US012532662B2

(12) United States Patent
Mitchell et al.

(10) Patent No.: US 12,532,662 B2
(45) Date of Patent: Jan. 20, 2026

(54) ORGANIC SEMICONDUCTING COMPOUNDS

(71) Applicant: RAYNERGY TEK INCORPORATION, Hsinchu (TW)

(72) Inventors: William Mitchell, Chandler's Ford (GB); Agnieszka Pron, Eastleigh (GB); Mansoor D'Lavari, Southampton (GB); Kane Heard, Southampton (GB); Jonathan Snow, Salisbury (GB)

(73) Assignee: RAYNERGY TEK INCORPORATION, Hsinchu (TW)

( * ) Notice: Subject to any disclaimer, the term of this patent is extended or adjusted under 35 U.S.C. 154(b) by 1121 days.

(21) Appl. No.: 17/042,468

(22) PCT Filed: Mar. 26, 2019

(86) PCT No.: PCT/EP2019/057501

§ 371 (c)(1),
(2) Date: Sep. 28, 2020

(87) PCT Pub. No.: WO2019/185580

PCT Pub. Date: Oct. 3, 2019

(65) Prior Publication Data

US 2021/0070770 A1 Mar. 11, 2021

(30) Foreign Application Priority Data

Mar. 28, 2018 (EP) .................................... 18164648

(51) Int. Cl.

| | |
|---|---|
| ***H10K 85/60*** | (2023.01) |
| ***C07D 495/14*** | (2006.01) |
| ***C07D 495/22*** | (2006.01) |
| ***C07D 519/00*** | (2006.01) |
| ***H10K 30/30*** | (2023.01) |
| ***H10K 30/50*** | (2023.01) |
| ***H10K 50/15*** | (2023.01) |
| ***H10K 50/16*** | (2023.01) |
| ***H10K 50/18*** | (2023.01) |
| ***H10K 85/10*** | (2023.01) |
| ***H10K 85/20*** | (2023.01) |
| ***H10K 85/40*** | (2023.01) |

(52) U.S. Cl.

CPC ....... *H10K 85/6576* (2023.02); *C07D 495/14* (2013.01); *C07D 495/22* (2013.01); *C07D 519/00* (2013.01); *H10K 85/1135* (2023.02); *H10K 85/211* (2023.02); *H10K 85/40* (2023.02); *H10K 85/656* (2023.02); *H10K 85/6572* (2023.02); *H10K 85/6574* (2023.02); *H10K 30/30* (2023.02); *H10K 30/50* (2023.02); *H10K 50/15* (2023.02); *H10K 50/16* (2023.02); *H10K 50/18* (2023.02)

(58) Field of Classification Search

CPC .................................................... C07D 495/22

See application file for complete search history.

(56) References Cited

FOREIGN PATENT DOCUMENTS

| | | | |
|---|---|---|---|
| CN | 106103436 | A | 11/2016 |
| WO | 2011/161262 | A1 | 12/2011 |
| WO | 2015/044377 | A1 | 2/2015 |
| WO | 2015139802 | A1 | 9/2015 |
| WO | 2018036914 | A1 | 3/2018 |

OTHER PUBLICATIONS

First Office Action mailed to Taiwanese Corresponding Patent Application No. 201980036621.6 on Aug. 24, 2023.
X. Li, et al., Journal of Materials Chemistry A, Royal Society of Chemistry, J. Mater. Chem. A, 2017, DOI: 10.1039/C7TA07049G.
PCT International Search Report.

*Primary Examiner* — William D Young
(74) *Attorney, Agent, or Firm* — WPAT, PC

(57) ABSTRACT

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these compounds, compositions or polymer blends.

18 Claims, No Drawings

ORGANIC SEMICONDUCTING COMPOUNDS

TECHNICAL FIELD

The invention relates to novel organic semiconducting compounds containing a polycyclic unit, to methods for their preparation and educts or intermediates used therein, to compositions, polymer blends and formulations containing them, to the use of the compounds, compositions and polymer blends as organic semiconductors in, or for the preparation of, organic electronic (OE) devices, especially organic photovoltaic (OPV) devices, perovskite-based solar cell (PSC) devices, organic photo-detectors (OPD), organic field effect transistors (OFET) and organic light emitting diodes (OLED), and to OE, OPV, PSC, OPD, OFET and OLED devices comprising these compounds, compositions or polymer blends.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, perovskite-based solar cell (PSC) devices, sensors, memory elements and logic circuits to name just a few. The organic semiconducting materials are typically present in the electronic device in the form of a thin layer, for example of between 50 and 300 nm thickness.

One particular area of importance is organic photovoltaics (OPV). Conjugated polymers have found use in OPVs as they allow devices to be manufactured by solution-processing techniques such as spin casting, dip coating or ink jet printing. Solution processing can be carried out cheaper and on a larger scale compared to the evaporative techniques used to make inorganic thin film devices. Currently, polymer based photovoltaic devices are achieving efficiencies above 10%.

Another particular area of importance is OFETs. The performance of OFET devices is principally based upon the charge carrier mobility of the semiconducting material and the current on/off ratio, so the ideal semiconductor should have a low conductivity in the off state, combined with high charge carrier mobility ($>1\times10^{-3}$ $cm^2$ $V^{-1}$ $s^{-1}$). In addition, it is important that the semiconducting material is stable to oxidation i.e. it has a high ionisation potential, as oxidation leads to reduced device performance. Further requirements for the semiconducting material are good processibility, especially for large-scale production of thin layers and desired patterns, and high stability, film uniformity and integrity of the organic semiconductor layer.

Organic photodetectors (OPDs) are a further particular area of importance, for which conjugated light-absorbing polymers offer the hope of allowing efficient devices to be produced by solution-processing technologies, such as spin casting, dip coating or ink jet printing, to name a few only.

The photosensitive layer in an OPV or OPD device is usually composed of at least two materials, a p-type semiconductor, which is typically a conjugated polymer, an oligomer or a defined molecular unit, and an n-type semiconductor, which is typically a fullerene or substituted fullerene, graphene, a metal oxide, or quantum dots.

However, the OSC materials disclosed in prior art for use in OE devices have several drawbacks. For example, the fullerenes or fullerene derivatives which have hitherto been used as electron acceptors in OPV or OPD devices are often difficult to synthesize or purify, and/or do not absorb light strongly in the near IR spectrum >700 nm, or do often not form a favourable morphology and/or miscibility with the donor material. Furthermore, the necessary phase separated bulk heterojunction morphology can be negatively impacted by heat and/or light.

Therefore, there is still a need for OSC materials for use in OE devices like OPVs, PSCs, OPDs and OFETs, which have advantageous properties, in particular good processability, a high solubility in organic solvents, good structural organization and film-forming properties. In addition, the OSC materials should be easy to synthesize, especially by methods suitable for mass production. For use in OPV cells, the OSC materials should especially have a low bandgap, which enables improved light harvesting by the photoactive layer and can lead to higher cell efficiencies, high stability and long lifetime. For use in OFETs the OSC materials should especially have high charge-carrier mobility, high on/off ratio in transistor devices, high oxidative stability and long lifetime.

It was an aim of the present invention to provide new OSC compounds, especially n-type OSCs, which can overcome the drawbacks of the OSCs from prior art, and which provide one or more of the above-mentioned advantageous properties, especially easy synthesis by methods suitable for mass production, good processability, high stability, long lifetime in OE devices, good solubility in organic solvents, high charge carrier mobility, and a low bandgap. Another aim of the invention was to extend the pool of OSC materials and n-type OSCs available to the expert. Other aims of the present invention are immediately evident to the expert from the following detailed description.

The inventors of the present invention have found that one or more of the above aims can be achieved by providing compounds as disclosed and claimed hereinafter.

These compounds represent a novel, alternative type of n-type organic semiconductors, which do not include a fullerene moiety, and which are hereinafter also referred to as "non-fullerene acceptor(s)" or "NFA(s)".

These NFA compounds comprise a polycyclic core, as shown in formula I, and further comprise one or two terminal acceptor groups, attached to the core via vinyl spacer groups, which are electron withdrawing relative to the central polycyclic core, and do optionally further comprise one or more aromatic or heteroaromatic spacer groups which are located either between the vinyl spacer and the polycyclic core and/or between the vinyl spacer and the terminal groups and which can be electron withdrawing or electron donating relative to the polycyclic core.

As a result these compounds have an acceptor-donor-acceptor (A-D-A) structure, wherein the polycyclic core acts as donor and the terminal groups, optionally together with the spacer groups, act as acceptor.

It has been found that compounds comprising the aforementioned structural features can be used as n-type OSCs which show advantageous properties as described above.

In prior art A-D-A type NFA compounds have been reported comprising an IDT core that is flanked by two terminal 2-(3-oxo-2,3-dihydroinden-1-ylidene)malononitrile withdrawing groups, as disclosed for example in Y. Lin et al., *Adv. Mater.,* 2015, 27, 1170; H. Lin et al., *Adv. Mater.,* 2015, 27, 7299; N. Qiu et al., *Adv. Mater.,* 2017, 29, 1604964; CN104557968 A and CN105315298 A.

X. Li et al., *Chem. Mater.* 2017, 29, 10130 discloses A-D-A type NFA compounds ITVIC, ITVfIC and ITVffIC, which consist of an indaceno-dithienothiophene core and two terminal acceptor groups attached thereto via vinyl spacer groups, and their use as acceptor for polymer solar cells. X. Li et al., *J. Mater. Chem. A.* 2018, DOI: 10.1039/C8TA00581H also discloses the compound ITVffIC.

ITVIC

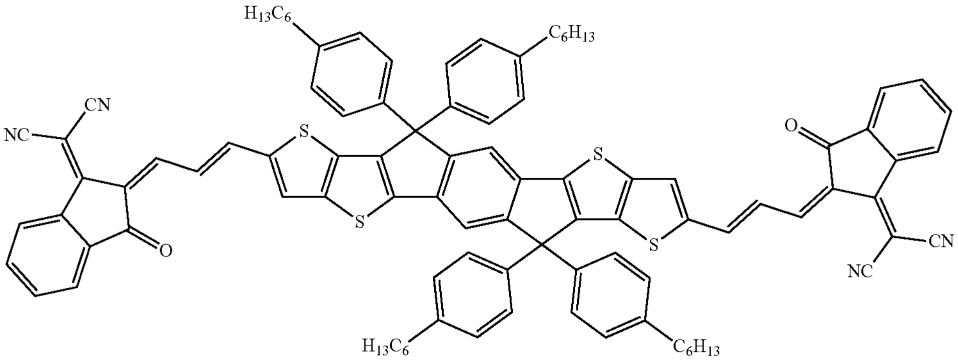

ITVfIC

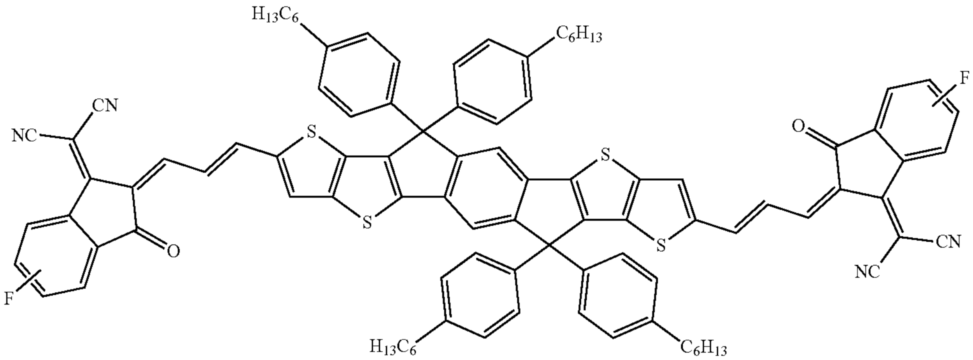

ITVffIC

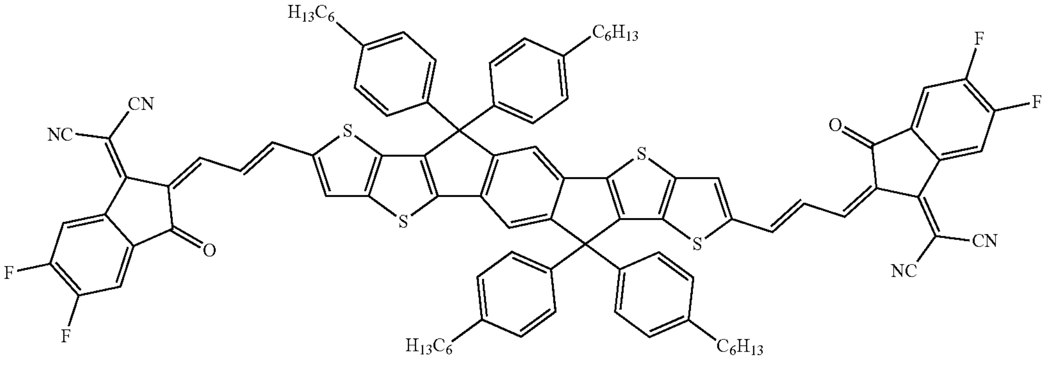

However, compounds as disclosed and claimed hereinafter have hitherto not been disclosed in prior art for use as n-type semiconductors.

SUMMARY

The invention relates to a compound of formula I

I

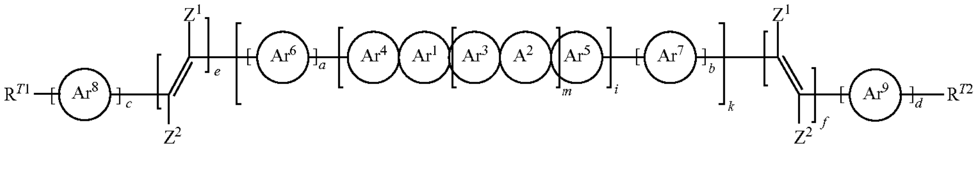

wherein the individual radicals, independently of each other and on each occurrence identically or differently, have the following meanings $Ar^1$, $Ar^2$ a group selected from the following formulae

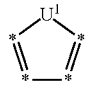

A1

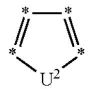

A2

$Ar^{3-5}$ arylene or heteroarylene that has from 5 to 20 ring atoms, is mono- or polycyclic, optionally contains fused rings, and is unsubstituted or substituted by one or more identical or different groups $R^1$ or $L^S$, $Ar^{6-9}$ arylene or heteroarylene that has from 5 to 20 ring atoms, is mono- or polycyclic, optionally contains fused rings, and is unsubstituted or substituted by one or more identical or different groups $R^1$ or $L^S$, or $CY^1{=}CY^2$ or —C≡C—, $U^1$, $U^2$ $CR^1R^2$, $SiR^1R^2$, $GeR^1R^2$, $C{=}CR^1R^2$, $NR^1$ or C=O, preferably $CR^1R^2$ or $SiR^1R^2$, very preferably $CR^1R^2$, $R^1$, $R^2$ $R^W$, H, F, Cl, CN, or straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0{=}CR^{00}$—, —$CY^1{=}CY^2$— or —C≡C— in such a manner that 0 and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups $L^S$, and the pair of $R^1$ and $R^2$, together with the C, Si or Ge atom to which they are attached, may also form a spiro group with 5 to 20 ring atoms which is mono- or polycyclic, does optionally contain fused rings, and is unsubstituted or substituted by one or more identical or different groups $L^S$, $R^W$ an electron withdrawing group, which preferably has one of the meanings given for an electron withdrawing group $R^{T1}$, $R^{T1}$, $R^{T2}$ H, F, Cl, CN, $NO_2$, or a carbyl or hydrocarbyl group with 1 to 30 C atoms that is optionally substituted by one or more groups $L^S$ and optionally comprises one or more hetero atoms, and which is preferably selected from electron withdrawing groups, $Z^1$, $Z^2$ one of the meanings given for $R^1$, preferably one of the meanings given for $Y^1$, $Y^1$, $Y^2$H, F, Cl or CN, $L^S$ F, Cl, —$NO_2$, —CN, —NC, —NCO, —NCS, —OCN, —SCN, $R^0$, $OR^0$, $SR^0$, —C(=O)$X^0$, —C(=O)$R^0$, —C(=O)—$OR^0$, —O—C(=O)—$R^0$, —$NH_2$, —$NHR^0$, —$NR^0R^{00}$, —C(=O)$NHR^0$, —C(=O)$NR^0R^{00}$, —$SO_3R^0$, —$SO_2R^0$, —OH, —$NO_2$, —$CF_3$, —$SF_5$, or optionally substituted silyl, or carbyl or hydrocarbyl with 1 to 30, preferably 1 to 20 C atoms that is optionally substituted and optionally comprises one or more hetero atoms, preferably F, —CN, $R^0$, —$OR^0$, —$SR^0$, —C(=O)—$R^0$, —C(=O)—$OR^0$, —O—C(=O)—$R^0$, —O—C(=O)—$OR^0$, —C(=O)—$NHR^0$, or —C(=O)—$NR^0R^{00}$, $R^0$, $R^{00}$H or straight-chain or branched alkyl with 1 to 20, preferably 1 to 12, C atoms that is optionally fluorinated, $X^0$ halogen, preferably F or Cl, a, b, c, d 0 or an integer from 1 to 10, preferably 0, 1, 2, 3, 4 or 5, very preferably 0, 1, 2 or 3, e, f 0 or 1, with e+f being 1 or 2, m 0 or an integer from 1 to 10, preferably 0, 1, 2, 3, 4, 5, 6 or 7, very preferably 0, 1, 2 or 3, k an integer from 1 to 10, preferably 1, 2, 3, 4, 5, 6 or 7, very preferably 1, 2 or 3, most preferably 1, i an integer from 1 to 10, preferably 0, 1, 2, 3, 4, 5, 6 or 7, very preferably 1, 2 or 3, most preferably 1, wherein at least one of $R^{T1}$ and $R^{T2}$ is an electron withdrawing group, and wherein, if i is 1 and $Ar^3$ is benzene, at least one of $Ar^4$ and $Ar^5$ is different from thieno[3,2b]thiophene.

The invention further relates to novel synthesis methods for preparing compounds of formula I, and novel intermediates used therein.

The invention further relates to the use of compounds of formula I as semiconductor, preferably as electron acceptor or n-type semiconductor, preferably in a semiconducting material, an electronic or optoelectronic device, or a component of an electronic or optoelectronic device.

The invention further relates to the use of compounds of formula I as dyes or pigments.

The invention further relates to a composition comprising one or more compounds of formula I, and further comprising one or more compounds having one or more of a semiconducting, hole or electron transport, hole or electron blocking, insulating, binding, electrically conducting, photoconducting, photoactive or light emitting property.

The invention further relates to a composition comprising one or more compounds of formula I, and further comprising a binder, preferably an electrically inert binder, very preferably an electrically inert polymeric binder.

The invention further relates to a composition comprising a compound of formula I, and further comprising one or more electron donors or p-type semiconductors, preferably selected from conjugated polymers.

The invention further relates to a composition comprising one or more n-type semiconductors, at least one of which is a compound of formula I, and further comprising one or more p-type semiconductors.

The invention further relates to a composition comprising one or more n-type semiconductors, at least one of which is a compound of formula I, and at least one other of which is a fullerene or fullerene derivative, and further comprising one or more p-type semiconductors, preferably selected from conjugated polymers.

The invention further relates to a bulk heterojunction (BHJ) formed from a composition comprising a compound of formula I as electron acceptor or n-type semiconductor, and one or more compounds which are electron donor or p-type semiconductors, and are preferably selected from conjugated polymers.

The invention further relates to the use of a compound of formula I or a composition as described above and below, as semiconducting, charge transporting, electrically conducting, photoconducting, photoactive or light emitting material.

The invention further relates to the use of a compound of formula I or a composition as described above and below, in an electronic or optoelectronic device, or in a component of such a device or in an assembly comprising such a device.

The invention further relates to a semiconducting, charge transporting, electrically conducting, photoconducting, photoactive or light emitting material, comprising a compound of formula I or a composition as described above and below.

The invention further relates to an electronic or optoelectronic device, or a component thereof, or an assembly comprising it, which comprises a compound of formula I or a composition as described above and below.

The invention further relates to an electronic or optoelectronic device, or a component thereof, or an assembly comprising it, which comprises a semiconducting, charge transporting, electrically conducting, photoconducting or light emitting material as described above and below.

The invention further relates to a formulation comprising one or more compounds of formula I, or comprising a composition or semiconducting material as described above and below, and further comprising one or more solvents, preferably selected from organic solvents.

The invention further relates to the use of a formulation as described above and below for the preparation of an electronic or optoelectronic device or a component thereof.

The invention further relates to an electronic or optoelectronic device or a component thereof, which is obtained through the use of a formulation as described above and below.

The electronic or optoelectronic device includes, without limitation, organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cells (PSC), laser diodes, Schottky diodes, photoconductors, photodetectors, thermoelectric devices.

Preferred devices are OFETs, OTFTs, OPVs, PSCs, OPDs and OLEDs, in particular OPDs and BHJ OPVs or inverted BHJ OPVs.

The component of the electronic or optoelectronic device includes, without limitation, charge injection layers, charge transport layers, interlayers, planarizing layers, antistatic films, polymer electrolyte membranes (PEM), conducting substrates and conducting patterns.

The assembly comprising an electronic or optoelectronic device includes, without limitation, integrated circuits (IC), radio frequency identification (RFID) tags, security markings, security devices, flat panel displays, LC windows, backlights of flat panel displays, electrophotographic devices, electrophotographic recording devices, organic memory devices, sensor devices, biosensors and biochips.

In addition the compounds of formula I and compositions as described above and below can be used as dichroitic dyes, especially in smart windows such as LC windows, as electrode materials in batteries, or in components or devices for detecting and discriminating DNA sequences.

Terms and Definitions

Unless stated otherwise, in the units, polymers and compounds according to the present invention the electron withdrawing groups $R^{T1}$ and $R^{T2}$ are understood to be electron withdrawing relative to the polycyclic core.

As used herein, the terms "indaceno group" and "indaceno-type group" will be understood to mean a group comprising two cyclopentadiene rings, or heterocyclic, vinylidene or ketone derivatives thereof, that are fused to a central aromatic or heteroaromatic aromatic ring Ar, and which can have cis- or trans-configuration, as exemplarily shown below

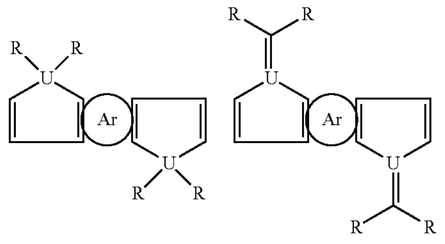

(trans-configuration)

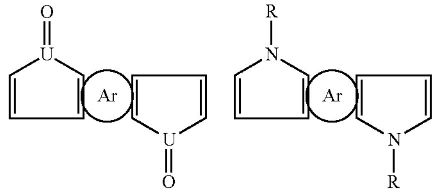

(trans-configuration)

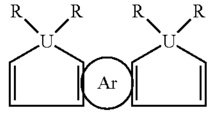

(cis-configuration)

wherein U is e.g. C, Si or Ge and R is a carbyl or hydrocarbyl group.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "donor unit" will be understood to mean a unit, preferably a conjugated arylene or heteroarylene unit, which has an electron donating or electron pushing property towards a neighboured conjugated unit. The term "acceptor unit" will be understood to mean a unit, preferably a conjugated arylene or heteroarylene unit, which has an electron accepting or electron withdrawing property towards a neighboured conjugated unit. The term "spacer unit" will be understood to mean a unit which can be conjugated or non-conjugated and is located between the polycyclic donor core and the terminal group $R^{T1}$ or $R^{T2}$ As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "conjugated" will be understood to mean a compound (for example a polymer) that contains mainly C atoms with $sp^2$-hybridization (or optionally also sp-hybridization), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the term "polymer" will be understood to mean a molecule of high relative molecular mass, the structure of which essentially comprises multiple repetitions of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5, very preferably ≥10, repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit an asterisk (*) will be understood to mean a chemical linkage, usually a single bond, to an adjacent unit or to a terminal group in the polymer backbone.

In a ring, like for example a benzene or thiophene ring, an asterisk (*) will be understood to mean a C atom that is fused to an adjacent ring.

As used herein, in a formula showing a ring, a polymer or a repeat unit a dashed line (- - - - - ) will be understood to mean a single bond.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerization reaction, like for example a group having the meaning of $R^{31}$ or $R^{32}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerization reaction.

Alternatively the endcapper can be added in situ to the reaction mixture before or during the polymerization reaction. In situ addition of an endcapper can also be used to terminate the polymerization reaction and thus control the molecular weight of the forming polymer. Typical endcap groups are for example H, phenyl and lower alkyl.

As used herein, unless stated otherwise the molecular weight is given as the number average molecular weight $M_n$ or weight average molecular weight $M_W$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, chlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, Sn, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has up to 40, preferably up to 25, very preferably up to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 1 to 40, preferably 6 to 40 C atoms, wherein each of these groups optionally contains one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_1$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are each optionally replaced by a hetero atom, preferably selected from N, O, P, S, Si and Se, or by a —S(O)— or —$S(O)_2$— group. The non-aromatic carbo- and heterocyclic groups are mono- or polycyclic, may also contain fused rings, preferably contain 1, 2, 3 or 4 fused or unfused rings, and are optionally substituted with one or more groups $L^S$.

$L^S$ is preferably selected from F, Cl, —CN, —$NO_2$, —NC, —NCO, —NCS, —OCN, —SCN, —$R^0$, —$OR^0$, —$SR^0$, —C(═O)$X^0$, —C(═O)$R^0$, —C(═O)—$OR^0$, —O—C(═O)—$R^0$, —$NH_2$, —$NHR^0$, —$NR^0R^{00}$, —C(═O)$NHR^0$, —C(═O)$NR^0R^{00}$, —$SO_3R^0$, —$SO_2R^0$, —OH, —$CF_3$, —$SF_5$, or optionally substituted silyl, or carbyl or hydrocarbyl with 1 to 30, preferably 1 to 20 C atoms that is optionally substituted and optionally comprises one or more hetero atoms, wherein $X^0$ is halogen, preferably F or Cl, and $R^0$, $R^{00}$ each independently denote H or straight-chain or branched alkyl with 1 to 20, preferably 1 to 12 C atoms that is optionally fluorinated.

Preferably $L^S$ is selected from F, —CN, $R^0$, —$OR^0$, —$SR^0$, —C(═O)—$R^0$, —C(═O)—$OR^0$, —O—C(═O)—$R^0$, —O—C(═O)—$OR^0$, —C(═O)—$NHR^0$ and —C(═O)—$NR^0R^0$.

Further preferably $L^S$ is selected from F or alkyl, alkoxy, oxaalkyl, thioalkyl, fluoroalkyl, fluoroalkoxy, alkylcarbonyl, alkoxycarbonyl, with 1 to 16 C atoms, or alkenyl or alkynyl with 2 to 16 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30, very preferably 5 to 20, ring C atoms, is mono- or polycyclic and may also contain fused rings, preferably contains 1, 2, 3 or 4 fused or unfused rings, and is optionally substituted with one or more groups $L^S$ as defined above.

A heteroaryl group as referred to above and below preferably has 4 to 30, very preferably 5 to 20, ring C atoms, wherein one or more of the ring C atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups $L^S$ as defined above.

An arylalkyl or heteroarylalkyl group as referred to above and below preferably denotes —$(CH_2)_z$-aryl or —$(CH_2)_z$-heteroaryl, wherein z is an integer from 1 to 6, preferably 1, and "aryl" and "heteroaryl" have the meanings given above and below. A preferred arylalkyl group is benzyl which is optionally substituted by $L^S$.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may each be replaced by N, naphthalene, thiophene, selenophene, thienothiophene, dithienothiophene, fluorene and oxazole, all of which can be unsubstituted, mono- or polysubstituted with $L^S$ as defined above. Very preferred aryl and heteroaryl groups are selected from phenyl, pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, 2,5-dithiophene-2',5'-diyl, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with $L^S$ as defined above. Further examples of aryl and heteroaryl groups are those selected from the groups shown hereinafter.

An alkyl group or an alkoxy group, i.e., where the terminal $CH_2$ group is replaced by —O—, can be straight-chain or branched. Particularly preferred straight-chains have 2, 3, 4, 5, 6, 7, 8, 12 or 16 carbon atoms and accordingly denote preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are each replaced by —CH═CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, can be straight-chain. Particularly preferred straight-chains are 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly, it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl or 5,5-bis-(ethoxycarbonyl)-hexyl.

A thioalkyl group, i.e., where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridized vinyl carbon atom is replaced.

A fluoroalkyl group can be perfluoroalkyl $C_hF_{2h+1}$, wherein h is an integer from 1 to 15, in particular $CF_3$, $C_2F_5$, $C_3F_7$, $C_4F_9$, $C_5F_{15}$, $C_6F_{13}$, $C_7F_{15}$ or $CF_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 3,7-dimethyloctyl, 3,7,11-trimethyldodecyl, 2-propylpentyl, in particular 2-methylbutyl, 2-methylbutoxy, 2-methylpentoxy, 3-methyl-pentoxy, 2-ethyl-hexoxy, 2-butyloctoxyo, 2-hexyldecoxy, 2-octyldodecoxy, 3,7-dimethyloctoxy, 3,7,11-trimethyldodecoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloro-propionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl and 2-fluoromethyloctyloxy for example. Very preferred are 2-methylbutyl, 2-ethylhexyl, 2-butyloctyl, 2-hexyldecyl, 2-octyldodecyl, 3,7-dimethyloctyl, 3,7,11-trimethyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the substituents on an aryl or heteroaryl ring are independently of each other selected from primary, secondary or tertiary alkyl, alkoxy, oxaalkyl, thioalkyl, alkylcarbonyl or alkoxycarbonyl with 1 to 30 C atoms, wherein one or more H atoms are each optionally replaced by F, or aryl, aryloxy, heteroaryl or heteroaryloxy that is optionally alkylated, alkoxylated, alkylthiolated or esterified and has 4 to 30, preferably 5 to 20, ring atoms. Further preferred substituents are selected from the group consisting of the following formulae

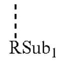

SUB1

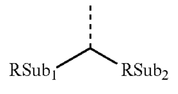

SUB2

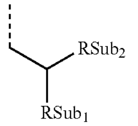

SUB3

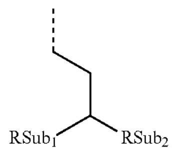

SUB4

-continued

SUB5

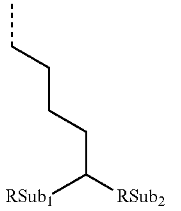

SUB6

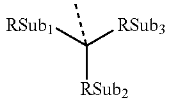

SUB7

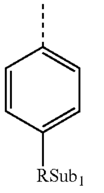

SUB8

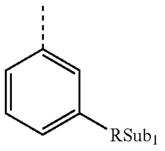

SUB9

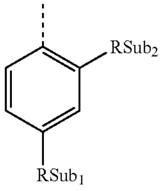

SUB10

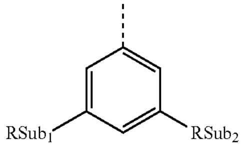

SUB11

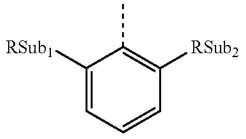

SUB12

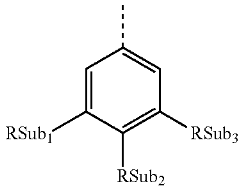

SUB13

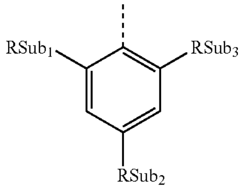

-continued

SUB14

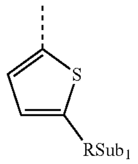

SUB15

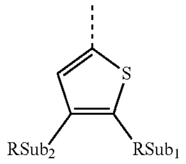

SUB16

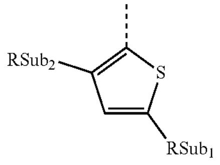

SUB17

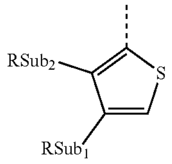

SUB18

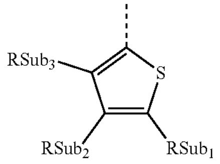

wherein $RSub_{1-3}$ each denote $L^S$ as defined above and below and where at least, preferably all, of $RSub_{1-3}$ is alkyl, alkoxy, oxaalkyl, thioalkyl, alkyl-carbonyl or alkoxycarbonyl with up to 24 C atoms, preferably up to 20 C atoms, that is optionally fluorinated, and wherein the dashed line denotes the link to the ring to which these groups are attached. Very preferred among these substituents are those wherein all $RSub_{1-3}$ subgroups are identical.

As used herein, if an aryl(oxy) or heteroaryl(oxy) group is "alkylated or alkoxylated", this means that it is substituted with one or more alkyl or alkoxy groups having from 1 to 24 C-atoms and being straight-chain or branched and wherein one or more H atoms are each optionally substituted by an F atom.

Above and below, $Y^1$ and $Y^2$ are independently of each other H, F, C or CN.

As used herein, —CO—, —C(═O)— and —C(O)— will be understood to mean a carbonyl group, i.e. a group having the structure

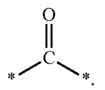

As used herein C═CR$^1$R$^2$ will be understood to mean a group having the structure

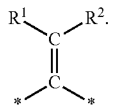

As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer or an intermediate is preferably Br or I.

Above and below, the term "mirror image" means a moiety that can be obtained from another moiety by flipping it vertically or horizontally across an external symmetry plane or a symmetry plane extending through the moiety. For example the moiety

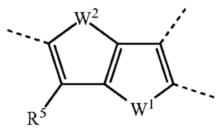

also includes the mirror images

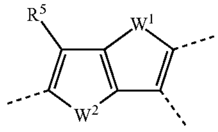

and

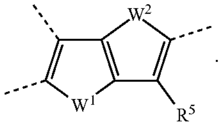

.

DETAILED DESCRIPTION

The compounds of the present invention are easy to synthesize and exhibit advantageous properties. They show good processibility for the device manufacture process, high solubility in organic solvents, and are especially suitable for large scale production using solution processing methods.

The compounds of formula I are especially suitable as (electron) acceptor or n-type semiconductor, and for the preparation of blends of n-type and p-type semiconductors which are suitable for use in OPD or BHJ OPV devices.

The compounds of formula I are further suitable to replace the fullerene compounds that have hitherto been used as n-type semiconductor in OPV or OPD devices.

Besides, the compounds of formula I show the following advantageous properties:

i) Substitution in positions R$^{1-2}$ and/or Ar$^{1-9}$ and/or Z$^{1-2}$ for example with solubilising groups enables greater light stability of the bulk heterojunction.

ii) Substitution in positions R$^{1-2}$ and/or Ar$^{1-9}$ and/or Z$^{1-2}$ for example with solubilising groups enables greater stability towards light illumination of the bulk heterojunction through mediation of the crystallisation and/or phase separation kinetic, thus stabilising the initial equilibrium thermodynamics in the BHJ.

iii) Substitution in positions R$^{1-2}$ and/or Ar$^{1-9}$ and/or Z$^{1-2}$ for example with solubilising groups enables greater thermal stability of the bulk heterojunction through mediation of the crystallisation and/or phase separation kinetic, thus stabilising the initial equilibrium thermodynamics in the BHJ.

iv) Compared to previously disclosed n-type OSCs for OPV/OPD application, the compounds of formula I provide the advantage that they enable further optimization of the HOMO and LUMO levels of the polycyclic unit through substitution, and careful selection of the Ar$^{1-9}$ units can give improved light absorption.

v) Further optimization of the HOMO and LUMO levels of the polycyclic unit in formula I through substitution and/or careful selection of the Ar$^{1-9}$ units can increase the open circuit potential ($V_{oc}$).

vi) When using the compounds as n-type OSC in a composition with a p-type OSC in the photoactive layer of an OPV or OPD, additional fine-tuning of the HOMO and LUMO levels of the polycyclic unit in formula I, for example through substitution and/or careful selection of the Ar$^{1-9}$ units, can reduce the energy loss in the electron transfer process between the n-type acceptor and the p-type donor material in the photoactive layer.

vii) Substitution in positions R$^{1-2}$ and/or Ar$^{1-9}$ and/or Z$^{1-2}$ can enable higher solubility in non-halogenated solvents due to the increased number of solubilising groups.

viii) Solubility can be modified by the careful selection of the Ar$^{1-9}$ units, for example by rendering the molecule asymmetric.

ix) Compared to previously disclosed n-type OSCs for OPV/OPD application, the compounds of formula I provide the advantage that they enable further optimization of the HOMO and LUMO levels of the polycyclic unit through careful selection of the vinyl units giving improved light absorption.

The synthesis of the compounds of formula I can be achieved based on methods that are known to the skilled person and described in the literature, as will be further illustrated herein.

In the compounds of formula I, if i is 1 and Ar$^3$ is benzene, at least one of Ar$^4$ and Ar$^5$ is different from thieno[3,2b]thiophene.

Preferred compounds of formula I are those wherein at least one of Ar$^4$ and Ar$^5$ is different from thieno[3,2b]thiophene.

Further preferred compounds of formula I are those wherein Ar$^3$ is thieno[3,2b]thiophene.

Preferred compounds of formula I are those wherein i is 0, 1, 2 or 3.

Further preferred compounds of formula I are those wherein m is 1 and k is 1.

Further preferred compounds of formula I are those wherein c is 0 and d is 0.

Further preferred compounds of formula I are those wherein e is 1 and f is 0.

Further preferred compounds of formula I are those wherein e is 1 and f is 1.

Preferred groups Ar$^1$ and Ar$^2$ in formula I are on each occurrence identically or differently selected from the following formulae and their mirror images A1a

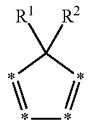

-continued

A2a

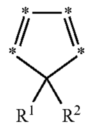

A1b

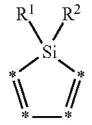

A2b

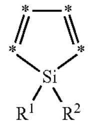

Especially preferred groups $Ar^1$ and $Ar^2$ are selected from formulae Ala and A2a.

In the compounds of formula I the groups $Ar^1$ and $Ar^2$ can be selected such that the indaceno-type groups have trans- or cis-configuration.

A first preferred embodiment of the present invention relates to compounds of formula I wherein m>0 and all indaceno-type groups have trans-configuration, i.e. one of the two groups $Ar^1$ and $Ar^2$ that are fused to the same group $Ar^3$ is of formula A1 and the other is of formula A2, as exemplarily illustrated below.

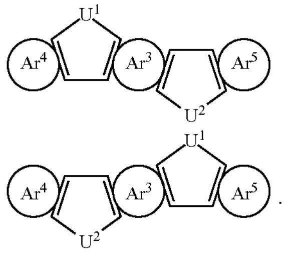

trans-configuration

Preferred compounds units of formula I according to this first preferred embodiment are selected from the following subformulae

I1

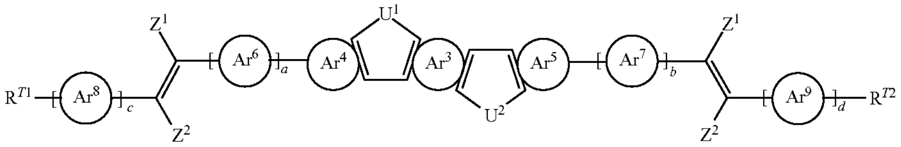

I2

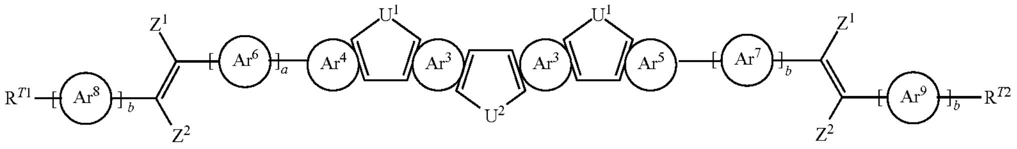

wherein $U^1$, $U^2$, $Ar^{3-9}$, $R^{T1}$, $R^{T2}$, $Z^1$, $Z^2$, a, b, c and d, independently of each other and on each occurrence identically or differently, have the meanings given in formula I or one of the preferred meanings given above and below.

Preferred compounds of formula I1 and I2 are those wherein c=d=0.

Preferred compounds of formula I1 and I2 are those wherein all of $U^1$ and $U^2$ denote $CR^1CR^2$.

A second preferred embodiment of the present invention relates to compounds of formula I wherein m>0 and at least one, preferably all, indaceno-type groups have cis-configuration, i.e. the groups $Ar^1$ and $Ar^2$ that are fused to the same group $Ar^3$ are both of formula A1 or both of formula A2, as exemplarily illustrated below.

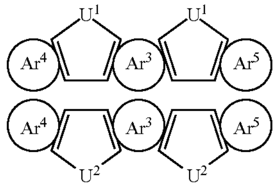

cis-configuration

This second preferred embodiment includes compounds of formula I having an "all-cis" configuration as exemplarily shown in formula I3 and I4 below, and compounds of formula I including both trans-configuration and cis-configuration, as exemplarily shown in formula I5 below.

Preferred compounds of formula I according to this second preferred embodiment are selected from the following subformulae

I3

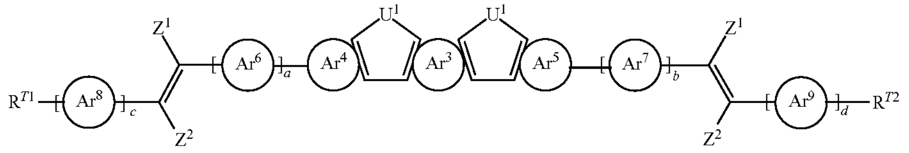

I4

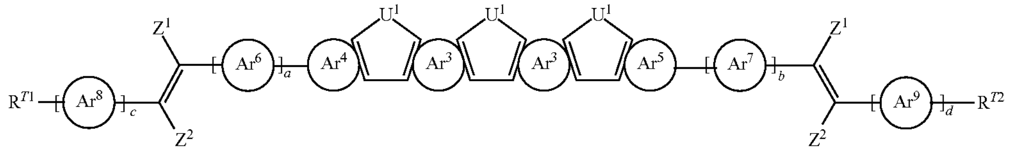

I5

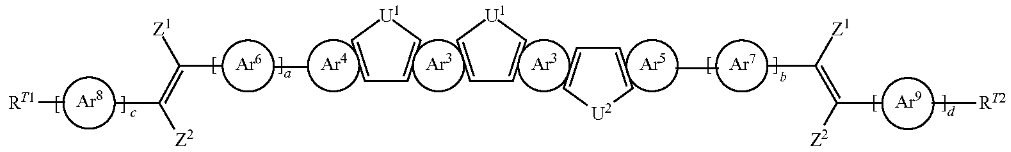

wherein $U^1$, $U^2$, $Ar^{3-9}$, $R^{T1}$, $R^{T2}$, $Z^1$, $Z^2$, a, b, c and d, independently of each other and on each occurrence identically or differently, have the meanings given in formula I or one of the preferred meanings given above and below.

Preferred compounds of formula I3, I4 and I5 are those wherein c=d=0.

Preferred compounds of formula I3, I4 and I5 are those wherein all of U and $U^2$ denote $CR^1CR^2$.

A third preferred embodiment of the present invention relates to compounds of formula I wherein m=0. Preferred compounds of formula I according to this third preferred embodiment are selected from the following subformulae

I6

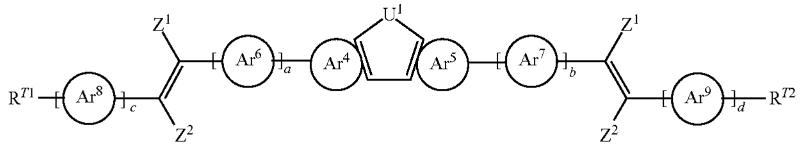

wherein $U^1$, $U^2$, $Ar^4$-9, $R^T$, $R^{T2}$, $Z^1$, $Z^2$, a, b, c and d, independently of each other and on each occurrence identically or differently, have the meanings given in formula I or one of the preferred meanings given above and below.

Preferred compounds of formula I6 are those wherein c=d=0.

Preferred compounds of formula I6 are those wherein U is $CR^1CR^2$.

Preferred groups $Ar^3$ in formula I and I1-I5 and their subformulae are on each occurrence identically or differently selected from the following formulae and their mirror images A3a

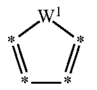

A3b

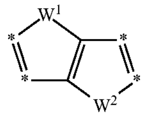

-continued

A3c

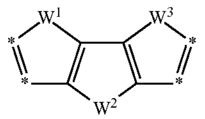

-continued
A3d
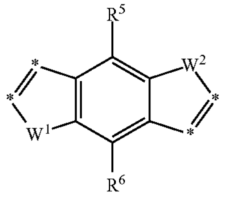
A3e
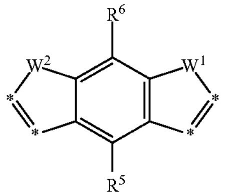
A3f
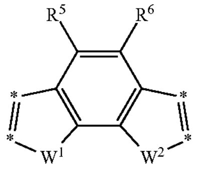
A3g
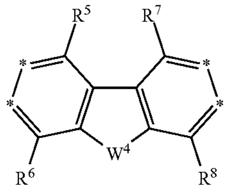
A3h
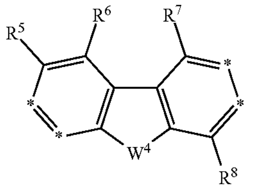
A3i
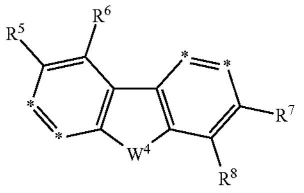
A3j
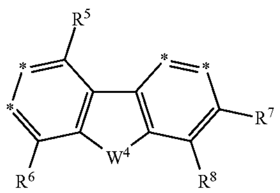
A3k
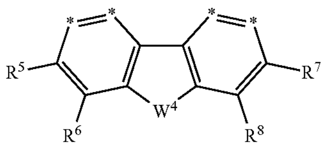
-continued
A3l
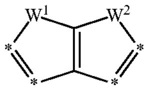
A3m
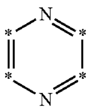
A3n
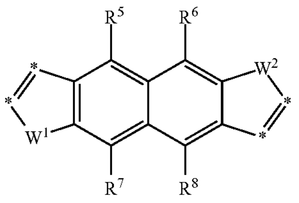
A3o
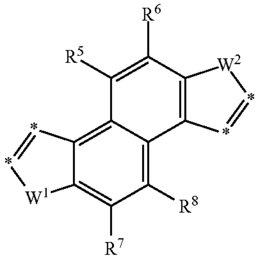
A3p
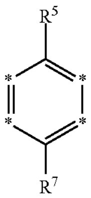
A3q
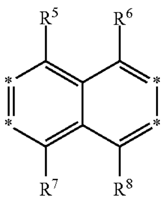
A3r
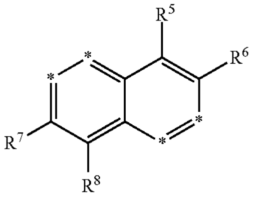
A3s
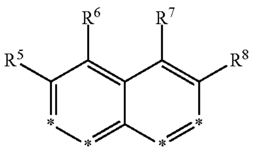

-continued

A3t

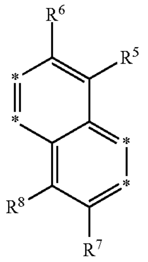

wherein the individual radicals, independently of each other and on each occurrence identically or differently, have the following meanings $W^1$, $W^2$, $W^3$ S, O, Se or C═O, preferably S, $W^4$ S, O or $NR^3$, preferably S, $R^{3-8}$ one of the meanings given for $R^1$ in formula I, Very preferred groups $Ar^3$ in formula I and I1-I5 and their subformulae are on each occurrence identically or differently selected from the following formulae and their mirror images A3a1

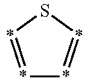

A3b1

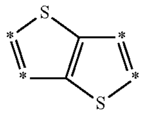

A3c1

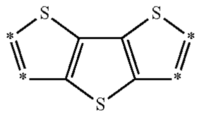

A3d1

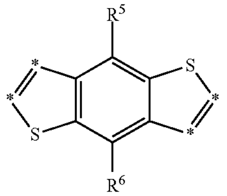

A3e1

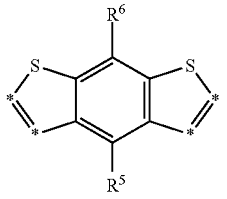

A3f1

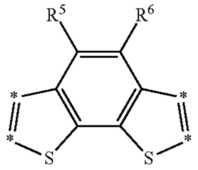

-continued

A3g1

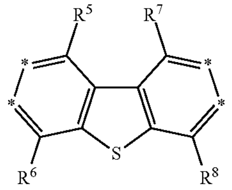

A3h1

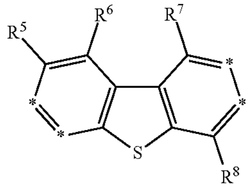

A3i1

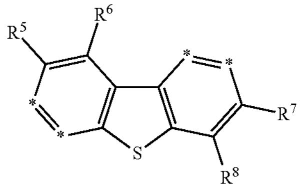

A3j1

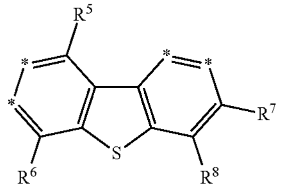

A3g2

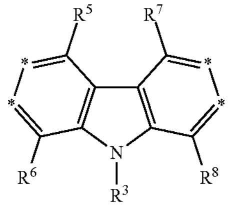

A3h2

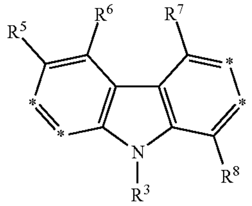

A3i2

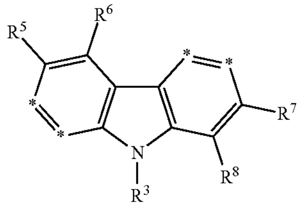

-continued

A3j2

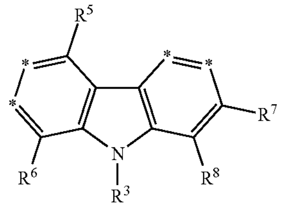

A3l1

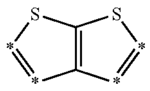

A3p

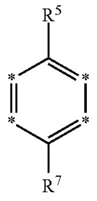

A3q

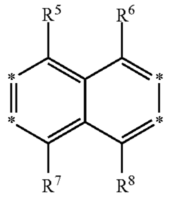

wherein $R^{5-8}$ have the meanings given above and below.

Very preferred groups $Ar^3$ are on each occurrence identically or differently selected from formula A3b, A3d and A3p, more preferably from formula A3b1, A3d1 and A3p, very preferably of formula A3b, most preferably of formula A3b1.

In a further preferred embodiment $Ar^3$ contains at least one heteroaryl ring, and is preferably selected from formulae A3a-A3o, more preferably from formulae A3a1-A3l1.

Preferred groups $Ar^4$ in formula I and I1-I6 and their subformulae are on each occurrence identically or differently selected from the following formulae and their mirror images A4a

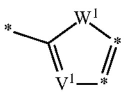

A4b

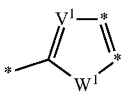

A4c

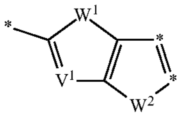

A4d

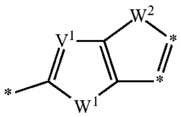

-continued

A4e

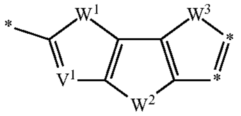

A4f

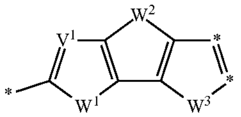

A4g

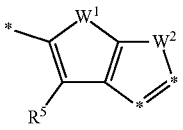

A4h

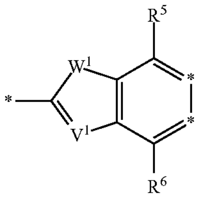

A4i

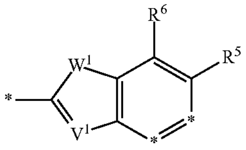

A4j

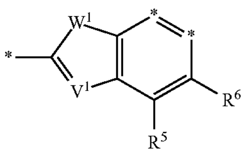

A4k

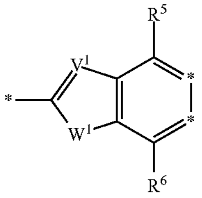

A4l

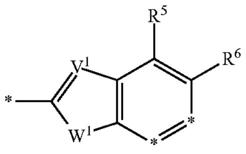

A4m

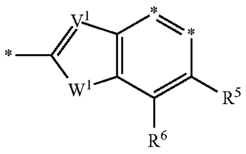

-continued

A4n

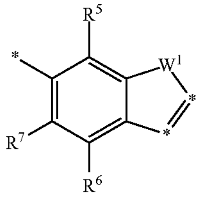

A4o

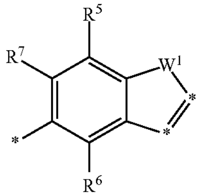

A4p

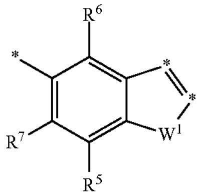

A4q

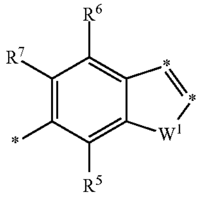

A4r

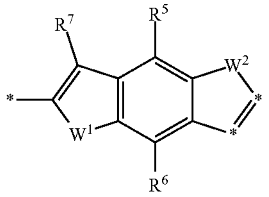

A4s

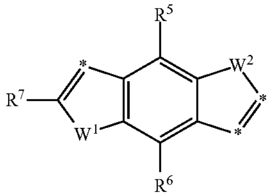

A4t

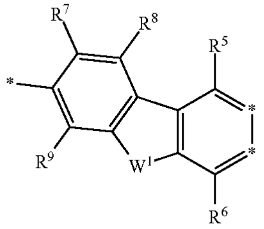

-continued

A4u

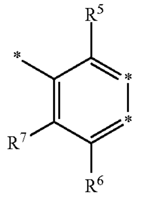

A4v

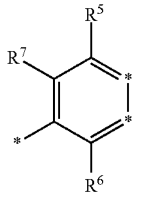

A4w

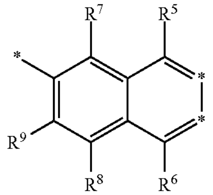

A4x

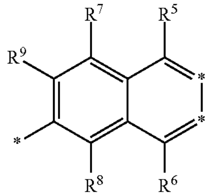

wherein $W^{1-3}$ and $R^{5-8}$ have the meanings given above and below, $V^1$ is $CR^5$ or N, and $R^9$ has one of the meanings given for $R^5$.

Very preferred groups $Ar^4$ in formula I and I1-I6 and their subformulae are on each occurrence identically or differently selected from the following formulae and their mirror images A4a1

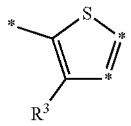

A4b1

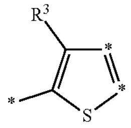

A4c1

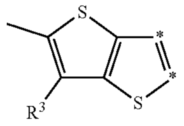

A4d1

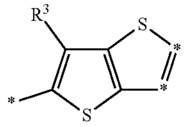

-continued
A4e1
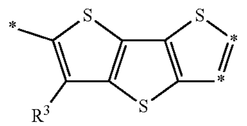
A4f1
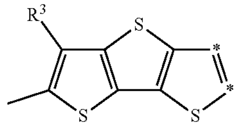
A4g1
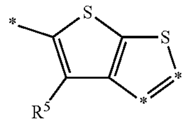
A4h1
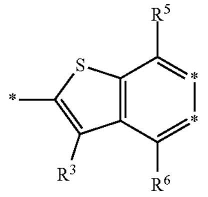
A4i1
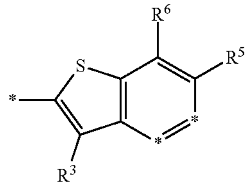
A4j1
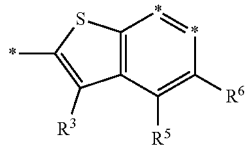
A4k1
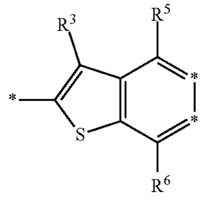
A4l1
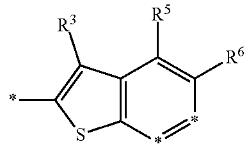
A4m1
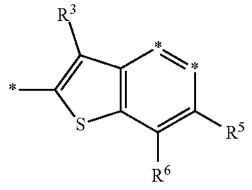
-continued
A4n1
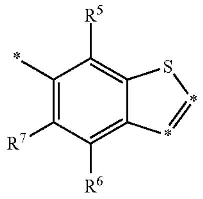
A4o1
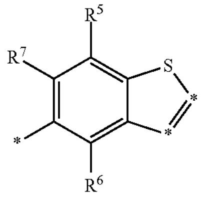
A4p1
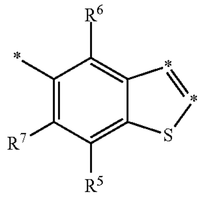
A4q1
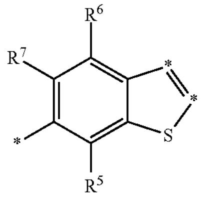
A4r1
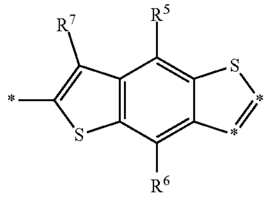
A4s1
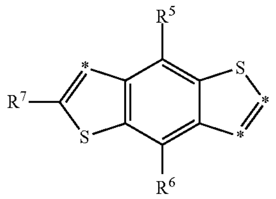
A4t1
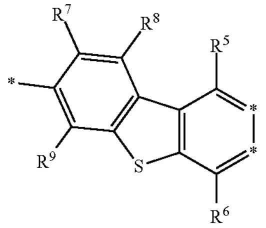

-continued

A4u

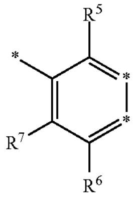

A4v

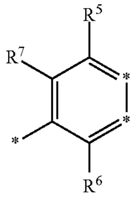

A4w

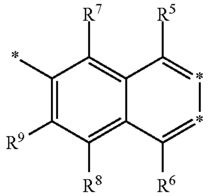

A4x

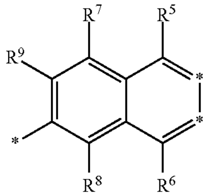

wherein $R^{5-7}$ have the meanings given above and below.

Very preferred groups $Ar^4$ are selected from formulae A4a, A4b, A4c, A4d, A4e, A4f, A4h, A4i, A4j, A4k, A4l, A4m, A4n, A4q, A4u and A4v, more preferably from formulae A4a1, A4b1, A4c1, A4d1, A4e1, A4f1, A4h1, A4i1, A4j1, A4k1, A4l1, A4m1, A4n1, A4q1, A4u and A4v.

Preferred groups $Ar^5$ in formula I and I1-I6 and their subformulae are on each occurrence identically or differently selected from the following formulae and their mirror images A5a

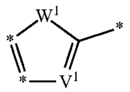

A5b

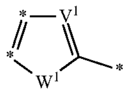

A5c

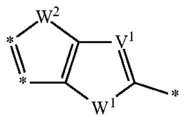

A5d

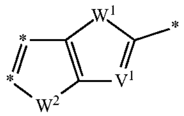

-continued

A5e

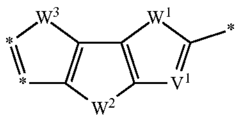

A5f

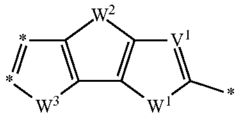

A5g

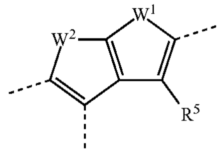

A5h

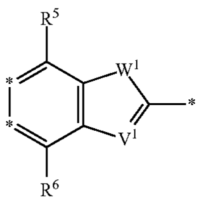

A5i

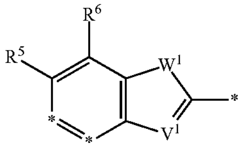

A5j

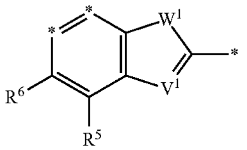

A5k

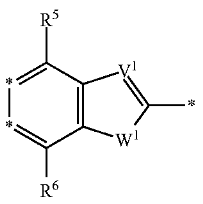

A5l

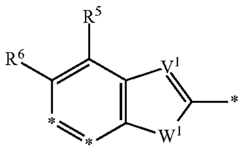

A5m

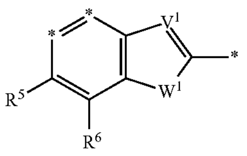

-continued
A5n
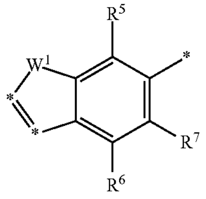
A5o
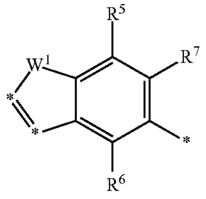
A5p
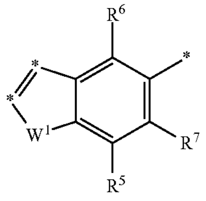
A5q
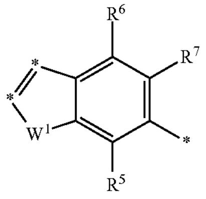
A5r
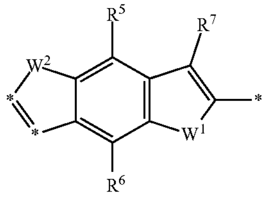
A5s
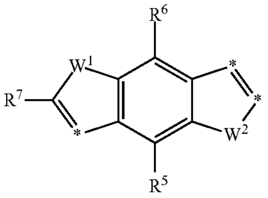
A5t
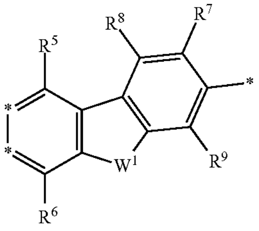
-continued
A5u
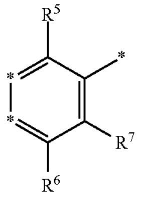
A5v
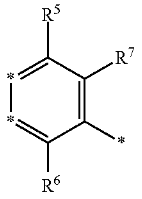
A5w
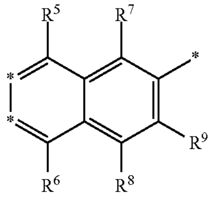
A5x
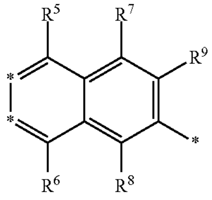
wherein $V^1$, $W^{1-3}$ and $R^{5-9}$ have the meanings given above and below.
Very preferred groups $Ar^5$ in formula I and I1-I6 and their subformulae are on each occurrence identically or differently selected from the following formulae and their mirror images
A5a1
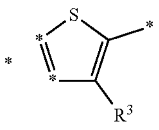
A5b1
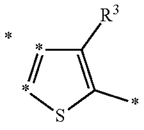
A5c1
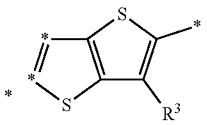
A5d1
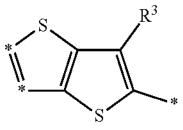

-continued
A5e1
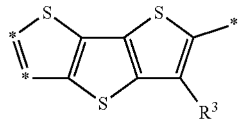
A5f1
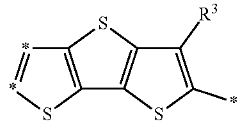
A5g1
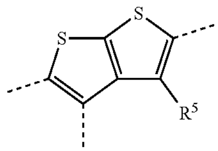
A5h1
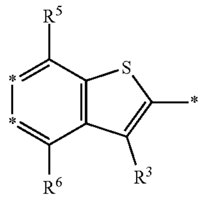
A5i1
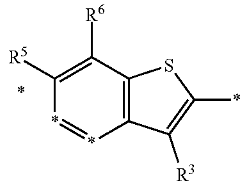
A5j1
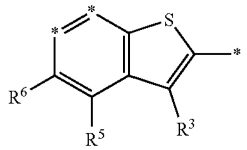
A5k1
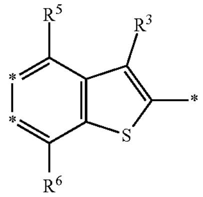
A5l1
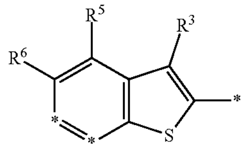
A5m1
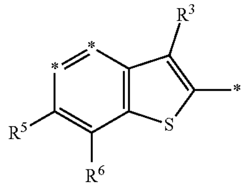
-continued
A5n1
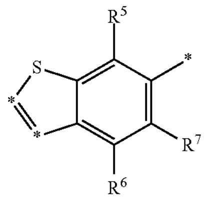
A5o1
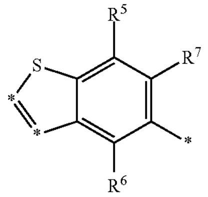
A5p1
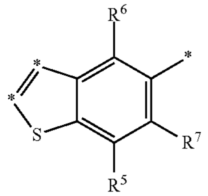
A5q1
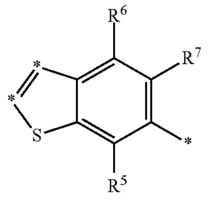
A5r1
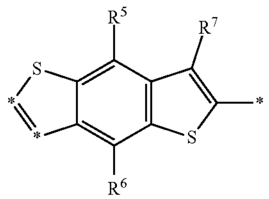
A5s1
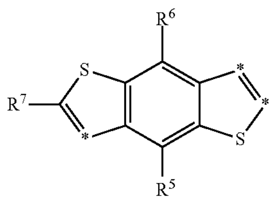
A5t1
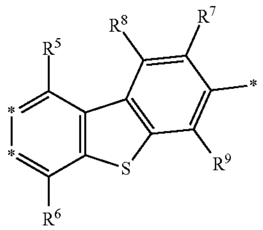

-continued

A5u

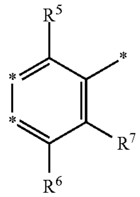

A5v

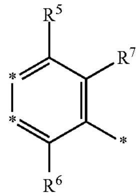

A5w

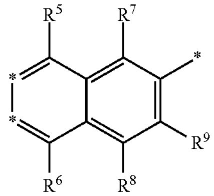

A5x

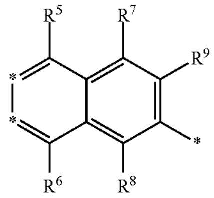

wherein $R^{5-7}$ have the meanings given above and below.

Very preferred groups $Ar^5$ are selected from formulae A5a, A5b, A5c, A5d, A5e, A5f, A5h, A5i, A5j, A5k, A5l, A5m, A5n, A5q, A5u and A5v, more preferably from formulae A5a1, A5b1, A5c1, A5d1, A5e1, A5f1, A5h1, A5i, A5j1, A5k1, A5l1, A5m1, A5n1, A5q1, A5u and A5v.

Preferred groups $Ar^{6-9}$ in formula I and I1-I6 and their subformulae are each independently and on each occurrence identically or differently selected from arylene or heteroarylene which has from 5 to 20 ring atoms, which is mono- or polycyclic, which optionally contains fused rings, and which is unsubstituted or substituted by one or more identical or different groups $L^S$, or from $—CY^1═CY^2—$.

Very preferred groups $Ar^{6-9}$ in formula I and I1-I6 and their subformulae are each independently and on each occurrence identically or differently selected from the following formulae and their mirror images:

AR1

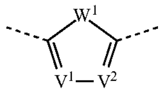

AR2

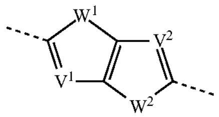

-continued

AR3

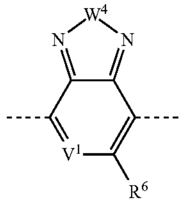

AR4

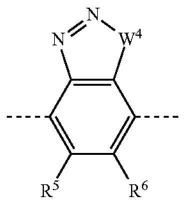

AR5

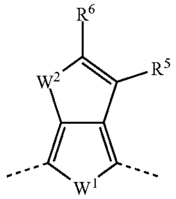

AR6

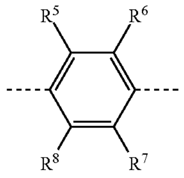

AR7

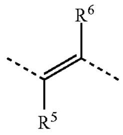

wherein, independently of each other and on each occurrence identically or differently, $V^2$ is $CR^5$ or N, and $V^1$, $W^1$, $W^2$, $W^4$ and $R^{5-8}$ are as defined above and below.

More preferred groups $Ar^{6-9}$ in formula I and I1-I6 and their subformulae are each independently, and on each occurrence identically or differently, selected from the following formulae and their mirror images

AR1-1

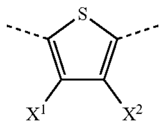

AR1-2

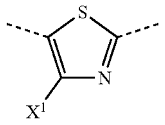

AR1-3

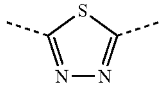

-continued

AR2-1

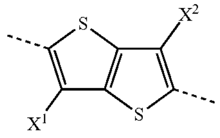

AR2-2

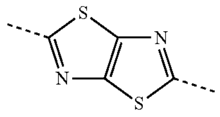

AR3-1

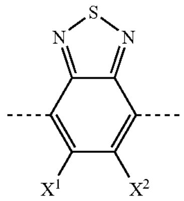

AR3-2

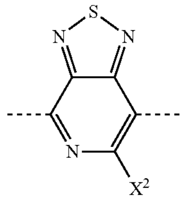

AR3-3

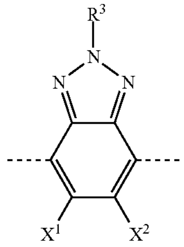

AR4-1

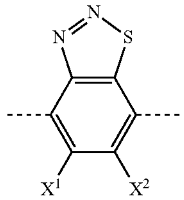

AR5-1

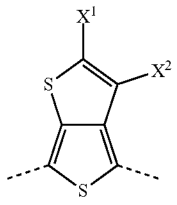

AR6-1

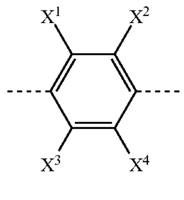

-continued

AR7-1

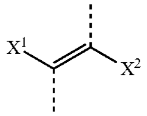

wherein $X^1$, $X^2$, $X^3$ and $X^4$ have one of the meanings given for $R^1$ above and below, and preferably denote H, F, Cl, —CN, $R^0$, $OR^0$ or $C(=O)OR^0$, and $R^0$ is as defined above and below.

Preferred formulae AR1-1 to AR7-1 are those containing at least one, preferably one, two or four substituents $X^{1-4}$ selected from F and Cl, very preferably F.

In formula AR6-1 preferably one or two, very preferably all of $X^{1-4}$ are F.

Preferred groups $Ar^{6-9}$ are selected from formulae AR1, AR2, AR3 and AR5. Very preferred groups $Ar^6$ and $Ar^7$ are selected from formulae AR1-1, AR1-2, AR2-1, AR3-1, AR3-2 and AR5-1, most preferably from formulae AR1-1, AR1-2, AR2-1, AR2-2 and AR3-1.

In formula I and I1-I6 and their subformulae both $R^{T1}$ and $R^{T2}$ are electron withdrawing groups, at least one of which is selected of formula TG.

In a preferred embodiment of the present invention both $R^{T1}$ and $R^{T2}$ are an electron withdrawing group.

In this preferred embodiment, the groups $R^{T1}$ and $R^{T2}$ are, independently of each other, preferably selected from the group consisting of F, Cl, Br, $—NO_2$, —CN, $—CF_3$, $—CF_2—R^*$, —O—R*, —S—R*, $—SO_2—R^*$, $—SO_3—R^*$, —C(=O)—H, —C(=O)—R*, —C(=S)—R*, $—C(=O)—CF_2—R^*$, —C(=O)—OR*, —C(=S)—OR*, —O—C(=O)—R*, —O—C(=S)—R*, —C(=O)—SR*, —S—C(=O)—R*, —C(=O)NR*R**, —NR*—C(=O)—R*, —NHR*, —NR*R**, —CR*=CR*R**, —C≡C—R*, —C≡C—SiR*RR*, —SiR*RR*, —CH=CH(CN), $—CH=C(CN)_2$, $—C(CN)=C(CN)_2$, $—CH=C(CN)(R^a)$, CH=C(CN)—C(=O)—OR*, $—CH=C(CO—OR^*)_2$, $—CH=C(CO—NR^*R^{**})_2$, and the group consisting of the following formulae

T1

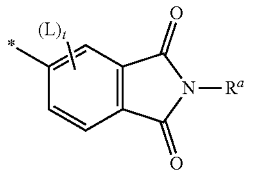

T2

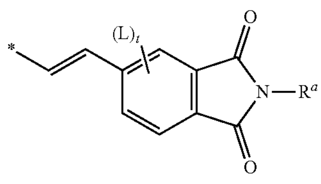

T3

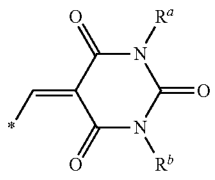

-continued
T4
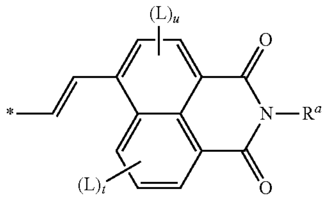
T5
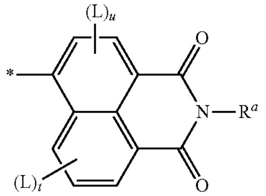
T6
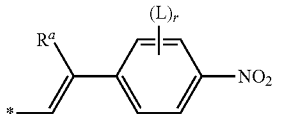
T7
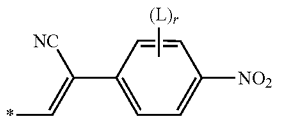
T8
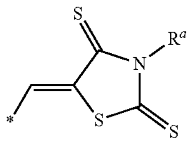
T9
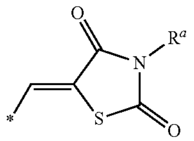
T10
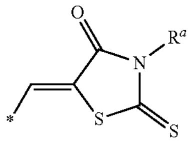
T11
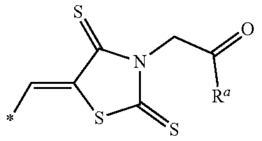
T12
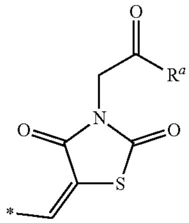
-continued
T13
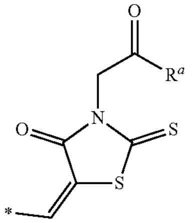
T14
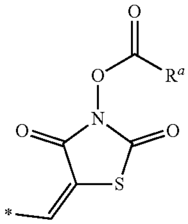
T15
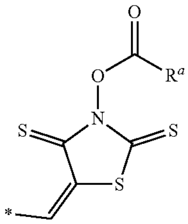
T16
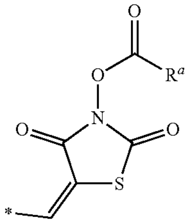
T17
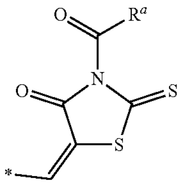
T18
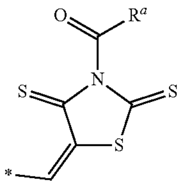
T19
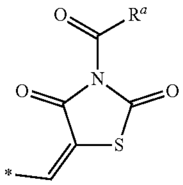

-continued
T20
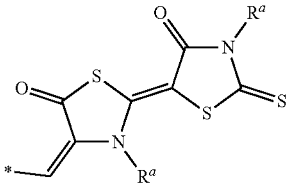
T21
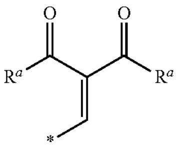
T22
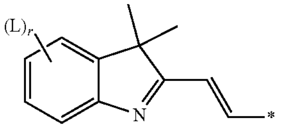
T23
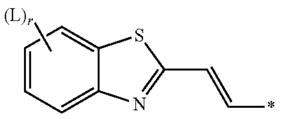
T24
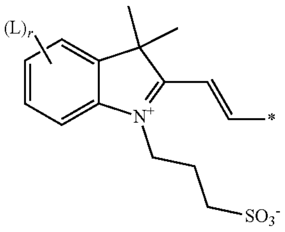
T25
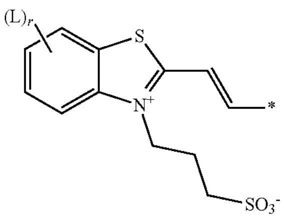
T26
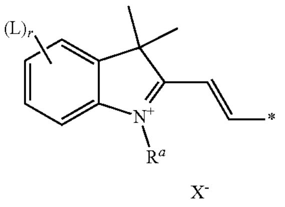
T27
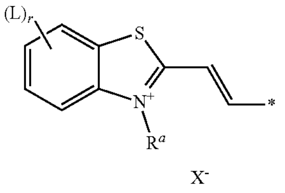
T28
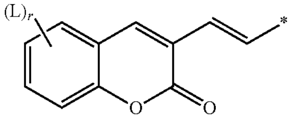
-continued
T29
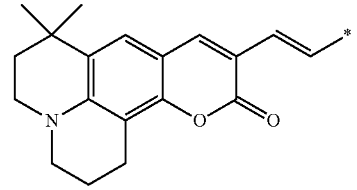
T30
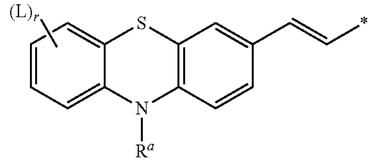
T31
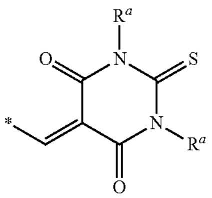
T32
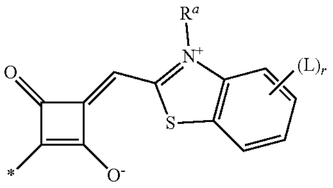
T33
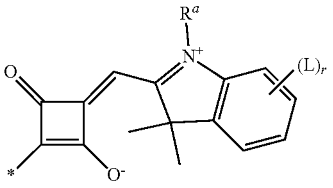
T34
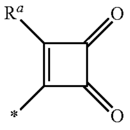
T35
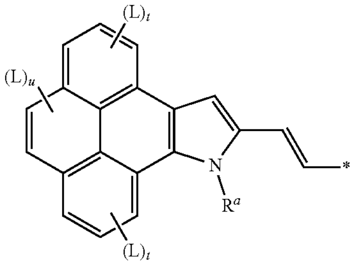
T36
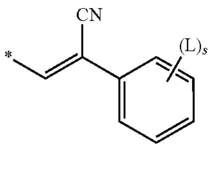

-continued
T37
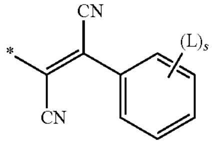
T38
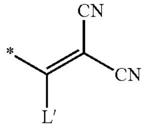
T39
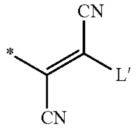
T40
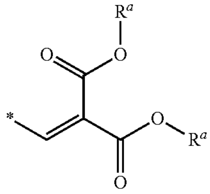
T41
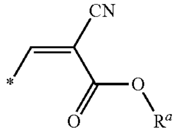
T42
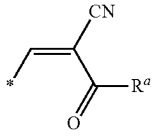
T43
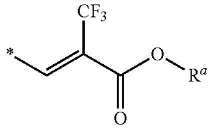
T44
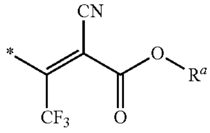
T45
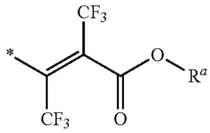
T46
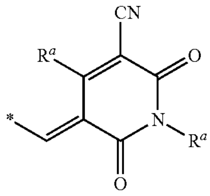
-continued
T47
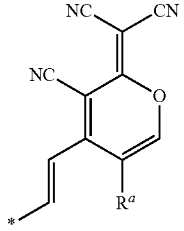
T48
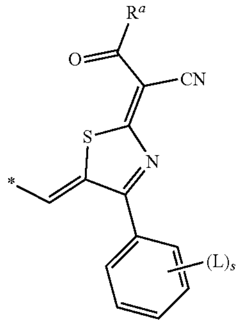
T49
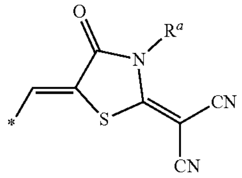
T50
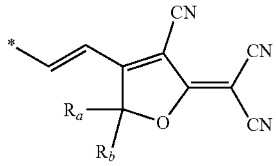
T51
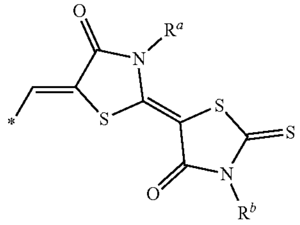
T52
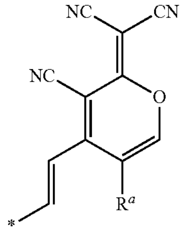
T53
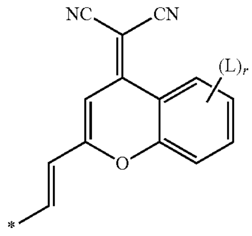

-continued
T54
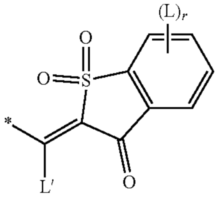
T55
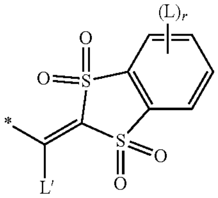
T56
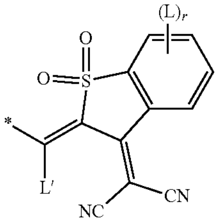
T57
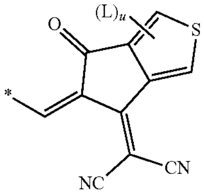
T58
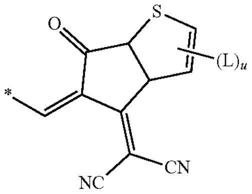
T59
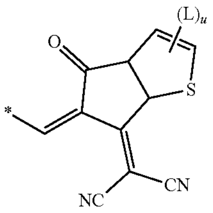
T60
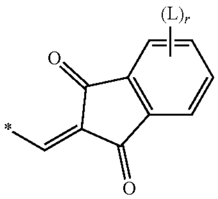
-continued
T61
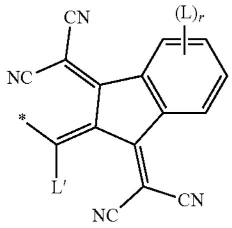
T62
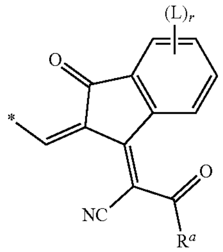
T63
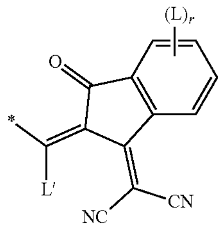
T64
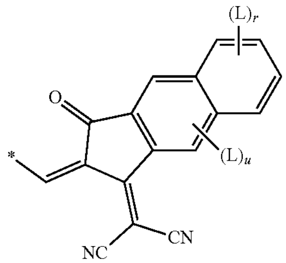
T65
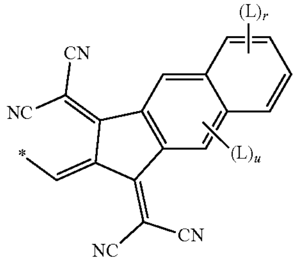
T66
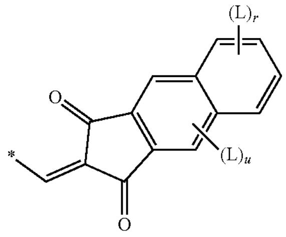

-continued
T67
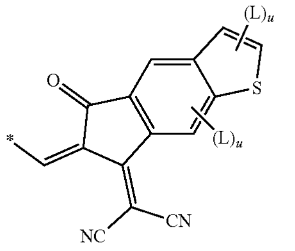
T68
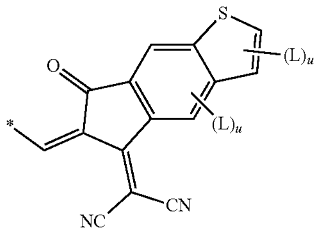
T69
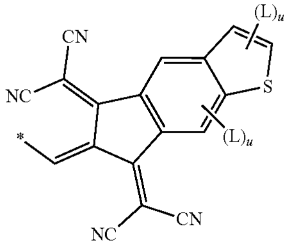
T70
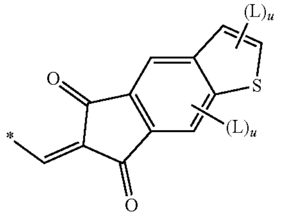
T71
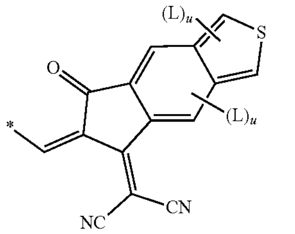
T72
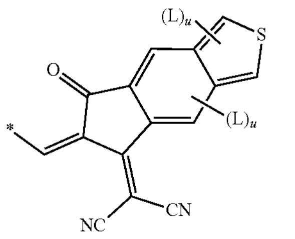
-continued
T73
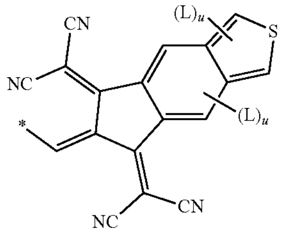
T74
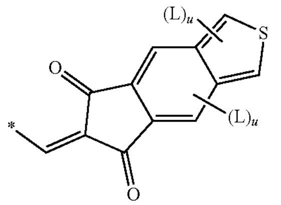
T75
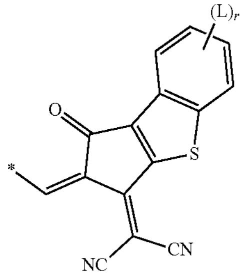
T76
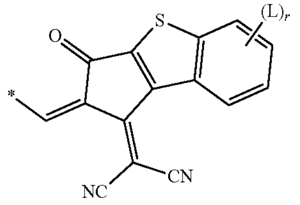
T77
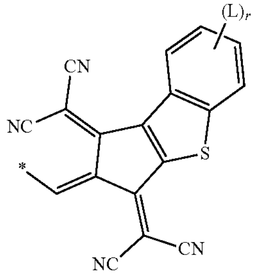
T78
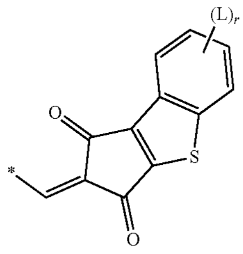
wherein the individual radicals, independently of each other and on each occurrence identically or differently, have the following meanings
$R^a$, $R^b$ aryl or heteroaryl, each having from 4 to 30, preferably from 5 to 20, ring atoms, optionally containing fused rings and being unsubstituted or substituted with one or more groups L, or one of the meanings given for L, R*, R, R* alkyl with 1 to 20 C atoms which is straight-chain, branched or cyclic, and is unsubstituted, or substituted with one or more F or Cl atoms or CN groups, or perfluorinated, and in which one or more C atoms are optionally replaced by —O—, —S—, —C(═O)—, —C(═S)—, $—SiR^0R^{00}—$, $—NR^0R^{00}—$, $—CHR^0═CR^{00}—$ or —C≡C— such that O- and/or S-atoms are not directly linked to each other, L F, Cl, $—NO_2$, —CN, —NC, —NCO, —NCS, —OCN, —SCN, $R^0$, $OR^0$, $SR^0$, $—C(═O)X^0$, $—C(═O)R^0$, $—C(═O)—OR^0$, $—O—C(═O)—R^0$, $—NH_2$, $—NHR^0$, $—NR^0R^{00}$, $—C(═O)NHR^0$, $—C(═O)NR^0R^{00}$, $—SO_3R^0$, $—SO_2R^0$, —OH, $—NO_2$, $—CF_3$, $—SF_5$, or optionally substituted silyl, or carbyl or hydrocarbyl with 1 to 30, preferably 1 to 20 C atoms that is optionally substituted and optionally comprises one or more hetero atoms, preferably F, —CN, $R^0$, $—OR^0$, $—SR^0$, $—C(═O)—R^0$, $—C(═O)—OR^0$, $—O—C(═O)—R^0$, $—O—C(═O)—OR^0$, $—C(═O)—NHR^0$, $—C(═O)—NR^0R^{00}$, L' H or one of the meanings of L, $R^0$, $R^{00}$H or straight-chain or branched alkyl with 1 to 20, preferably 1 to 12 C atoms that is optionally fluorinated, $Y^1$, $Y^2$H, F, C or CN, $X^0$ halogen, preferably F or Cl, r 0, 1, 2, 3 or 4, s 0, 1, 2, 3, 4 or 5, t 0, 1, 2 or 3, u 0, 1 or 2.

Preferred groups $R^{T1}$ and $R^{T2}$ which are different from formula TG are each independently selected from —CN, —C(═O)—OR*, —C(═S)—OR*, —CH═CH(CN), $—CH═C(CN)_2$, $—C(CN)═C(CN)_2$, $—CH═C(CN)(R^a)$, CH═C(CN)—C(═O)—OR*, $—CH═C(CO—OR*)_2$, and formulae T1-T78.

Very preferred groups $R^{T1}$ and $R^{T2}$ are each independently selected from formulae T1-T78 wherein preferably L' is H, $R^a$ and $R^b$ denote H or $C_1$-$C_{12}$-alkyl, r is 0 and s is 0.

Further preferred groups $R^{T1}$ and $R^{T2}$ are selected from formulae T54-78, preferably from formulae T60-T78, more preferably from formulae T63-T78, very preferably from formulae T63, T64, T67, T68, T71, T72, T75 and T76, most preferably from formula T63 and T64, wherein r is 0, 1 or 2 and L is F.

The above formulae T1-T78 are meant to also include their respective E- or Z-stereoisomer with respect to the C≡C bond in α-position to the adjacent group $Ar^{47}$, thus for example the group

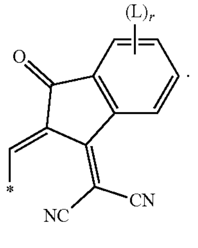

may also denote

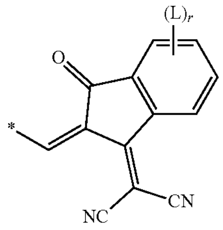

In the compounds of formula I, I1-I6 and their subformulae $R^1$ and $R^2$ are preferably different from H.

In a preferred embodiment of the present invention, in the compounds of formula I, I1-I6 and their subformulae $R^1$ and $R^2$ are selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, C or formulae SUB1-SUB6 above.

In another preferred embodiment of the present invention, in the compounds of formula I, I1-I6 and their subformulae $R^1$ and $R^2$ are selected from mono- or polycyclic aryl or heteroaryl, each of which is optionally substituted with one or more groups $L^S$ as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, most preferably from formulae SUB7-SUB18 above.

In a preferred embodiment of the present invention, in the compounds of formula I, I1-I6 and their subformulae $R^{5-9}$ are H.

In another preferred embodiment of the present invention, in the compounds of formula I, I1-I6 and their subformulae at least one of $R^{5-9}$ is different from H.

In a preferred embodiment of the present invention, in the compounds of formula I, I1-I6 and their subformulae $R^{5-9}$, when being different from H, are each independently selected from F, Cl, CN, or from straight-chain or branched alkyl, alkoxy, sulfanylalkyl, sulfonylalkyl, alkylcarbonyl, alkoxycarbonyl and alkylcarbonyloxy, each of which has 1 to 20 C atoms and is unsubstituted or substituted by one or more F atoms, most preferably from F, Cl or formulae SUB1-SUB6 above.

In another preferred embodiment of the present invention, in the compounds of formula I, I1-I6 and their subformulae $R^{5-9}$, when being different from H, are each independently selected are selected from mono- or polycyclic aryl or heteroaryl, each of which is optionally substituted with one or more groups $L^S$ as defined in formula I and has 5 to 20 ring atoms, and wherein two or more rings may be fused to each other or connected with each other by a covalent bond, very preferably phenyl that is optionally substituted, preferably in 4-position, 2,4-positions, 2,4,6-positions or 3,5-positions, or thiophene that is optionally substituted, preferably in 5-position, 4,5-positions or 3,5-positions, with alkyl, alkoxy or thioalkyl having 1 to 16 C atoms, more preferably from formulae SUB7-SUB18 above, most preferably from formulae SUB14-SUB18 above.

Preferred aryl and heteroaryl groups $R^{1-9}$, when being different from H, are each independently selected from the following formulae S1
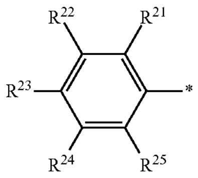
S2
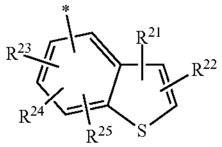
S3
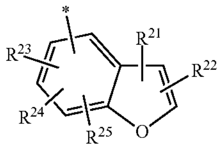
S4
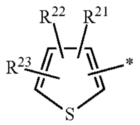
S5
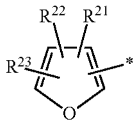
S6
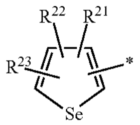
S7
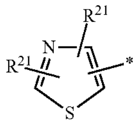
S8
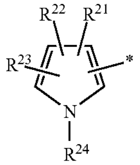
S9
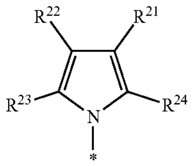
S10
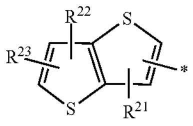
-continued
S11
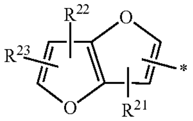
S12
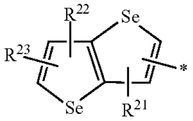
S13
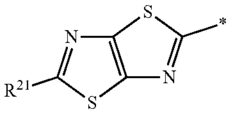
S14
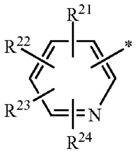
S15
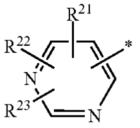
S16
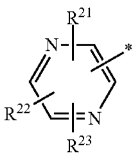
S17
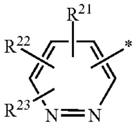
S18
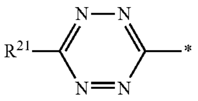
S19
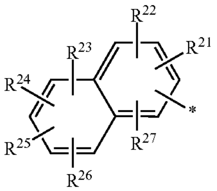
S20
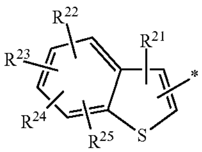

-continued

S21

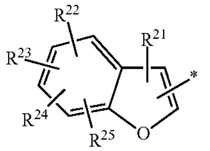

S22

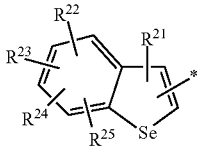

S23

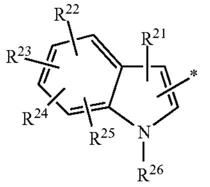

S24

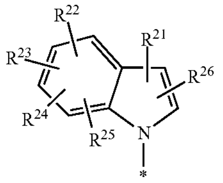

S25

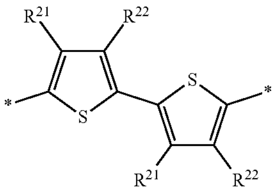

S26

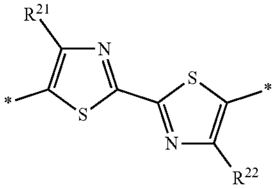

S27

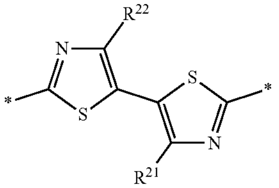

wherein $R^{21-27}$, independently of each other, and on each occurrence identically or differently, denote H, F, Cl, CN, or straight-chain, branched or cyclic alkyl with 1 to 30, preferably 1 to 20, C atoms, in which one or more $CH_2$ groups are each optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are each optionally replaced by F, Cl, Br, I or CN, and in which one or more $CH_2$ or $CH_3$ groups are each optionally replaced by a cationic or anionic group.

Very preferred aryl and heteroaryl groups $R^{1-9}$, when being different from H, are each independently selected from formulae S1, S4, S5, S7 and S10.

Most preferred aryl and heteroaryl groups $R^{1-9}$ are each independently selected from formulae SUB7-SUB16 as defined above.

In another preferred embodiment one or more of $R^{1-9}$ denote a straight-chain, branched or cyclic alkyl group with 1 to 50, preferably 2 to 50, very preferably 2 to 30, more preferably 2 to 24, most preferably 2 to 16 C atoms, in which one or more $CH_2$ or $CH_3$ groups are replaced by a cationic or anionic group.

The cationic group is preferably selected from the group consisting of phosphonium, sulfonium, ammonium, uronium, thiouronium, guanidinium or heterocyclic cations such as imidazolium, pyridinium, pyrrolidinium, triazolium, morpholinium or piperidinium cation.

Preferred cationic groups are selected from the group consisting of tetraalkylammonium, tetraalkylphosphonium, N-alkylpyridinium, N,N-dialkylpyrrolidinium, 1,3-dialkylimidazolium, wherein "alkyl" preferably denotes a straight-chain or branched alkyl group with 1 to 12 C atoms and very preferably is selected from formulae SUB1-6.

Further preferred cationic groups are selected from the group consisting of the following formulae

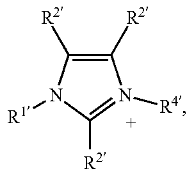

imidazolium

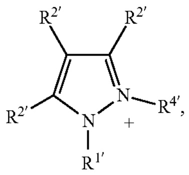

1H-pyrazolium

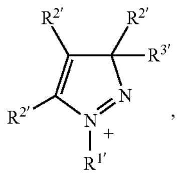

, 3H-pyrazolium

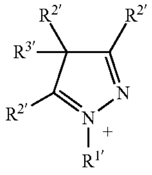

, 4H-pyrazolium

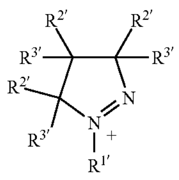

, 1-pyrazolinium

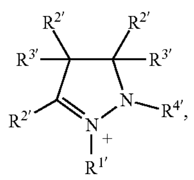

2-pyrazolinium

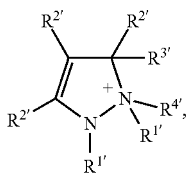

3-pyrazolinium

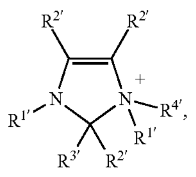

2,3-dihydroimidazolinium

-continued

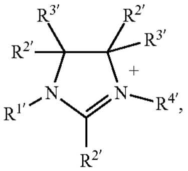

4,5-dihydroimidazolinium

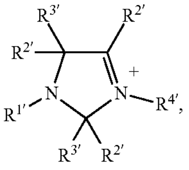

2,5-dihydroimidazolinium

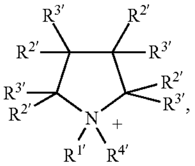

pyrrolidinium

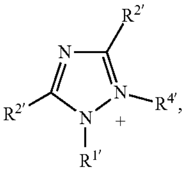

1,2,4-triazolium

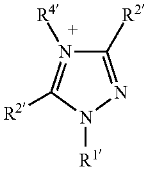

, 1,2,4-triazolium

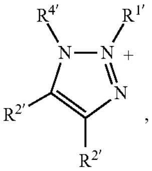

, 1,2,3-triazolium

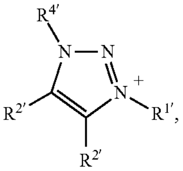

1,2,3-triazolium

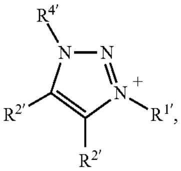

1,2,3-triazolium

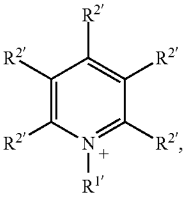

pyridinium

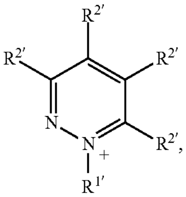

pyridazinium

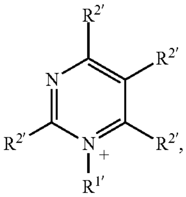

pyrimidinium

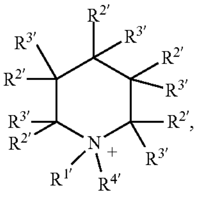

piperidinium

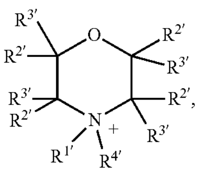

morpholinium

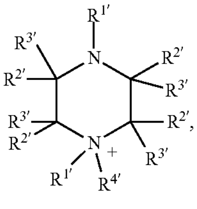

piperazinium

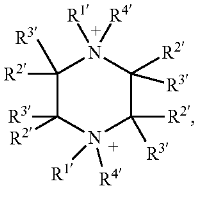

piperazinium

-continued

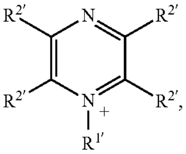

pyrazinium

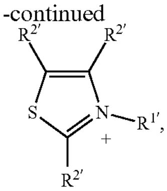

thiazolium

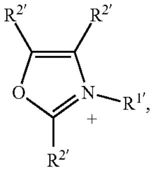

oxazolium

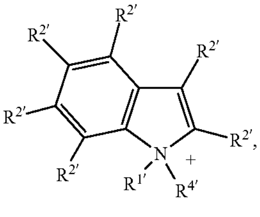

indolium

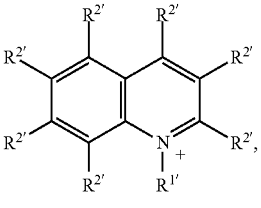

quinolinium

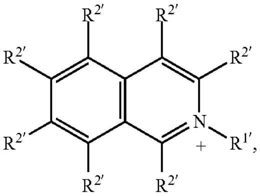

isoquinolinium

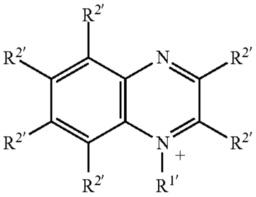

quinoxalinium or

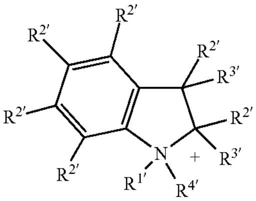

indolinium wherein $R^{1'}$, $R^{2'}$, $R^{3'}$ and $R^{4'}$ denote, independently of each other, H, a straight-chain or branched alkyl group with 1 to 12 C atoms or non-aromatic carbo- or heterocyclic group or an aryl or heteroaryl group, each of the aforementioned groups having 3 to 20, preferably 5 to 15, ring atoms, being mono- or polycyclic, and optionally being substituted by one or more identical or different substituents $L^S$ as defined above, or denote a link to the respective group $R^{1-9}$.

In the above cationic groups of the above-mentioned formulae any one of the groups $R^{1'}$, $R^{2'}$, $R^{3'}$ and $R^{4'}$ (if they replace a $CH_3$ group) can denote a link to the respective group $R^{1-9}$, or two neighbored groups $R^{1'}$, $R^{2'}$, $R^{3'}$ or $R^{4'}$ (if they replace a $CH_2$ group) can denote a link to the respective group $R^1$.

The anionic group is preferably selected from the group consisting of borate, imide, phosphate, sulfonate, sulfate, succinate, naphthenate or carboxylate, very preferably from phosphate, sulfonate or carboxylate.

Preferred compounds of formula I and I1-I6 are selected from formula IA

IA

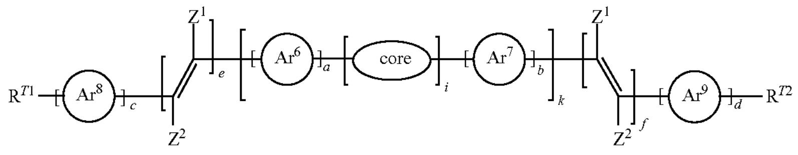

wherein $Ar^{6-9}$, $R^{T1}$, $R^{T2}$, $Z^1$, $Z^2$, a, b, c, d, e, f, i and k, independently of each other and on each occurrence identically or differently, have the meanings given in formula I or one of the preferred meanings given above and below, and "core" is, on each occurrence identically or differently, a polycyclic divalent group selected from the following formulae

C1

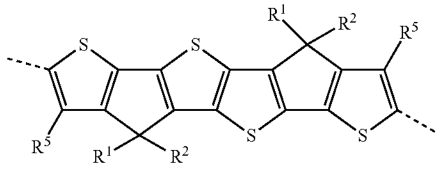

C2

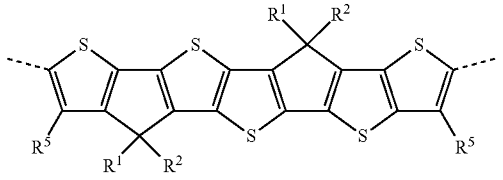

C3

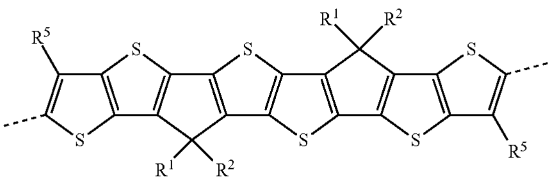

C4

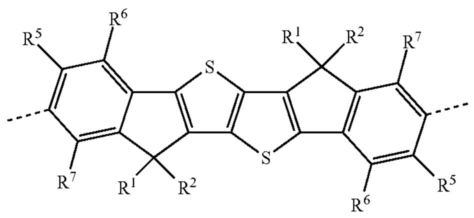

C5

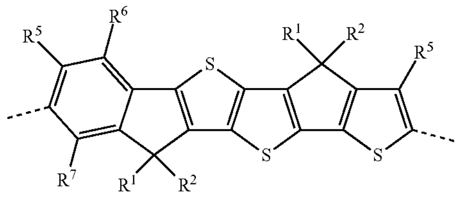

-continued

C6

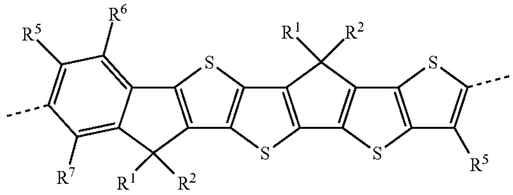

C7

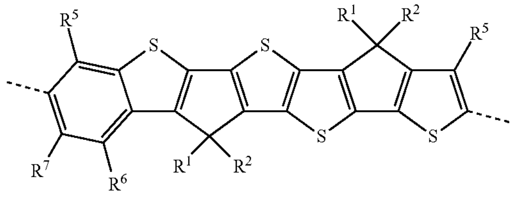

C8

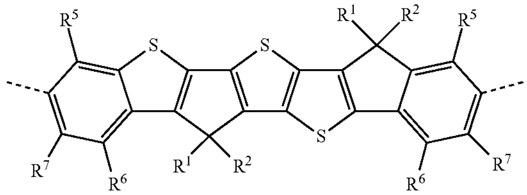

C9

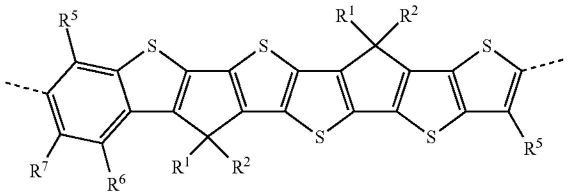

C10

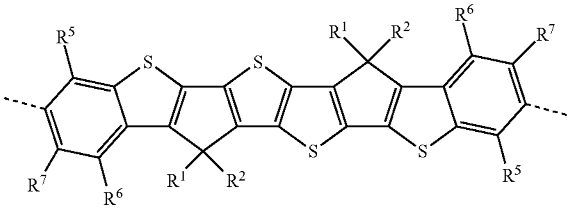

-continued
C11
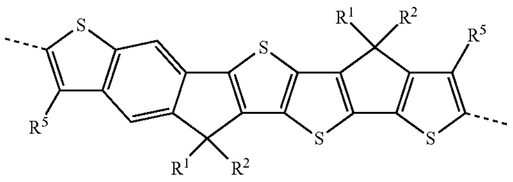
C12
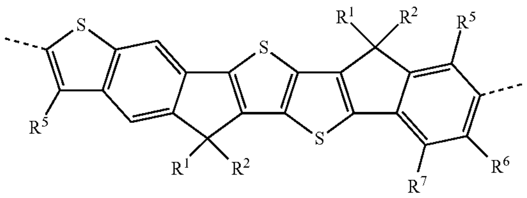
C13
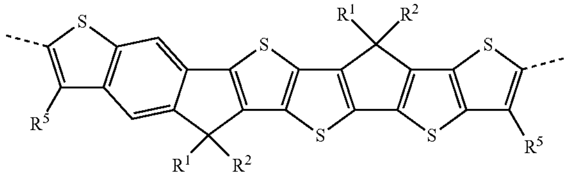
C14
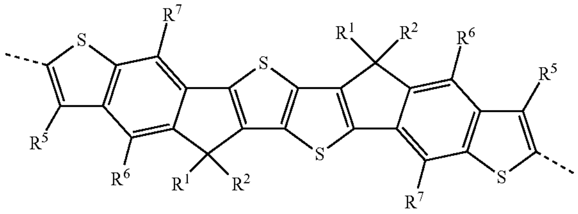
C15
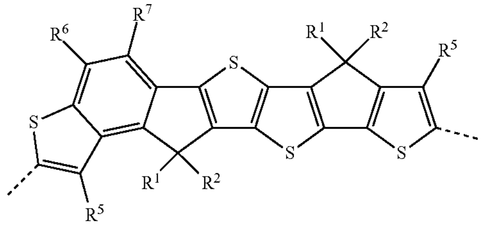
C16
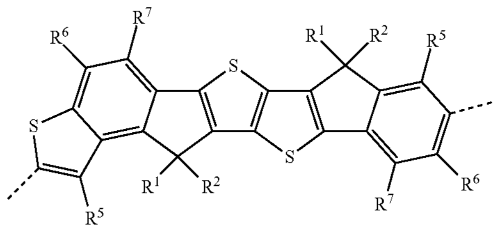
C17
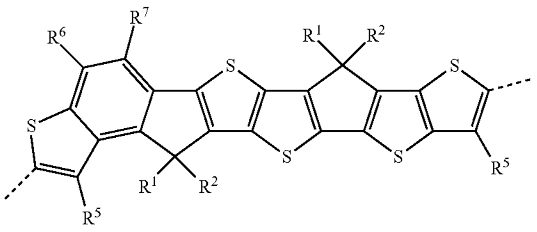
-continued
C18
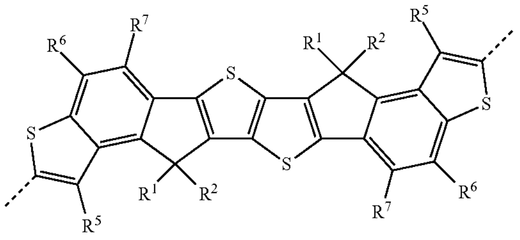
C19
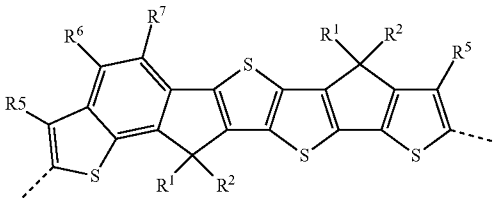
C20
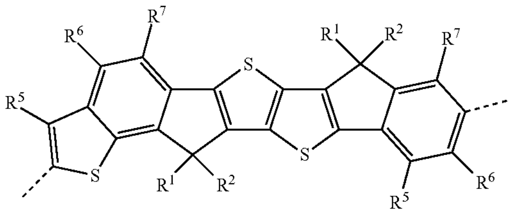
C21
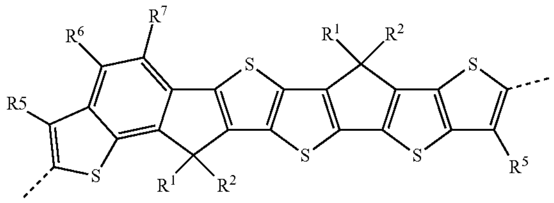
C22
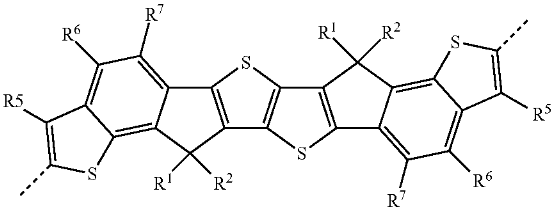
C23
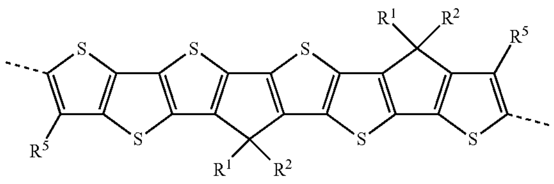
C24
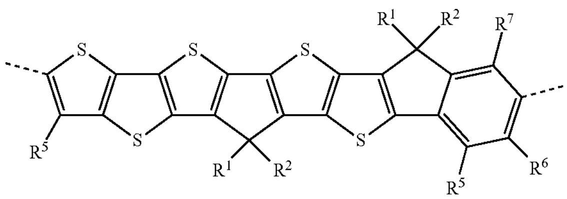

-continued
C25
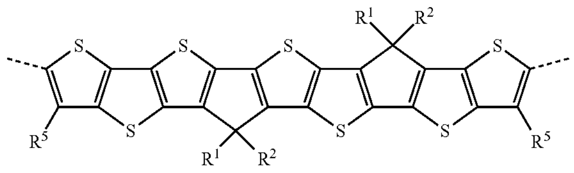
C26
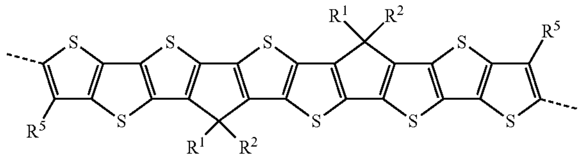
C27
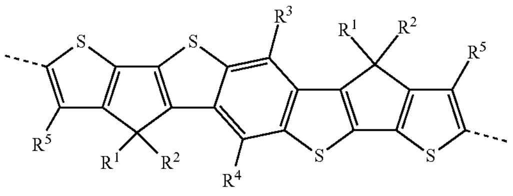
C28
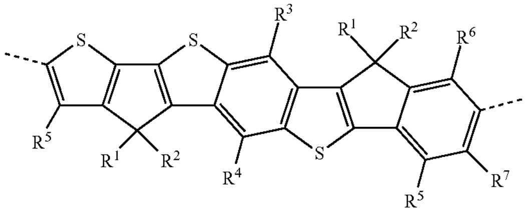
C29
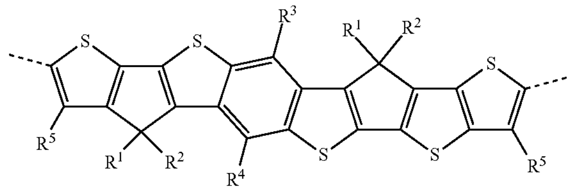
C30
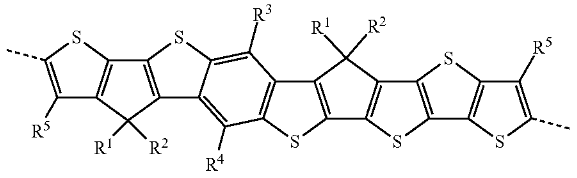
C31
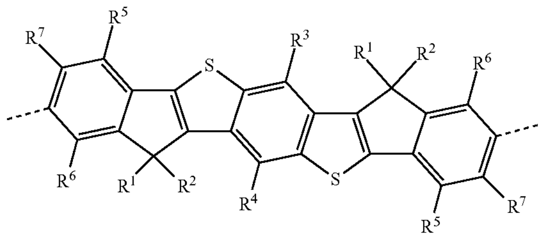
-continued
C32
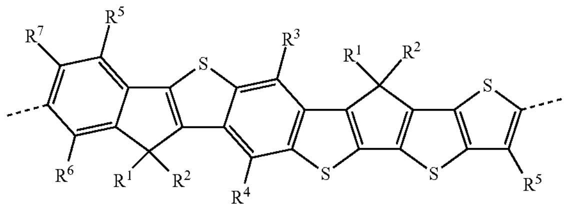
C33
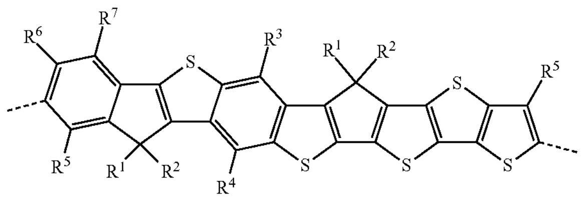
C34
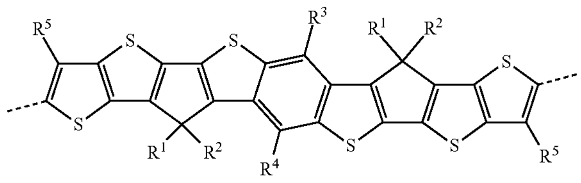
C35
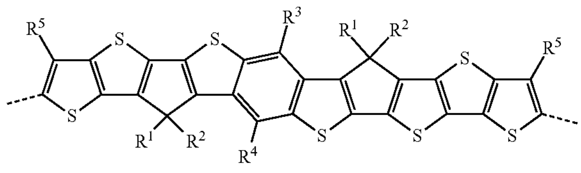
C36
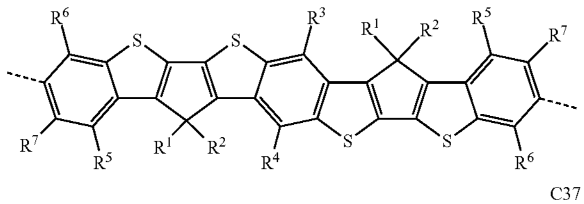
C37
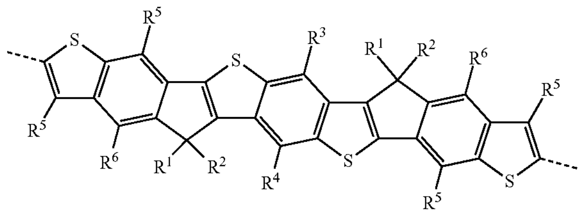
C38
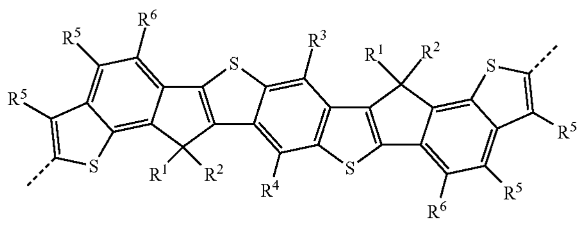

-continued
C39
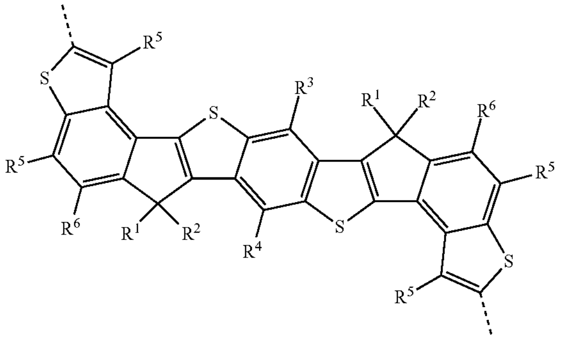
C40
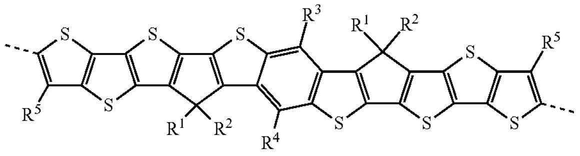
C41
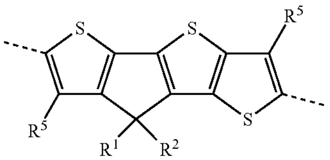
C42
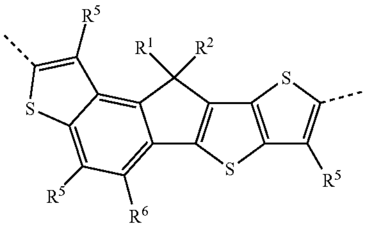
C43
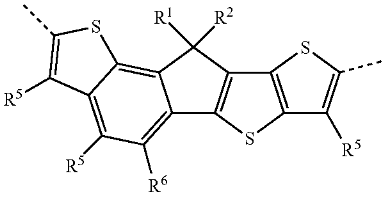
C44
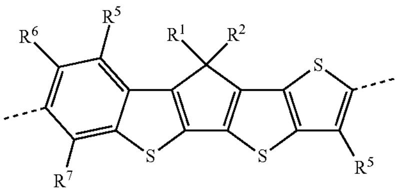
C45
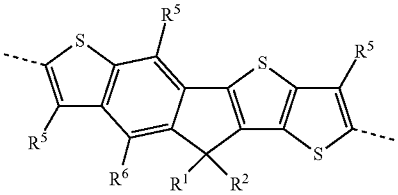
-continued
C46
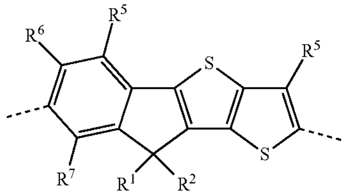
C47
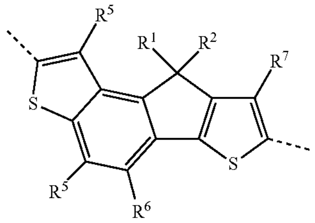
C48
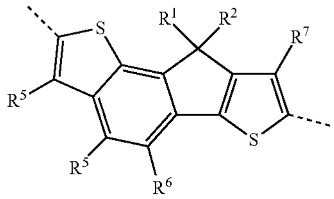
C49
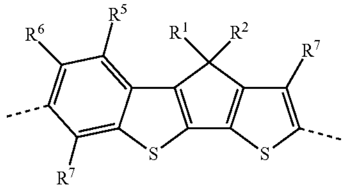
C50
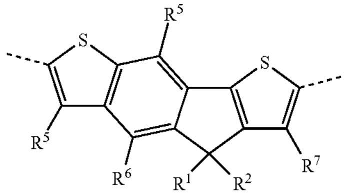
C51
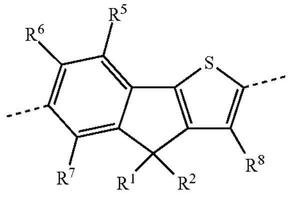
C52
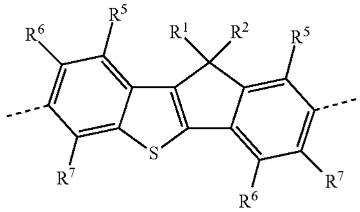
C53
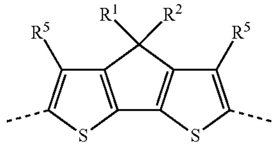

-continued

C54

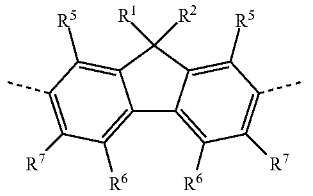

C55

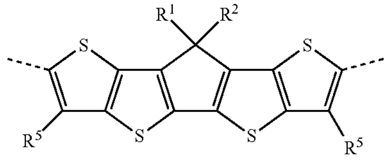

C56

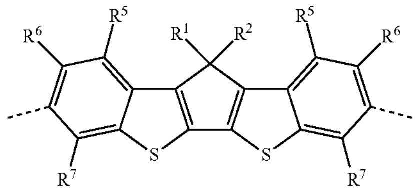

C57

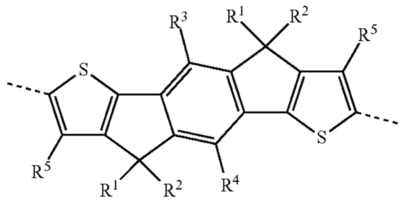

C58

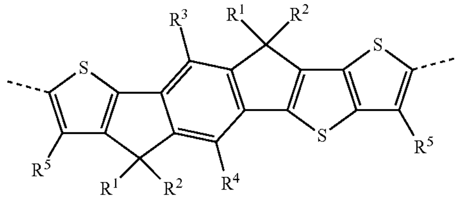

C59

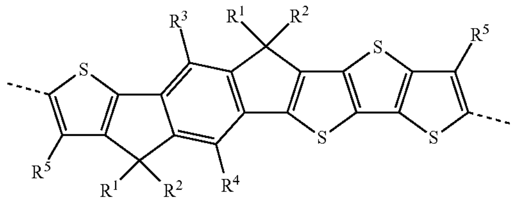

C60

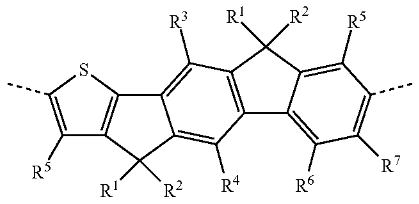

-continued

C61

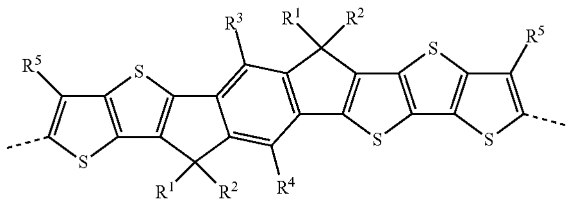

C62

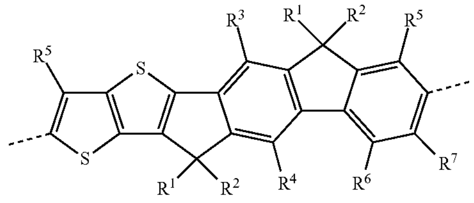

C63

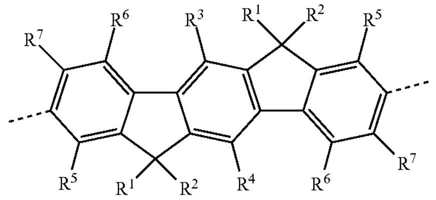

C64

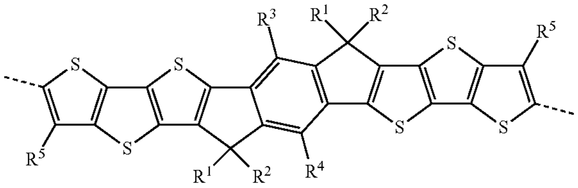

C65

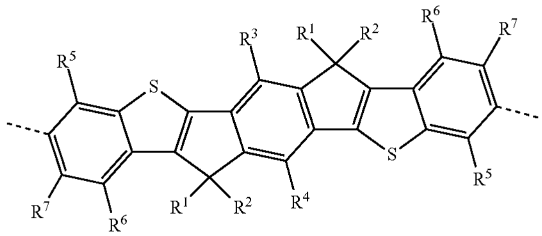

wherein $R^{1-7}$ have the meanings given above.

Very preferred are the core groups of formula C1, C2, C3, C4, C10, C27, C29, C34, C41, C51, C53, C54, C55, C57, C58 and C63.

Preferred compounds of formula IA are those wherein e=f=1, i is 1 and k is 1.

Further preferred compounds of formula IA are those wherein a=b=0, c=d=0, e=f=1, i is 1 and k is 1.

Further preferred compounds of formula IA are those wherein a and b are independently of each other 1 or 2, c=d=0, e=f=1, i is 1 and k is 1.

Further preferred compounds of formula IA are those wherein c and d are independently of each other 1 or 2, a=b=0, e=f=1, i is 1 and k is 1.

Further preferred compounds of formula IA are those wherein a, b, c and d are independently of each other 1 or 2, e=f=1, i is 1 and k is 1.

Further preferred compounds of formula IA are selected from formula IA1-IA4

IA1

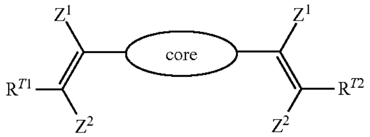

IA2

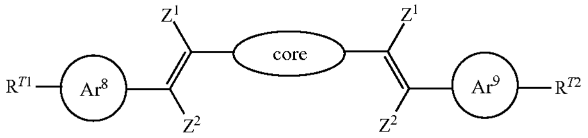

IA3

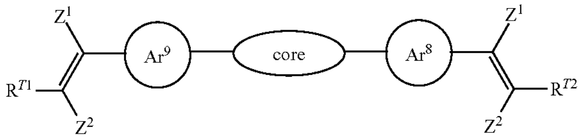

IA4

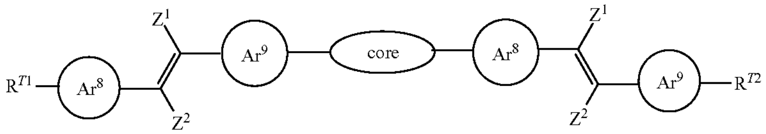

wherein $Ar^8$, $Ar^9$, $R^{T1}$, $R^{T2}$, $Z^1$, $Z^2$ and "core" have the meanings given in formula IA or one of the preferred meanings given above and below, and "core" is preferably selected from formula C1-C65 above, very preferably from formulae C1, C2, C3, C4, C10, C27, C29, C34, C41, C51, C53, C54, C55, C57, C58 and C63.

Very preferred compounds of formula I, I1-I6, IA and IA1-4 are selected from the following subformulae IA1a

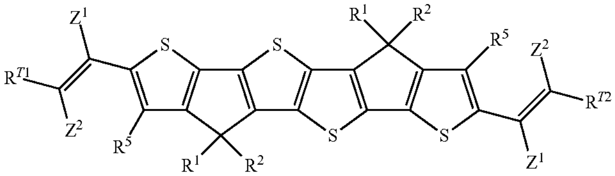

IA1b

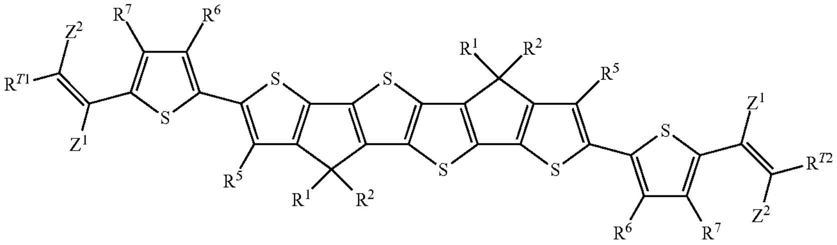

IA1c

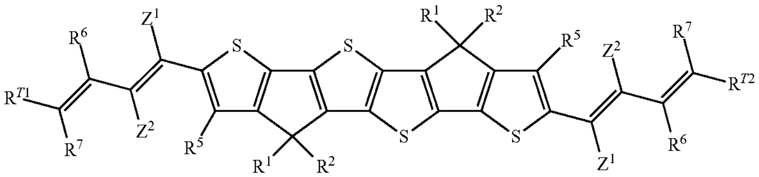

-continued
IA1d
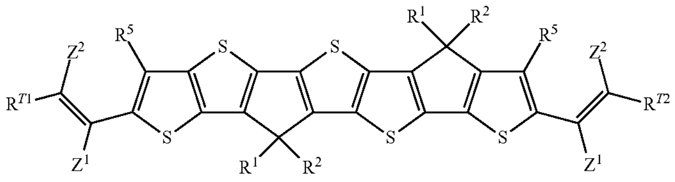
IA1e
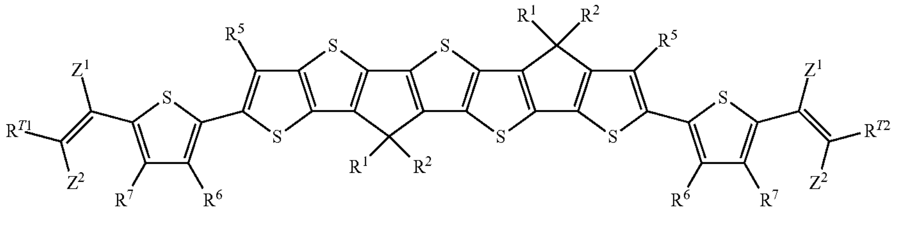
IA1f
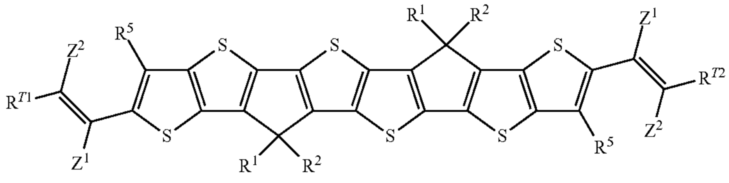
IA1g
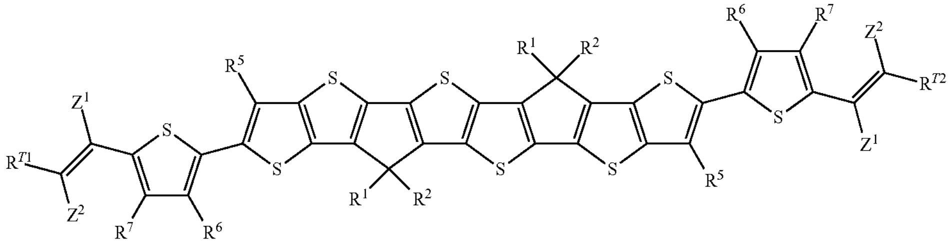
IA1h
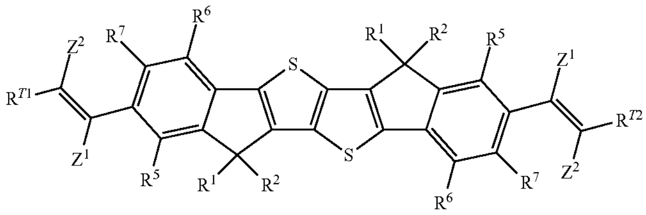
IA1i
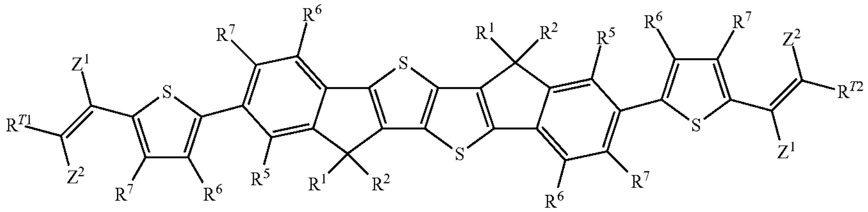
IA1j
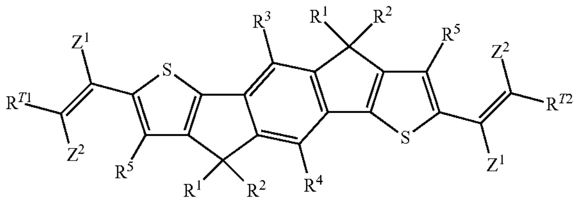

-continued
IA1k
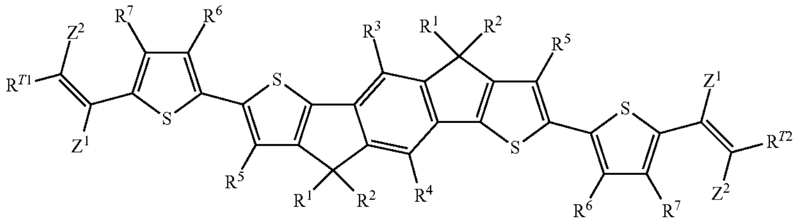
IA1l
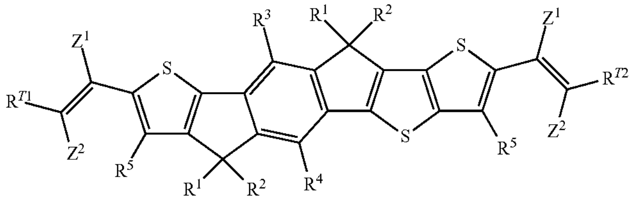
IA1m
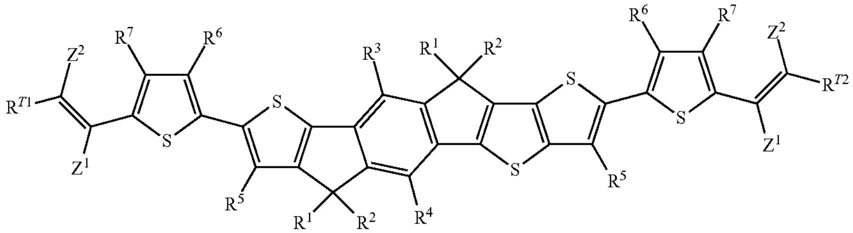
IA1n
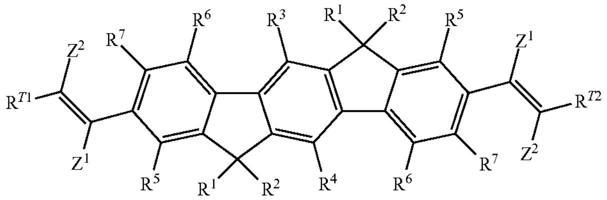
IA1o
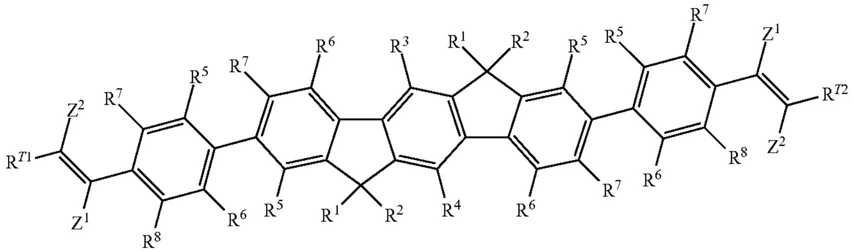
IA1p
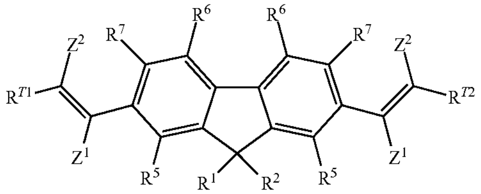
IA1q
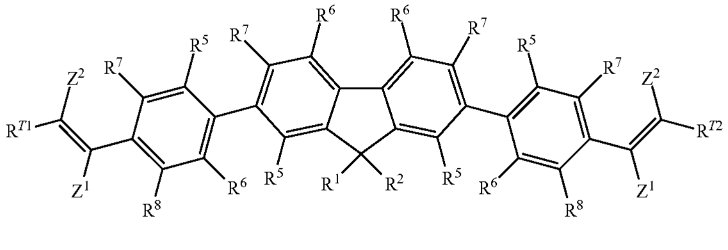

-continued

IA1r

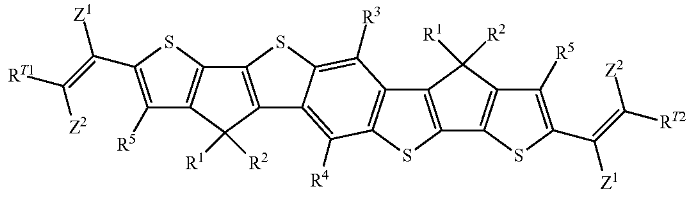

IA1s

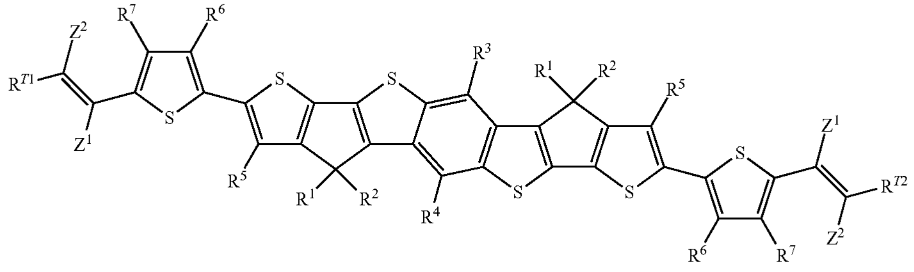

wherein $R^{1-8}$ and $Z^{1-2}$ have the meanings given above and below.

Further preferred compounds of formula I, I1-I6, IA, I1AA, I1A1-I1A4 and their subformulae are selected from the following preferred embodiments or any combination thereof:

a is 1 or 2, preferably 1,
b is 1 or 2, preferably 1,
a=b=0,
a=b=1 or 2,
c is 1 or 2, preferably 1,
d is 1 or 2, preferably 1,
c=d=0,
c=d=1 or 2,
e is 1 and f is 0,
i is 1,
k is 1,
m is 0,
m is >0, preferably 1, 2 or 3, very preferably 1,
$U^1$ and $U^2$ denote $CRR^2$ or $SiR^1R^2$, very preferably $CRR^2$,
$W^1$, $W^2$ and $W^3$ are S or Se, preferably S,
$W^4$ is S or $NR^0$, preferably S,
$V^1$ is $CR^3$,
$V^2$ is $CR^4$,
$V^1$ is N,
$V^2$ is N,
$V^1$ is $CR^3$ and $V^2$ is $CR^4$,
$V^1$ is $CR^3$ and $V^2$ is N,
$V^1$ and $V^2$ are N,
$Z^1$ and $Z^2$ are independently of each other H, F, Cl or CN, preferably H,
$Ar^1$ is selected from formula A1a, A2a, A1b and A2b, more preferably from formula A1a and A2a.
$Ar^3$ is selected from formulae A3b, A3d and A3p, more preferably from formula A3b1, A3d1 and A3p,
$Ar^4$ is selected from formulae A4a, A4b, A4c, A4d, A4e, A4f, A4h, A4i, A4j, A4k, A4l, A4m, A4n, A4q, A4u and A4v, more preferably from formulae A4a1, A4b1, A4c1, A4d1, A4e1, A4f1, A4h1, A4i, A4j1, A4k1, A4l1, A4m1, A4n1, A4q1, A4u and A4v.
$Ar^5$ is selected from formulae A5a, A5b, A5c, A5d, A5e, A5f, A5h, A5i, A5j, A5k, A5l, A5m, A5n, A5q, A5u and A5v, more preferably from formulae A5a1, A5b1, A5c1, A5d1, A5e1, A5f1, A5h1, A5i1, A5j1, A5k1, A5l1, A5m1, A5n1, A5q1, A5u and A5v.
in one or both of $Ar^4$ and $Ar^5$ all substituents $R^{5-9}$ are H,
in one or both of $Ar^4$ and $Ar^5$ at least one, preferably one or two of $R^{5-9}$ are different from H,
$Ar^{6-9}$ are selected from formulae AR1, AR2, AR3, AR5 and AR7,
$Ar^{6-9}$ are selected from formulae AR1-1, AR1-2, AR2-1, AR3-1, AR3-2, AR5-1 and AR7-1, most preferably from formulae AR1-1, AR2-1, AR3-1 and AR7-1,
$Ar^{6-9}$ are selected from thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene, benzotriazole, thiadiazole[3,4-c]pyridine and vinyl, which are substituted by $X^1$, $X^2$, $X^3$ and $X^4$ as defined above,
$Ar^{6-9}$ are selected from thiophene, thiazole, thieno[3,2-b]thiophene, thiazolo[5,4-d]thiazole, benzene, 2,1,3-benzothiadiazole, 1,2,3-benzothiadiazole, thieno[3,4-b]thiophene, benzotriazole, thiadiazole[3,4-c]pyridine and vinyl, wherein $X^1$, $X^2$, $X^3$ and $X^4$ are H,
$Ar^{6-9}$ are selected from thiophene, thiazole, thieno[3,2-b]thiophene, thiazolothiazole, benzene, 2,1,3-benzothiadiazole, 1,2,3-benzothiadiazole, thieno[3,4-b]thiophene, benzotriazole, thiadiazole[3,4-c]pyridine and vinyl, wherein one or more of $X^1$, $X^2$, $X^3$ and $X^4$ are different from H,
$R^{T1}$ and $R^{T2}$ are both an electron withdrawing group,
$R^{T1}$ and $R^{T2}$ are selected from formulae T1-T78 wherein preferably L' is H, $R^a$ and $R^b$ denote H or $C_1$-$C_{12}$-alkyl, r is 0 and s is 0, preferably from formulae T64, T67, T68, T71, T72, T75 and T76, most preferably from formula T64, wherein r is 0, 1 or 2 and L is F.
L' is H,
L denotes F, Cl, CN, $NO_2$, or alkyl or alkoxy with 1 to 16 C atoms that is optionally fluorinated,
t is 1 and L is F, Cl, CN, $NO_2$, or alkyl or alkoxy with 1 to 16 C atoms that is optionally fluorinated,
u is 1 or 2 and L is F, Cl, CN, $NO_2$, or alkyl or alkoxy with 1 to 16 C atoms that is optionally fluorinated,
$R^1$ and $R^2$ are different from H,
$R^1$ and $R^2$, when being different from H, are each independently selected from F, Cl or straight-chain or branched alkyl, alkoxy, sulfanylalkyl, sulfonylalkyl, alkylcarbonyl, alkoxycarbonyl and alkylcarbonyloxy, each having 1 to 20 C atoms and being unsubstituted or substituted by one or more F atoms, or alkyl or alkoxy having 1 to 12 C atoms that is optionally fluorinated, more preferably from formulae SUB1-SUB6 above, $R^1$ and $R^2$, when being different from H, and are each independently selected from phenyl that is substituted, preferably in 4-position, or in 2,4-positions, or in 2,4,6-positions or in 3,5-positions, with alkyl or alkoxy having 1 to 20 C atoms, preferably 1 to 16 C atoms, very preferably 4-alkylphenyl wherein alkyl is C1-16 alkyl, most preferably 4-methylphenyl, 4-hexylphenyl, 4-octylphenyl or 4-dodecylphenyl, or 4-alkoxyphenyl wherein alkoxy is C1-16 alkoxy, most preferably 4-hexyloxyphenyl, 4-octyloxyphenyl or 4-dodecyloxyphenyl or 2,4-dialkylphenyl wherein alkyl is C1-16 alkyl, most preferably 2,4-dihexylphenyl or 2,4-dioctylphenyl or 2,4-dialkoxyphenyl wherein alkoxy is C1-16 alkoxy, most preferably 2,4-dihexyloxyphenyl or 2,4-dioctyloxyphenyl or 3,5-dialkylphenyl wherein alkyl is C1-16 alkyl, most preferably 3,5-dihexylphenyl or 3,5-dioctylphenyl or 3,5-dialkoxyphenyl wherein alkoxy is C1-16 alkoxy, most preferably 3,5-dihexyloxyphenyl or 3,5-dioctyloxyphenyl, or 2,4,6-trialkylphenyl wherein alkyl is C1-16 alkyl, most preferably 2,4,6-trihexylphenyl or 2,4,6-trioctylphenyl or 2,4,6-trialkoxyphenyl wherein alkoxy is C1-16 alkoxy, most preferably 2,4,6-trihexyloxyphenyl or 2,4,6-trioctyloxyphenyl or 4-thioalkylphenyl wherein thioalkyl is C1-16 thioalkyl, most preferably 4-thiohexylphenyl, 4-thiooctylphenyl or 4-thiododecylphenyl, or 2,4-dithioalkylphenyl wherein thioalkyl is C1-16 thioalkyl, most preferably 2,4-dithiohexylphenyl or 2,4-dithiooctylphenyl, or 3,5-dithioalkylphenyl wherein thioalkyl is C1-16 thioalkyl, most preferably 3,5-dithiohexylphenyl or 3,5-dithiooctylphenyl, or 2,4,6-trithioalkylphenyl wherein thioalkyl is C1-16 thioalkyl, most preferably 2,4,6-trithiohexylphenyl or 2,4,6-trithiooctylphenyl, or from thiophene that is optionally substituted, preferably in 5-position, 4,5-positions or 3,5-positions, with alkyl, alkoxy or thioalkyl having 1 to 16 C atoms, most preferably from formulae SUB7-SUB18 above, $R^{5-9}$ are H, at least one of $R^{5-9}$ is different from H, $R^{59}$, when being different from H, are each independently selected from F, Cl, CN or straight-chain or branched alkyl, alkoxy, sulfanylalkyl, sulfonylalkyl, alkylcarbonyl, alkoxycarbonyl and alkylcarbonyloxy, each having up to 20 C atoms and being unsubstituted or substituted by one or more F atoms, preferably from F, or alkyl or alkoxy having up to 16 C atoms that is optionally fluorinated, more preferably from formulae SUB1-SUB6 above, $R^{59}$, when being different from H, are each independently selected from aryl or heteroaryl, preferably phenyl or thiophene, each of which is optionally substituted with one or more groups $L^S$ as defined in formula IA and has 4 to 30 ring atoms, preferably from phenyl that is optionally substituted, preferably in 4-position, 2,4-positions, 2,4,6-positions or 3,5-positions, with alkyl or alkoxy having 1 to 20 C atoms, preferably 1 to 16 C atoms, more preferably from formulae SUB7-SUB18 above.

Another embodiment of the invention relates to a composition comprising a compound of formula I, and further comprising one or more electron donors or p-type semiconductors, preferably selected from conjugated polymers. Preferably, the conjugated polymer used in the said composition comprises at least one electron donating unit ("donor unit") and at least one electron accepting unit ("acceptor unit"), and optionally at least one spacer unit separating a donor unit from an acceptor unit, wherein each donor and acceptor units is directly connected to another donor or acceptor unit or to a spacer unit, and wherein all of the donor, acceptor and spacer units are each independently selected from arylene or heteroarylene that has from 5 to 20 ring atoms, is mono- or polycyclic, optionally contains fused rings, are is unsubstituted or substituted by one or more identical or different groups $L^S$ as defined above.

Preferably the spacer units, if present, are located between the donor and acceptor units such that a donor unit and an acceptor unit are not directly connected to each other.

Preferred conjugated polymers comprise, very preferably consist of, one or more units selected from formula U1, U2 and U3, and/or one or more units selected from formula U4, U5, U6 and U7

-(D-Sp)- U1

-(A-Sp)- U2

-(A-D)- U3

-(D)- U4

-(Sp-D-Sp)- U5

-(A)- U6

-(Sp-A-Sp)- U7 wherein D denotes a donor unit, A denotes an acceptor unit and Sp denotes a spacer unit, all of which are selected, independently of each other and on each occurrence identically or differently, from arylene or heteroarylene that has from 5 to 20 ring atoms, is mono- or polycyclic, optionally contains fused rings, are is unsubstituted or substituted by one or more identical or different groups $L^S$ as defined above.

Very preferred are polymers of formula Pi-Pviii $-[(D-Sp)_x-(A-Sp)_y]_n-$ Pi $-[(A-D)_x-(A-Sp)_y]_n-$ Pi $-[(D)_x-(Sp-A-Sp)y]_n-$ Piii $-[D-Sp-A-Sp]_n-$ Piv $-[D-A]_n-$ Pv $-[D-Sp-A-Sp]_n$ Pvi $-[D^1-A-D^2-A]_n$ Pvii $-[D-A^1-D-A^2]_n$ Pviii wherein A, D and Sp are as defined in formula U1-U7, A and D can each, in case of multiple occurrence, also have different meanings, $D^1$ and $D^2$ have one of the meanings given for D and are different from each other, $A^1$ and $A^2$ have one of the meanings given for A and are different from each other, x and y denote the molar fractions of the corresponding units, x and y are each, independently of one another, a non-integer >0 and <1, with x+y=1, and n is an integer >1.

Especially preferred are repeating units and polymers of formulae U1-U7 and Pi-viii wherein D, $D^1$ and $D^2$ are selected from the group consisting of the following formulae
(D1)
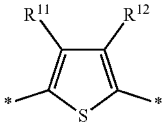
(D7)
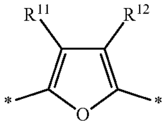
(D10)
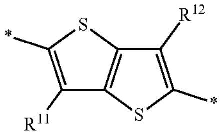
(D11)
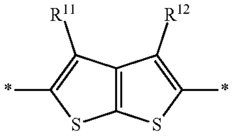
(D19)
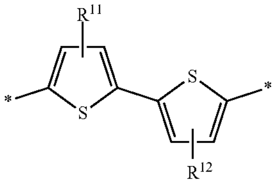
(D22)
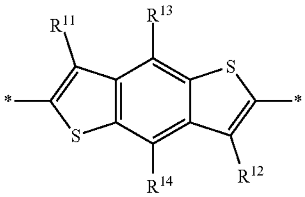
(D29)
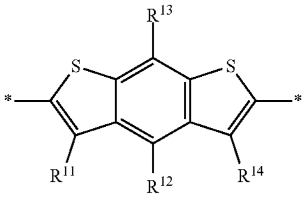
(D30)
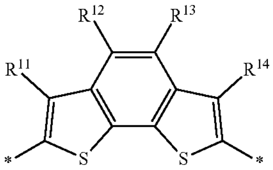
(D35)
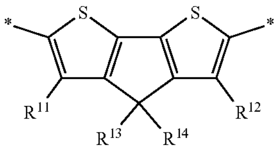
-continued
(D36)
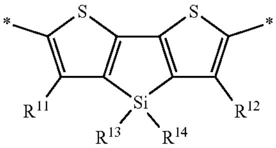
(D37)
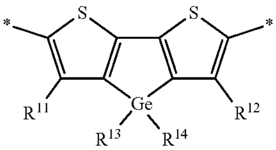
(D44)
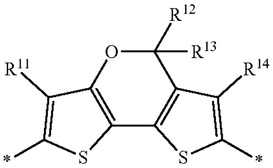
(D55)
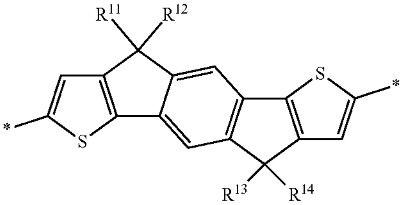
(D84)
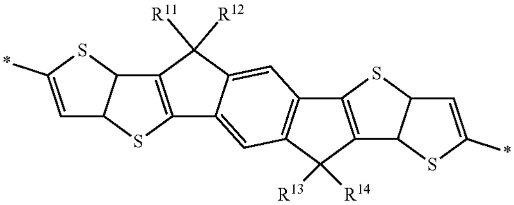
(D87)
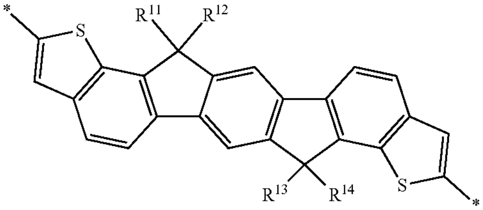
(D88)
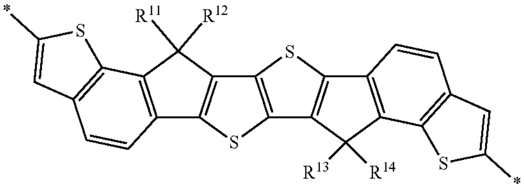
(D89)
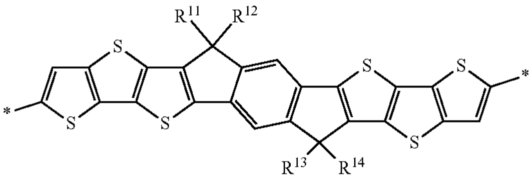

-continued (D93)

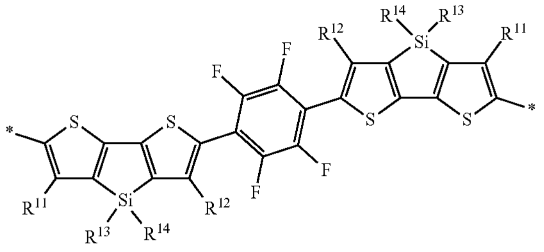

(D106)

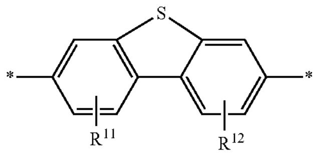

(D111)

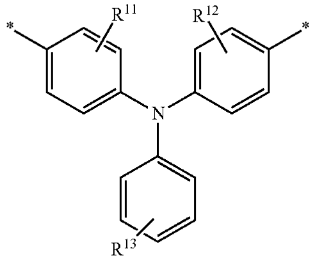

(D119)

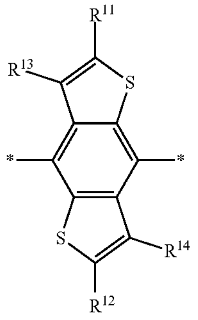

(D140)

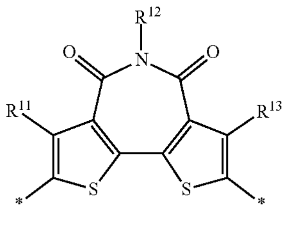

(D141)

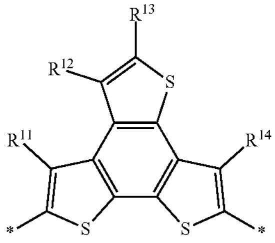

-continued (D146)

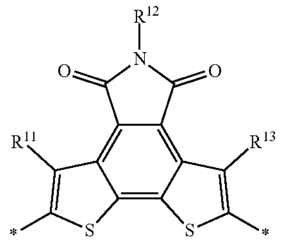

(D147)

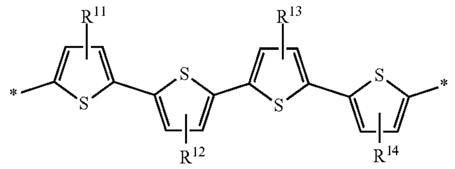

wherein $R^{11}$, $R^{12}$, $R^{13}$, $R^{14}$ independently of each other denote H or have one of the meanings of L, preferably of $R^7$, as defined above, and wherein preferably at least one of $R^{11}$, $R^{12}$, $R^{13}$ and $R^{14}$ is different from H and in formula D147 preferably $R^{12}$ and $R^{13}$ are F and $R^{11}$ and $R^{14}$ are H or C1-C30 alkyl.

Further preferred are repeating units and polymers of formulae U1-U7 and Pi-viii wherein A, $A^1$ and $A^2$ are selected from the group consisting of the following formulae (A1)

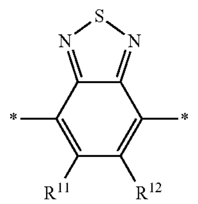

(A2)

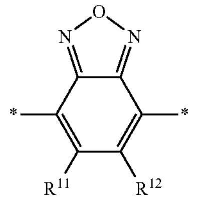

(A5)

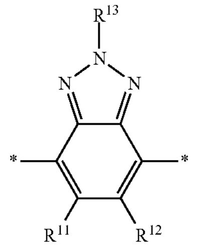

(A15)

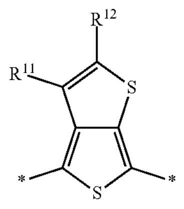

-continued
(A16)
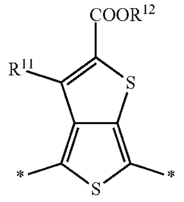
(A20)
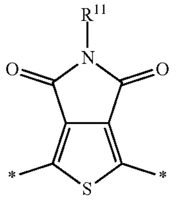
(A74)
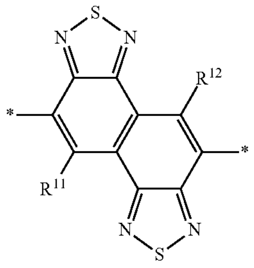
(A88)
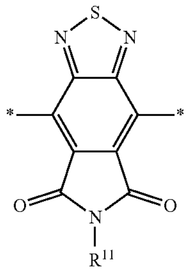
(A92)
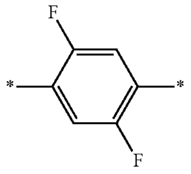
(A94)
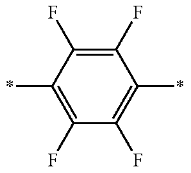
(A98)
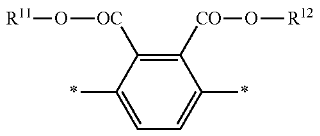
-continued
(A99)
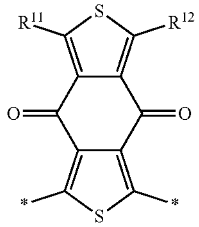
(A100)
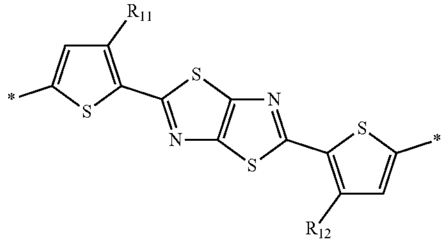
wherein $R^{11}$, $R^{12}$, $R^{13}$, $R^{14}$ independently of each other denote H or have one of the meanings of L, preferably of $R^7$, as defined above.
Further preferred are repeating units and polymers of formulae U1-U7 and Pi-Pviii wherein Sp is selected from the group consisting of the following formulae
Sp1
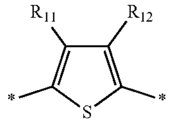
Sp2
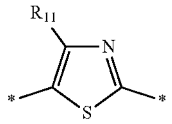
Sp3
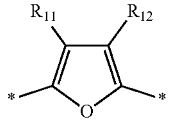
Sp4
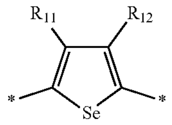
Sp5
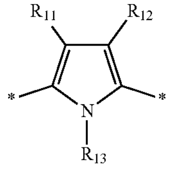
Sp6
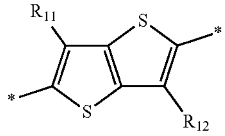

-continued

Sp7

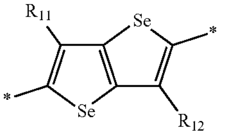

Sp8

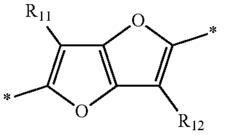

Sp9

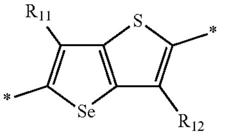

Sp10

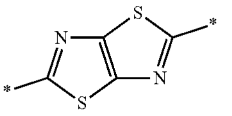

Sp11

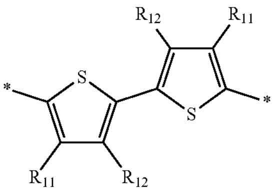

Sp12

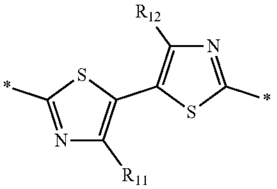

Sp13

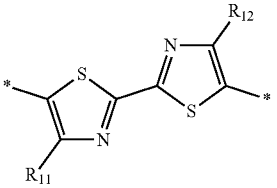

Sp14

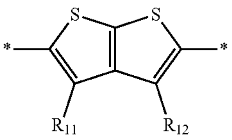

Sp15

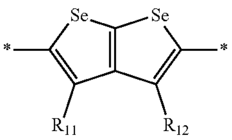

Sp16

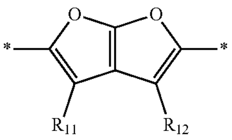

-continued

Sp17

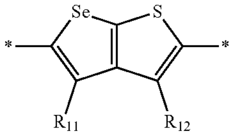

Sp18

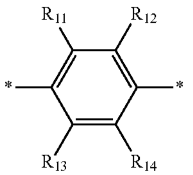

wherein $R^{11}$, $R^{12}$, $R^{13}$, $R^{14}$ independently of each other denote H or have one of the meanings of $L^S$ as defined above.

In the formulae Sp1 to Sp17 preferably $R^{11}$ and $R^{12}$ are H. In formula Sp18 preferably $R^{11-14}$ are H or F.

Preferably the conjugated polymer contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or b) one or more acceptor units selected from the group consisting of the formulae A1, A2, A5, A15, A16, A20, A74, A88, A92, A94 and A98, A99, A100 and c) optionally one or more spacer units selected from the group consisting of the formulae Sp1-Sp18, very preferably of the formulae Sp1, Sp6, Sp11 and Sp14, wherein the spacer units, if present, are preferably located between the donor and acceptor units such that a donor unit and an acceptor unit are not directly connected to each other.

In a second preferred embodiment the conjugated polymer comprises, preferably consists of one or more, preferably one, two, three or four, distinct repeating units D, and one or more, preferably one, two or three, distinct repeating units A.

Preferably the conjugated polymer according to this second preferred embodiment contains from one to six, very preferably one, two, three or four distinct units D and from one to six, very preferably one, two, three or four distinct units A, wherein d1, d2, d3, d4, d5 and d6 denote the molar ratio of each distinct unit D, and a1, a2, a3, a4, a5 and a6 denote the molar ratio of each distinct unit A, and each of d1, d2, d3, d4, d5 and d6 is from 0 to 0.6, and d1+d2+d3+d4+d5+d6 is from 0.2 to 0.8, preferably from 0.3 to 0.7, and each of a1, a2, a3, a4, a5 and a6 is from 0 to 0.6, and a1+a2+a3+a4+a5+d6 is from 0.2 to 0.8, preferably from 0.3 to 0.7, and d1+d2+d3+d4+d5+d6+a1+a2+a3+a4+a5+a6 is from 0.8 to 1, preferably 1.

Preferably the conjugated polymer according to this second preferred embodiment contains, preferably consists of a) one or more donor units selected from the group consisting of the formulae D1, D7, D10, D11, D19, D22, D29, D30, D35, D36, D37, D44, D55, D84, D87, D88, D89, D93, D106, D111, D119, D140, D141, D146, and D147 and/or b) one or more acceptor units selected from the group consisting of the formulae A1, A2, A5, A15, A16, A20, A74, A88, A92, A94, A98, A99 and A100.

In the above conjugated polymers, like those of formula P and its subformulae, the total number of repeating units n is preferably from 2 to 10,000. The total number of repeating units n is preferably ≥5, very preferably ≥10, most preferably ≥50, and preferably ≤500, very preferably ≤1,000, most preferably ≤2,000, including any combination of the aforementioned lower and upper limits of n.

The conjugated polymers are preferably statistical or random copolymers.

Very preferred conjugated polymers are selected from the following formulae

P1

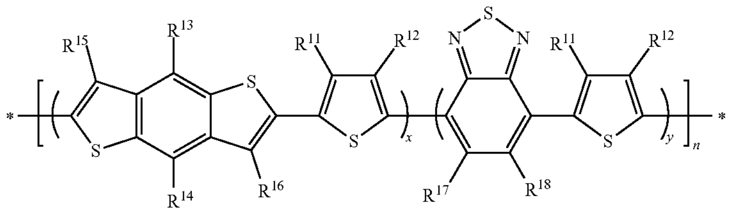

P2

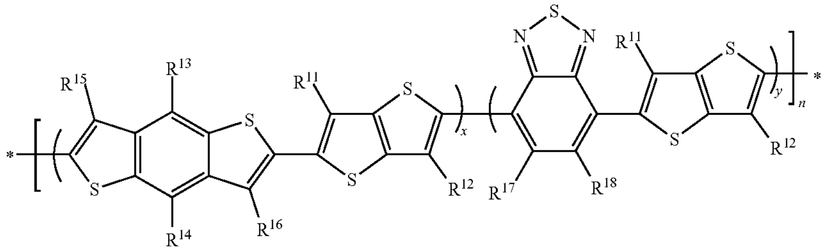

P3

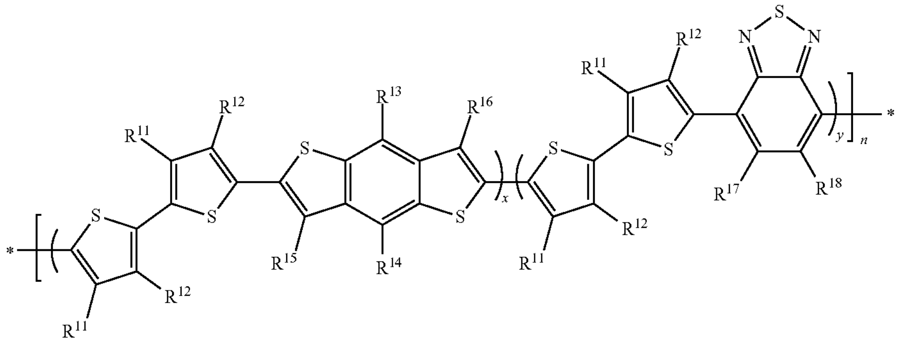

P4

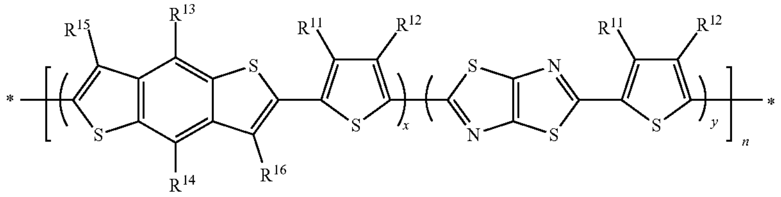

P5

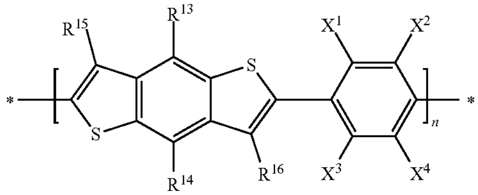

-continued
P6
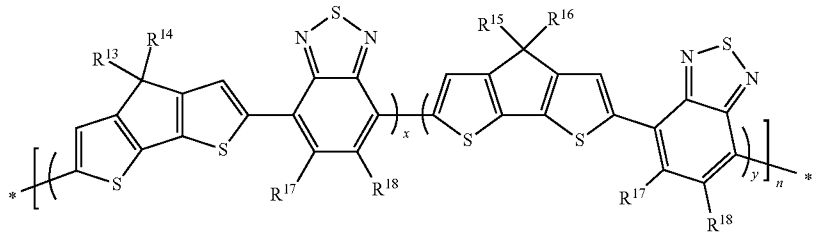
P7
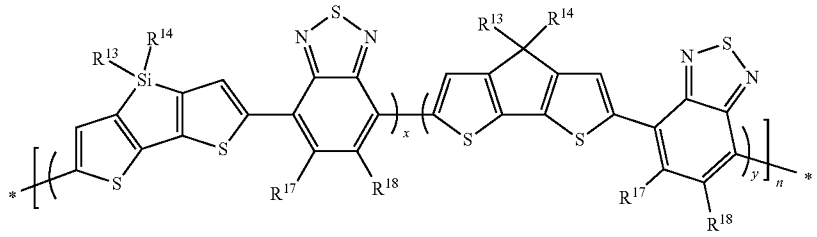
P8
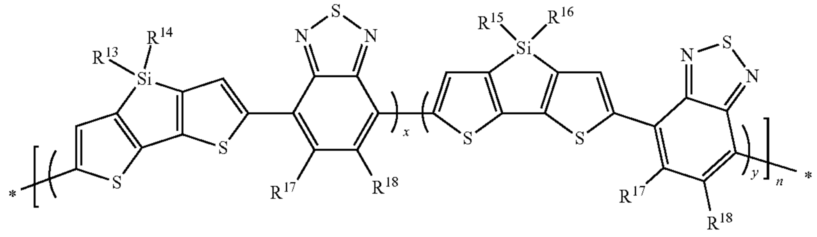
P9
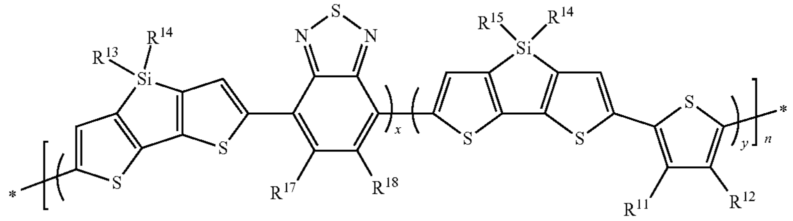
P10
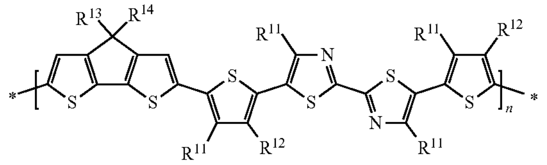
P11
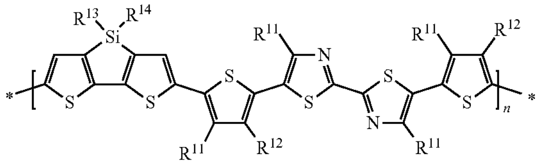
P12
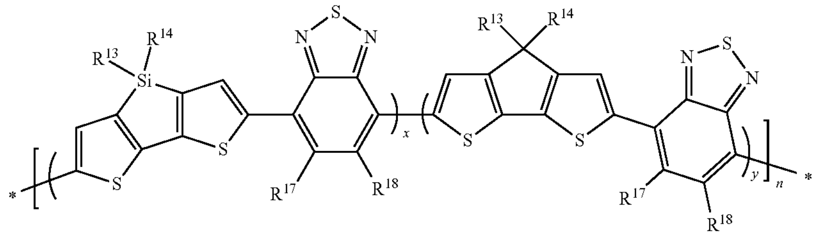
P13
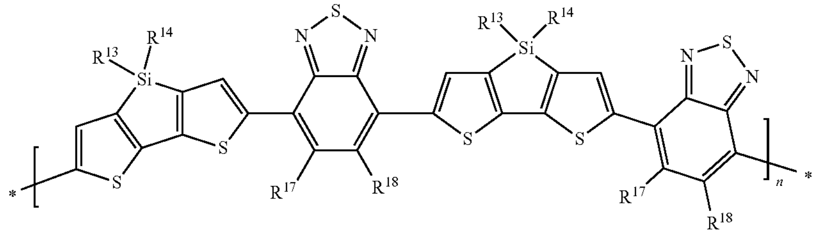

-continued
P14
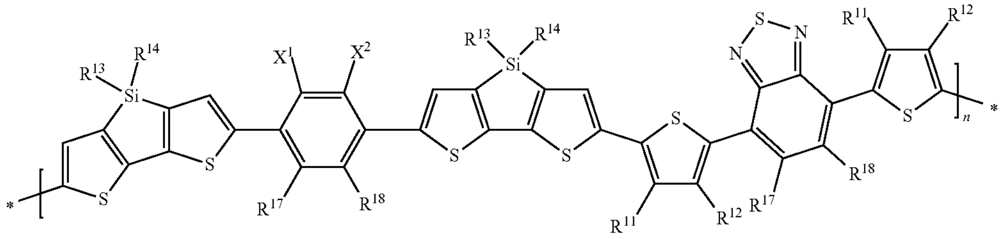
P15
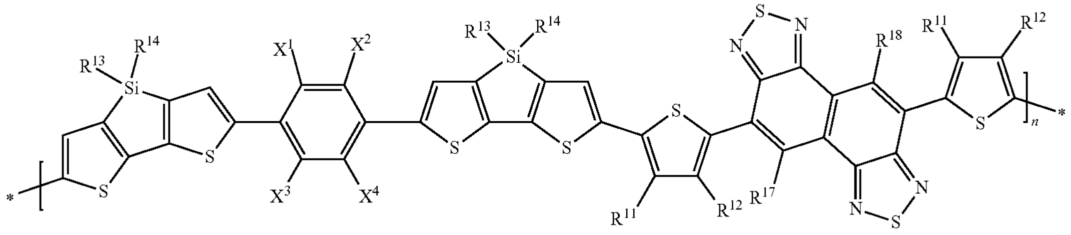
P16
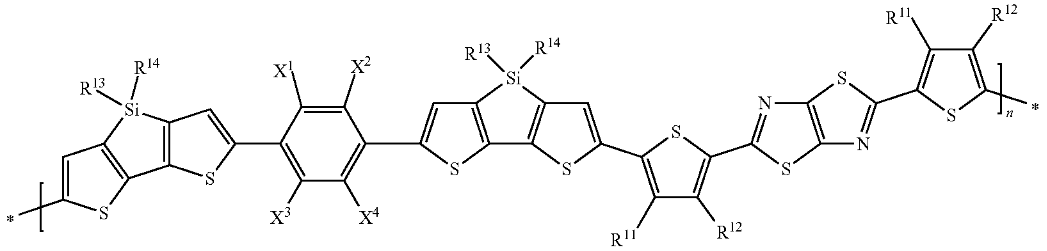
P17
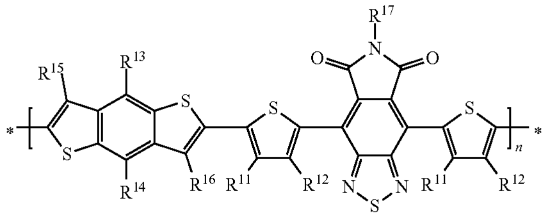
P18
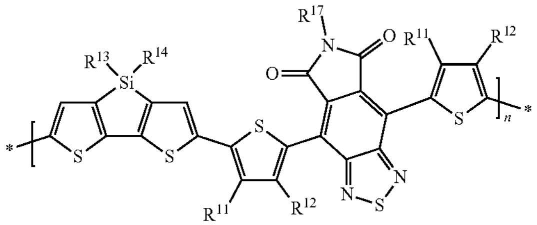
P19
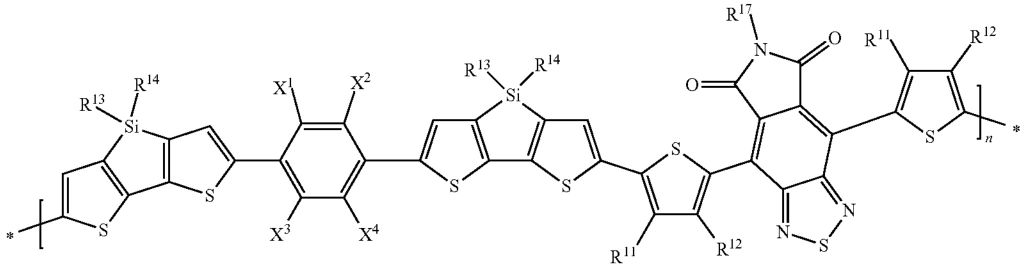
P20
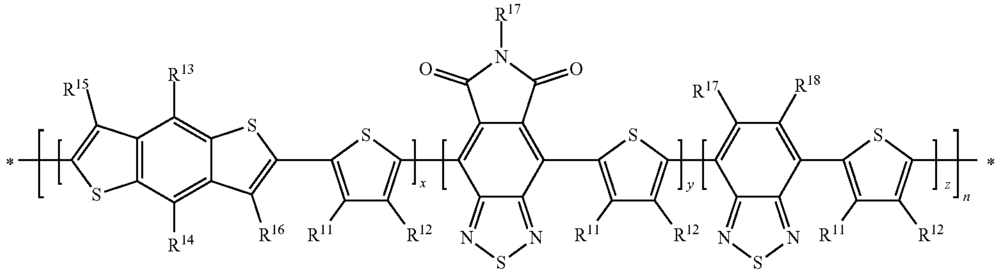

-continued
P21
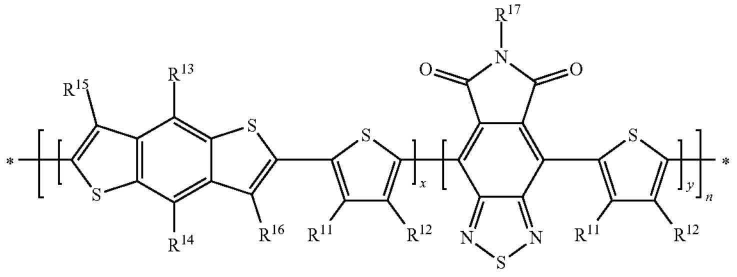
P22
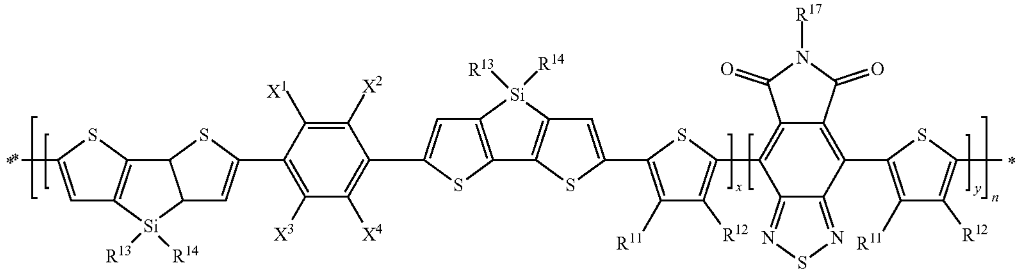
P23
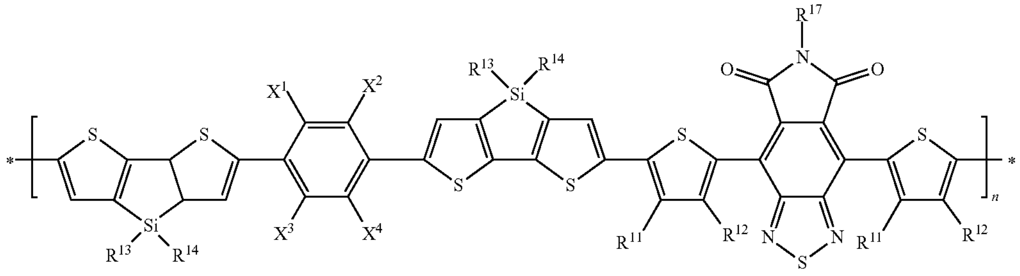
P24
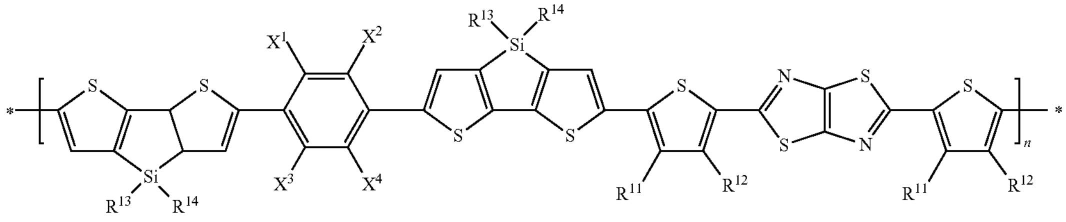
P25
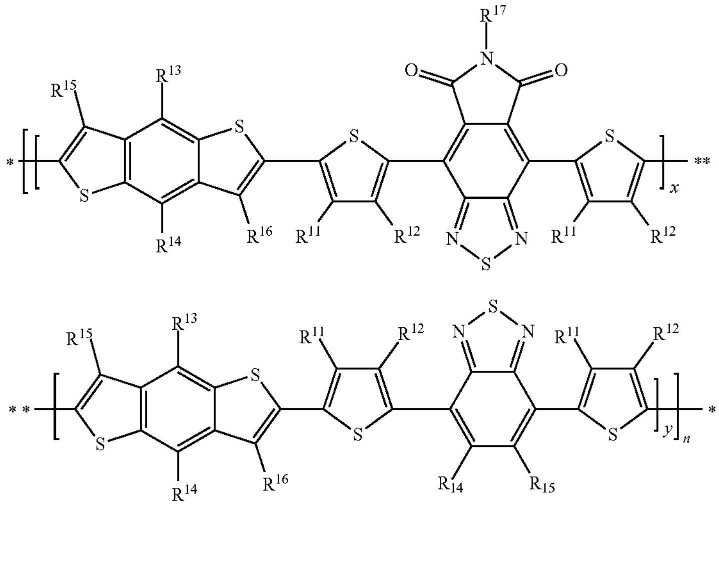

-continued
P26
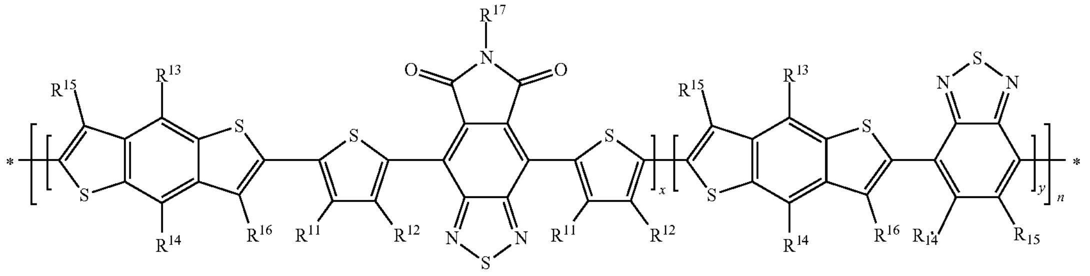
P27
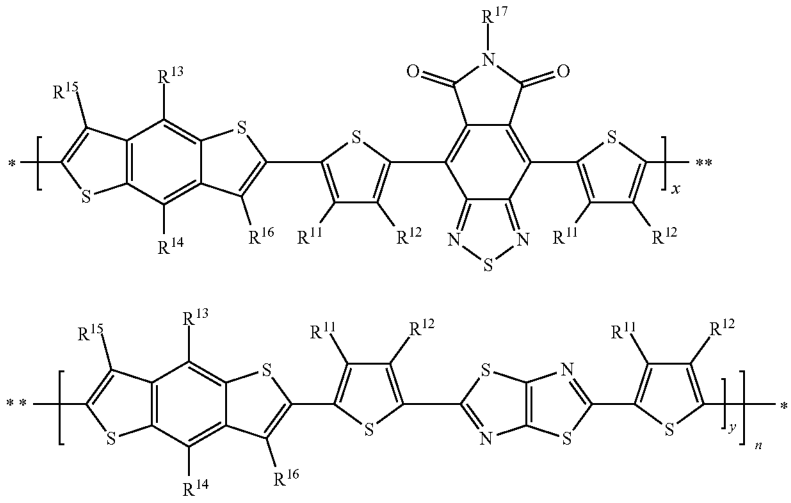
P28
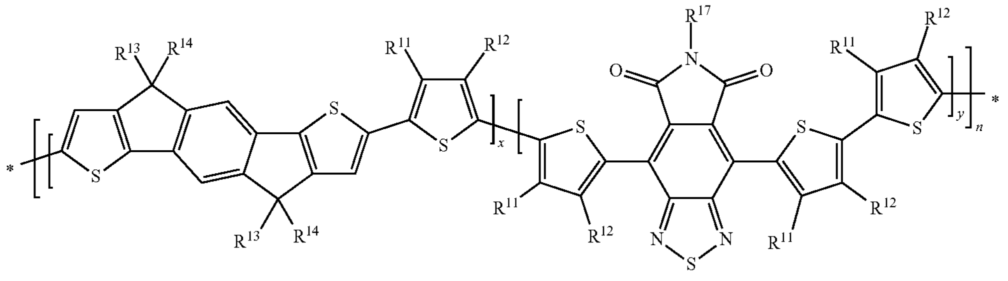
P29
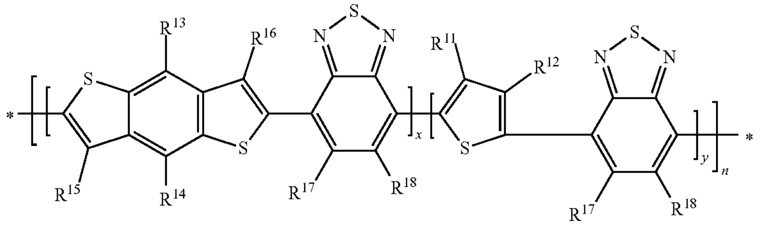
P30
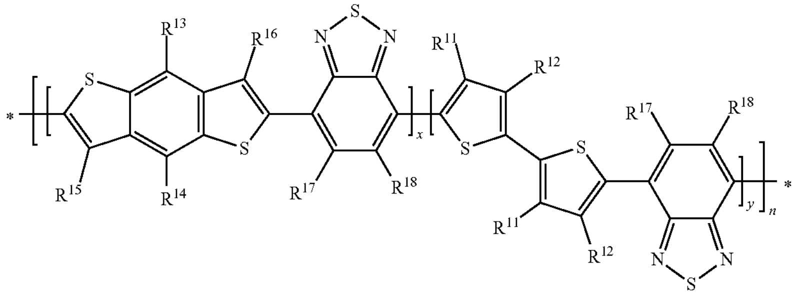

-continued
P31
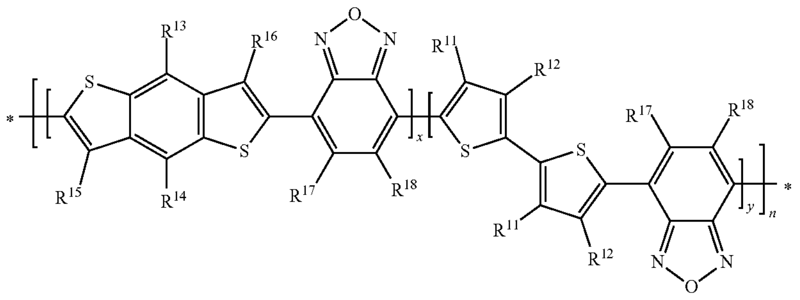
P32
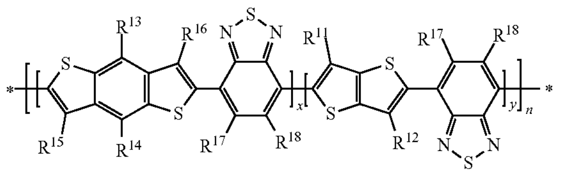
P33
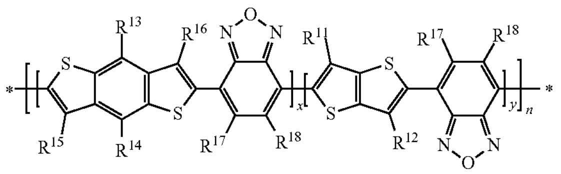
P34
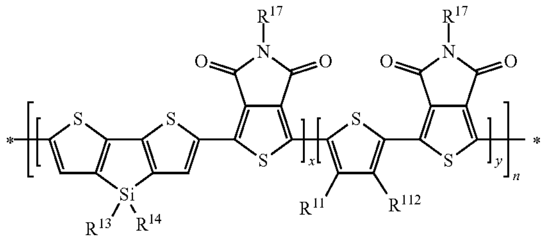
P35
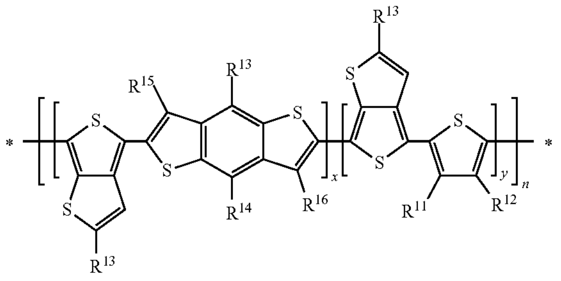
P36
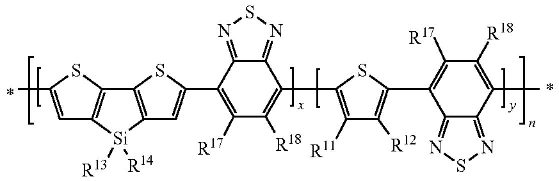
P37
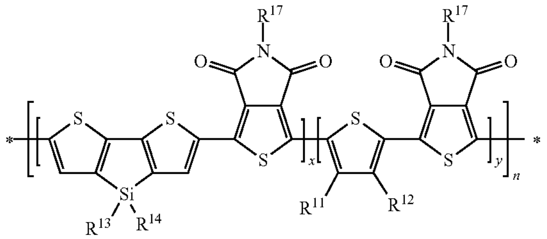
P38
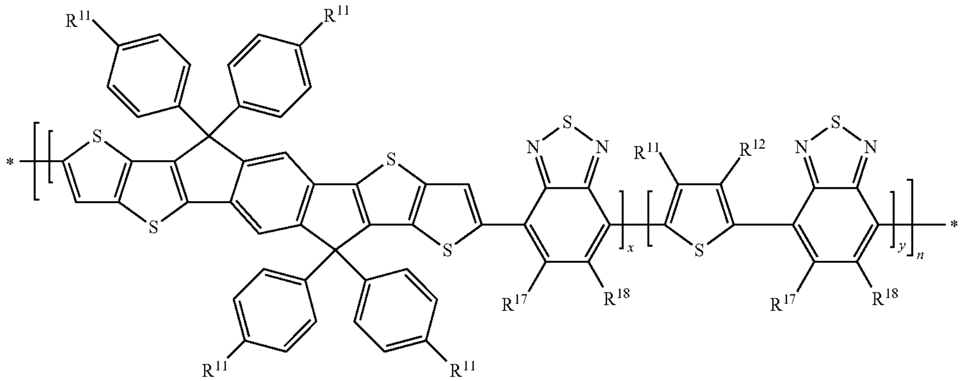

-continued
P39
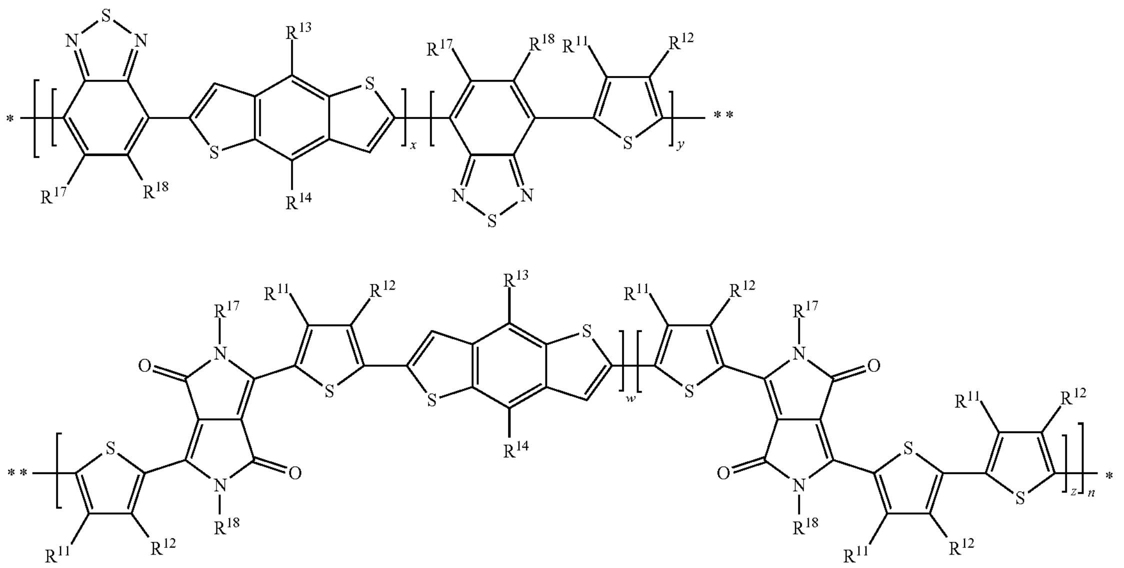
P40
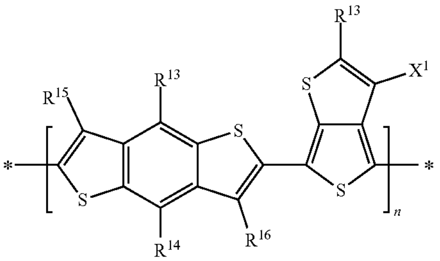
P41
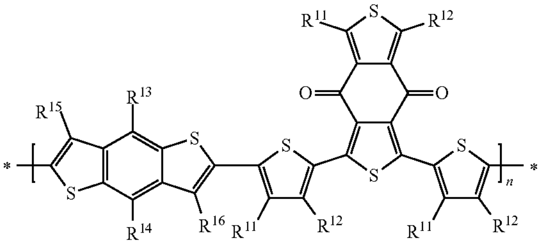
P42
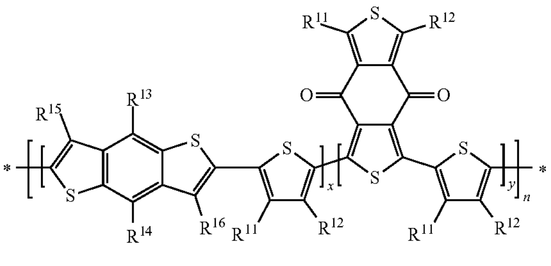
P43
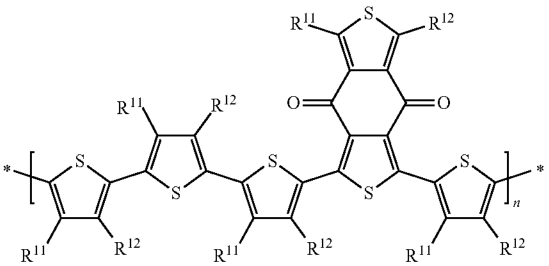
P44
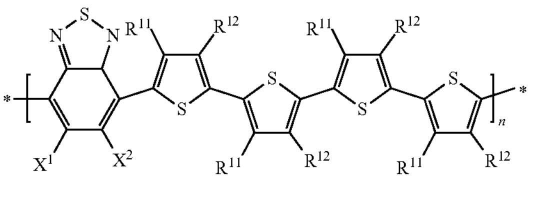
P45
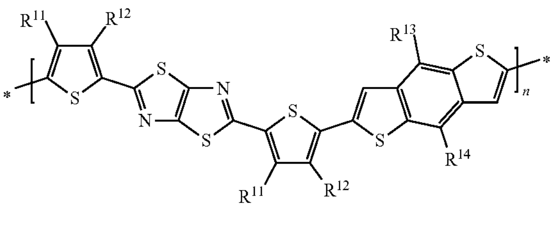

-continued
P46
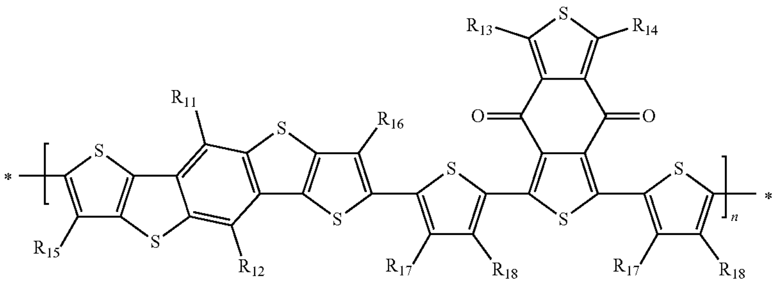
P47
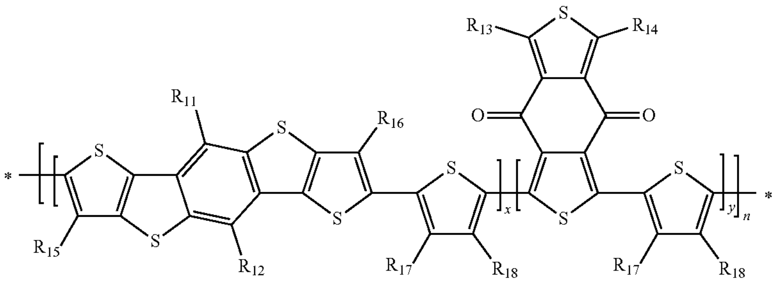
P48
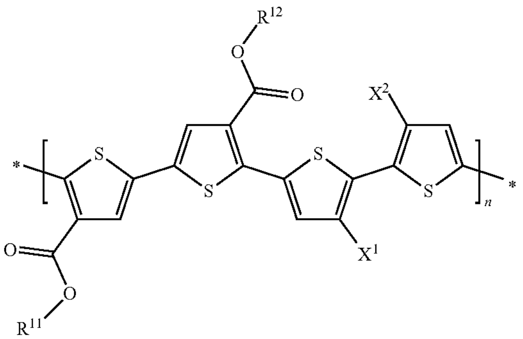
P49
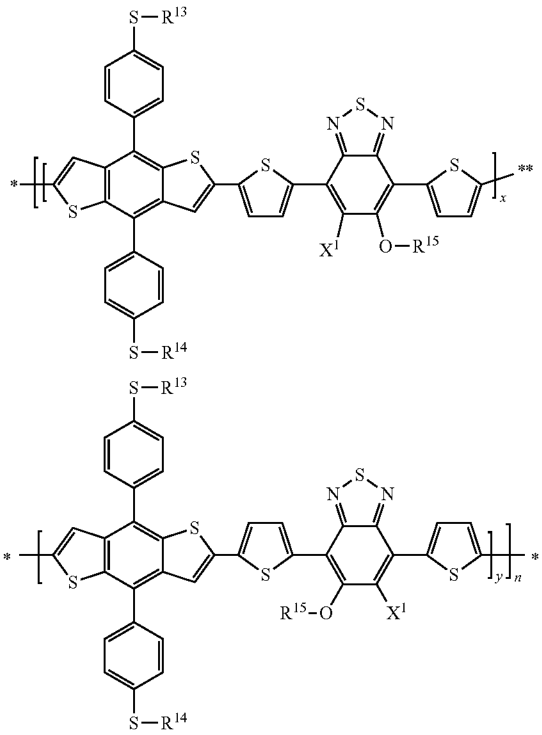

-continued
P50
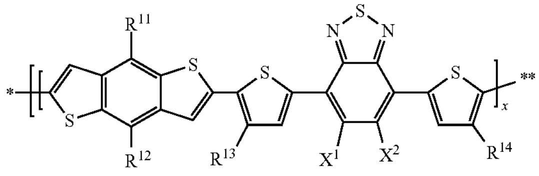
P51
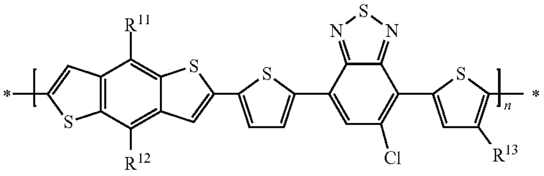
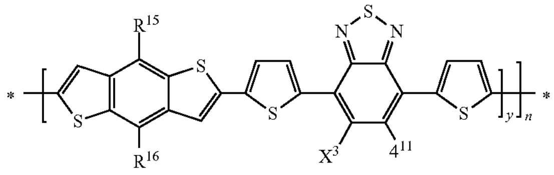
P52
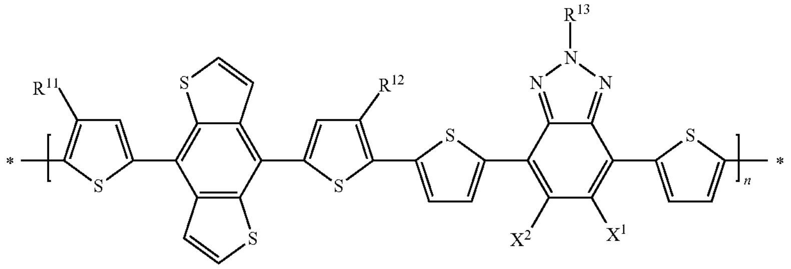
P53
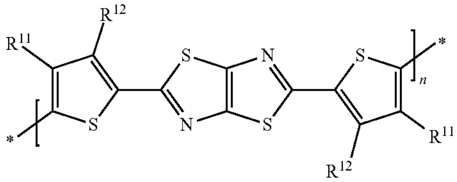
P54
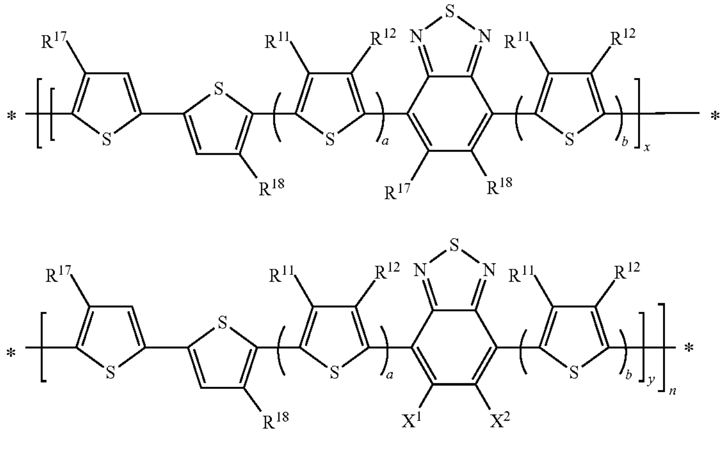

wherein $R^{11-14}$, x, y and n are as defined above, w and z have one of the meanings given for y, x+y+w+z=1, $R^{15}$, $R^{16}$, $R^{17}$ and $R^{18}$ have one of the meanings given for $R^{11}$, and $X^1$, $X^2$, $X^3$ and $X^4$ denote H, F or Cl.

Further preferred are polymers comprising one of the formulae P1-P54 as one or more repeating unit.

In the polymers of formula Pi-viii and P1-P54 which are composed of two building blocks [ ]x and [ ]y, x and y are preferably from 0.1 to 0.9, very preferably from 0.25 to 0.75, most preferably from 0.4 to 0.6.

In the polymers of formula Pi-viii which are composed of three building blocks $[\ ]_x$, [ ]y, and [ ]z, x, y and z are preferably from 0.1 to 0.8, very preferably from 0.2 to 0.6, most preferably from 0.25 to 0.4.

In the formulae P1-P54 preferably one or more of $X^1$, $X^2$, $X^3$ and $X^4$ denote F, very preferably all of $X^1$, $X^2$, $X^3$ and $X^4$ denote F or $X^1$ and $X^2$ denote H and $X^3$ and $X^4$ denote F.

In the formulae P1-P54 preferably $R^{11}$ and $R^{12}$ are H. Further preferably $R^{11}$ and $R^{12}$, when being different from H, denote straight-chain or branched alkyl with 1 to 30, preferably 1 to 20, C atoms that is optionally fluorinated.

In the formulae P1-P54, preferably $R^{15}$ and $R^{16}$ are H, and $R^{13}$ and $R^{14}$ are different from H.

In formula P54 preferably $R^{17}$ and $R^{18}$ are F. Further preferably in formula P54 one or both of $R^{11}$ and $R^{12}$ are C1-C30 alkyl.

In the formulae P1-P54, preferably $R^{13}$, $R^{14}$, $R^{15}$ and $R^{16}$, when being different from H, are each independently selected from the following groups:

- the group consisting of straight-chain or branched alkyl, alkoxy or sulfanylalkyl with 1 to 30, preferably 1 to 20, C atoms that is optionally fluorinated,
- the group consisting of straight-chain or branched alkylcarbonyl or alkylcarbonyloxy with 2 to 30, preferably 2 to 20, C atoms, that is optionally fluorinated.

In the formulae P1-P54, preferably $R^{17}$ and $R^{18}$, when being different from H, are each independently selected from the following groups:

- the group consisting of straight-chain or branched alkyl, alkoxy or sulfanylalkyl with 1 to 30, preferably 1 to 20, C atoms that is optionally fluorinated,
- the group consisting of straight-chain or branched alkylcarbonyl or alkylcarbonyloxy with 2 to 30, preferably 2 to 20, C atoms, that is optionally fluorinated.
- the group consisting of F and Cl.

Further preferred are conjugated polymers selected of formula PT $R^{31}$-chain-$R^{32}$ PT wherein "chain" denotes a polymer chain selected of formula Pi-Pviii or P1-P54, and $R^{31}$ and $R^{32}$ have independently of each other one of the meanings of $R^{11}$ as defined above, or denote, independently of each other, H, F, Br, Cl, I, —$CH_2Cl$, —CHO, —CR'═CR"$_2$, —SiR'R"R'", —SiR'X'X", —SiR'R"X', —SnR'R"R'", —BR'R", —B(OR')(OR"), —$B(OH)_2$, —O—$SO_2$—R', —C≡CH, —C≡C—SiR'$_3$, —ZnX' or an endcap group, X' and X" denote halogen, R', R" and R'" have independently of each other one of the meanings of $R^0$ given in formula 1, and preferably denote alkyl with 1 to 12 C atoms, and two of R', R" and R'" may also form a cyclosilyl, cyclostannyl, cycloborane or cycloboronate group with 2 to 20 C atoms together with the respective hetero atom to which they are attached.

Preferred endcap groups $R^{31}$ and $R^{32}$ are H, $C_{1-20}$ alkyl, or optionally substituted $C_{6-12}$ aryl or $C_{2-10}$ heteroaryl, very preferably H, phenyl or thiophene.

The compounds of formula IA, IB and their subformulae and the conjugated polymers of formula Pi-viii, P1-P54 and PT can be synthesized according to or in analogy to methods that are known to the skilled person and are described in the literature. Other methods of preparation can be taken from the examples.

For example, the compounds of the present invention can be suitably prepared by aryl-aryl coupling reactions, such as Yamamoto coupling, Suzuki coupling, Stille coupling, Sonogashira coupling, Heck coupling or Buchwald coupling. The educts can be prepared according to methods which are known to the person skilled in the art.

Preferred aryl-aryl coupling methods used in the synthesis methods as described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.,* 1977, 683-684. Yamamoto coupling is described in for example in T. Yamamoto et al., *Prog. Polym. Sci.,* 1993, 17, 1153-1205, or WO 2004/022626 A1. Stille coupling is described for example in Z. Bao et al., *J. Am. Chem. Soc.,* 1995, 117, 12426-12435 and C—H activation is described for example in M. Leclerc et al, *Angew. Chem. Int. Ed.,* 2012, 51, 2068-2071. For example, when using Yamamoto coupling, educts having two reactive halide groups are preferably used.

When using Suzuki coupling, educts having two reactive boronic acid or boronic acid ester groups or two reactive halide groups are preferably used. When using Stille coupling, edcuts having two reactive stannane groups or two reactive halide groups are preferably used. When using Negishi coupling, educts having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as $Pd(Ph_3P)_4$. Another preferred phosphine ligand is tris(ortho-tolyl)phosphine, i.e. Pd(o-$Tol_3P)_4$. Preferred Pd(II) salts include palladium acetate, i.e. $Pd(OAc)_2$. Alternatively the Pd(0) complex can be prepared by mixing a Pd(0) dibenzylideneacetone complex, for example tris(dibenzyl-ideneacetone)dipalladium(0), bis(dibenzylideneacetone)palladium(0), or Pd(II) salts e.g. palladium acetate, with a phosphine ligand, for example triphenylphosphine, tris(ortho-tolyl)phosphine or tri(tert-butyl) phosphine. Suzuki coupling is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto coupling employs a Ni(0) complex, for example bis(1,5-cyclooctadienyl) nickel(0).

As alternatives to halogens as described above, leaving groups of formula —O—$SO_2Z^0$ can be used wherein $Z^0$ is an alkyl or aryl group, preferably $C_{1-10}$ alkyl or $C_{6-12}$ aryl. Particular examples of such leaving groups are tosylate, mesylate and triflate.

Especially suitable and preferred synthesis methods of the compounds of formula I and its subformulae are illustrated in the synthesis schemes shown hereinafter.

Scheme 1a
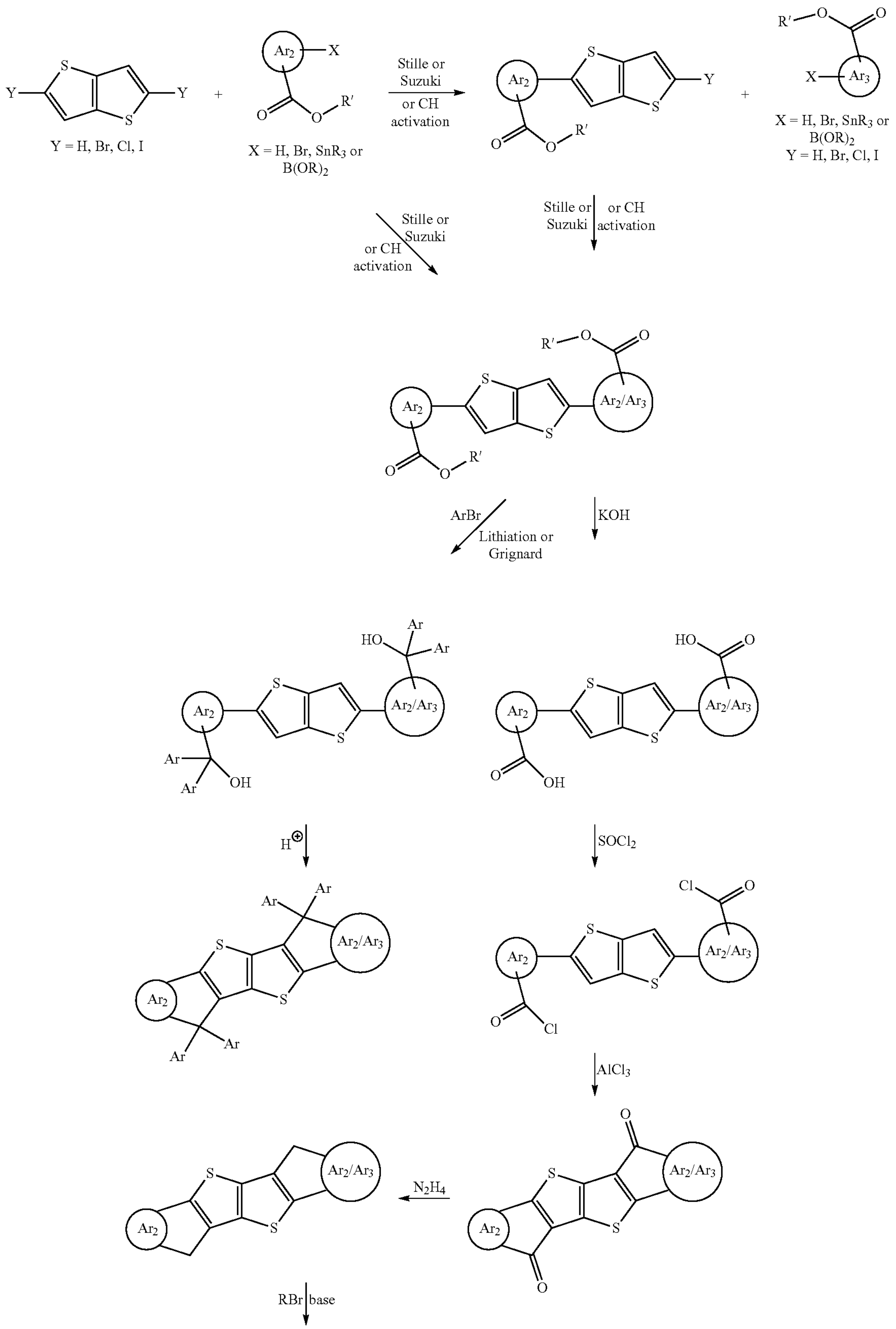

-continued
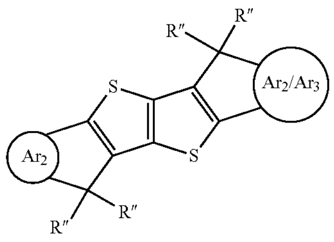
Scheme 1b
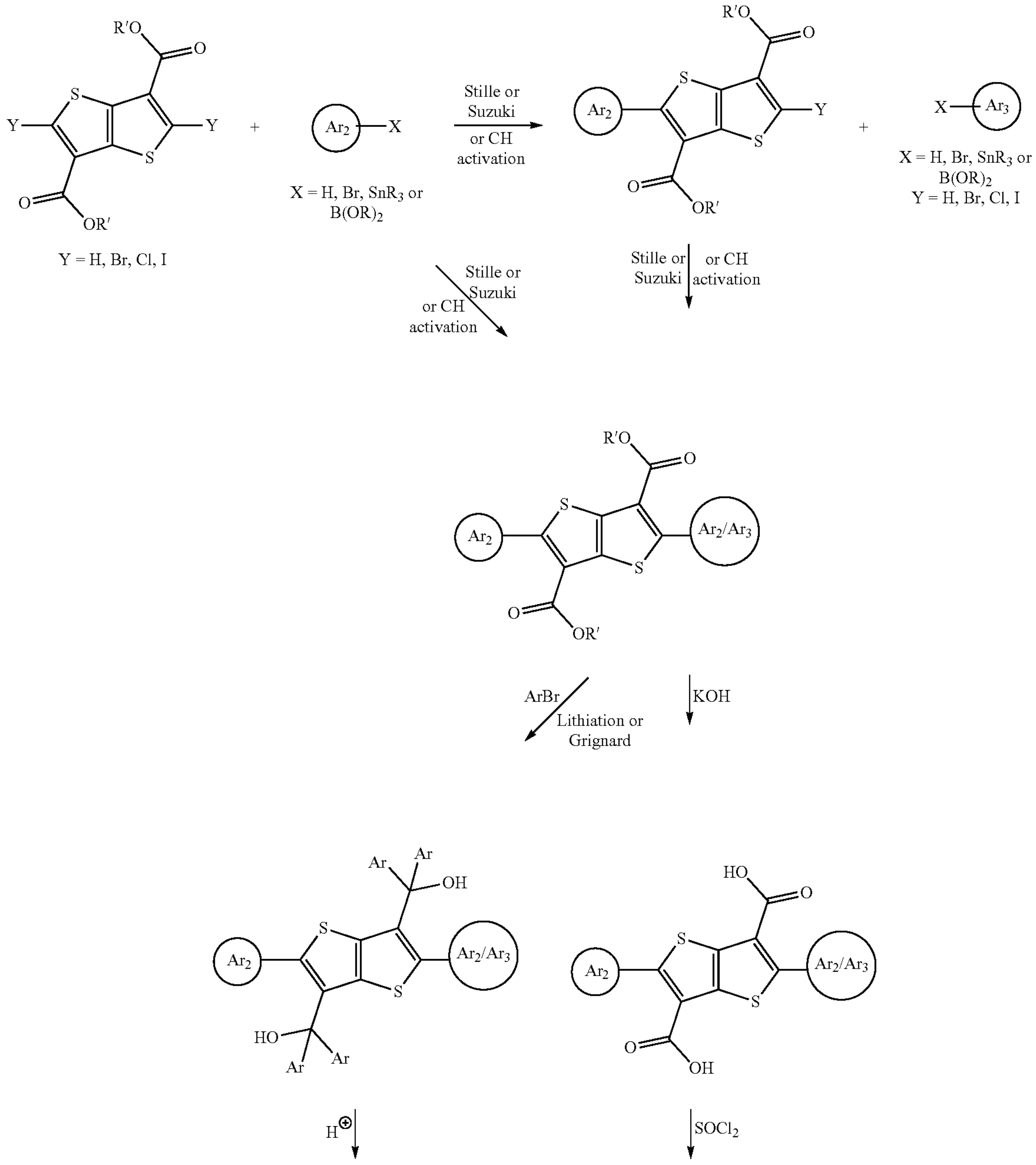

-continued
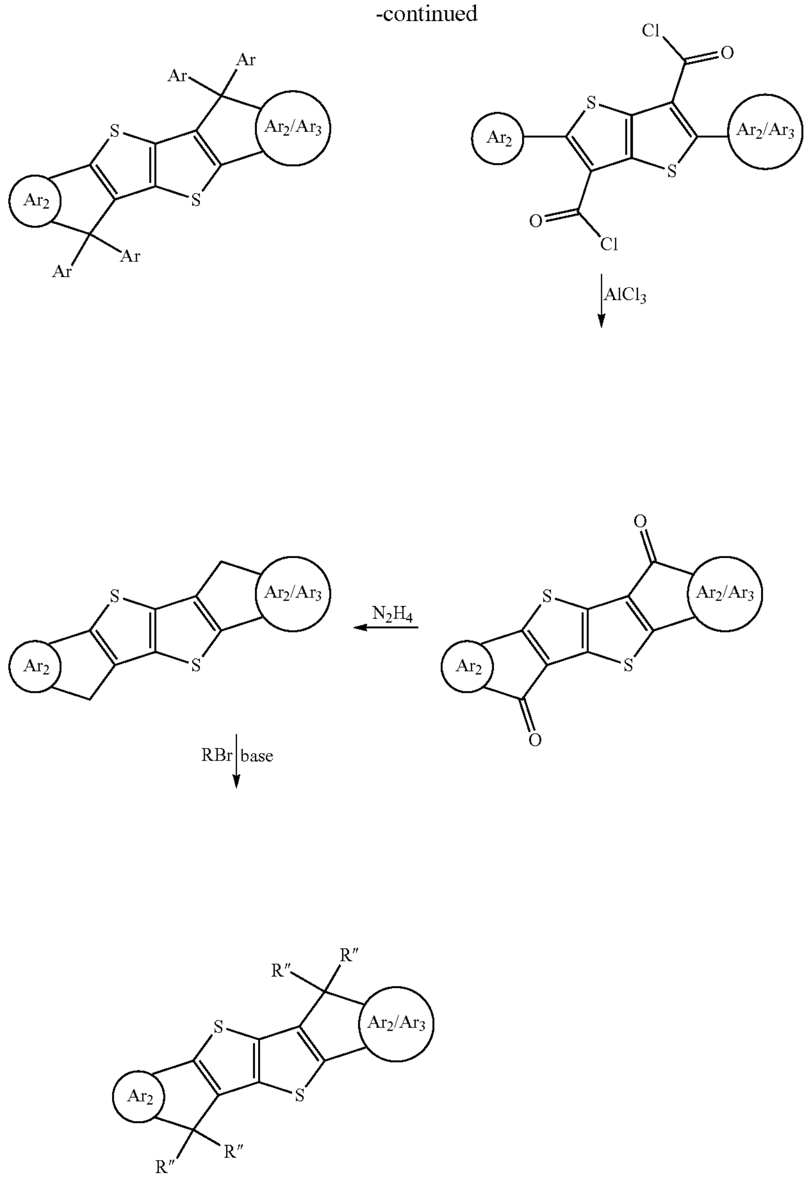
Scheme 2
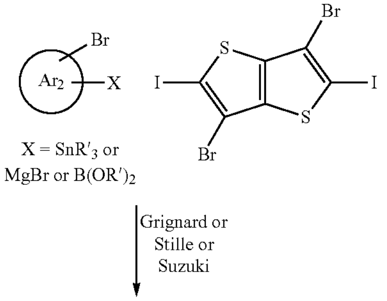
-continued
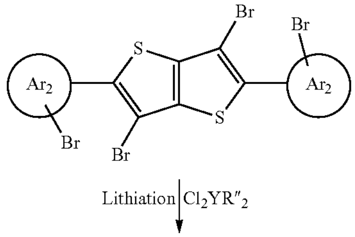

-continued
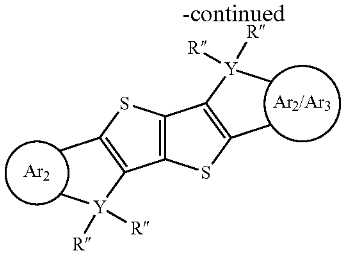
Y = Si or Ge
Scheme 3
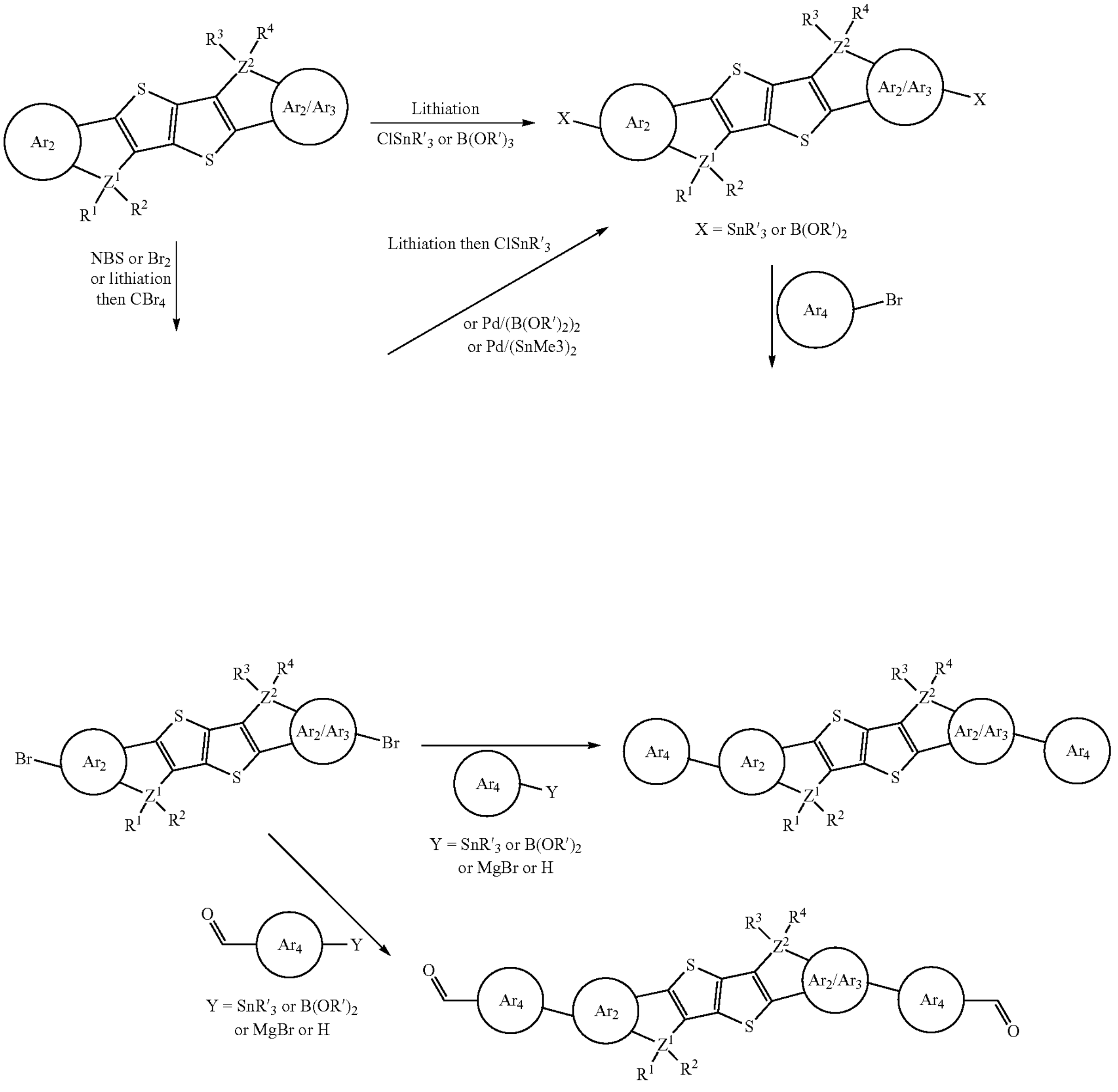

Scheme 4
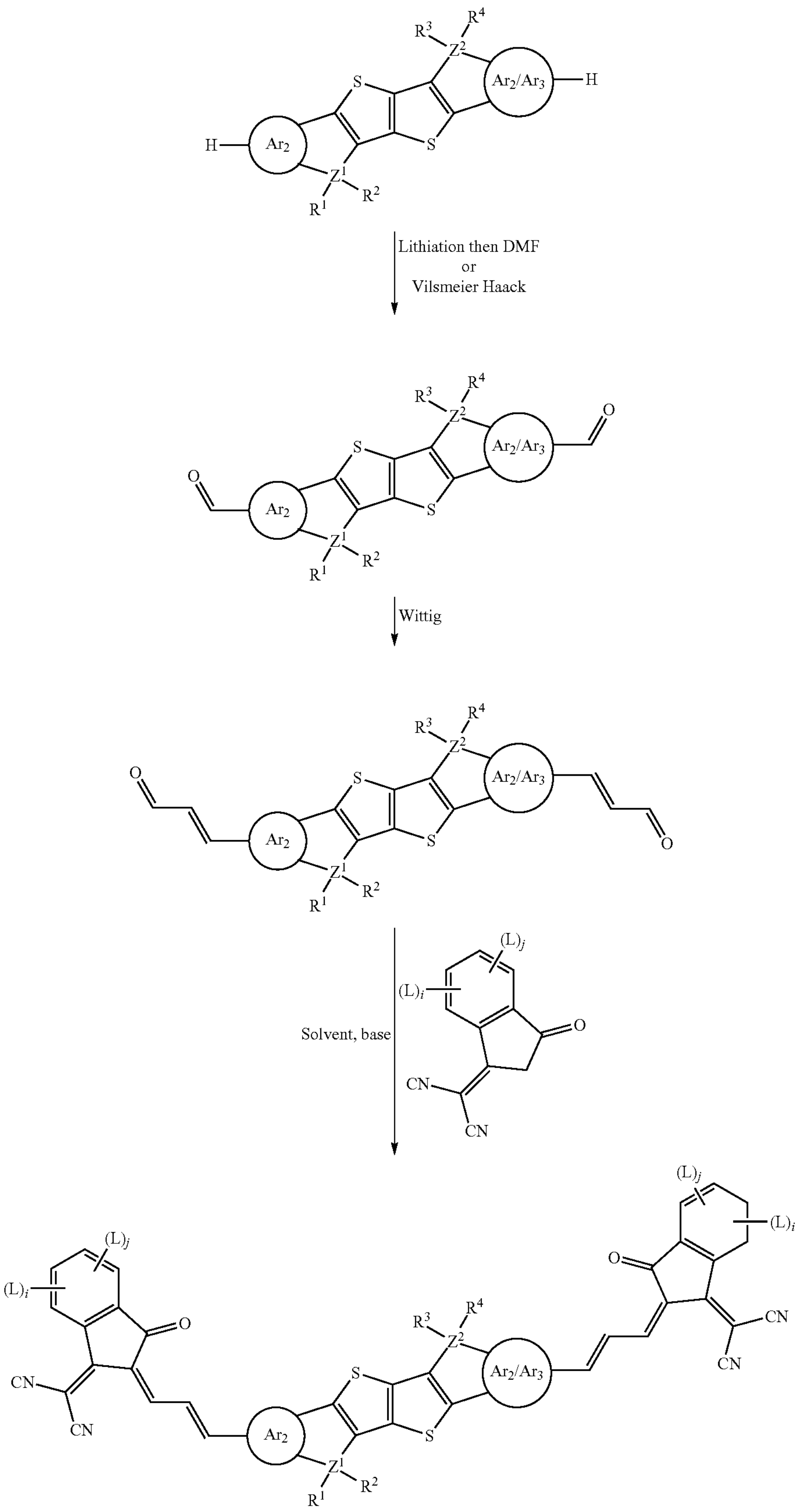

Scheme 5

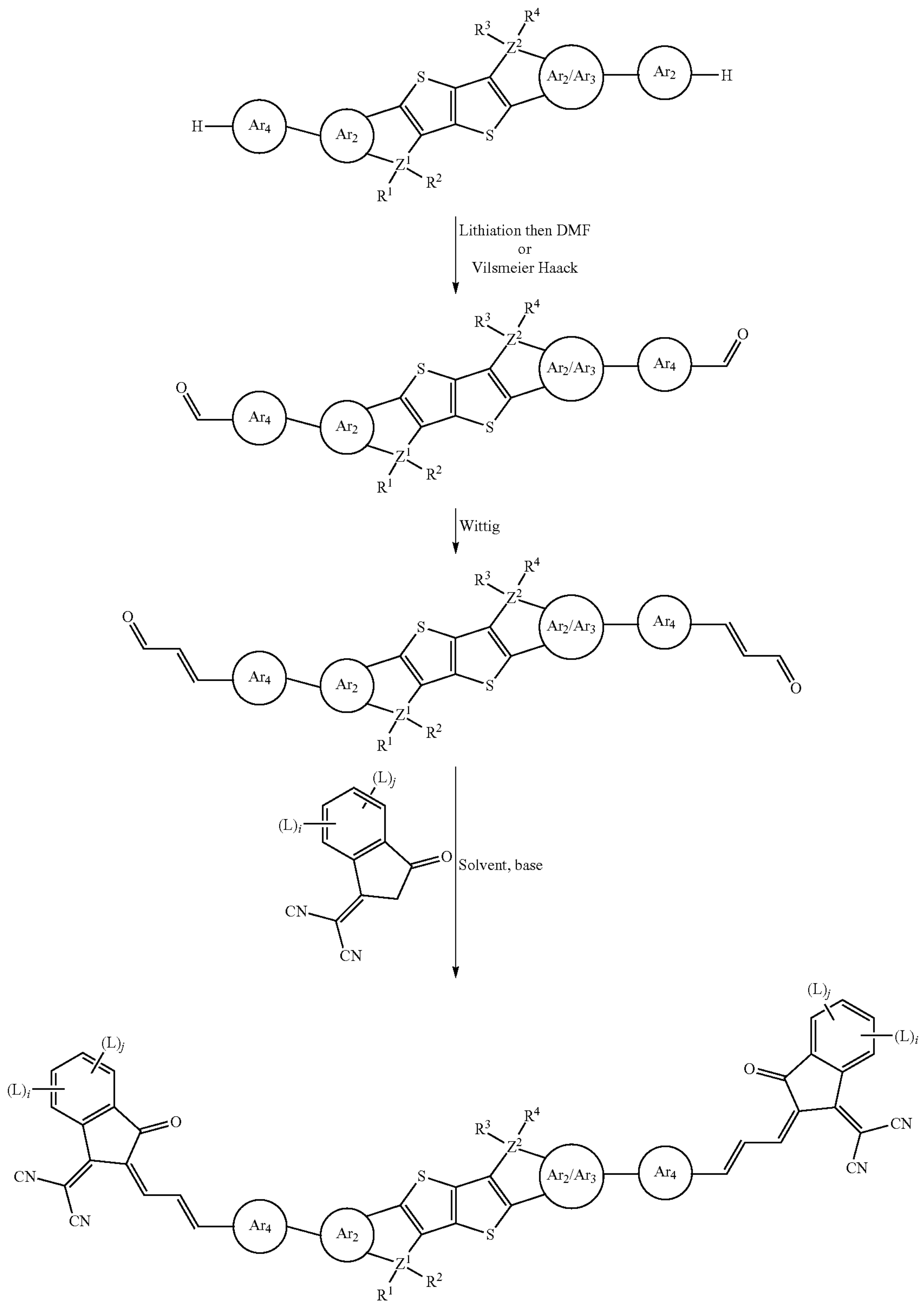

Novel methods of preparing compounds of formula I are another aspect of the invention.

The compound according to the present invention can also be used in compositions, for example together with monomeric or polymeric compounds having charge-transport, semiconducting, electrically conducting, photoconducting and/or light emitting semiconducting properties, or for example with compounds having hole blocking or electron blocking properties for use as interlayers or charge blocking layers in PSCs or OLEDs.

Thus, another aspect of the invention relates to a composition comprising one or more compounds according to the present invention and one or more small molecule compounds and/or polymers having one or more of a charge-transport, semiconducting, electrically conducting, photoconducting, hole blocking and electron blocking property.

The invention further relates to a composition comprising one or more compounds according to the present invention, and further comprising one or more p-type organic semiconductors, preferably selected from conjugated polymers.

The invention further relates to a composition comprising a first n-type semiconductor which is a compound according to the present invention, a second n-type semiconductor, which is preferably a fullerene or fullerene derivative, a non-fullerene acceptor small molecule, or an n-type conjugated polymer, and a p-type semiconductor, which is preferably a conjugated polymer.

In a preferred embodiment the second n-type OSC compound is a non-fullerene acceptor (NFA) small molecule having an A-D-A structure as described above with an electron donating polycyclic core and two terminal electron withdrawing groups attached thereto.

Suitable and preferred NFA small molecules for use as second n-type OSC in this preferred embodiment are for example those disclosed in Y. Lin et al., *Adv. Mater.,* 2015, 27, 1170; H. Lin et al., *Adv. Mater.,* 2015, 27, 7299; N. Qiu et al., *Adv. Mater.,* 2017, 29, 1604964; CN104557968 A and CN105315298 A, furthermore those disclosed in WO 2018/007479 A1.

In another preferred embodiment the second n-type OSC compound is a fullerene or substituted fullerene.

The fullerene is for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. *Chem. Mater.* 2004, 16, 4533).

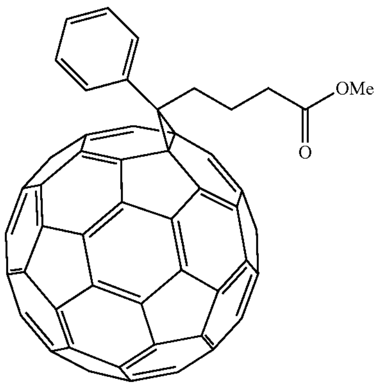

PCBM-$C_{60}$

-continued

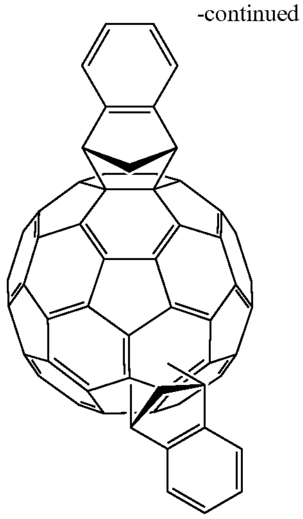

ICBA-$C_{60}$

Preferably the compound according to the present invention is blended with an n-type semiconductor such as a fullerene or substituted fullerene of formula Full-I to form the active layer in an OPV or OPD device,

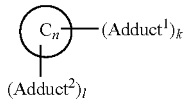

Full-I wherein $C_n$ denotes a fullerene composed of n carbon atoms, optionally with one or more atoms trapped inside, Adduct$^1$ is a primary adduct appended to the fullerene $C_n$ with any connectivity, Adduct$^2$ is a secondary adduct, or a combination of secondary adducts, appended to the fullerene $C_n$ with any connectivity, k is an integer ≥1, and l is 0, an integer ≥1, or a non-integer >0.

In the formula Full-I and its subformulae, k preferably denotes 1, 2, 3 or, 4, very preferably 1 or 2.

The fullerene $C_n$ in formula Full-I and its subformulae may be composed of any number n of carbon atoms Preferably, in the compounds of formula XII and its subformulae the number of carbon atoms n of which the fullerene $C_n$ is composed is 60, 70, 76, 78, 82, 84, 90, 94 or 96, very preferably 60 or 70.

The fullerene $C_n$ in formula Full-I and its subformulae is preferably selected from carbon based fullerenes, endohedral fullerenes, or mixtures thereof, very preferably from carbon based fullerenes.

Suitable and preferred carbon based fullerenes include, without limitation, $(C_{60\text{-}Ih})$[5,6]fullerene, $(C_{70\text{-}D5h})$[5,6] fullerene, $(C_{76\text{-}D2*})$[5,6]fullerene, $(C_{84\text{-}D2*})$[5,6]fullerene, $(C_{84\text{-}D2d})$[5,6]fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, $Sc_3N$@$C_{80}$, $Y_3N@C_{80}$, $Sc_3C_2@C_{80}$ or a mixture of two or more of the aforementioned metallofullerenes.

Preferably the fullerene $C_n$ is substituted at a [6,6] and/or [5,6] bond, preferably substituted on at least one [6,6] bond.

Primary and secondary adducts, named "Adduct1" and "Adduct 2" in formula Full-I and its subformulae, are each preferably selected from the following formulae

S-1

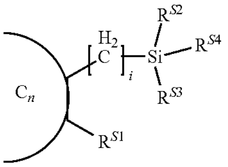

S-2

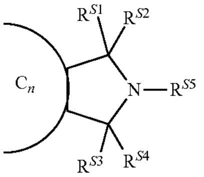

S-3

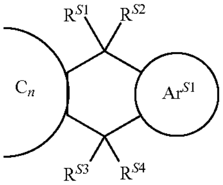

S-4

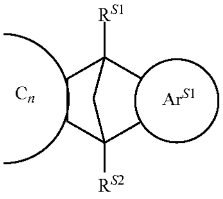

S-4

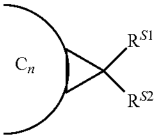

S-5

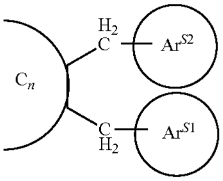

S-6

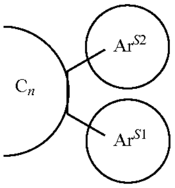

-continued

S-7

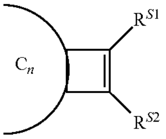

S-8

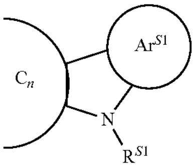

S-9

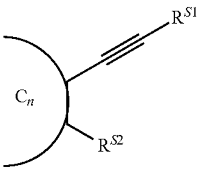

S-10

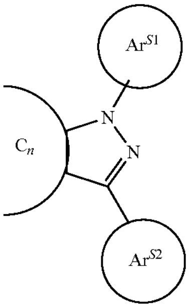

S-11

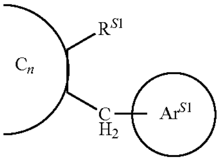

S-12

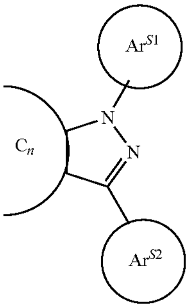

-continued

S-13

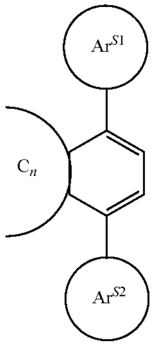

S-14

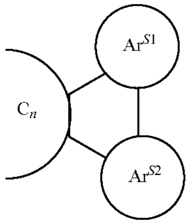

wherein $Ar^{S1}$, $Ar^{S2}$ denote, independently of each other, an aryl or heteroaryl group with 5 to 20, preferably 5 to 15, ring atoms, which is mono- or polycyclic, and which is optionally substituted by one or more identical or different substituents having one of the meanings of $L^S$ as defined above and below, $R^{S1}$, $R^{S2}$, $R^{S3}$, $R^{S4}$ and $R^{S5}$ independently of each other denote H, CN or have one of the meanings of $L^S$ as defined above and below, and i is an integer from 1 to 20, preferably from 1 to 12.

Preferred compounds of formula Full-I are selected from the following subformulae:

Full-Ia

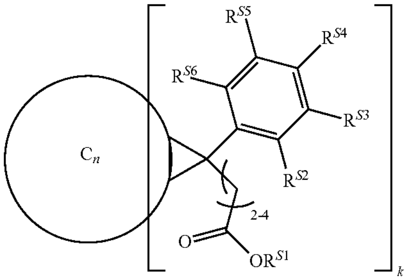

Full-Ib

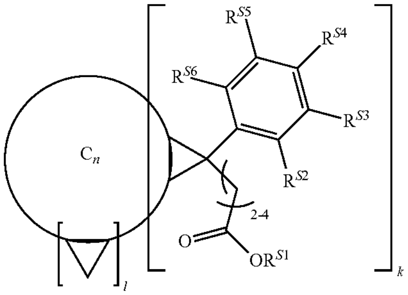

-continued

Full-Ic

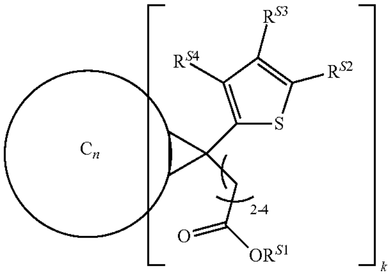

Full-Id

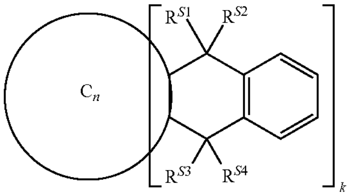

Full-Ie

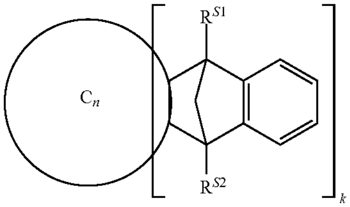

Full-If

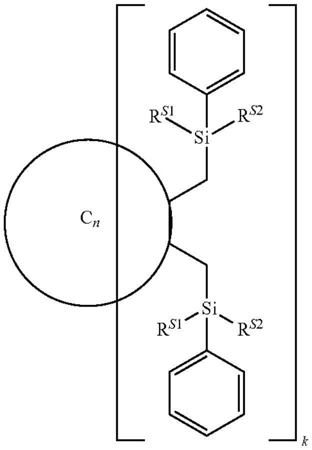

Full-Ig

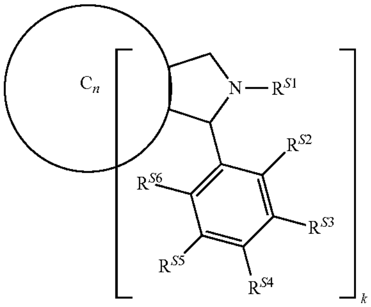

-continued

Full-Ih

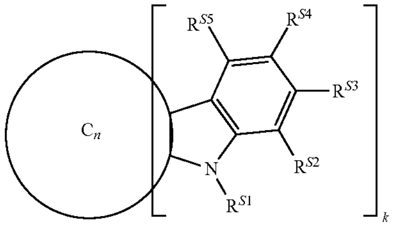

wherein $R^{S1}$, $R^{S2}$, $R^{S3}$, $R^{S4}$ $R^{S5}$ and $R^{S6}$ independently of each other denote H or have one of the meanings of $R^S$ as defined above and below.

Most preferably the fullerene is PCBM-C60, PCBM-C70, bis-PCBM-C60, bis-PCBM-C70, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-Ih), or bis-oQDM-C60.

In another preferred embodiment the second n-type OSC compound is a small molecule which does not contain a fullerene moiety, and which is selected from naphthalene or perylene carboximide derivatives.

Preferred naphthalene or perylene carboximide derivatives for use as n-type OSC compounds are described for example in Adv. Sci. 2016, 3, 1600117, *Adv. Mater.* 2016, 28, 8546-8551, *J. Am. Chem. Soc.*, 2016, 138, 7248-7251 and *J. Mater. Chem.* A, 2016, 4, 17604.

Preferred n-type OSC compounds of this preferred embodiment are selected from the following formulae

NDI1

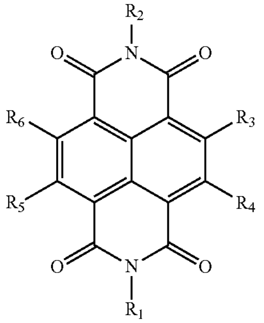

NDI2

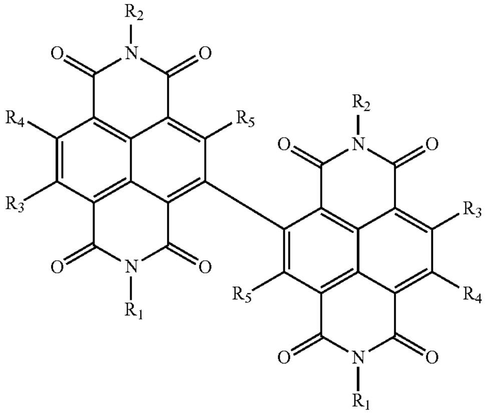

NDI3

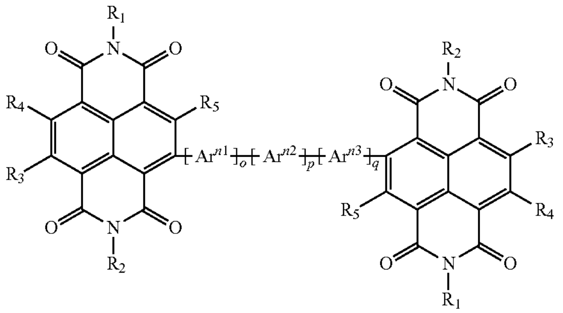

NDI4

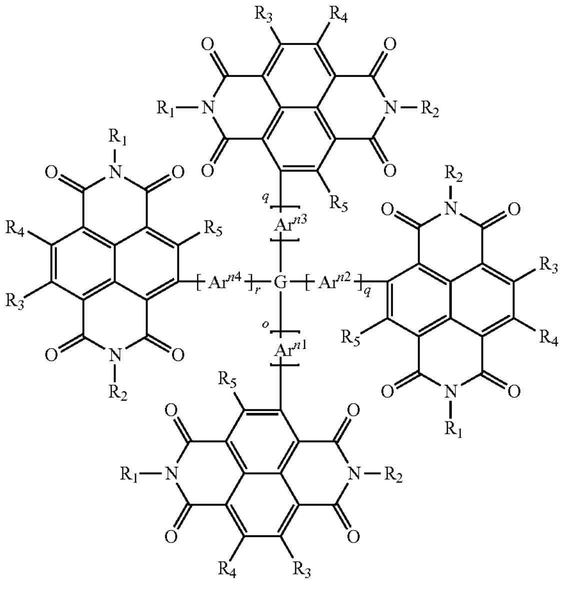

-continued
PDI1
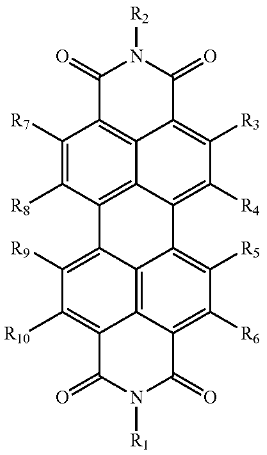
PDI2
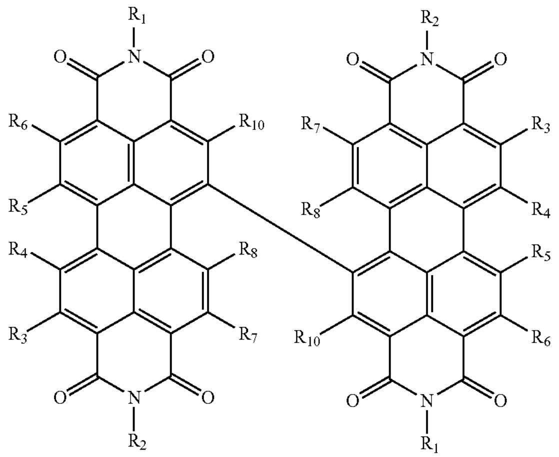
PDI3
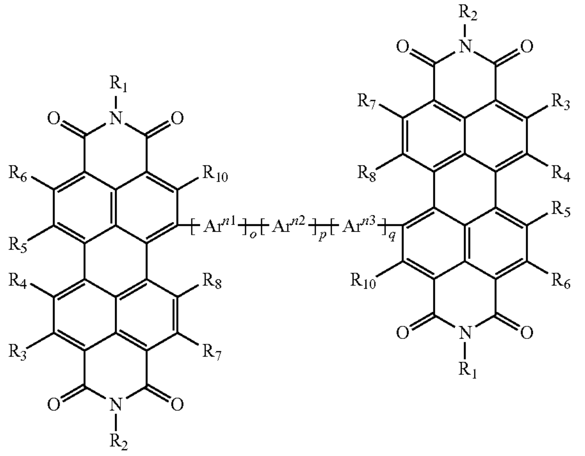
PDI4
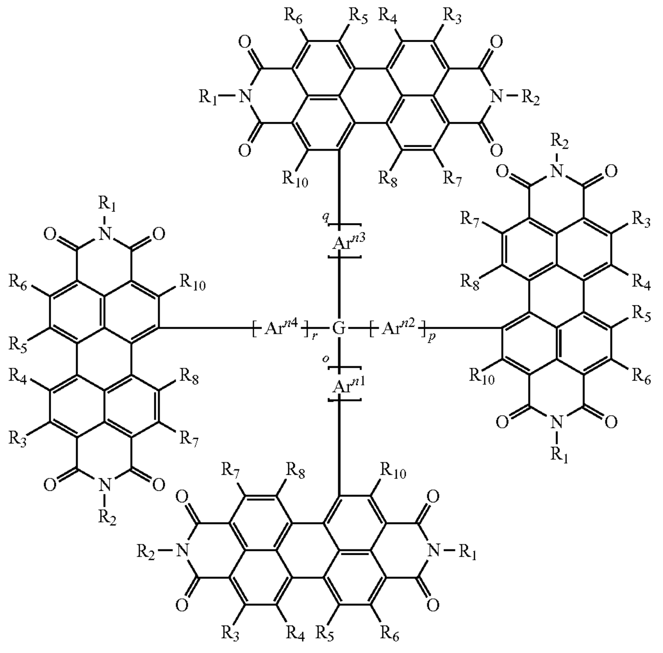

-continued
PDI5
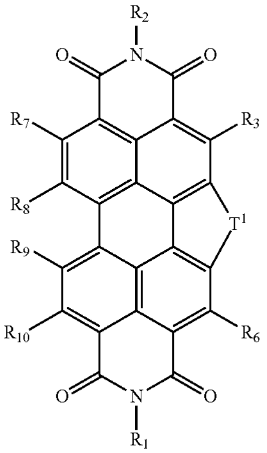
PDI6
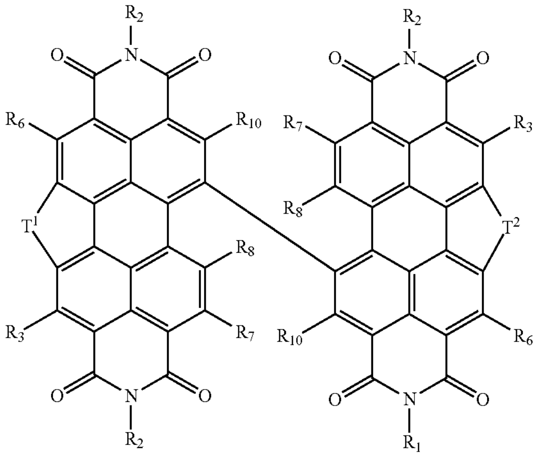
PDI7
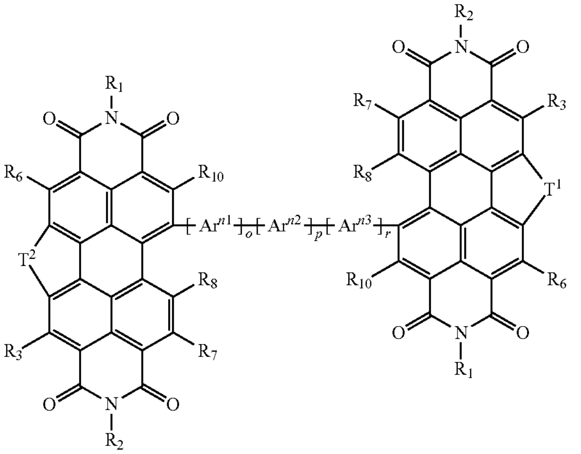
PDI8
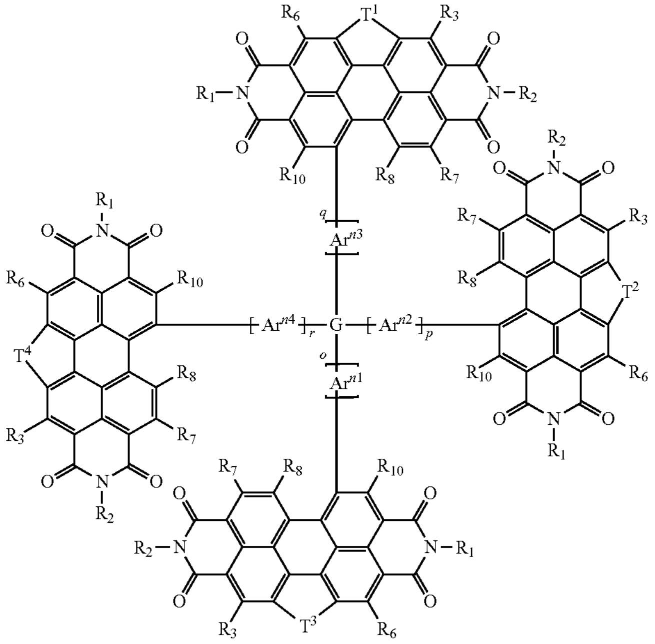

-continued

PDI9

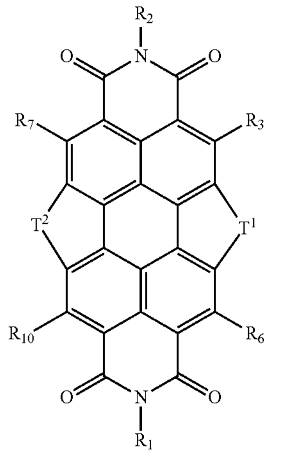

wherein the individual radicals, independently of each other and on each occurrence identically or differently, have the following meanings $R^{1-10}$ $R^W$, H, F, Cl, or straight-chain, branched or cyclic alkyl with 1 to 30, preferably 1 to 20, C atoms, in which one or more $CH_2$ groups are optionally replaced by —O—, —S—, —C(═O)—, —C(═S)—, —C(═O)—O—, —O—C(═O)—, —$NR^0$—, —$SiR^0R^{00}$—, —$CF_2$—, —$CR^0$═$CR^{00}$—, —$CY^1$═$CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono- or polycyclic, does optionally contain fused rings, and is unsubstituted or substituted by one or more identical or different groups $L^S$, $R^W$ an electron withdrawing group, preferably having one of the preferred meanings as given above for $R^{T1}$, very preferably CN, $Y^1$, $Y^2$H, F, C or CN, $L^S$ F, Cl, —$NO_2$, —CN, —NC, —NCO, —NCS, —OCN, —SCN, $R^0$, $OR^0$, $SR^0$, —C(═O)$X^0$, —C(═O)$R^0$, —C(═O)—$OR^0$, —O—C(═O)—$R^0$, —$NH_2$, —$NHR^0$, —$NR^0R^{00}$, —C(═O)$NHR^0$, —C(═O)$NR^0R^{00}$, —$SO_3R^0$, —$SO_2R^0$, —OH, —$NO_2$, —$CF_3$, —$SF_5$, or optionally substituted silyl, or carbyl or hydrocarbyl with 1 to 30, preferably 1 to 20 C atoms that is optionally substituted and optionally comprises one or more hetero atoms, preferably F, —CN, $R^0$, —$OR^0$, —$SR^0$, —C(═O)—$R^0$, —C(═O)—$OR^0$, —O—C(═O)—$R^0$, —O—C(═O)—$OR^0$, —C(═O)—$NHR^0$, or —C(═O)—$NR^0R^{00}$, $T^{1-4}$ —O—, —S—, —C(═O)—, —C(═S)—, —$CR^0R^{00}$—, —$SiR^0R^{00}$—, —$NR^0$—, —$CR^0$═$CR^{00}$— or —C≡C—, G C, Si, Ge, C═C or a four-valent aryl or heteroaryl group that has from 5 to 20 ring atoms, is mono- or polycyclic, optionally contains fused rings, and is unsubstituted or substituted by one or more identical or different groups $R^1$ or $L^S$, $Ar^{n1-n4}$ independently of each other, and on each occurrence identically or differently arylene or heteroarylene that has from 5 to 20 ring atoms, is mono- or polycyclic, optionally contains fused rings, and is unsubstituted or substituted by one or more identical or different groups $R^1$ or $L^S$, or $CY^1$═$CY^2$ or —C≡C—, o, p, q, r 0 or an integer from 1 to 10.

In another preferred embodiment the second n-type OSC compound is a conjugated OSC polymer. Preferred n-type OSC polymers are described, for example, in *Acc. Chem. Res.,* 2016, 49 (11), pp 2424-2434 and WO 2013/142841 A1.

Preferred n-type conjugated OSC polymers for use as second n-type OSC compound in this preferred embodiment comprise one or more units derived from perylene or naphthalene are poly[[N,N'-bis(2-octyldodecyl)naphthalene-1,4,5,8-bis(dicarboximide)-2,6-diyl]-alt-5,5'-(2,2'-bithiophene)], poly[[N,N'-bis(2-hexyldecyl)naphthalene-1,4,5,8-bis(dicarboximide)-2,6-diyl]-alt-5,5'-thiophene].

The composition according to the present invention can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more compounds according to the present invention or compositions as described above and below and one or more organic solvents.

Preferred solvents are aliphatic hydrocarbons, chlorinated hydrocarbons, aromatic hydrocarbons, ketones, ethers and mixtures thereof. Further suitable and preferred solvents used include 1,2,4-trimethylbenzene, 1,2,3,4-tetra-methyl benzene, pentylbenzene, mesitylene, cumene, cymene, cyclohexylbenzene, diethylbenzene, tetralin, indane, 1,5-dimethyltetraline, decalin, 1-methylnaphthalene, 2,6-lutidine, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoromethylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene, a mixture of o-, m-, and p-xylene, 2-fluoro-m-xylene, 3-fluoro-o-xylene, tetrahydrofuran, morpholine, 1,4-dioxane, 2-methylthiophene, 3-methylthiophene, chloroform, 1,2-dichloroethane, dichloromethane, carbon tetrachloride, 1,2-dichloroethane, 1,1,1-trichloroethane, 1,1,2,2-tetrachloroethane, acetone, methylethylketone, propiophenone, acetophenone, cyclohexanone, ethyl acetate, n-butyl acetate, ethyl benzoate, ethyl benzoate, dimethylacetamide, dimethylsulfoxide, or mixtures of the aforementioned. Solvents with relatively low polarity are generally preferred.

Examples of especially preferred solvents include, without limitation, dichloromethane, trichloromethane, chlorobenzene, o-dichlorobenzene, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetralin, 2-methylthiophene, 3-methylthiophene, decaline, indane, methyl benzoate, ethyl benzoate, mesitylene, or mixtures thereof.

The concentration of the compounds or polymers in the solution is preferably 0.1 to 10% by weight, more preferably 0.5 to 5% by weight.

Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p 9-10, 1986". Such a procedure may lead to a blend of 'non' solvents that will dissolve both the polymers and compounds of the present invention, although it is desirable to have at least one true solvent in a blend.

The compositions and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

In a composition according to the present invention comprising a compound according to the present invention, and a polymer, the ratio compound:polymer is preferably from 5:1 to 1:5 by weight, more preferably from 3:1 to 1:3 by weight, most preferably 2:1 to 1:2 by weight.

The composition according to the present invention may also comprise a polymeric binder, preferably from 0.001 to 95% by weight. Examples of binder include polystyrene (PS), polydimethylsilane (PDMS), polypropylene (PP) and polymethylmethacrylate (PMMA).

A binder to be used in the formulation as described before, which is preferably a polymer, may comprise either an insulating binder or a semiconducting binder, or mixtures thereof, may be referred to herein as the organic binder, the polymeric binder or simply the binder.

Preferably, the polymeric binder comprises a weight average molecular weight in the range of 1,000 to 5,000,000 g/mol, especially 1,500 to 1,000,000 g/mol and more preferable 2,000 to 500,000 g/mol. Surprising effects can be achieved with polymers having a weight average molecular weight of at least 10,000 g/mol, more preferably at least 100,000 g/mol.

In particular, the polymer can have a polydispersity index $M_w/M_n$ in the range of 1.0 to 10.0, more preferably in the range of 1.1 to 5.0 and most preferably in the range of 1.2 to 3.

Preferably, the inert binder is a polymer having a glass transition temperature in the range of −70 to 160° C., preferably 0 to 150° C., more preferably 50 to 140° C. and most preferably 70 to 130° C. The glass transition temperature can be determined by measuring the DSC of the polymer (DIN EN ISO 11357, heating rate 10° C. per minute).

The weight ratio of the polymeric binder to the compound according to the present invention is preferably in the range of 30:1 to 1:30, particularly in the range of 5:1 to 1:20 and more preferably in the range of 1:2 to 1:10.

According to a preferred embodiment the binder preferably comprises repeating units derived from styrene monomers and/or olefin monomers. Preferred polymeric binders can comprise at least 80%, preferably 90% and more preferably 99% by weight of repeating units derived from styrene monomers and/or olefins.

Styrene monomers are well known in the art. These monomers include styrene, substituted styrenes with an alkyl substituent in the side chain, such as α-methylstyrene and α-ethylstyrene, substituted styrenes with an alkyl substituent on the ring such as vinyltoluene and p-methylstyrene, halogenated styrenes such as monochlorostyrenes, dichlorostyrenes, tribromostyrenes and tetrabromostyrenes.

Olefin monomers consist of hydrogen and carbon atoms. These monomers include ethylene, propylene, butylenes, isoprene and 1,3-butadiene.

According to a preferred embodiment of the present invention, the polymeric binder is polystyrene having a weight average molecular weight in the range of 50,000 to 2,000,000 g/mol, preferably 100,000 to 750,000 g/mol, more preferably in the range of 150,000 to 600,000 g/mol and most preferably in the range of 200,000 to 500,000 g/mol.

Further examples of suitable binders are disclosed for example in US 2007/0102696 A1. Especially suitable and preferred binders are described in the following.

The binder should preferably be capable of forming a film, more preferably a flexible film.

Suitable polymers as binders include poly(1,3-butadiene), polyphenylene, polystyrene, poly(α-methylstyrene), poly(α-vinylnaphtalene), poly(vinyltoluene), polyethylene, cis-polybutadiene, polypropylene, polyisoprene, poly(4-methyl-1-pentene), poly (4-methylstyrene), poly (chorotrifluoroethylene), poly(2-methyl-1,3-butadiene), poly(p-xylylene), poly(α-α-α'-α' tetrafluoro-p-xylylene), poly[1,1-(2-methyl propane)bis(4-phenyl)carbonate], poly (cyclohexyl methacrylate), poly(chlorostyrene), poly(2,6-dimethyl-1,4-phenylene ether), polyisobutylene, poly(vinyl cyclohexane), poly(vinylcinnamate), poly(4-vinylbiphenyl), 1,4-polyisoprene, polynorbornene, poly(styrene-block-butadiene); 31% wt styrene, poly(styrene-block-butadiene-block-styrene) 30% wt styrene, poly(styrene-co-maleic anhydride) (and ethylene/butylene) 1-1.7% maleic anhydride, poly(styrene-block-ethylene/butylene-block-styrene) triblock polymer 13% styrene, poly(styrene-block-ethylene-propylene-block-styrene) triblock polymer 37% wt styrene, poly(styrene-block-ethylene/butylene-block-styrene) triblock polymer 29% wt styrene, poly(1-vinylnaphthalene), poly(1-vinylpyrrolidone-co-styrene) 64% styrene, poly(1-vinylpyrrolidone-co-vinyl acetate) 1.3:1, poly(2-chlorostyrene), poly(2-vinylnaphthalene), poly(2-vinylpyridine-co-styrene) 1:1, poly(4,5-Difluoro-2,2-bis(CF3)-1,3-dioxole-co-tetrafluoroethylene) Teflon, poly(4-chlorostyrene), poly (4-methyl-1-pentene), poly(4-methylstyrene), poly(4-vinylpyridine-co-styrene) 1:1, poly(alpha-methylstyrene), poly(butadiene-graft-poly(methyl acrylate-co-acrylonitrile)) 1:1:1, poly(butyl methacrylate-co-isobutyl methacrylate) 1:1, poly(butyl methacrylate-co-methyl methacrylate) 1:1, poly(cyclohexylmethacrylate), poly(ethylene-co-1-butene-co-1-hexene) 1:1:1, poly(ethylene-co-ethylacrylate-co-maleic anhydride); 2% anhydride, 32% ethyl acrylate, poly (ethylene-co-glycidyl methacrylate) 8% glycidyl methacrylate, poly(ethylene-co-methyl acrylate-co-glycidyl meth-acrylate) 8% glycidyl metha-crylate 25% methyl acrylate, poly(ethylene-co-octene) 1:1, poly(ethylene-co-propylene-co-5-methylene-2-norbornene) 50% ethylene, poly(ethylene-co-tetrafluoroethylene) 1:1, poly(isobutyl methacrylate), poly(isobutylene), poly(methyl methacrylate)-co-(fluorescein O-methacrylate) 80% methyl methacrylate, poly(methyl methacrylate-co-butyl methacrylate) 85% methyl methacrylate, poly(methyl methacrylate-co-ethyl acrylate) 5% ethyl acrylate, poly(propylene-co-butene) 12% 1-butene, poly(styrene-co-allyl alcohol) 40% allyl alcohol, poly(styrene-co-maleic anhydride) 7% maleic anhydride, poly(styrene-co-maleic anhydride) cumene terminated (1.3:1), poly(styrene-co-methyl methacrylate) 40% styrene, poly(vinyltoluene-co-alpha-methylstyrene) 1:1, poly-2-vinylpyridine, poly-4-vinylpyridine, poly-alpha-pinene, polymethylmethacrylate, polybenzylmethacrylate, polyethylmethacrylate, polyethylene, polyethylene terephthalate, polyethylene-co-ethylacrylate 18% ethyl acrylate, polyethylene-co-vinylacetate 12% vinyl acetate, polyethylene-graft-maleic anhydride 0.5% maleic anhydride, polypropylene, polypropylene-graft-maleic anhydride 8-10% maleic anhydride, polystyrene poly(styrene-block-ethylene/butylene-block-styrene) graft maleic anhydride 2% maleic anhydride 1:1:1 others, poly(styrene-block-butadiene) branched 1:1, poly(styrene-block-butadiene-block-styrene), 30% styrene, poly(styrene-block-isoprene) 10% wt styrene, poly(styrene-block-isoprene-block-styrene) 17% wt styrene, poly(styrene-co-4-chloromethylstyrene-co-4-methoxymethylstyrene 2:1:1, polystyrene-co-acrylonitrile 25% acrylonitrile, polystyrene-co-alpha-methylstyrene 1:1, polystyrene-co-butadiene 4% butadiene, polystyrene-co-butadiene 45% styrene, polystyrene-co-chloromethylstyrene 1:1, polyvinylchloride, polyvinylcinnamate, polyvinylcyclohexane, polyvinylidenefluoride, polyvinylidenefluoride-co-hexafluoropropylene assume 1:1, poly(styrene-block-ethylene/propylene-block-styrene) 30% styrene, poly(styrene-block-ethylene/propylene-block-styrene) 18% styrene, poly (styrene-block-ethylene/propylene-block-styrene) 13% styrene, poly(styrene-block ethylene block-ethylene/propylene-block styrene) 32% styrene, poly(styrene-block ethylene block-ethylene/propylene-block styrene) 30% styrene, poly(styrene-block-ethylene/butylene-block-styrene) 31% styrene, poly(styrene-block-ethylene/butylene-block-styrene) 34% styrene, poly(styrene-block-ethylene/butylene-block-styrene) 30% styrene, poly(styrene-block-ethylene/butylene-block-styrene) 60%, styrene, branched or non-branched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders to be used in the formulations as described before are polystryrene, poly(α-methylstyrene), polyvinylcinnamate, poly(4-vinylbiphenyl), poly(4-methylstyrene), and polymethyl methacrylate.

Most preferred insulating binders are polystyrene and polymethyl methacrylate.

The binder can also be selected from crosslinkable binders, like e.g. acrylates, epoxies, vinylethers, thiolenes etc. The binder can also be mesogenic or liquid crstalline.

The organic binder may itself be a semiconductor, in which case it will be referred to herein as a semiconducting binder. The semiconducting binder is still preferably a binder of low permittivity as herein defined.

Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility of at least $10^{-5}$ $cm^2V^{-1}s^{-1}$, more preferably at least $10^{-4}$ $cm^2V^{-1}s^{-1}$.

A preferred semiconducting binder comprises a homopolymer or copolymer (including block-copolymer) containing arylamine (preferably triarylamine).

The compounds and compositions according to the present invention are useful as charge transport, semiconducting, electrically conducting, photoconducting or light emitting materials in optical, electronic, optoelectronic, electroluminescent or photoluminescent components or devices. In these devices, the compounds and compositions of the present invention are typically applied as thin layers or films.

Thus, the present invention also provides the use of the compound or composition or layer in an electronic device. The compound or composition may be used as a high mobility semiconducting material in various devices and apparatus. The compound or composition may be used, for example, in the form of a semiconducting layer or film. Accordingly, in another aspect, the present invention provides a semiconducting layer for use in an electronic device, the layer comprising a compound or composition according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The compounds according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a compound according to the present invention can be carried out for example by photolithography, electron beam lithography or laser patterning.

For use as thin layers in electronic or optoelectronic devices the compounds, compositions or formulations of the present invention may be deposited by any suitable method.

Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, inkjet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

For the fabrication of OPV devices and modules area printing method compatible with flexible substrates are preferred, for example slot dye coating, spray coating and the like.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent.

Suitable solvents should be selected to ensure full dissolution of all components, like p-type and n-type OSCs, and take into account the boundary conditions (for example rheological properties) introduced by the chosen printing method. For inkjet printing solvents and solvent mixtures with high boiling temperatures are preferred. For spin coating alkylated benzenes like xylene and toluene are preferred.

Apart from the requirements stated above the solvents should not have any detrimental effect on the chosen print head. Additionally, the solvents should preferably have boiling points >100° C., preferably >140° C. and more preferably >150° C. in order to prevent operability problems caused by the solution drying out inside the print head.

Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{12}$-alkylanilines and other fluorinated or chlorinated aromatics.

A preferred solvent for depositing a compound by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total.

Such a solvent enables an inkjet fluid to be formed comprising the solvent with the compound, which reduces or prevents clogging of the jets and separation of the components during spraying. The solvent(s) may include those selected from the following list of examples: dodecylbenzene, 1-methyl-4-tert-butylbenzene, terpineol, limonene, isodurene, terpinolene, cymene, and diethylbenzene. The solvent may be a solvent mixture, that is a combination of two or more solvents, each solvent preferably having a boiling point >100° C. more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa-s, more preferably 1-50 mPa-s and most preferably 1-30 mPa-s.

The invention additionally provides an OE device comprising a compound or composition or organic semiconducting layer according to the present invention.

Preferred OE devices are OFETs, TFTs, ICs, logic circuits, capacitors, RFID tags, OLEDs, OLETs, OPEDs, OPVs, PSCs, OPDs, solar cells, laser diodes, photoconductors, photodetectors, electrophotographic devices, electrophotographic recording devices, organic memory devices, sensor devices, charge injection layers, Schottky diodes, planarizing layers, antistatic films, conducting substrates and conducting patterns.

Very preferred OE devices are OPV, PSC and OPD devices, OFETs, and OLEDs, in particular OPD, PSC and bulk heterojunction (BHJ) OPV devices. In an OFET, for example, the active semiconductor channel between the drain and source may comprise the compound or composition of the invention. As another example, in an OLED device, the charge (hole or electron) injection or transport layer may comprise the compound or composition of the invention.

An OPV or OPD device according to the present invention preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, $MoO_x$, $NiO_x$, a conjugated polymer electrolyte, like for example PEDOT:PSS, a conjugated polymer, like for example polytriarylamine (PTAA), an insulating polymer, like for example nafion, polyethyleneimine or polystyrenesulphonate, an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammoniumhexyl)thiophene], or poly [(9,9-bis(3'-(N,N-dimethylamino)propyl)-2,7-fluorene)-alt-2,7-(9,9-dioctylfluorene)] or an organic compound, like for example tris(8-quinolinolato)-aluminum(III) ($Alq_3$), 4,7-diphenyl-1,10-phenanthroline.

The OPV device can for example be of any type known from the literature (see e.g. Waldauf et al., *Appl. Phys. Lett.*, 2006, 89, 233517).

A first preferred OPV device according to the invention comprises the following layers (in the sequence from bottom to top):

- optionally a substrate,
- a high work function electrode, preferably comprising a metal oxide, like for example ITO, serving as anode, an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1, 1'biphenyl-4,4'-diamine) or NBD (N,N'-dyphenyl-N—N'-bis(1-napthylphenyl)-1,1'biphenyl-4,4'-diamine), a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ, optionally a layer having electron transport properties, for example comprising LiF or PFN, a low work function electrode, preferably comprising a metal like for example aluminum, serving as cathode, wherein at least one of the electrodes, preferably the anode, is transparent to visible light, and wherein the n-type semiconductor is a compound according to the present invention.

A second preferred OPV device according to the invention is an inverted OPV device and comprises the following layers (in the sequence from bottom to top):

optionally a substrate, a high work function metal or metal oxide electrode, comprising for example ITO, serving as cathode, a layer having hole blocking properties, preferably comprising an organic polymer, polymer blend, metal or metal oxide like $TiO_x$, $ZnO_x$, Ca, Mg, poly(ethyleneimine), poly(ethyleneimine) ethoxylated or poly [(9,9-bis(3'-(N,N-dimethylamino)propyl)-2,7-fluorene)-alt-2,7-(9,9-dioctylfluorene)], a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ, an optional conducting polymer layer or hole transport layer, preferably comprising an organic polymer or polymer blend, metal or metal oxide, for example PEDOT:PSS, nafion, a substituted triaryl amine derivative like for example TBD or NBD, or $WO_x$, $MoO_x$, $NiO_x$, Pd or Au, an electrode comprising a high work function metal like for example silver, serving as anode, wherein at least one of the electrodes, preferably the cathode, is transparent to visible light, and wherein the n-type semiconductor is a compound according to the present invention.

In the OPV devices of the present invention the p-type and n-type semiconductor materials are preferably selected from the materials, like the compound/polymer/fullerene systems, as described above.

When the photoactive layer is deposited on the substrate, it forms a BHJ that phase separates at nanoscale level. For discussion on nanoscale phase separation see Dennler et al, *Proceedings of the IEEE,* 2005, 93 (8), 1429 or Hoppe et al, *Adv. Func. Mater,* 2004, 14(10), 1005. An optional annealing step may be then necessary to optimize blend morpohology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.,* 2007, 6, 497 or Fréchet et al. J. *Am. Chem. Soc.,* 2010, 132, 7595-7597.

Another preferred embodiment of the present invention relates to the use of a compound or composition according to the present invention as dye, hole transport layer, hole blocking layer, electron transport layer and/or electron blocking layer in a DSSC or a perovskite-based solar cell (PSC), and to a DSSC or PSC comprising a compound or composition according to the present invention.

DSSCs and PSCs can be manufactured as described in the literature, for example in Chem. Rev. 2010, 110, 6595-6663, Angew. Chem. Int. Ed. 2014, 53, 2-15 or in WO2013171520A1 A preferred OE device according to the invention is a solar cell, preferably a PSC, comprising a light absorber which is at least in part inorganic as described below.

In a solar cell comprising the light absorber according to the invention there are no restrictions per se with respect to the choice of the light absorber material which is at least in part inorganic.

The term "at least in part inorganic" means that the light absorber material may be selected from metalorganic complexes or materials which are substantially inorganic and possess preferably a crystalline structure where single positions in the crystalline structure may be allocated by organic ions.

Preferably, the light absorber comprised in the solar cell according to the invention has an optical band-gap ≤2.8 eV and ≥0.8 eV.

Very preferably, the light absorber in the solar cell according to the invention has an optical band-gap ≤2.2 eV and ≥1.0 eV.

The light absorber used in the solar cell according to the invention does preferably not contain a fullerene. The chemistry of fullerenes belongs to the field of organic chemistry. Therefore fullerenes do not fulfil the definition of being "at least in part inorganic" according to the invention.

Preferably, the light absorber which is at least in part inorganic is a material having perovskite structure or a material having 2D crystalline perovskite structure.

The term "perovskite" as used above and below denotes generally a material having a perovskite crystalline structure or a 2D crystalline perovskite structure.

The term perovskite solar cell (PSC) means a solar cell comprising a light absorber which is a material having perovskite structure or a material having 2D crystalline perovskite structure.

The light absorber which is at least in part inorganic is without limitation composed of a material having perovskite crystalline structure, a material having 2D crystalline perovskite structure (e.g. CrystEngComm, 2010, 12, 2646-2662), $Sb_2S_3$ (stibnite), $Sb_2(S_xSe_{(x-1)})_3$, $PbS_xSe_{(x-1)}$, $CdS_xSe_{(x-1)}$, ZnTe, CdTe, $ZnS_xSe_{(x-1)}$, InP, FeS, $FeS_2$, $Fe_2S_3$, $Fe_2SiS_4$, $Fe_2GeS_4$, $Cu_2S$, CuInGa, $CuIn(Se_xS_{(1-x)})_2$, $Cu_3Sb_xBi_{(x-1)}$, $(S_ySe_{(y-1)})_3$, $Cu_2SnS_3$, $SnS_xSe_{(x-1)}$, $Ag_2S$, $AgBiS_2$, BiSI, BiSeI, $Bi_2(S_xSe_{(x-1)})_3$, $BiS_{(1-x)}Se_xI$, $WSe_2$, AlSb, metal halides (e.g. $BiI_3$, $Cs_2SnI_6$), chalcopyrite (e.g. $CuIn_xGa_{(1-x)}(S_ySe_{(1-y)})_2$), kesterite (e.g. $Cu_2ZnSnS_4$, $Cu_2ZnSn(Se_xS_{(1-x)})_4$, $Cu_2Zn(Sn_{1-x}Ge_x)S_4$) and metal oxide (e.g. CuO, $Cu_2O$) or a mixture thereof.

Preferably, the light absorber which is at least in part inorganic is a perovskite.

In the above definition for light absorber, x and y are each independently defined as follows: (0≤x≤1) and (0≤y≤1).

Very preferably, the light absorber is a special perovskite namely a metal halide perovskite as described in detail above and below. Most preferably, the light absorber is an organic-inorganic hybrid metal halide perovskite contained in the perovskite solar cell (PSC).

In one particularly preferred embodiment of the invention, the perovskite denotes a metal halide perovskite with the formula $ABX_3$, where A is a monovalent organic cation, a metal cation or a mixture of two or more of these cations B is a divalent cation and X is F, Cl, Br, I, $BF_4$ or a combination thereof.

Preferably, the monovalent organic cation of the perovskite is selected from alkylammonium, wherein the alkyl group is straight chain or branched having 1 to 6 C atoms, formamidinium or guanidinium or wherein the metal cation is selected from $K^+$, $Cs^+$ or $Rb^+$.

Suitable and preferred divalent cations B are $Ge^{2+}$, $Sn^{2+}$ or $Pb^{2+}$.

Suitable and preferred perovskite materials are $CsSnI_3$, $CH_3NH_3Pb(I_{1-x}Cl_x)_3$, $CH_3NH_3PbI_3$, $CH_3NH_3Pb(I_{1-x}Br_x)_3$, $CH_3NH_3Pb(I_{1-x}(BF_4)_x)_3$, $CH_3NH_3Sn(I_{1-x}Cl_x)_3$, $CH_3NH_3SnI_3$ or $CH_3NH_3Sn(I_{1-x}Br_x)_3$ wherein x is each independently defined as follows: ($0 \leq x \leq 1$).

Further suitable and preferred perovskites may comprise two halides corresponding to formula $Xa_{(3-x)}Xb_{(x)}$, wherein Xa and Xb are each independently selected from C, Br, or I, and x is greater than 0 and less than 3.

Suitable and preferred perovskites are also disclosed in WO 2013/171517, claims 52 to 71 and claims 72 to 79, which is entirely incorporated herein by reference. The materials are defined as mixed-anion perovskites comprising two or more different anions selected from halide anions and chalcogenide anions. Preferred perovskites are disclosed on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N{=}CH{-}NH_2)PbI_{3z}Br_{3(1-z)}$, wherein z is greater than 0 and less than 1.

The invention further relates to a solar cell comprising the light absorber, preferably a PSC, as described above and below, wherein the compound according to the present invention is employed as a layer between one electrode and the light absorber layer.

The invention further relates to a solar cell comprising the light absorber, preferably a PSC, as described above and below, wherein the compound according to the present invention is comprised in an electron-selective layer.

The electron selective layer is defined as a layer providing a high electron conductivity and a low hole conductivity favoring electron-charge transport.

The invention further relates to a solar cell comprising the light absorber, preferably a PSC, as described above and below, wherein the compound according to the present invention is employed as electron transport material (ETM) or as hole blocking material as part of the electron selective layer.

Preferably, the compound according to the present invention is employed as electron transport material (ETM).

In an alternative preferred embodiment, the compound according to the present invention is employed as hole blocking material.

The device architecture of a PSC device according to the invention can be of any type known from the literature.

A first preferred device architecture of a PSC device according to the invention comprises the following layers (in the sequence from bottom to top):

- optionally a substrate which, in any combination, can be flexible or rigid and transparent, semi-transparent or non-transparent and electrically conductive or non-conductive;
- a high work function electrode, preferably comprising a doped metal oxide, for example fluorine-doped tin oxide (FTO), tin-doped indium oxide (ITO), or aluminum-doped zinc oxide;
- an electron-selective layer which comprises one or more electron-transporting materials, at least one of which is a compound according to the present invention, and which, in some cases, can also be a dense layer and/or be composed of nanoparticles, and which preferably comprises a metal oxide such as $TiO_2$, $ZnO_2$, $SnO_2$, $Y_2O_5$, $Ga_2O_3$, $SrTiO_3$, $BaTiO_3$ or combinations thereof;
- optionally a porous scaffold which can be conducting, semi-conducting or insulating, and which preferably comprises a metal oxide such as $TiO_2$, $ZnO_2$, $SnO_2$, $Y_2O_5$, $Ga_2O_3$, $SrTiO_3$, $BaTiO_3$, $Al_2O_3$, $ZrO_2$, $SiO_2$ or combinations thereof, and which is preferably composed of nanoparticles, nanorods, nanoflakes, nanotubes or nanocolumns;
- a layer comprising a light absorber which is at least in part inorganic, particularly preferably a metal halide perovskite as described above which, in some cases, can also be a dense or porous layer and which optionally partly or fully infiltrates into the underlying layer;
- optionally a hole selective layer, which comprises one or more hole-transporting materials, and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;

and a back electrode which can be metallic, for example made of Au, Ag, Al, Cu, Ca, Ni or combinations thereof, or non-metallic and transparent, semi-transparent or non-transparent.

A second preferred device architecture of a PSC device according to the invention comprises the following layers (in the sequence from bottom to top):

- optionally a substrate which, in any combination, can be flexible or rigid and transparent, semi-transparent or non-transparent and electrically conductive or non-conductive;
- a high work function electrode, preferably comprising a doped metal oxide, for example fluorine-doped tin oxide (FTO), tin-doped indium oxide (ITO), or aluminum-doped zinc oxide;
- optionally a hole injection layer which, for example, changes the work function of the underlying electrode, and/or modifies the surface of the underlying layer and/or helps to planarize the rough surface of the underlying layer and which, in some cases, can also be a monolayer;
- optionally a hole selective layer, which comprises one or more hole-transporting materials and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris (bis(trifluoromethylsulfonyl)imide)), which can enhance the properties of the hole selective layer, for example the electrical conductivity, and/or facilitate its processing;

a layer comprising a light absorber which is at least in part inorganic, particularly preferably a metal halide perovskite as described or preferably described above;

an electron-selective layer, which comprises one or more electron-transporting materials, at least one of which is a compound according to the present invention and which, in some cases, can also be a dense layer and/or be composed of nanoparticles, and which, for example, can comprise a metal oxide such as $TiO_2$, $ZnO_2$, $SnO_2$, $Y_2O_5$, $Ga_2O_3$, $SrTiO_3$, $BaTiO_3$ or combinations thereof, and/or which can comprise a substituted fullerene, for example [6,6]-phenyl C61-butyric acid methyl ester, and/or which can comprise a molecular, oligomeric or polymeric electron-transport material, for example 2,9-Dimethyl-4,7-diphenyl-1,10-phenanthroline, or a mixture thereof;

and a back electrode which can be metallic, for example made of Au, Ag, A1, Cu, Ca, Ni or combinations thereof, or non-metallic and transparent, semi-transparent or non-transparent.

To produce electron selective layers in PSC devices according to the invention, the compounds according to the present invention, optionally together with other compounds or additives in the form of blends or mixtures, may be deposited by any suitable method. Liquid coating of devices is more desirable than vacuum deposition techniques. Solution deposition methods are especially preferred. Formulations comprising the compounds according to the present invention enable the use of a number of liquid coating techniques. Preferred deposition techniques include, without limitation, dip coating, spin coating, inkjet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot die coating or pad printing. For the fabrication of PSC devices and modules, deposition techniques for large area coating are preferred, for example slot die coating or spray coating.

Formulations that can be used to produce electron selective layers in optoelectronic devices according to the invention, preferably in PSC devices comprise one or more compounds according to the present invention or preferred embodiments as described above in the form of blends or mixtures optionally together with one or more further electron transport materials and/or hole blocking materials and/or binders and/or other additives as described above and below, and one or more solvents.

The formulation may include or comprise, essentially consist of or consist of the said necessary or optional constituents as described above or below. All compounds or components which can be used in the formulations are either known or commercially available, or can be synthesized by known processes.

The formulation as described before may be prepared by a process which comprises:

(i) first mixing a compound according to the present invention, optionally a binder or a precursor of a binder as described before, optionally a further electron transport material, optionally one or more further additives as described above and below and a solvent or solvent mixture as described above and below and (ii) applying such mixture to a substrate; and optionally evaporating the solvent(s) to form an electron selective layer according to the present invention.

In step (i) the solvent may be a single solvent for the compound according to the present invention and the organic binder and/or further electron transport material may each be dissolved in a separate solvent followed by mixing the resultant solutions to mix the compounds.

Alternatively, the binder may be formed in situ by mixing or dissolving a compound according to the present invention in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound in a suitable solvent as described before, and the solution deposited for example by dipping, spraying, painting or printing it on a substrate to form a liquid layer and then removing the solvent to leave a solid layer. It will be appreciated that solvents are chosen which are able to dissolve all ingredients of the formulation, and which upon evaporation from the solution blend give a coherent defect free layer.

Besides the said components, the formulation as described before may comprise further additives and processing assistants. These include, inter alia, surface-active substances (surfactants), lubricants and greases, additives which modify the viscosity, additives which increase the conductivity, dispersants, hydrophobicizing agents, adhesion promoters, flow improvers, antifoams, deaerating agents, diluents, which may be reactive or unreactive, fillers, assistants, processing assistants, dyes, pigments, stabilizers, sensitizers, nanoparticles and inhibitors.

Additives can be used to enhance the properties of the electron selective layer and/or the properties of any of the neighbouring layers and/or the performance of the optoelectronic device according to the invention. Additives can also be used to facilitate the deposition, the processing or the formation of the electron selective layer and/or the deposition, the processing or the formation of any of the neighbouring layers. Preferably, one or more additives are used which enhance the electrical conductivity of the electron selective layer and/or passivate the surface of any of the neighbouring layers.

Suitable methods to incorporate one or more additives include, for example exposure to a vapor of the additive at atmospheric pressure or at reduced pressure, mixing a solution or solid containing one or more additives and a material or a formulation as described or preferably described before, bringing one or more additives into contact with a material or a formulation as described before, by thermal diffusion of one or more additives into a material or a formulation as described before, or by ion-implantation of one or more additives into a material or a formulation as described before.

Additives used for this purpose can be organic, inorganic, metallic or hybrid materials. Additives can be molecular compounds, for example organic molecules, salts, ionic liquids, coordination complexes or organometallic compounds, polymers or mixtures thereof. Additives can also be particles, for example hybrid or inorganic particles, preferably nanoparticles, or carbon based materials such as fullerenes, carbon nanotubes or graphene flakes.

Examples for additives that can enhance the electrical conductivity are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$), cations (e.g. $H^+$, $Li^+$, $Na^+$, $K^+$, $Rb^+$, $Cs^+$, $Co^{3+}$ and $Fe^{3+}$), $O_2$, redox active salts (e.g. $XeOF_4$, $(NO_2^+)$ $(SbF_6^-)$, $(NO_2^-)$ $(SbCl_6^-)$, $(NO_2^+)$ $(BF_4^-)$, $NOBF_4$, $NOPF_6$, $AgClO_4$, $H_2IrCl_6$ and $La(NO_3)_3.6H_2O$), strongly electron-accepting organic molecules (e.g. 2,3,5,6-tetrafluoro-7,7,8,8-tetracyanoquinodimethane (F4-TCNQ)), transition metal oxides (e.g. $WO_3$, $Re_2O_7$ and $MoO_3$), metal-organic complexes of cobalt, iron, bismuth and molybdenum, $(p\text{-}BrC_6H_4)_3NSbCl_6$, bismuth (III) tris(trifluoroacetate), $FSO_2OOSO_2F$, acetylcholine, $R_4N^+$, (R is an alkyl group), $R_4P^+$ (R is a straight-chain or branched alkyl group 1 to 20), $R_6As^+$ (R is an alkyl group), $R_3S^+$ (R is an alkyl group) and ionic liquids (e.g. 1-Ethyl-3-methylimidazolium bis(trifluoromethylsulfonyl)imide). Suitable cobalt complexes beside of tris(2-(1H-pyrazol-1-yl)-4-tert-butylpyridine)-cobalt(III) tris(bis(trifluoromethylsulfonyl)imide)) are cobalt complex salts as described in WO 2012/114315, WO 2012/114316, WO 2014/082706, WO 2014/082704, EP 2883881 or JP 2013-131477.

Suitable lithium salts are beside of lithium bis(trifluoromethylsulfonyl)imide, lithium tris(pentafluoroethyl)trifluorophosphate, lithium dicyanamide, lithium methylsulfate, lithium trifluormethanesulfonate, lithium tetracyanoborate, lithium dicyanamide, lithium tricyanomethide, lithium thiocyanate, lithium chloride, lithium bromide, lithium iodide, lithium hexafluorophosphate, lithium tetrafluoroborate, lithium perchlorate, lithium hexafluoroantimonate, lithium hexafluoroarsenate or a combination of two or more. A preferred lithium salt is lithium bis(trifluoromethylsulfonyl) imide.

Preferably, the formulation comprises from 0.1 mM to 50 mM, preferably from 5 to 20 mM of the lithium salt.

Suitable device structures for PSCs comprising a compound according to the present invention and a mixed halide perovskite are described in WO 2013/171517, claims 52 to 71 and claims 72 to 79, which is entirely incorporated herein by reference.

Suitable device structures for PSCs comprising a compound according to the present invention and a dielectric scaffold together with a perovskite are described in WO 2013/171518, claims 1 to 90 or WO 2013/171520, claims 1 to 94 which are entirely incorporated herein by reference.

Suitable device structures for PSCs comprising a compound according to the present invention, a semiconductor and a perovskite are described in WO 2014/020499, claims 1 and 3 to 14, which is entirely incorporated herein by reference The surface-increasing scaffold structure described therein comprises nanoparticles which are applied and/or fixed on a support layer, e.g. porous $TiO_2$.

Suitable device structures for PSCs comprising a compound according to the present invention and comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film.

The invention further relates to a method of preparing a PSC as described above or below, the method comprising the steps of:

providing a first and a second electrode, providing an electron selective layer comprising a compound according to the present invention.

The invention relates furthermore to a tandem device comprising at least one device according to the invention as described above and below. Preferably, the tandem device is a tandem solar cell.

The tandem device or tandem solar cell according to the invention may have two semi-cells wherein one of the semi cells comprises the compounds, oligomers or polymers in the active layer as described or preferably described above. There exists no restriction for the choice of the other type of semi cell which may be any other type of device or solar cell known in the art.

There are two different types of tandem solar cells known in the art. The so called 2-terminal or monolithic tandem solar cells have only two connections. The two subcells (or synonymously semi cells) are connected in series. Therefore, the current generated in both subcells is identical (current matching). The gain in power conversion efficiency is due to an increase in voltage as the voltages of the two subcells add up.

The other type of tandem solar cells is the so called 4-terminal or stacked tandem solar cell. In this case, both subcells are operated independently. Therefore, both subcells can be operated at different voltages and can also generate different currents. The power conversion efficiency of the tandem solar cell is the sum of the power conversion efficiencies of the two subcells.

The invention furthermore relates to a module comprising a device according to the invention as described before or preferably described before.

The compounds and compositions according to the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds and compositions of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound or a composition according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:

a source electrode, a drain electrode, a gate electrode, a semiconducting layer, one or more gate insulator layers, optionally a substrate.

wherein the semiconductor layer preferably comprises a compound according to the present invention.

The OFET device can be a top gate device or a bottom gate device.

Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF®1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds and compositions (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidized and reduced form of the materials according to the present invention. Either loss or gain of electrons results in formation of a highly delocalized ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalized ionic centers in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeC_3$, FeOCl, $Fe(ClO_4)_3$, $Fe(4\text{-}CH_3C_6H_4SO_3)_3$, $TiCl_4$, $ZrCl_4$, $HfCl_4$, $NbF_5$, $NbCl_5$, $TaC_5$, $MoF_5$, $MoC_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(N_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the materials according to the present invention can be used as an organic "metal" in applications including, but not limited to, charge injection layers and ITO planarizing layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., *Nat. Photonics,* 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarization charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

According to another use, the materials according to the present invention are suitable for use in liquid crystal (LC) windows, also known as smart windows, as described for example in US 2016/0108317 A1.

The materials according to the present invention may also be combined with photoisomerizable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.*, 1999, 96, 12287; D. Wang, X. Gong, P. S. Heeger, F. Rininsland, G. C. Bazan and A. J. Heeger, *Proc. Natl. Acad. Sci. U.S.A.*, 2002, 99, 49; N. DiCesare, M. R. Pinot, K. S. Schanze and J. R. Lakowicz, *Langmuir*, 2002, 18, 7785; D. T. McQuade, A. E. Pullen, T. M. Swager, *Chem. Rev.*, 2000, 100, 2537.

Unless the context clearly indicates otherwise, as used herein plural forms of the terms herein are to be construed as including the singular form and vice versa.

Throughout the description and claims of this specification, the words “comprise” and “contain” and variations of the words, for example “comprising” and “comprises”, mean “including but not limited to”, and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius.

The invention will now be described in more detail by reference to the following examples, which are illustrative only and do not limit the scope of the invention.

Example 1

Intermediate 1

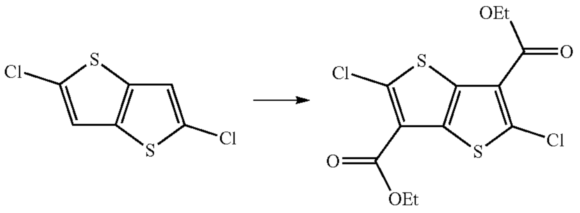 [SMILES: Clc1cc2sc(Cl)cc2s1 ; CCOC(=O)c1c(Cl)sc2c(C(=O)OCC)c(Cl)sc12]

To a solution of 2,5-dichloro-thieno[3,2-b]thiophene (17.3 g, 82.7 mmol) in anhydrous tetrahydrofuran (173 $cm^3$) at 5° C. is added ethyl chloroformate (23.7 $cm^3$, 248 mmol). A solution of 2,2,6,6-tetramethylpiperidinylmagnesium chloride lithium chloride complex (207 $cm^3$, 207 mmol, 1.0 M in tetrahydrofuran) is then added dropwise over 1 hour. The reaction is slowly warmed to 23° C. and stirred for 42 hours. Water (200 $cm^3$) is added, the mixture stirred for 10 minutes and the solid collected by filtration and washed with water (2×100 $cm^3$). The solid is triturated in acetone (200 $cm^3$), collected by filtration and washed with acetone (2×100 $cm^3$) to give intermediate 1 (26.6 g, 91%) as a white solid. $^1H$ NMR (400 MHz, $CDCl_3$) 4.46 (4H, q, J 7.1), 1.47 (6H, t, J 7.1).

Intermediate 2

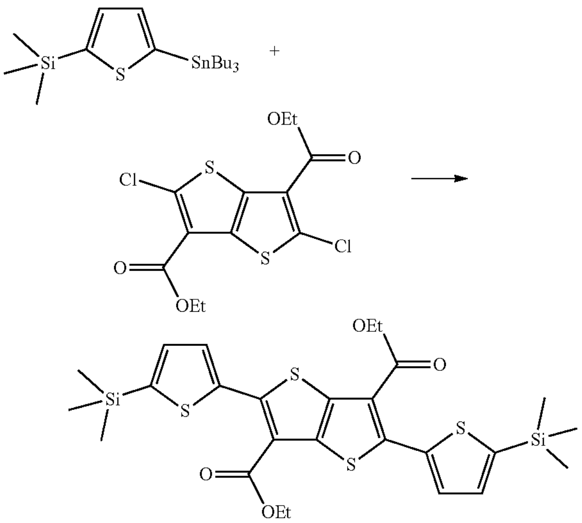

Trimethyl-(5-tributylstannanyl-thiophen-2-yl)-silane (30.5 g, 61.7 mmol), intermediate 1 (10.0 g, 28.3 mmol) and tetrakis(triphenylphosphine) palladium(0) (657 mg, 0.57 mmol) are suspended in anhydrous toluene (100 $cm^3$) and heated at 100° C. for 18 hours. The reaction is cooled to 23° C. and methanol (250 $cm^3$) added. The suspension is cooled in an ice-bath, the solid collected by filtration and washed with methanol (200 $cm^3$). The crude is purified by silica pad (dichloromethane) followed by column chromatography (40-60 petrol:dichloromethane; 60:40) to give intermediate 2 (7.68 g, 46%) as a yellow solid. $^1H$ NMR (400 MHz, $CDCl_3$) 7.42 (2H, d, J 3.5), 7.02 (2H, d, J 3.5), 4.19 (4H, q, J 7.1), 1.19 (6H, t, J 7.1), 0.15 (18H, s).

Intermediate 3

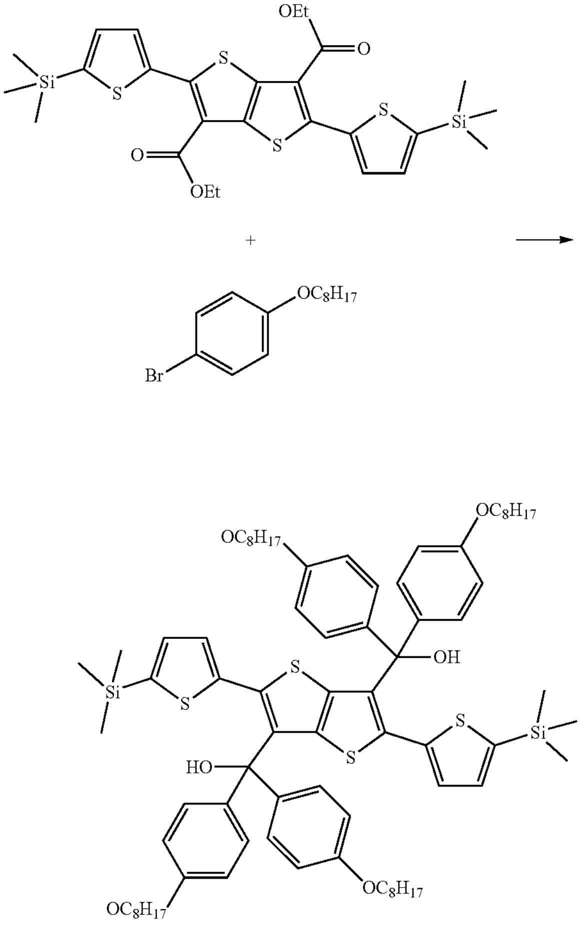

To a solution of 1-bromo-4-octyloxy-benzene (14.1 g, 49.5 mmol) in anhydrous tetrahydrofuran (73 $cm^3$) at −78° C. is added dropwise t-butyllithium (58.2 $cm^3$, 99.0 mmol, 1.7 M in pentane) over 20 minutes. The reaction is warmed to between −28° C. and −35° C. for 30 minutes. A second portion of 1-bromo-4-octyloxy-benzene (3.0 g, 11 mmol) is added and the reaction mixture stirred for 30 minutes. The reaction is cooled to −78° C. and a solution of intermediate 2 (4.89 g, 8.25 mmol) in anhydrous tetrahydrofuran (30 $cm^3$) is rapidly added. The reaction is warmed to 23° C. and stirred for 60 hours. Water (50 $cm^3$) is added and the organics extracted with ether (300 $cm^3$). The organic phase is washed with water (3×100 $cm^3$), dried over anhydrous magnesium sulfate, filtered and the solvent removed in vacuo. The crude is purified by column chromatography using a graded solvent system (40-60 petrol:dichloromethane; 9:1 to 8:2) to give intermediate 3 (3.17 g, 29%) as a pale brown solid. $^1H$ NMR (400 MHz, $CDCl_3$) 7.16-7.23 (8H, m), 6.88 (2H, d, J 3.4), 6.78-6.85 (8H, m), 6.51 (2H, d, J 3.4), 3.97 (8H, t, J 6.6), 3.37 (2H, s), 1.75-1.84 (8H, m), 1.27-1.52 (40H, m), 0.82-0.95 (12H, m), 0.25 (18H, s).

Intermediate 4—Route A

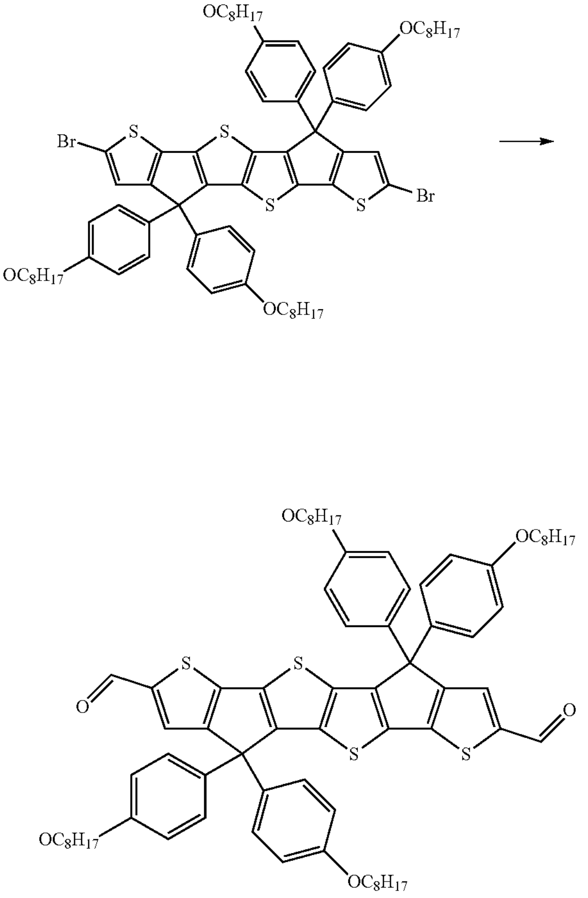

To a solution of 2,7-dibromo-4,4,9,9-tetrakis(4-(octyloxy) phenyl)-4,9-dihydro-thieno[3',2':4,5]cyclopenta[1,2-b] thieno[2",3":3',4']cyclopenta[1', 2':4,5]thieno[2,3-d]thiophene (1.00 g, 0.77 mmol) in anhydrous tetrahydrofuran (25 $cm^3$) cooled to −78° C. is added dropwise n-butyllithium (0.92 $cm^3$, 2.30 mmol, 2.5 M in hexanes). The reaction is stirred for 1 hour and then N,N-dimethylformamide (1.13 $cm^3$, 23.0 mmol) is added in a single portion. The reaction is warmed to 23° C. and stirred for 18 hours. The reaction is quenched with water (50 $cm^3$), extracted with dichloromethane (3×30 $cm^3$). The resulting organic phase is washed with water (2×20 $cm^3$), dried over anhydrous magnesium sulfate, filtered and concentrated in vacuo. The crude is purified by column chromatography eluting with a graded solvent system (40-60 petrol:dichloromethane; 6:4 to 4:6) to give intermediate 4 (330 mg, 36%) as an orange oil. $^1H$ NMR (400 MHz, $CDCl_3$) 9.72 (2H, s), 7.58 (2H, s), 7.00-7.08 (8H, m), 6.69-6.82 (8H, m), 3.83 (8H, t, J 6.5), 1.61-1.71 (8H, m), 1.34 (8H, m), 1.11-1.33 (32H, m), 0.72-0.90 (12H, m).

Intermediate 4—Route B

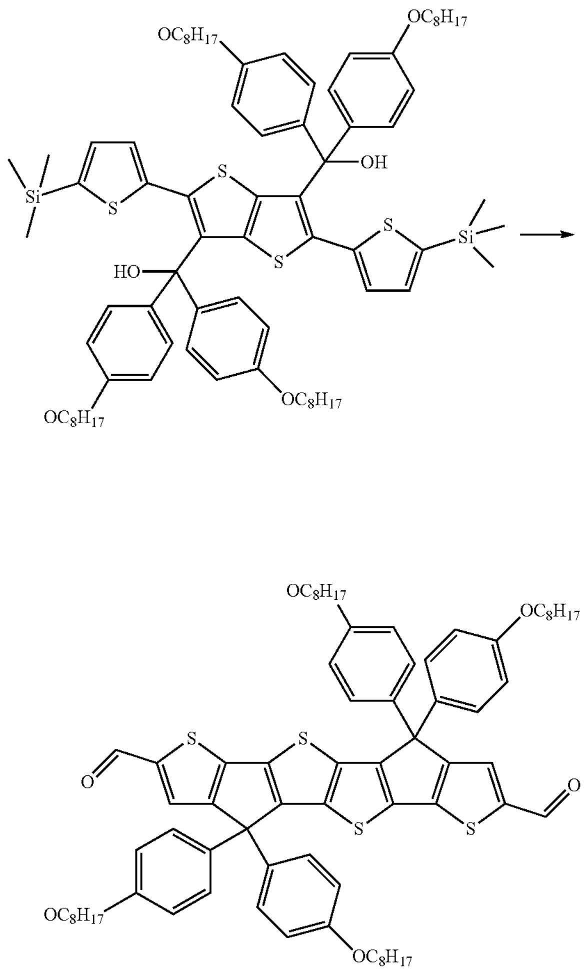

To a degassed solution of intermediate 3 (6.00 g, 4.52 mmol) in toluene (240 $cm^3$) is added amberlyst 15 strong acid (24 g), the mixture further degassed and then heated at 75° C. for 18 hours. The solution is cooled to about 50° C., filtered and the solid washed with toluene (200 $cm^3$). The filtrate is concentrated, triturated with 80-100 petrol (3×30 $cm^3$) and the solid collected by filtration. The solid is dissolved in chloroform (120 $cm^3$) N,N-dimethylformamide (5.3 g, 72 mmol) added and the solution cooled to 0° C. Phosphorus(V) oxychloride (10.4 g, 67.9 mmol) is added over 10 minutes. The reaction mixture is then heated at 65° C. for 18 hours. Aqueous sodium acetate solution (150 $cm^3$, 2 M) is added at 65° C. and the reaction mixture stirred for 1 hour. Saturated aqueous sodium acetate solution is added until the mixture is pH 6 and the reaction stirred for a further 30 minutes. The aqueous phase is extracted with chloroform (2×25 $cm^3$) and the combined organic layers washed with water (50 $cm^3$), dried over anhydrous magnesium sulfate, filtered and the solvent removed in vacuo. The solid is triturated in 80-100 petrol and the solid collected by filtration to give intermediate 4 (3.06 g, 56%) as an orange oil. $^1H$ NMR (400 MHz, $CDCl_3$) 9.72 (2H, s), 7.58 (2H, s), 7.00-7.08 (8H, m), 6.69-6.82 (8H, m), 3.83 (8H, t, J 6.5), 1.61-1.71 (8H, m), 1.34 (8H, m), 1.11-1.33 (32H, m), 0.72-0.90 (12H, m).

Intermediate 5

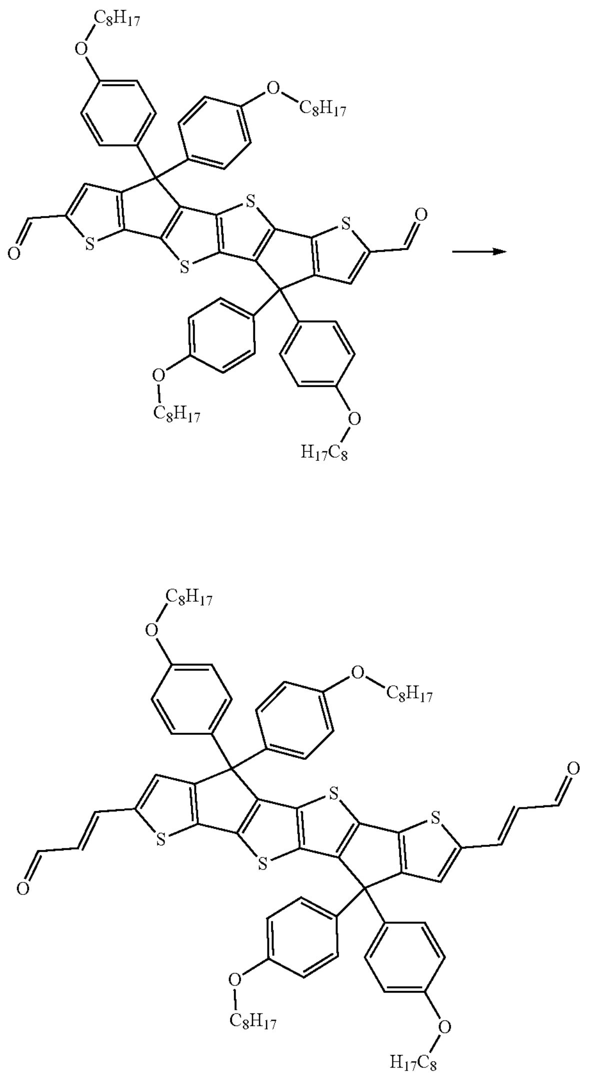

To a solution of intermediate 4 (1.00 g, 0.83 mmol) and tributyl(1,3-dioxolan-2-ylmethyl)-phosphonium bromide (676 mg, 1.83 mmol) in anhydrous tetrahydrofuran (61 $cm^3$) is added sodium hydride (200 mg, 4.99 mmol, 60% dispersion in mineral oil). The reaction mixture is then stirred at 23° C. for 18 hours, cooled to ° C. and hydrochloric acid (5 $cm^3$, 10% solution in water) added. The reaction mixture is stirred at 0° C. for 40 minutes then at 23° C. for 2 hours. Water (25 $cm^3$) is then added and the organics extracted with ether (3×50 $cm^3$). The combined organic layer is washed with brine (50 $cm^3$), dried over anhydrous magnesium sulfate, filtered and the solvent removed in vacuo. The crude is triturated in n-pentane (100 $cm^3$), the solid collected by filtration and washed with acetonitrile (50 $cm^3$) to give intermediate 5 (1.01 g, 97%) as a dark red/purple solid. $^1H$ NMR (400 MHz, $CDCl_3$) 9.50 (2H, d, J 7.8), 7.43 (2H, d, J 15.4), 7.19 (2H, s), 6.97-7.08 (8H, m), 6.65-6.82 (8H, m), 6.36 (2H, dd, J 15.5, 7.7), 3.82 (8H, t, J 6.6), 1.56-1.75 (8H, m), 1.30-1.42 (8H, m), 1.09-1.30 (32H, m), 0.74-0.86 (12H, m).

Compound 1

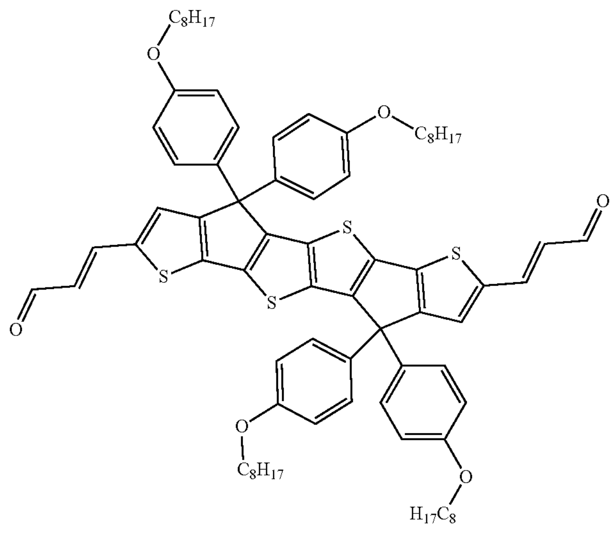

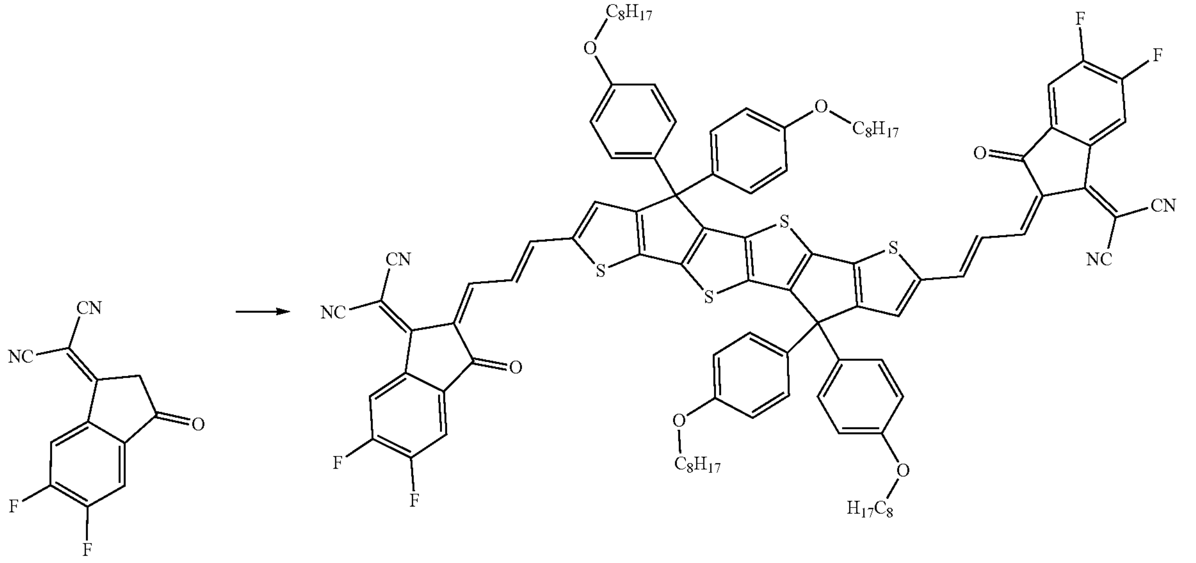

To a solution of intermediate 5 (200 mg, 0.16 mmol) in anhydrous chloroform (13 $cm^3$) at 0° C. is added 2-(5,6-difluoro-3-oxo-indan-1-ylidene)-malononitrile (147 mg, 0.638 mmol) followed by pyridine (0.90 $cm^3$). The resulting solution is degassed for 15 minutes. The ice bath is removed, the reaction mixture allowed to warm to 23° C. and stirred for 25 minutes. The reaction mixture is poured into acetonitrile (100 $cm^3$) and the mixture stirred for 17 hours. The solid collected by filtration to give compound 1 (259 mg, 97%) as a dark green solid. $^1H$ NMR (400 MHz, $CD_2Cl_2$) 8.36-8.49 (4H, 3 m), 8.26-8.34 (2H, m), 7.57 (2H, t, J 7.7), 7.45 (2H, d, J 14.2), 7.33 (2H, s), 7.06 (8H, d, J 8.8), 6.73 (8H, d, J 8.8), 3.82 (8H, t, J 6.6), 1.56-1.71 (8H, m), 1.09-1.41 (40H, m), 0.72-0.84 (12H, m).

Example 2

Compound 2

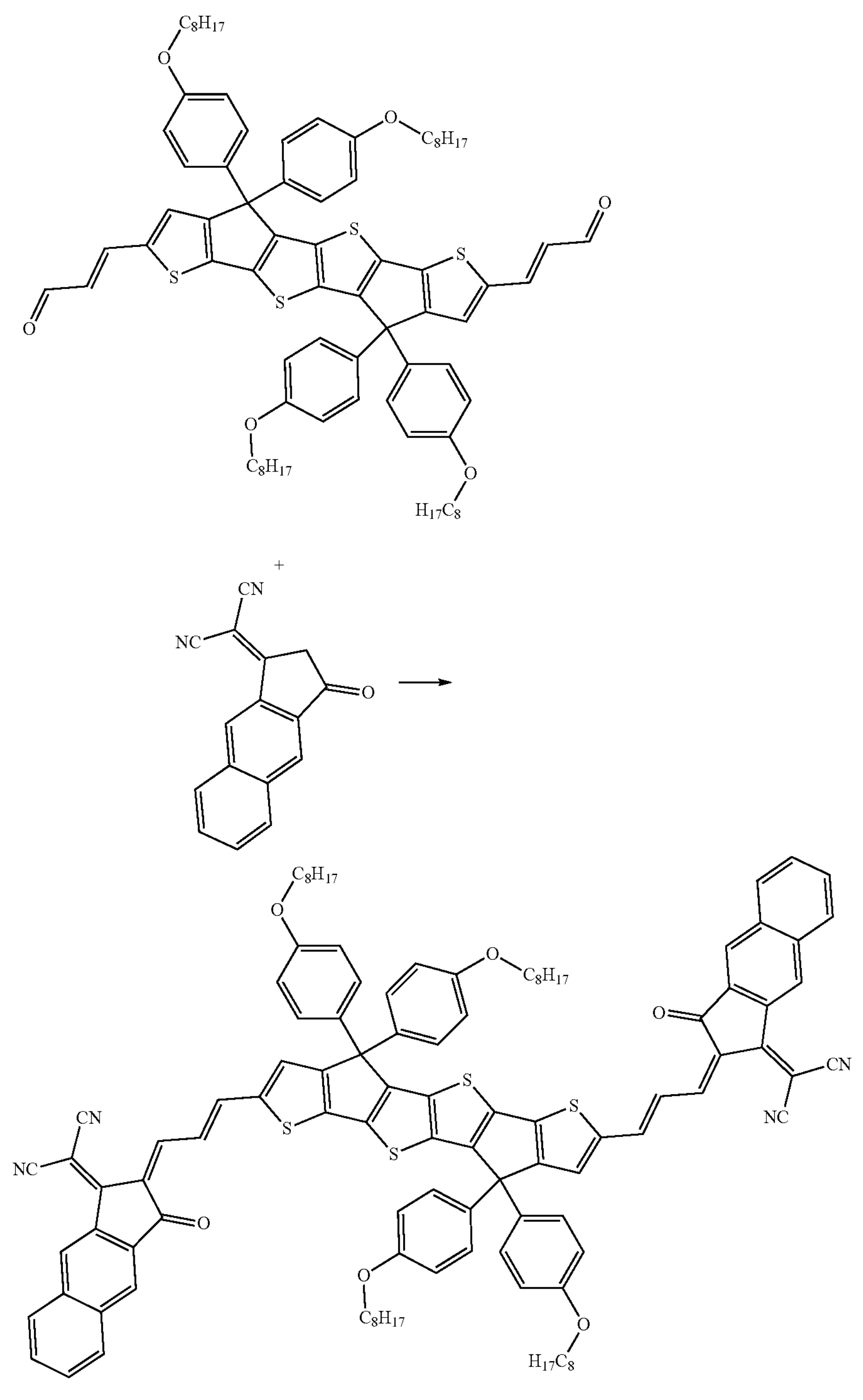

To a degassed mixture of intermediate 5 (200 mg, 0.16 mmol), 2-(3-oxo-2,3-dihydro-cyclopenta[b]naphthalen-1-ylidene)-malononitrile (195 mg, 0.80 mmol) and anhydrous chloroform (20 $cm^3$) is added pyridine (0.90 $cm^3$). The mixture is then heated at 40° C. for 4 hours. Methanol (50 $cm^3$) is then slowly added and the mixture stirred at 23° C. for 30 minutes. The solid is collected by filtration and washed with methanol (2×5 $cm^3$). The crude is purified by column chromatography using a graded solvent system (40-60 petrol:dichloromethane; 1:1 to 3:7). The material is recrystallised (chloroform/acetone) to give compound 2 (137 mg, 50%) as a dark solid. $^1H$ NMR (400 MHz, $CDCl_3$) 9.09 (2H, s), 8.61 (2H, dd, J 14.5, 11.8), 8.41 (2H, d, J 11.7), 8.27 (2H, s), 7.94-8.04 (4H, m), 7.57-7.67 (4H, m), 7.44

(2H, d, J 14.5), 7.34 (2H, s), 7.04-7.12 (8H, m), 6.73-6.82 (8H, m), 3.85 (8H, t, J 6.5), 1.69 (8H, p, J 6.7), 1.30-1.42 (8H, m), 1.16-1.30 (32H, m), 0.76-0.84 (12H, m).

Example 3

Compound 3

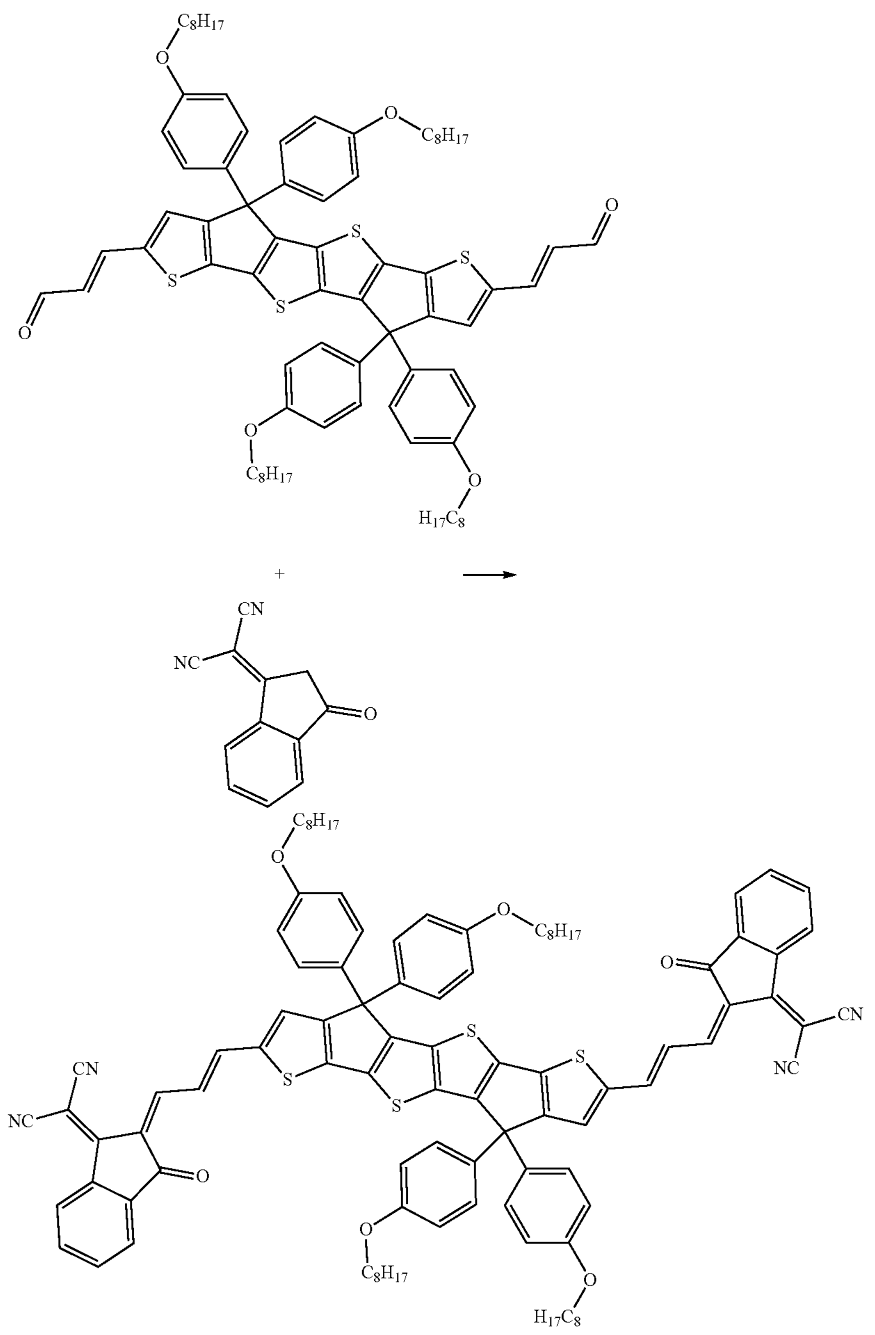

To a degassed mixture of intermediate 5 (100 mg, 0.08 mmol), 2-(3-oxo-indan-1-ylidene)-malononitrile (77 mg, 0.40 mmol) and anhydrous chloroform (10 $cm^3$) is added pyridine (0.45 $cm^3$). The reaction mixture is then heated at 40° C. for 4 hours. Methanol (15 $cm^3$) is then slowly added and the mixture cooled to 23° C. The solid is collected by filtration and washed with methanol (5 $cm^3$). The crude is purified by column chromatography using a graded solvent system (40-60 petrol:dichloromethane; 1:1 to 3:7). The material is recrystallised (dichloromethane/acetone/methanol) to give compound 3 (50 mg, 50%) as a blue/green solid.

$^1$H NMR (400 MHz, $CDCl_3$) 8.65-8.72 (2H, m), 8.58 (2H, dd, J 14.5, 11.7), 8.42 (2H, d, J 11.7), 7.86-7.94 (2H, m), 7.69-7.81 (4H, m), 7.48 (2H, d, J 14.5), 7.39 (2H, s), 7.11-7.21 (8H, m), 6.81-6.90 (8H, m), 3.93 (8H, t, J 6.5), 1.77 (8H, p, J 6.7), 1.39-1.50 (8H, m), 1.22-1.39 (32H, m), 0.85-0.93 (12H, m).

Example 4

Intermediate 6

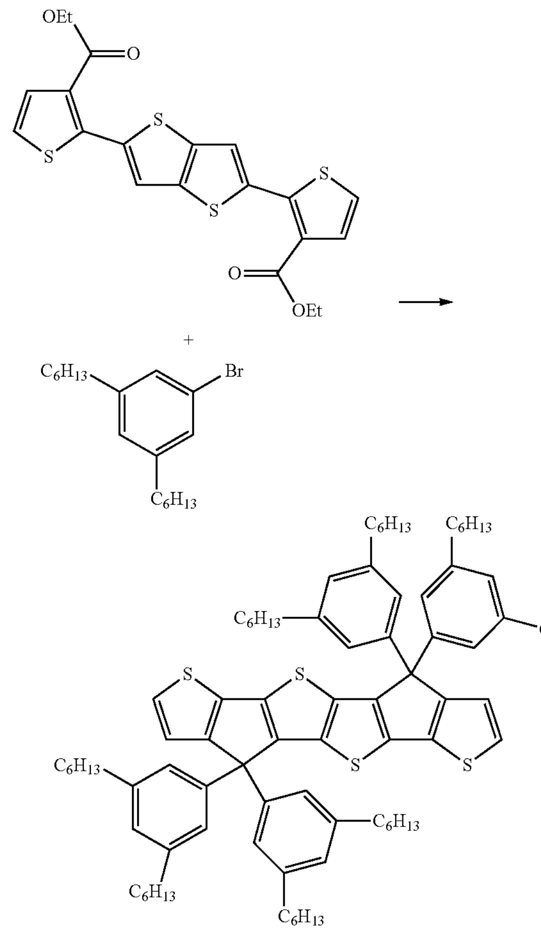

To a solution of 1-bromo-3,5-dihexyl-benzene (14.5 g, 44.6 mmol) in anhydrous tetrahydrofuran (60 $cm^3$) at −78° C. is added dropwise n-butyllithium (17.8 $cm^3$, 44.6 mmol, 2.5 M in hexane) over 10 minutes. The reaction is stirred for 2 hours and ethyl 2-[5-(3-ethoxycarbonyl-2-thienyl)thieno[3,2-b]thiophen-2-yl]thiophene-3-carboxylate (4.00 g, 8.92 mmol) added. The reaction is warmed to 23° C. and stirred for 17 hours. Water (100 $cm^3$) added and the product extracted with ether (100 $cm^3$). The organic phase is washed with water (2×50 $cm^3$), dried over anhydrous magnesium sulfate, filtered and the solvent removed in vacuo. The crude is purified by column chromatography (40-60 petrol then dichloromethane). The solid is suspended in toluene (40 $cm^3$), p-toluene sulphonic acid (2.0 g) added and the reaction mixture heated at 60° C. for 4 hours. The mixture allowed to cool to 23° C. and the solid collected by filtration, washed with toluene (50 $cm^3$) and purified by column chromatography using a graded solvent system (40-60 petrol:dichloromethane; 1:0 to 19:1) to give intermediate 6 (2.5 g, 21%) as a pale brown oil. $^1H$ NMR (400 MHz, $CDCl_3$) 7.07 (2H, d, J 4.9), 6.96 (2H, d, J 4.9), 6.78 (4H, d, J 1.6), 6.74 (8H, d, J 1.5), 2.40 (16H, t, J 8.0), 1.40-1.48 (16H, m), 1.10-1.26 (48H, m), 0.69-0.82 (24H, m).

Intermediate 7

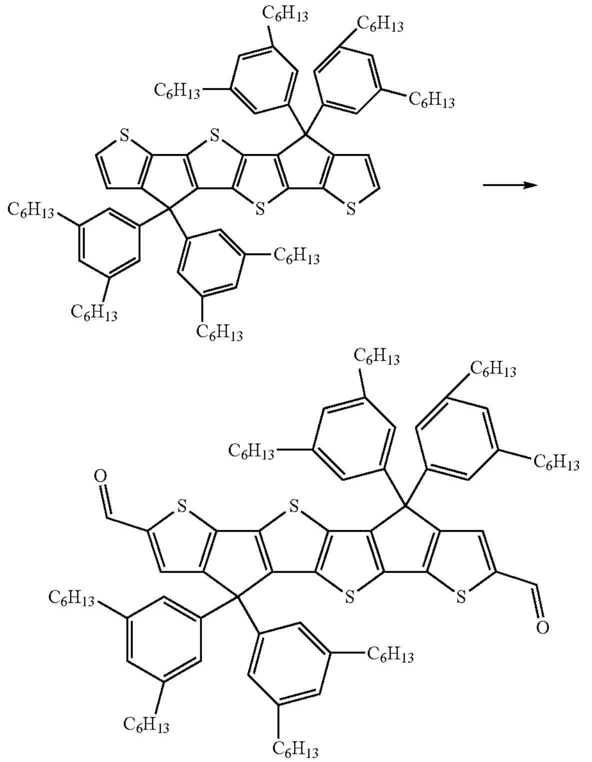

To a mixture of intermediate 6 (0.50 g, 0.38 mmol), anhydrous N,N-dimethylformamide (0.40 $cm^3$, 5.2 mmol) and chloroform (20 $cm^3$) at 0° C. is added dropwise phosphorus oxychloride (0.47 $cm^3$, 5.0 mmol). The reaction is heated at 70° C. for 18 hours before cooling to 60° C., saturated aqueous sodium acetate solution (7 $cm^3$) is added and the mixture stirred for 1 hour. The organic phase is separated, washed with water (20 $cm^3$) and dried with anhydrous sodium sulphate, filtered and the solvent removed in vacuo. The solid is triturated in acetone (3×5 $cm^3$) to give intermediate 7 (400 mg, 76%) as a bright orange solid. $^1H$ NMR (400 MHz, $CD_2Cl_2$) 9.78 (2H, s), 7.64 (2H, s), 6.90 (4H, d, J 1.6), 6.78 (8H, d, J 1.6), 2.46 (16H, d, J 7.9), 1.42-1.51 (16H, m), 1.17-1.28 (48H, m), 0.76-0.85 (24H, m).

Intermediate 8

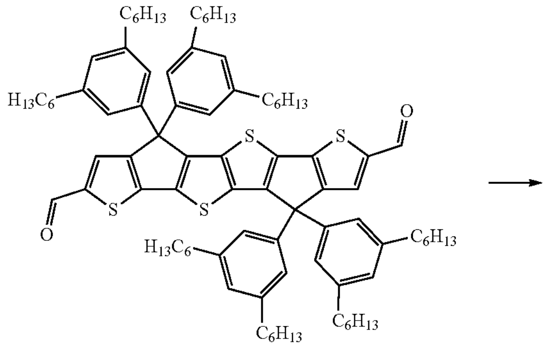

-continued

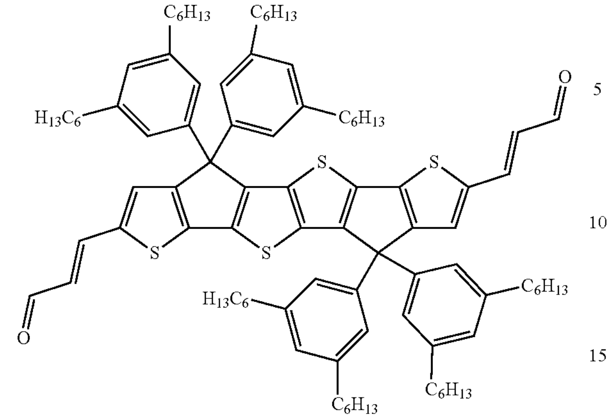

To a solution of tributyl(1,3-dioxolan-2-ylmethyl)-phosphonium bromide (1.03 g, 2.77 mmol) and intermediate 7 (1.72 g, 1.26 mmol) in anhydrous tetrahydrofuran (70 $cm^3$) is added sodium hydride (303 mg, 7.57 mmol, 60% dispersion in mineral oil) and the reaction stirred at 23° C. for 17 hours. The reaction is cooled to 0° C. before addition of hydrochloric acid (11 $cm^3$, 10% in water). The mixture is then stirred at 0° C. for 40 minutes and at 23° C. for 47 hours. Ethyl acetate (100 $cm^3$) and water (100 $cm^3$) are then added. The organic layer is then washed with water (100 $cm^3$), brine (25 $cm^3$) before drying over anhydrous magnesium sulfate, filtered and the solvent removed in vacuo. The crude is then purified by column chromatography using a graded solvent system (40-60 petrol:dichloromethane; 1:0 to 3:7) to give intermediate 8 (1.53 g, 86%) as a dark oily solid. $^{1}H$ NMR (400 MHz, $CDCl_3$) 9.54-9.60 (2H, m), 7.48-7.56 (2H, m), 7.24-7.26 (2H, m), 6.90 (4H, s), 6.78 (8H, s), 6.37-6.49 (2H, m), 2.42-2.55 (16H, m), 1.43-1.60 (16H, m), 1.17-1.30 (48H, m), 0.74-0.84 (24H, m).

Compound 4

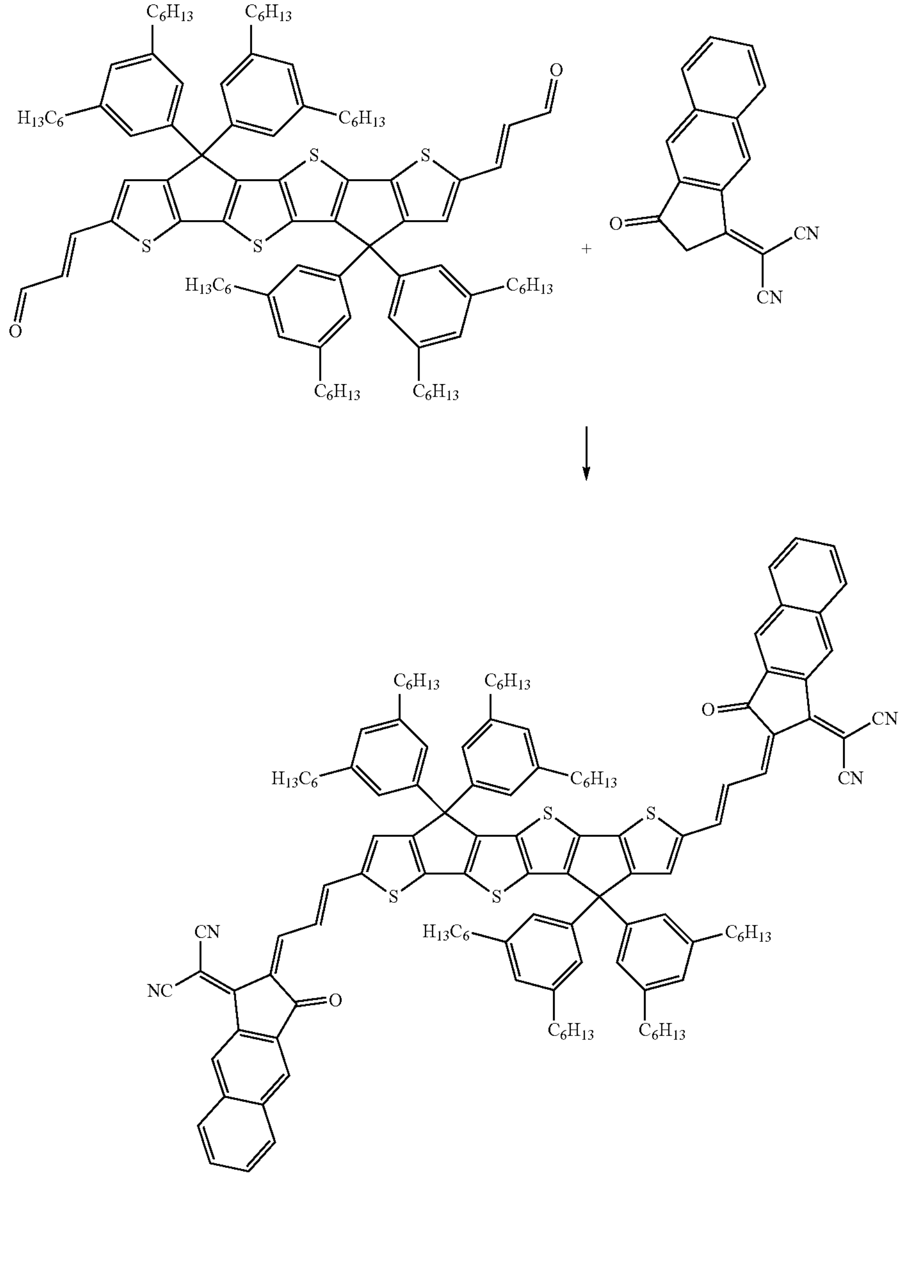

To a degassed solution of intermediate 8 (189 mg, 0.13 mmol), anhydrous chloroform (10 $cm^3$) and pyridine (0.76 $cm^3$, 9.4 mmol) at 0° C. is added 2-(3-oxo-2,3-dihydro-cyclopenta[b]naphthalen-1-ylidene)-malononitrile (131 mg, 0.535 mmol). The reaction mixture is then stirred for 2.5 hours at 0° C. and poured into stirred methanol (150 $cm^3$). The mixture stirred for 25 minutes, the solid collected by filtration and washed with methanol (3×10 $cm^3$), acetonitrile (3×10 $cm^3$) and 40-60 petrol (3×10 $cm^3$). The crude is then recrystallised (80-100 petrol:acetone) to give compound 4 (26 mg, 10%) as a black solid. $^1$H NMR (400 MHz, $CDCl_3$) 9.16 (2H, s), 8.69 (2H, dd, J 14.6, 11.9), 8.50 (2H, d, J 11.7), 8.35 (2H, s), 8.01-8.11 (4H, m), 7.66-7.73 (4H, m), 7.55 (2H, d, J 14.4), 7.38 (2H, s), 6.95 (4H, s), 6.81 (8H, d, J 1.2), 2.53 (16H, t, J 7.7), 1.49-1.66 (16H, m), 1.21-1.35 (48H, m), 0.81-0.89 (24H, m).

Example 5

To a degassed solution of intermediate 8 (100 mg, 0.071 mmol) in anhydrous chloroform (10 $cm^3$) and pyridine (0.40 $cm^3$) at 0° C. is added 2-(5,6-difluoro-3-oxo-indan-1-ylidene)-malononitrile (65 mg, 0.28 mmol). The reaction mixture is then stirred for 70 minutes before methanol (150 $cm^3$) is added. The mixture is then stirred for 80 minutes and the solid collected by filtration. The crude is purified by column chromatography using a graded solvent system (40-60 petrol:dichloromethane; 1:0 to 2:3) to give compound 5 (31 mg, 24%) as a black solid. $^1$H NMR (400 MHz, $CDCl_3$) 8.45-8.57 (4H, m), 8.40 (2H, d, J 11.7), 7.60-7.69 (2H, m), 7.53 (2H, d, J 14.2), 7.37 (2H, s), 6.95 (4H, s), 6.79 (8H, s), 2.52 (16H, t, J 7.5), 1.47-1.62 (16H, m), 1.19-1.35 (48H, m), 0.79-0.89 (24H, m).

Compound 5

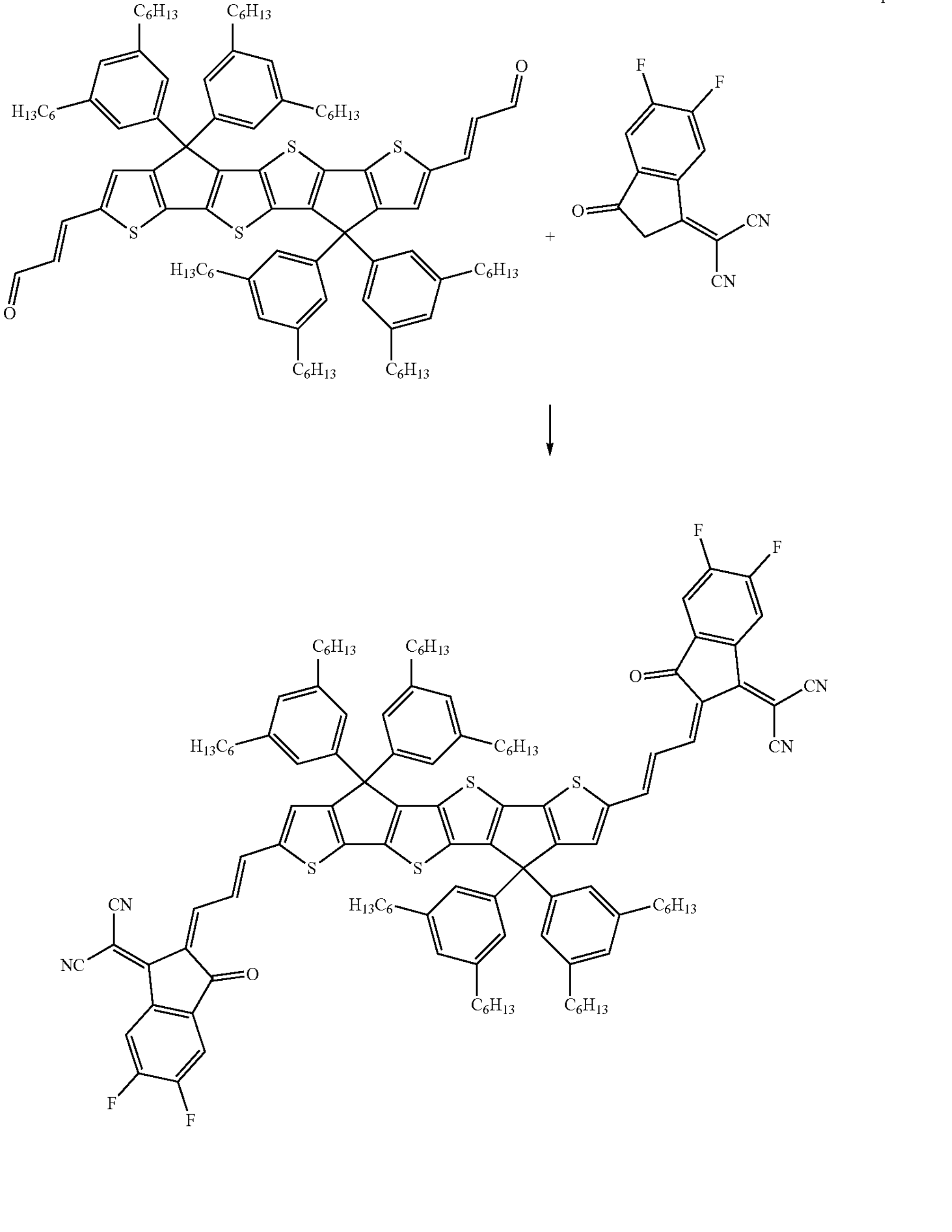

Example 6

Intermediate 9

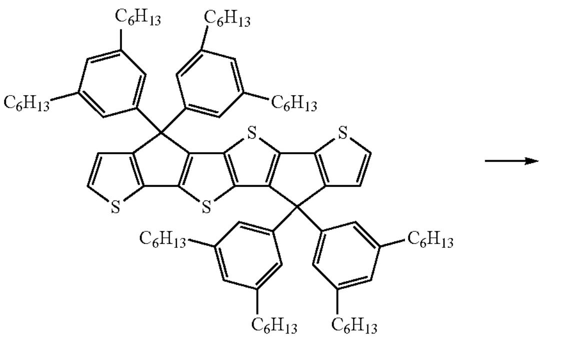

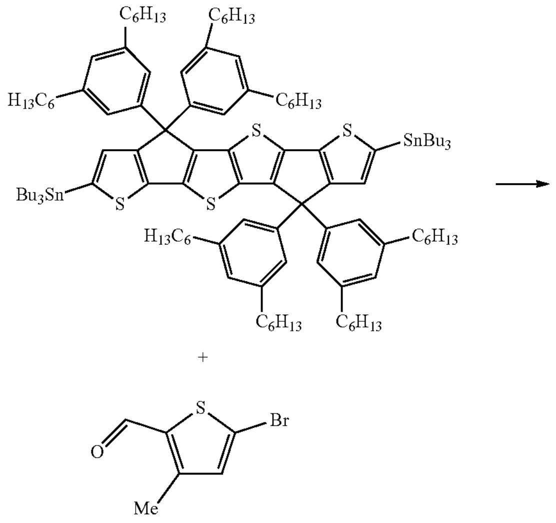

Intermediate 10

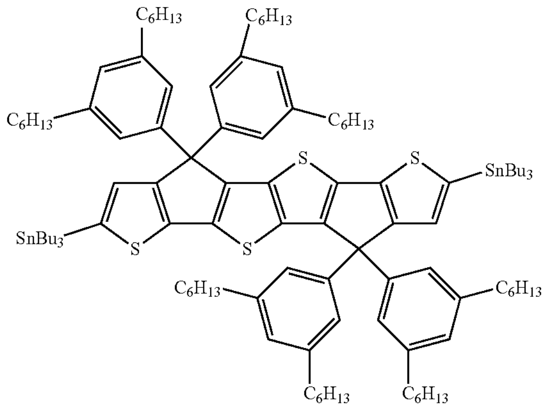

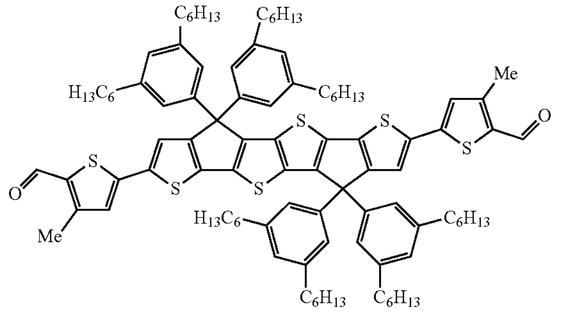

To a solution of intermediate 6 (1.60 g, 1.2 mmol) in anhydrous tetrahydro-furan (47 $cm^3$) at −78° C. is added dropwise n-butyllithium (1.96 $cm^3$ 4.9 mmol, 2.5 M in hexane) over 20 minutes. After addition, the reaction mixture is stirred at −78° C. for 60 minutes and then tributyltin chloride (1.5 $cm^3$, 5.5 mmol) is added in one go. The mixture is then allowed to warm to 23° C. over 72 hours and the solvent removed in vacuo. The crude is purified by passing through a zeolite plug (40-60 petrol) followed by trituration in ethanol (2×100 $cm^3$) to give a mixture of intermediate 9 and tributyltin chloride (2.7 g) as a dark brown oil. H NMR (400 MHz, $CD_2Cl_2$) 6.99 (2H, s), 6.64-6.85 (12H, m), 2.38 (16H, t, J 7.7), 0.57-1.69 (98H, m).

To a mixture of 5-bromo-3-methyl-thiophene-2-carbaldehyde (156 mg, 0.759 mmol) and anhydrous toluene (41 $cm^3$) is added intermediate 9 (650 mg, 0.34 mmol). The solution is then degassed for 20 minutes before tris(dibenzylideneacetone)dipalladium(0) (25 mg, 0.028 mmol) and tris(o-tolyl) phosphine (31.5 mg, 0.103 mmol) are added. The reaction is then degassed for a further 10 minutes before heating at 80° C. for 4 hours and at 23° C. for 90 hours. The reaction is then concentrated in vacuo. The crude is purified by column chromatography using a graded solvent system (40-60 petrol:dichloromethane; 1:0 to 0:1) followed by trituration in acetonitrile (50 $cm^3$). The solid is collected by filtration and washed with acetonitrile (3×10 $cm^3$) to give intermediate 10 (261 mg, 49%) as a red/black sticky solid. $^1H$ NMR (400 MHz, $CD_2Cl_2$) 9.94 (2H, s), 7.31 (2H, s), 7.02 (2H, s), 6.91 (4H, s), 6.83 (8H, s), 2.43-2.55 (22H, m), 1.46-1.58 (16H, m), 1.17-1.32 (48H, m), 0.79-0.87 (24H, m).

Intermediate 11

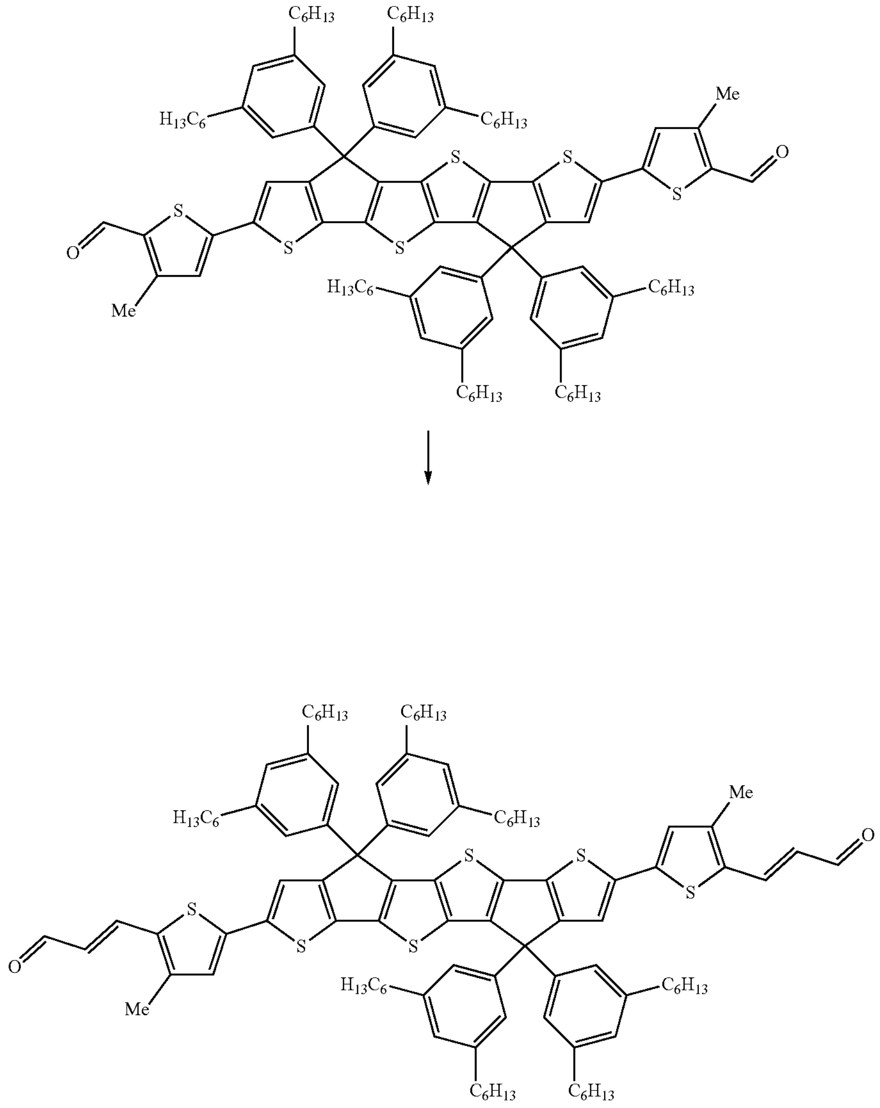

To a mixture of tributyl(1,3-dioxolan-2-ylmethyl)-phosphonium bromide (87 mg, 0.23 mmol), intermediate 10 (166 mg, 0.11 mmol) and anhydrous tetrahydrofuran (10 $cm^3$) is added sodium hydride (26 mg, 0.64 mmol, 60% dispersion in mineral oil) and the reaction stirred at 23° C. for 22 hours. Hydrochloric acid (1.5 $cm^3$, 10% in water) is then added and the mixture stirred for 5 hours. Ethyl acetate (25 $cm^3$) and water (50 $cm^3$) are then added and the aqueous layer extracted with ethyl acetate (25 $cm^3$). The combined organic extracts are then washed with water (75 $cm^3$), brine (25 $cm^3$) before drying over anhydrous magnesium sulfate, filtered and the solvent removed in vacuo. The crude is purified by column chromato-graphy using a graded solvent system (40-60 petrol:dichloro-methane; 1:0 to 1:4) to give intermediate 11 (129 mg, 75%) as a purple solid. $^1H$ NMR (400 MHz, $CD_2Cl_2$) 9.58 2H, (d, J 7.8), 7.60 (2H, d, J 15.4), 7.22 (2H, s), 7.00 (2H, s), 6.91 (4H, s), 6.83 (8H, d, J 1.5), 6.31 (2H, dd, J 15.3, 7.7), 2.48 (16H, t, J 7.6), 2.35 (6H, s), 1.45-1.60 (16H, m), 1.16-1.32 (48H, m), 0.78-0.87 (24H, m).

Compound 6

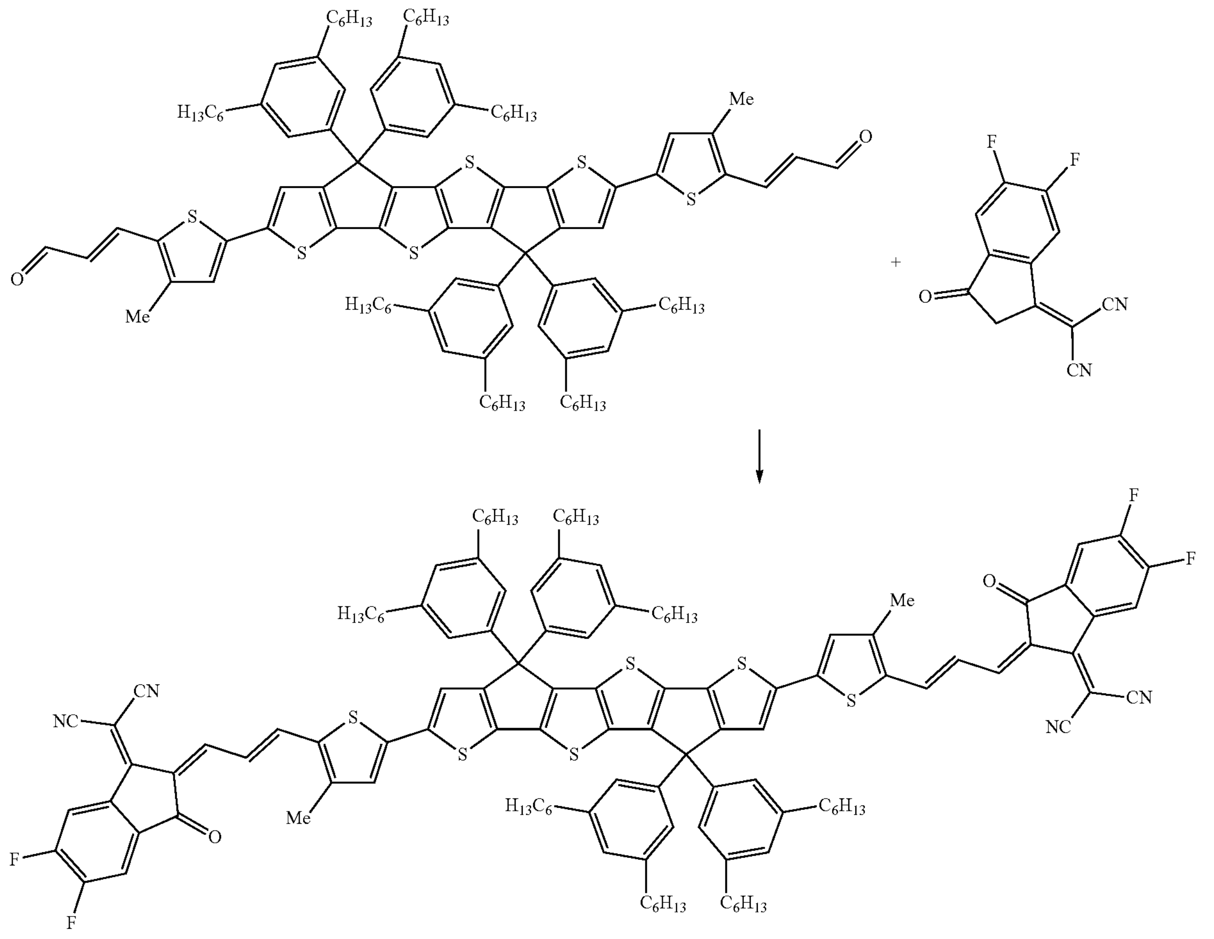

To a degassed mixture of intermediate 11 (124 mg, 0.0772 mmol), anhydrous chloroform (10 $cm^3$) and pyridine (0.44 $cm^3$) at 0° C. is added 2-(5,6-difluoro-3-oxo-indan-1-ylidene)-malononitrile (71 mg, 0.31 mmol). The reaction mixture is then stirred at 0° C. for 2.5 hours before methanol (150 $cm^3$) is added and the mixture stirred for 90 minutes. The solid is collected by filtration and washed with methanol (4×10 $cm^3$), acetonitrile (3×10 $cm^3$), 40-60 petrol (3×10 $cm^3$), cyclohexane (3×10 $cm^3$) and acetone (2×10 $cm^3$). The crude is purified by recrystallisation (80-100 petrol/2-butanone) to give compound 6 (55 mg, 35%) as a black solid. $^1H$ NMR (400 MHz, $CD_2Cl_2$) 8.45-8.52 (2H, m), 8.36-8.45 (4H, m), 7.61-7.68 (2H, m), 7.54-7.61 (2H, m), 7.36 (2H, s), 7.09 (2H, s), 6.93 (4H, s), 6.85 (8H, d, J 1.5), 2.51 (16H, t, J 7.6), 2.40 (6H, s), 1.48-1.58 (16H, m), 1.21-1.33 (48H, m), 0.80-0.86 (24H, m).

Example 7

Intermediate 12

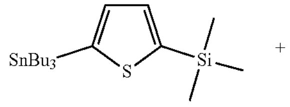

-continued

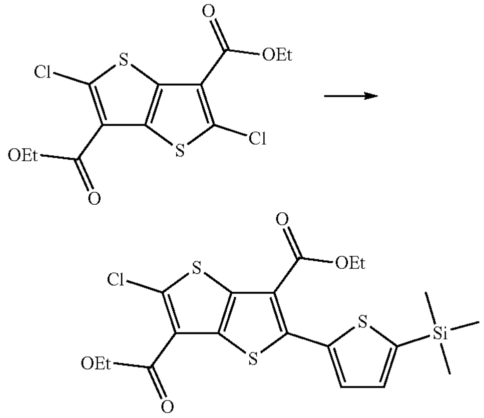

A mixture of intermediate 1 (7.1 g, 20 mmol), trimethyl-(5-tributylstannanyl-thiophen-2-yl)-silane (10 g, 23 mmol) and anhydrous toluene (300 $cm^3$) is degassed by nitrogen for 25 minutes. To the mixture is added tetrakis(triphenylphosphine)palladium(0) (0.5 g, 0.4 mmol) and the mixture further degassed for 15 minutes. The mixture is stirred at 85° C. for 17 hours. The reaction mixture is filtered hot through a celite plug and washed through with hot toluene. The crude is purified by column chromatography (40-60 petrol:dichloromethane: 4:1) to give intermediate 12 (2.3 g, 21%) as a pale yellow solid. $^1$H NMR (400 MHz, $CDCl_3$) 7.40 (1H, d, J 3.7), 6.99-7.03 (1H, m), 4.13-4.29 (4H, m), 1.15-1.28 (6H, m), 0.10-0.37 (9H, s).

Intermediate 13

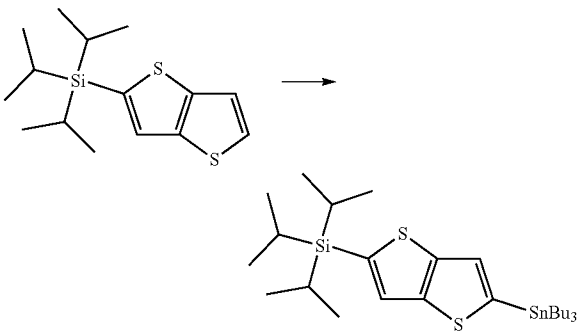

To a solution of triisopropyl-thieno[3,2-b]thiophen-2-yl-silane (11.9 g, 40.0 mmol) in anhydrous tetrahydrofuran (100 $cm^3$) at −78° C. is added drop-wise n-butyllithium (20.8 $cm^3$, 52.0 mmol, 2.5 M in hexane) over 20 minutes. After addition, the reaction mixture is stirred at −78° C. for 120 minutes and then tributyltin chloride (15.8 $cm^3$, 56.0 mmol) is added in one go. The mixture is then allowed to warm to 23° C. over 17 hours and the solvent removed in vacuo. The crude is diluted in 40-60 petrol (250 $cm^3$) and filtered through a zeolite plug (50 g). The plug is washed with additional 40-60 petrol (250 $cm^3$). The solvent is removed in vacuo to give intermediate 13 (23.1 g, 99%) as a clear oil. $^1$H-NMR (400 MHz, $CD_2Cl_2$) 7.27 (1H, d J 0.7), 7.1 (1H, s), 1.35-1.63 (9H, m), 1.17-1.34 (12H, m), 0.98-1.13 (18H, m), 0.65-0.91 (12H, m).

Intermediate 14

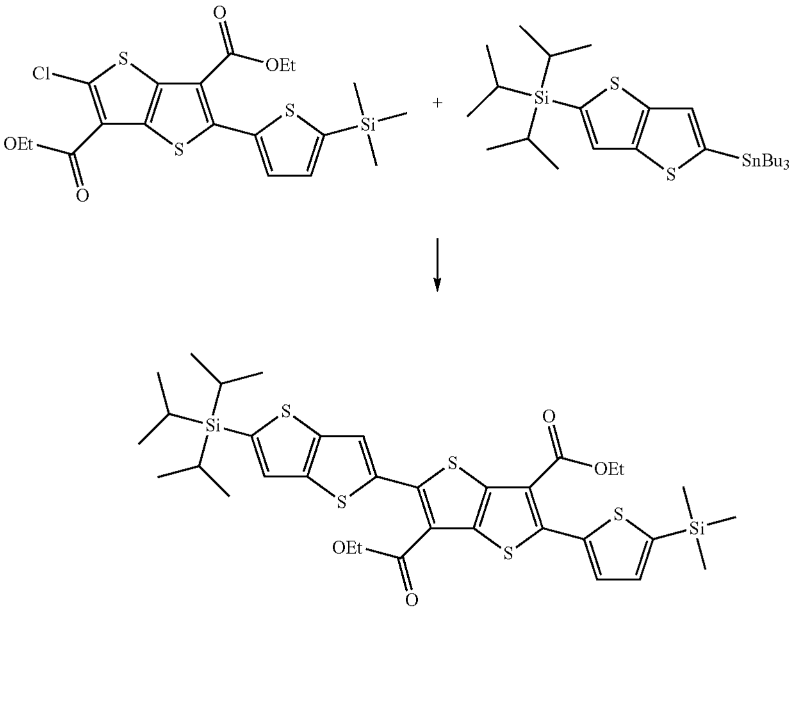

A mixture of intermediate 12 (2.2 g, 4.6 mmol), intermediate 13 (3.4 g, 5.8 mmol) and anhydrous toluene (300 $cm^3$) is degassed by nitrogen for 25 minutes. To the mixture is added tetrakis(triphenylphosphine)palladium(0) (0.5 g, 0.4 mmol) and the mixture further degassed for 15 minutes. The mixture is stirred at 85° C. for 17 hours. The reaction mixture is filtered hot through a celite plug and washed through with hot toluene. The crude product is stirred in acetone (100 $cm^3$) for 1 hour to form a heavy suspension. The solid is collected by filtration to give intermediate 14 (3.2 g, 75%) as a pale brown solid. $^1$H NMR (400 MHz, $CDCl_3$) 7.80-7.86 (1H, s), 7.65 (1H, d, J 3.4), 7.38 (1H, s), 7.24 (1H, d, J 3.4), 4.43 (4H, m), 1.31-1.51 (10H, m), 1.15 (18H, d, J 7.3), 0.38 (9H, s).

Intermediate 15

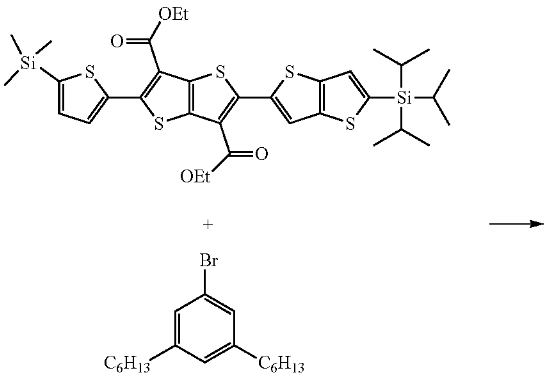

-continued

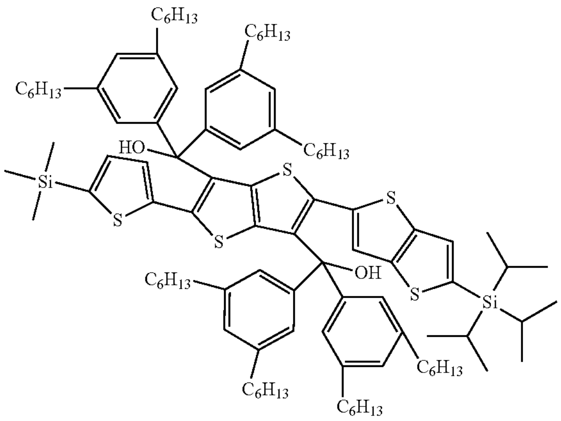

-continued

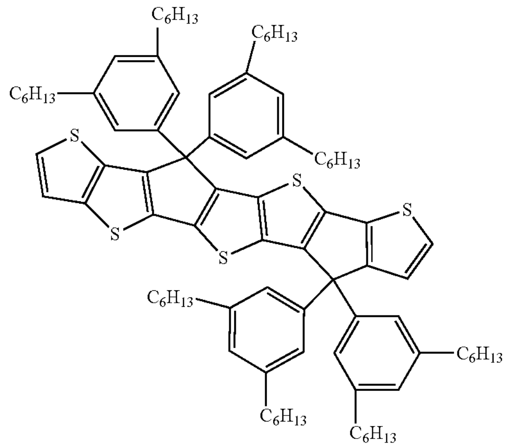

To a solution of 1-bromo-3,5-dihexyl-benzene (4.9 g, 15 mmol) in anhydrous tetrahydrofuran (100 $cm^3$) at −78° C. is added dropwise n-butyllithium (6.0 $cm^3$, 15.0 mmol, 2.5 M in hexane) over 30 minutes. After addition, the reaction mixture is stirred at −78° C. for 120 minutes. Intermediate 14 (2.2 g, 3.0 mmol) is added and the mixture allowed to warm to 23° C. over 17 hours. Ether (100 $cm^3$) and water (100 $cm^3$) are added and the mixture stirred at 23° C. for 30 minutes. The product is extracted with ether (3×100 $cm^3$). The organics are combined and dried over anhydrous magnesium sulfate, filtered and the solvent removed in vacuo to give intermediate 15 (2.30 g, 47%) as a brown oil. $^1$H NMR (400 MHz, $CD_2Cl_2$) 7.21 (1H, s), 7.06 (1H, s), 6.80-7.03 (12H, m), 6.42-6.55 (2H, m), 3.36 (2H, d, J 4.4), 2.44-2.62 (16H, m), 1.48-1.65 (16H, m), 1.24-1.35 (49H, m), 1.11-1.17 (18H, m), 0.83-0.94 (24H, m), 0.26 (9H, s).

Nitrogen gas is bubbled through a suspension of amberlyst 15 strong acid (8.8 g) in anhydrous ether (100 $cm^3$) at 0° C. for 60 minutes. Intermediate 15 (2.2 g, 1.4 mmol) is added whilst the mixture is degassed for a further 30 minutes. The resulting suspension is stirred at 23° C. for 2 hours. The reaction mixture is filtered and the solvent removed in vacuo. The crude is taken up in anhydrous tetrahydrofuran (50 $cm^3$) and tetrabutylammonium fluoride (2.7 $cm^3$, 2.7 mmol, 1 M in tetrahydrofuran) added. The mixture is stirred for 1 hour. Diethyl ether (100 $cm^3$) and water (200 $cm^3$) are added and the mixture stirred for 30 minutes. The product is extracted with ether (3×100 $cm^3$). The organics are combined and dried over anhydrous magnesium sulfate, filtered and the solvent removed in vacuo. The crude is purified using column chromatography (40-60 petrol:dichloromethane: 9:1) to give intermediate 16 (1.0 g, 54%) as a dark orange solid. $^1$H NMR (400 MHz, $CDCl_3$) 7.25-7.31 (1H, m), 7.21-7.25 (1H, m), 7.17 (1H, d, J 4.9), 7.05 (1H, d, J 4.9), 6.81-6.91 (12H, m), 2.40-2.57 (16H, m), 1.54 (16H, d, J 6.8), 1.25 (48H, d, J 7.3), 0.85 (24H, q, J 6.2).

Intermediate 16

Intermediate 17

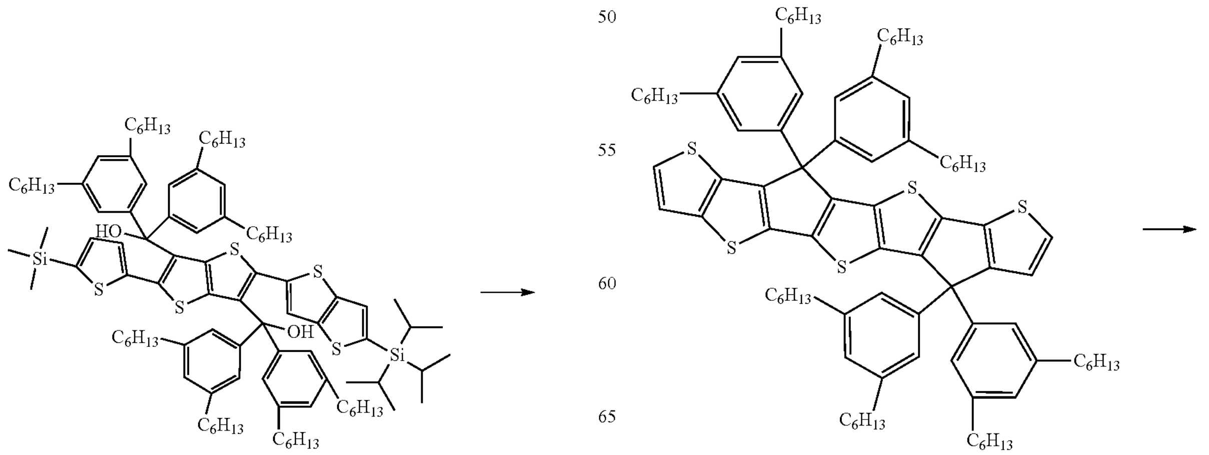

-continued

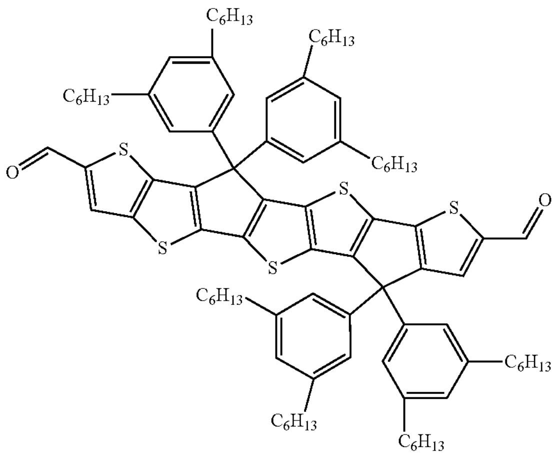

Intermediate 18 lp;3p

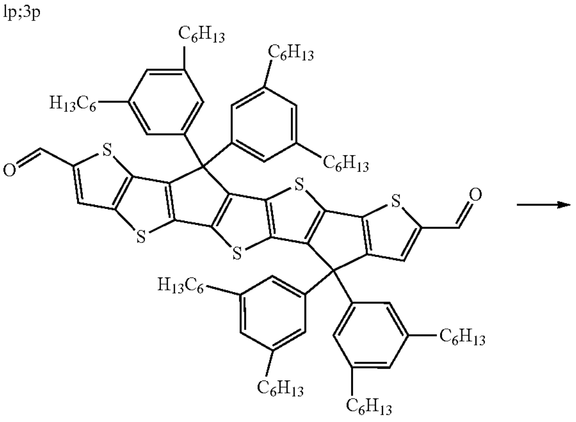

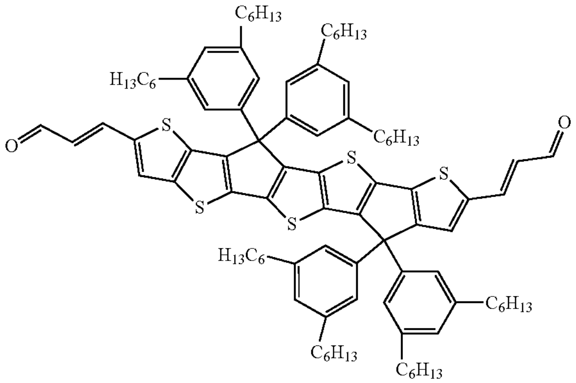

To a solution of intermediate 16 (500 mg, 0.37 mmol) in anhydrous tetrahydrofuran (22 $cm^3$) at −78° C. is added dropwise n-butyllithium (0.6 $cm^3$, 1.5 mmol, 2.5 M in hexane) over 10 minutes. After addition, the reaction mixture is stirred at −78° C. for 60 minutes. N,N-Dimethylformamide (0.15 $cm^3$, 2.2 mmol) is added and the mixture allowed to warm to 23° C. over 17 hours. Ether (50 $cm^3$) and water (50 $cm^3$) are added and the mixture stirred at 23° C. for 30 minutes. The product is extracted with ether (3×100 $cm^3$). The combined organics are dried over anhydrous magnesium sulfate, filtered and the solvent removed in vacuo. The crude is purified using column chromatography (40-60 petrol:dichloromethane; 8:2) to give intermediate 17 (95 mg, 18%) as a dark red oil. $^1H$ NMR (400 MHz, $CDCl_3$) 9.70-9.85 (1H, s), 9.69-9.75 (1H, s), 7.83-7.87 (1H, s), 7.56 (1H, s), 6.83 (4H, s), 6.71 (8H, dd, J 12.8, 1.3), 2.29-2.53 (16H, m), 1.36-1.55 (16H, m), 1.05-1.27 (48H, m), 0.76 (24H, q, J 6.8).

To a solution of intermediate 17 (1.00 g, 0.71 mmol) and tributyl(1,3-dioxolan-2-ylmethyl)-phosphonium bromide (573 mg, 1.55 mmol) in anhydrous tetrahydrofuran (50 $cm^3$) is added sodium hydride (169 mg, 4.23 mmol, 60% dispersion in mineral oil). The reaction is then stirred at 23° C. for 18 hours. The reaction is cooled to 0° C. and hydrochloric acid (5 $cm^3$, 10% in water) is added and the mixture stirred at 0° C. for 40 minutes and at 23° C. for 2 hours. Water (25 $cm^3$) is added and the mixture extracted with ether (3×50 $cm^3$). The combined organic layer is washed with brine (50 $cm^3$) before drying over anhydrous magnesium sulfate, filtered and the solvent removed in vacuo. The crude is triturated in acetonitrile (100 $cm^3$) at 50° C. for 1 hour. The solvent is decanted and the material dried to give intermediate 18 (920 mg, 89%) as a dark purple oil. $^1H$ NMR (400 MHz, $CDCl_3$) 9.48-9.55 (2H, m), 7.41-7.52 (3H, m), 7.18 (1H, s), 6.64-6.89 (12H, m), 6.27-6.42 (2H, m), 2.34-2.50 (16H, m), 1.39-1.54 (16H, m), 1.10-1.29 (48H, m), 0.70-0.80 (24H, m).

Compound 7

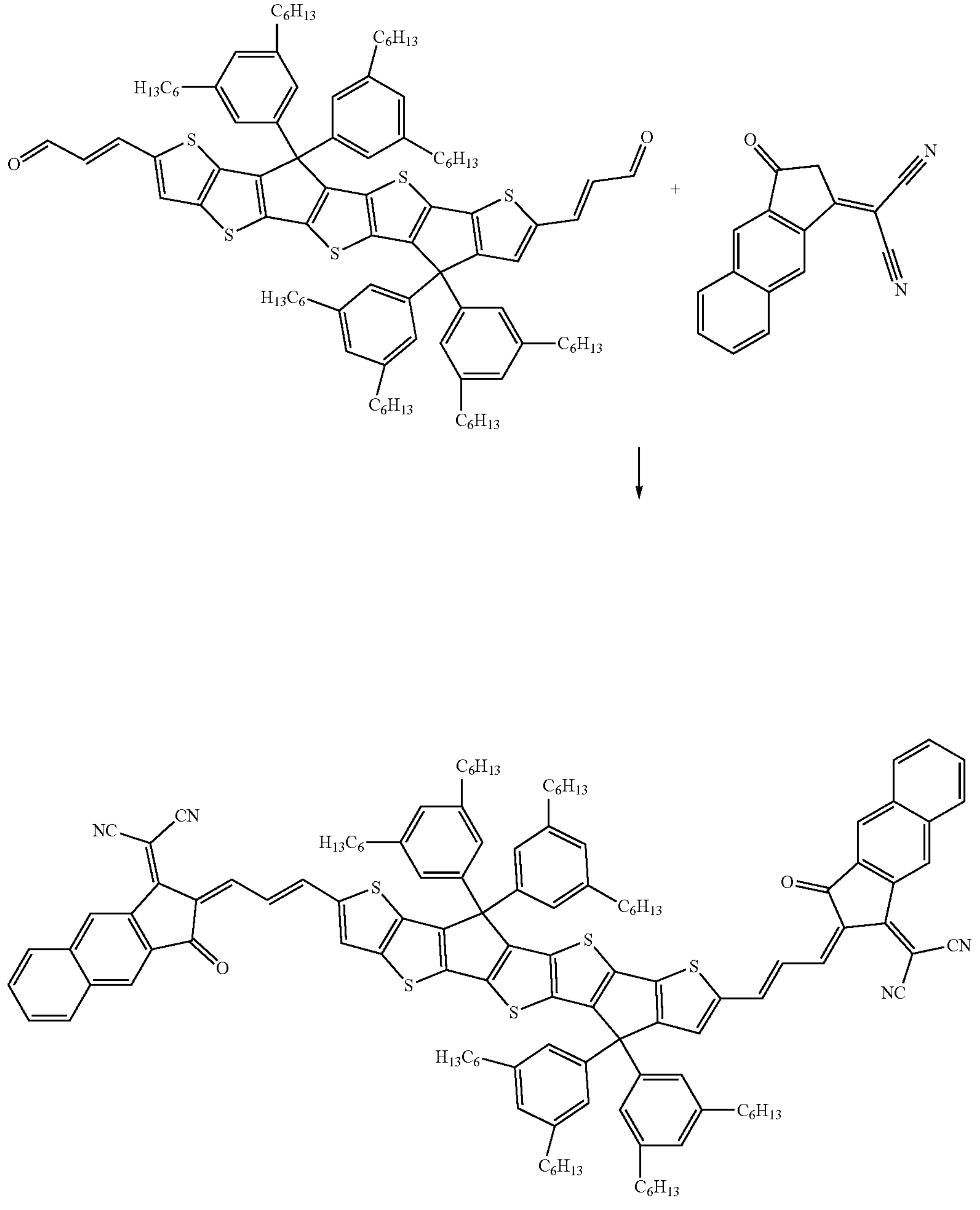

To a solution of intermediate 18 (120 mg, 0.082 mmol) in anhydrous chloroform (6.5 $cm^3$) at 0° C. is added 2-(3-oxo-2,3-dihydrocyclo-penta[b]naphthalen-1-ylidene)-malononitrile (79.7 mg, 0.326 mmol) followed by pyridine (0.46 $cm^3$). The resulting solution is then degassed for 15 minutes. The ice bath is removed and the mixture allowed to warm to 23° C. and stirred for 15 minutes. Acetonitrile (50 $cm^3$) is added to form a heavy suspension and the solid collected by filtration to give compound 7 (145 mg, 92%) as a dark brown solid. $^1H$ NMR (400 MHz, $CD_2Cl_2$) 9.07 (2H, d, J 5.4), 8.53-8.67 (2H, m), 8.36-8.44 (2H, m), 8.23-8.29 (2H, m), 7.94-8.05 (4H, m), 7.46-7.66 (7H, m), 7.34 (1H, s), 6.73-6.92 (12H, m), 2.35-2.48 (16H, m), 1.40-1.56 (16H, m), 1.17 (48H, d, J 2.4), 0.66-0.81 (24H, m).

Example 8

Compound 8

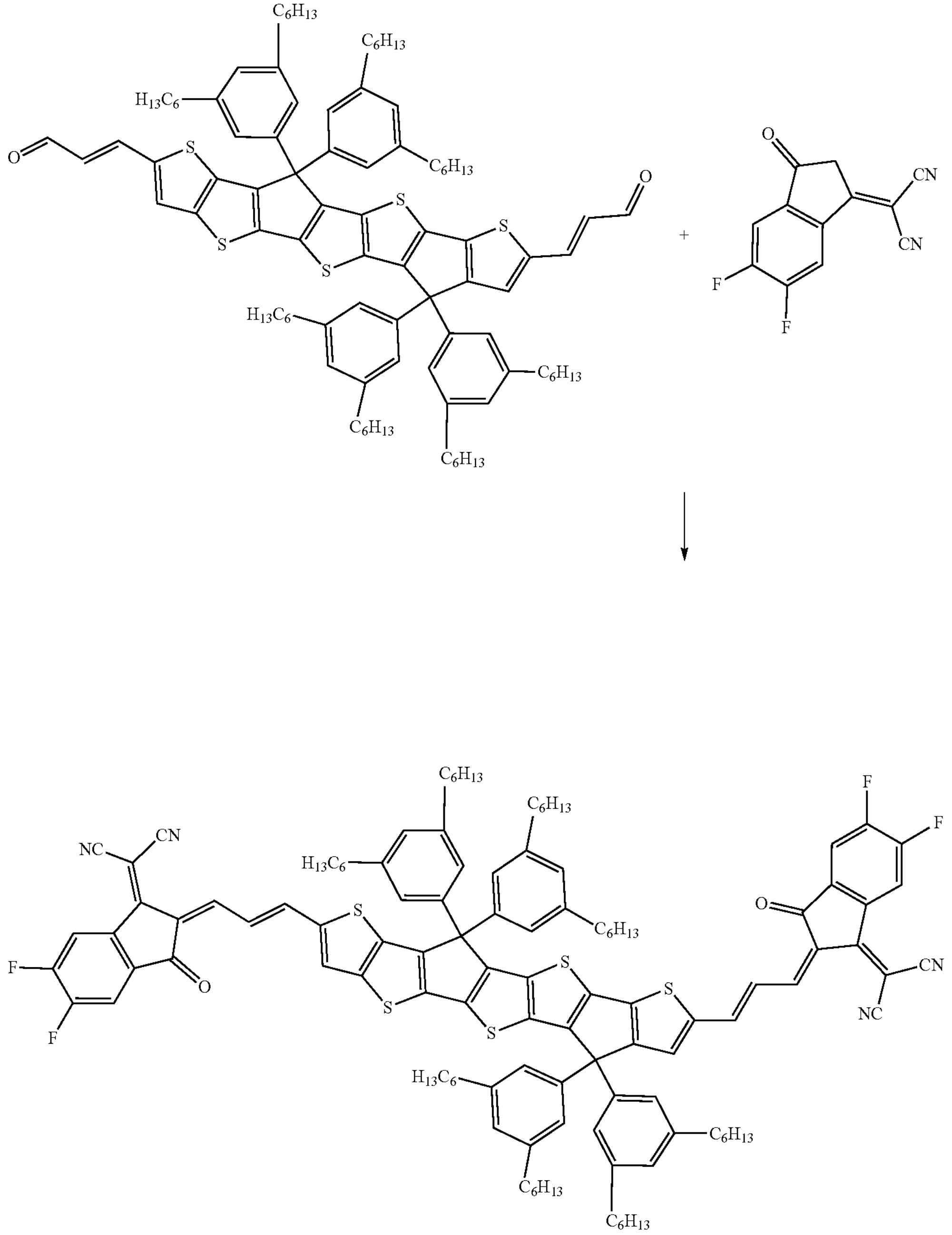

To a solution of intermediate 18 (70 mg, 0.048 mmol) in anhydrous chloroform (3.8 $cm^3$) at 0° C. is added 2-(5,6-difluoro-3-oxo-indan-1-ylidene)-malononitrile (43.8 mg, 0.190 mmol) followed by pyridine (0.27 $cm^3$). The resulting solution is degassed for 5 minutes. The ice bath is removed and the reaction mixture allowed to warm to 23° C. and stirred for 15 minutes. Acetonitrile (50 $cm^3$) is added and the solid collected by filtration to give compound 8 (78 mg, 87%) as a dark brown solid. $^1H$ NMR (400 MHz, $CD_2Cl_2$) 8.27-8.57 (6H, m), 7.46-7.61 (5H, m), 7.33 (1H, s), 6.66-6.94 (12H, m), 2.42 (16H, q, J 7.6), 1.35-1.57 (16H, m), 1.04-1.31 (48H, m), 0.64-0.82 (24H, m).

Example 9

Intermediate 19

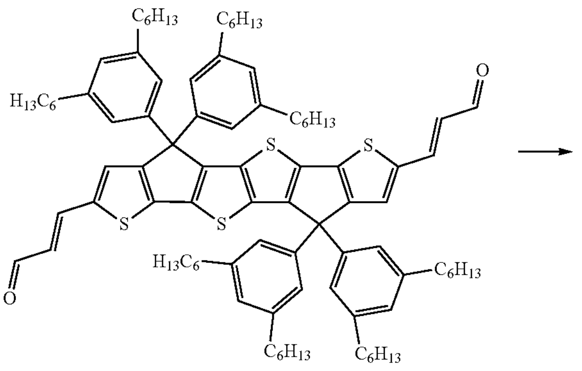

-continued

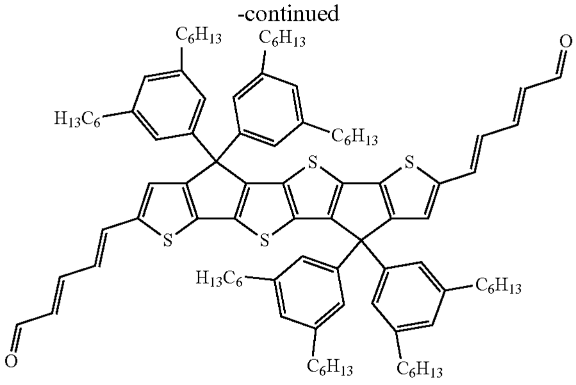

To a solution of tributyl(1,3-dioxolan-2-ylmethyl)-phosphonium bromide (591 mg, 1.60 mmol), intermediate 8 (1.03 g, 0.73 mmol) and anhydrous tetrahydrofuran (40 $cm^3$) at 0° C. is added sodium hydride (174 mg, 4.36 mmol, 60% dispersion in mineral oil). The reaction is then stirred at 23° C. for 16 hours and then cooled to 0° C. before hydrochloric acid (10 $cm^3$, 10% in water) is added. The mixture is then stirred at 0° C. for 20 minutes and at 23° C. for 6 hours. Ethyl acetate (100 $cm^3$) and water (100 $cm^3$) are added and the organic layer washed with water (100 $cm^3$), brine (100 $cm^3$) before drying over anhydrous magnesium sulfate, filtered and the solvent removed in vacuo. The crude is purified by column chromatography using a graded solvent system (40-60 petrol:ethyl acetate; 1:0 to 9:1) to give intermediate 19 (781 mg, 73%) as a purple/black oily solid. $^1$H NMR (400 MHz, $CD_2Cl_2$) 9.55 (2H, d, J 7.9), 7.20 (2H, dd, J 15.0, 11.1), 7.08-7.15 (4H, m), 6.91 (4H, s), 6.70-6.84 (10H, m), 6.16 (2H, dd, J 15.0, 7.9), 2.48 (16H, t, J 7.6), 1.45-1.57 (16H, m), 1.19-1.33 (48H, m), 0.80-0.87 (24H, m).

Compound 9

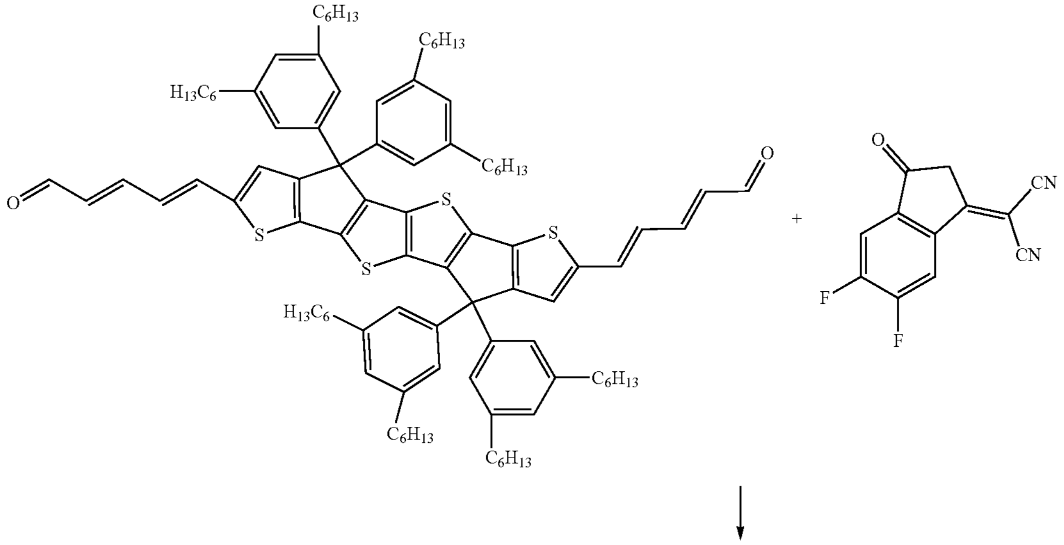

-continued

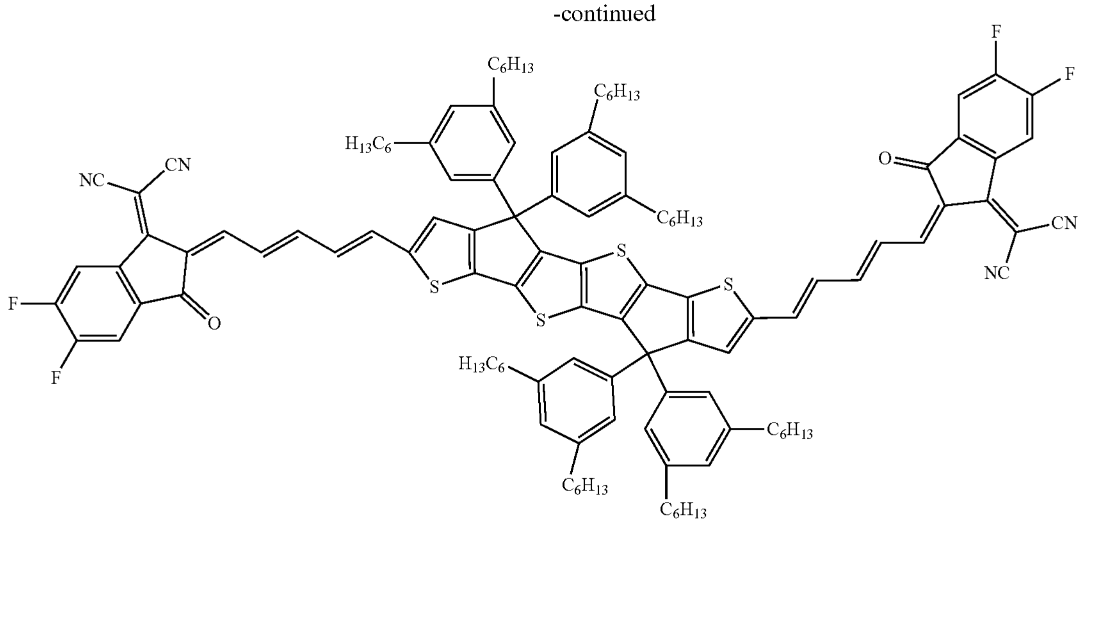

To a degassed solution of intermediate 19 (200 mg, 0.14 mmol), anhydrous chloroform (22 $cm^3$) and pyridine (0.77 $cm^3$, 9.6 mmol) at 0° C. is added 2-(5,6-difluoro-3-oxo-indan-1-ylidene)-malononitrile (126 mg, 0.55 mmol). The reaction mixture is then stirred at 0° C. for 70 minutes before adding to stirred methanol (150 $cm^3$) and the mixture stirred for 25 minutes at 23° C. The solid collected by filtration, washed with methanol (6×10 $cm^3$), acetonitrile (3×10 $cm^3$), 40-60 petrol (3×10 $cm^3$), cyclohexane (3×10 $cm^3$), diethyl ether (3×10 $cm^3$), ethyl acetate (3×10 $cm^3$), acetone (3×10 $cm^3$) and 2-butanone (3×10 $cm^3$). The solid is triturated with boiling ether (50 $cm^3$) and the collected solid washed with ether (2×50 $cm^3$) to give compound 9 (53 mg, 20%) as a black solid. $^1H$ NMR (400 MHz, $CD_2Cl_2$) 8.49 (2H, dd, J 10.1, 6.6), 8.37 (2H, d, J 12.0), 8.16-8.27 (2H, m), 7.60-7.69 (2H, m), 7.19-7.32 (6H, m), 6.89-7.03 (6H, m), 6.81 (8H, s), 2.49 (16H, t, J 7.6), 1.46-1.58 (16H, m), 1.19-1.34 (48H, m), 0.81-0.88 (24H, m).

Example 10

Compound 10

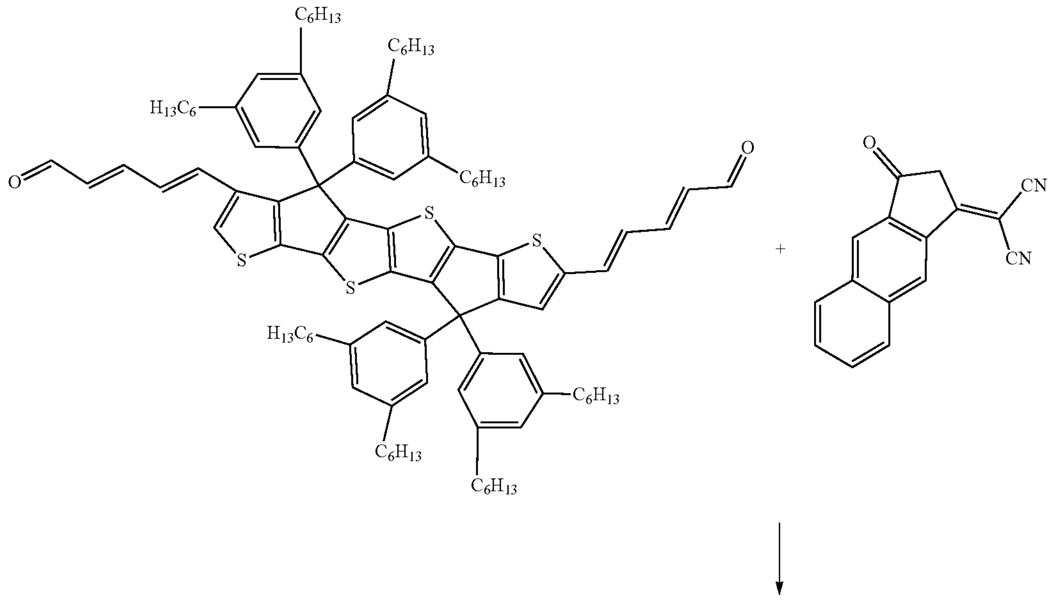

-continued

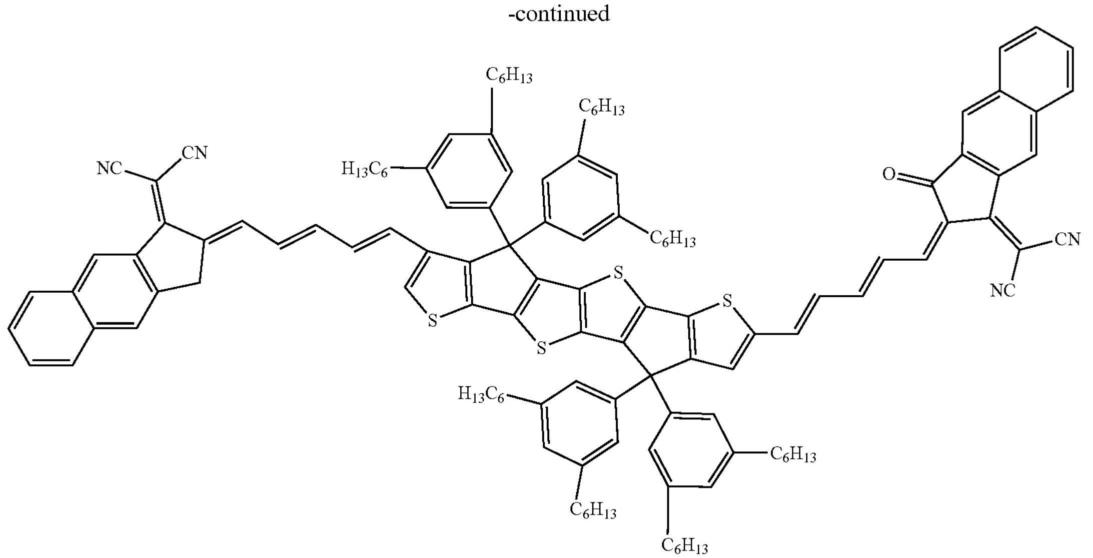

To a degassed solution of intermediate 19 (200 mg, 0.14 mmol), anhydrous chloroform (15 $cm^3$) and pyridine (0.77 $cm^3$, 9.6 mmol) at 0° C. is added 2-(3-oxo-2,3-dihydro-cyclopenta[b]naphthalen-1-ylidene)-malononitrile (133 mg, 0.55 mmol). The reaction mixture is then stirred at 0° C. for 110 minutes before adding to stirred methanol (150 $cm^3$) and the mixture stirred for 15 minutes at 23° C. The solid collected by filtration, washed with methanol (5x10 $cm^3$), acetonitrile (3x10 $cm^3$), 40-60 petrol (3x10 $cm^3$), cyclohexane (3x10 $cm^3$), ethyl acetate (3x10 $cm^3$), diethyl ether (3x10 $cm^3$), acetone (3x10 $cm^3$) and 2-butanone (3x10 $cm^3$). The solid is triturated with boiling ether (2x50 $cm^3$) and the collected solid washed with ether (2x50 $cm^3$) to give compound 10 (143 mg, 55%) as a black solid. $^1H$ NMR (400 MHz, $CD_2Cl_2$) 9.15 (2H, s), 8.30-8.49 (6H, m), 8.03-8.13 (4H, m), 7.66-7.74 (4H, m), 7.18-7.34 (6H, m), 7.01 (2H, dd, J 14.6, 11.6), 6.93 (4H, s), 6.83 (8H, s), 2.50 (16H, t, J 7.5), 1.46-1.61 (16H, m), 1.18-1.36 (48H, m), 0.78-0.90 (24H, m).

Example 11

Intermediate 20

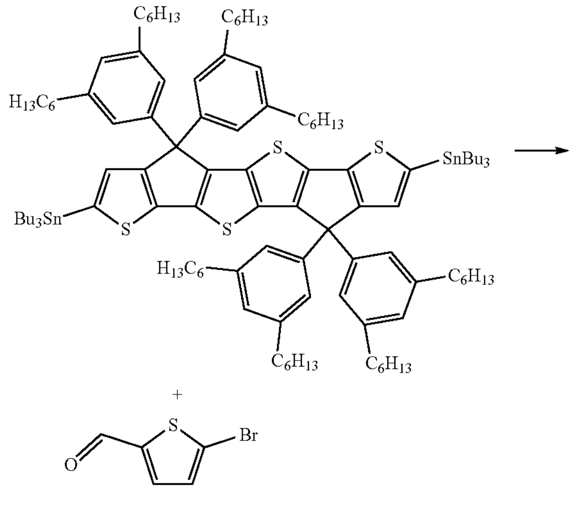

-continued

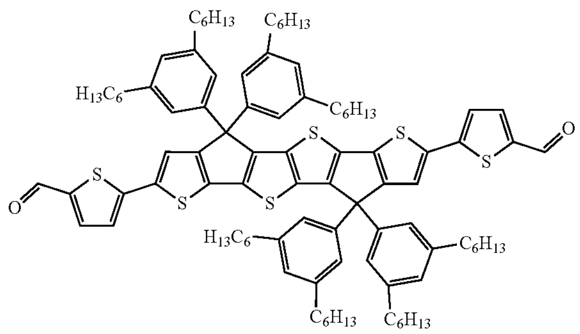

To a degassed solution of 5-bromo-thiophene-2-carbaldehyde (1.05 $cm^3$, 8.83 mmol), anhydrous toluene (240 $cm^3$) and intermediate 9 (7.56 g, 4.01 mmol) is added tris(dibenzylideneacetone)dipalladium(0) (294 mg, 0.32 mmol) and tris(o-tolyl)phosphine (366 mg, 1.20 mmol). The reaction mixture is then further degassed before heating at 80° C. for 45 hours. The reaction mixture is allowed to cool to 23° C. and the solvent removed in vacuo. The crude is purified by column chromatography using a graded solvent system (40-60 petrol:dichloromethane; 1:0 to 0:1) followed by trituration in acetonitrile (20 $cm^3$) to give intermediate 20 (1.30 g, 21%) as a dark red solid. $^1H$ NMR (400 MHz, $CDCl_3$) 9.82 (2H, s), 7.63 (2H, d, J 4.0), 7.29 (2H, s), 7.18 (2H, d, J 4.0), 6.90 (4H, s), 6.82 (8H, d, J 1.1), 2.49 (16H, t, J 7.6), 1.47-1.57 (16H, m), 1.19-1.32 (48H, m), 0.80-0.87 (24H, m).

Intermediate 21

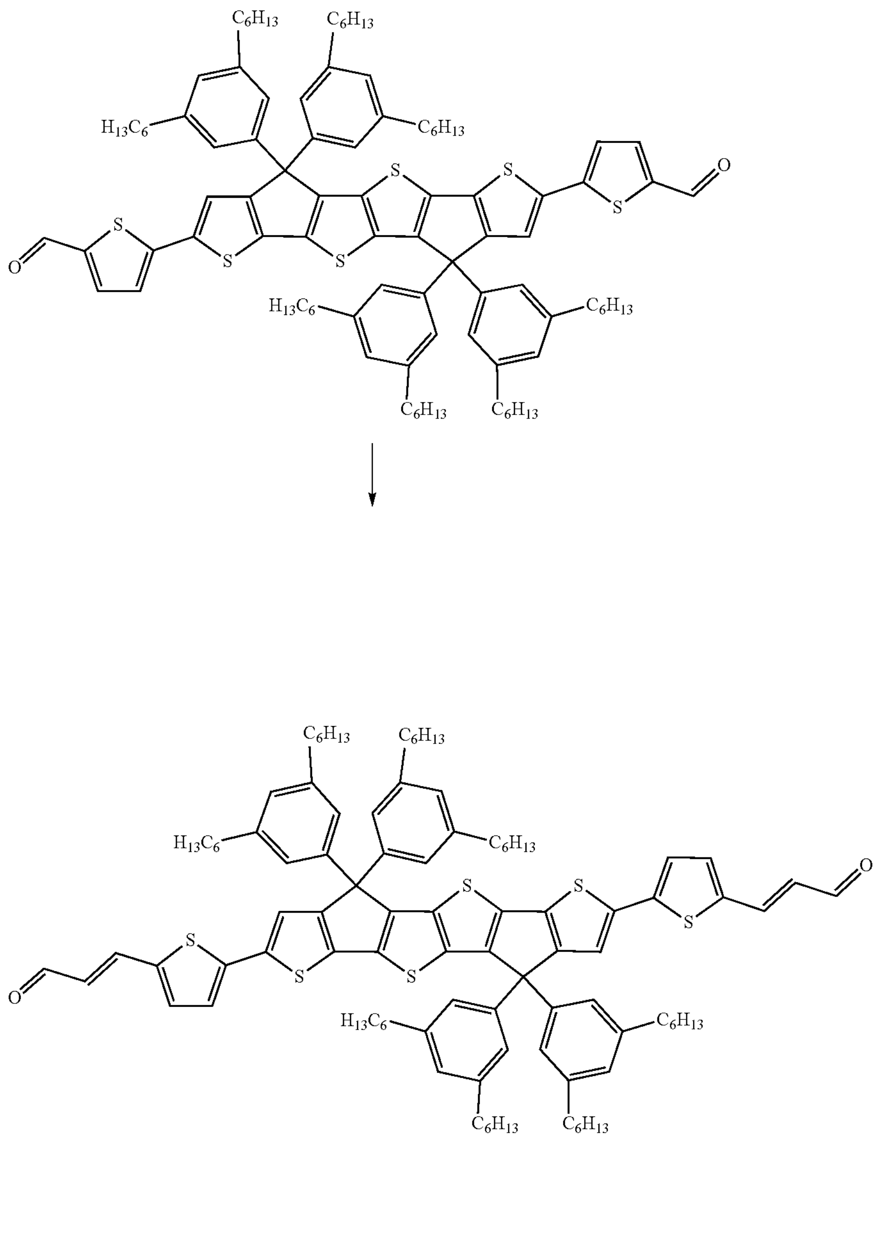

To a mixture of tributyl(1,3-dioxolan-2-ylmethyl)-phosphonium bromide (692 mg, 1.87 mmol), intermediate 20 (1.30 g, 0.85 mmol) and anhydrous tetrahydrofuran (46 $cm^3$) is added sodium hydride (204 mg, 5.11 mmol, 60% dispersion in mineral oil) and the reaction stirred at 23° C. for 70 hours. Hydrochloric acid (12 $cm^3$, 10% in water) is added and the mixture stirred for 3 hours. Ethyl acetate (75 $cm^3$) and water (75 $cm^3$) are then added and the organic layer extracted with ethyl acetate (10 $cm^3$). The combined organic layers are washed with water (75 $cm^3$) and brine (75 $cm^3$) before drying over anhydrous magnesium sulfate, filtered and the solvent removed in vacuo. The crude is triturated in warm acetonitrile (2×20 $cm^3$) to give intermediate 21 (1.29 g, 96%) as a purple solid. $^1H$ NMR (400 MHz, $CDCl_3$) 9.60 (2H, d, J 7.7), 7.50 (2H, d, J 15.5), 7.23 (2H, d, J 3.9), 7.20 (2H, s), 7.10 (2H, d, J 4.0), 6.89 (4H, s), 6.82 (8H, d, J 1.5), 6.40 (2H, dd, J 15.4, 7.7), 2.49 (16H, t, J 7.7), 1.47-1.56 (16H, m), 1.18-1.32 (48H, m), 0.78-0.87 (24H, m).

Compound 11

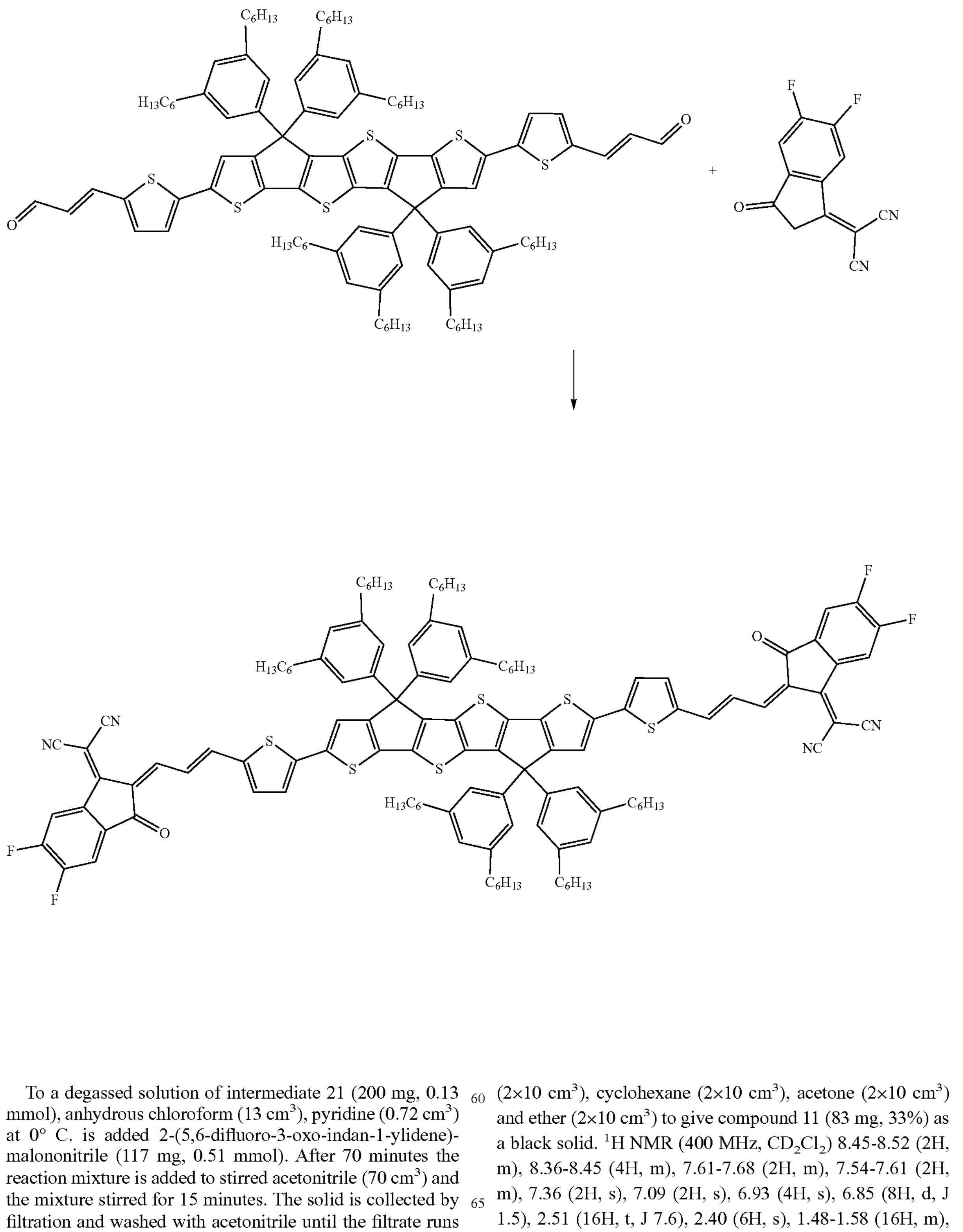

To a degassed solution of intermediate 21 (200 mg, 0.13 mmol), anhydrous chloroform (13 $cm^3$), pyridine (0.72 $cm^3$) at 0° C. is added 2-(5,6-difluoro-3-oxo-indan-1-ylidene)-malononitrile (117 mg, 0.51 mmol). After 70 minutes the reaction mixture is added to stirred acetonitrile (70 $cm^3$) and the mixture stirred for 15 minutes. The solid is collected by filtration and washed with acetonitrile until the filtrate runs colourless. The solid is further washed with 40-60 petrol (2×10 $cm^3$), cyclohexane (2×10 $cm^3$), acetone (2×10 $cm^3$) and ether (2×10 $cm^3$) to give compound 11 (83 mg, 33%) as a black solid. $^1H$ NMR (400 MHz, $CD_2Cl_2$) 8.45-8.52 (2H, m), 8.36-8.45 (4H, m), 7.61-7.68 (2H, m), 7.54-7.61 (2H, m), 7.36 (2H, s), 7.09 (2H, s), 6.93 (4H, s), 6.85 (8H, d, J 1.5), 2.51 (16H, t, J 7.6), 2.40 (6H, s), 1.48-1.58 (16H, m), 1.21-1.33 (48H, m), 0.80-0.86 (24H, m).

Example 12

Compound 12

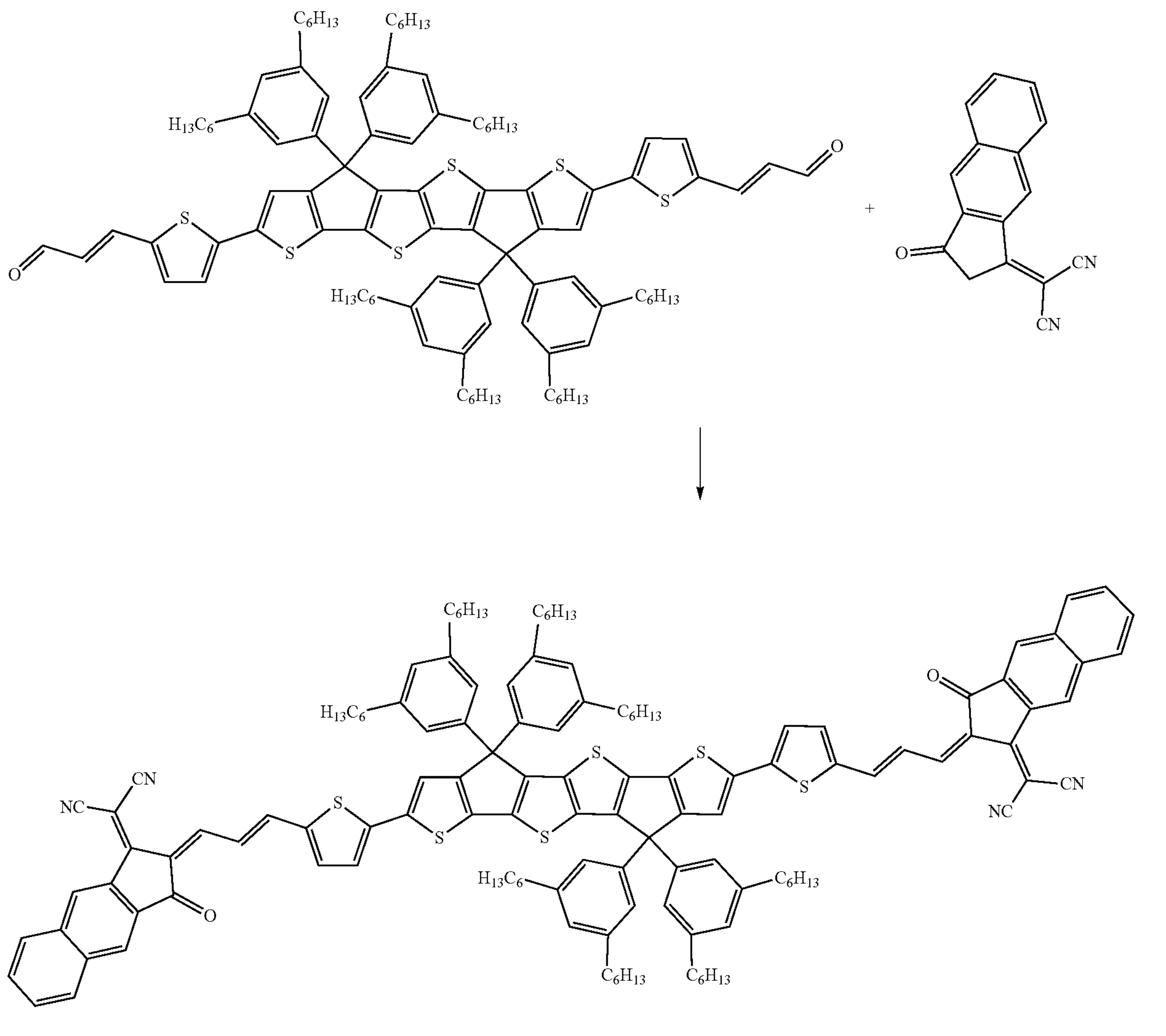

To a degassed solution of intermediate 21 (200 mg, 0.13 mmol), anhydrous chloroform (13 $cm^3$) and pyridine (0.72 $cm^3$) at 0° C. is added 2-(3-oxo-2,3-dihydro-cyclopenta[b] naphthalen-1-ylidene)-malononitrile (124 mg, 0.51 mmol). The reaction mixture is stirred for 165 minutes and then added to stirred acetonitrile (75 $cm^3$) and the mixture stirred for 45 minutes. The solid is collected by filtration and washed with acetonitrile until the filtrate runs colourless. The solid is further washed with 40-60 petrol (2×10 $cm^3$), cyclohexane (2×10 $cm^3$), acetone (2×10 $cm^3$) and ether (2×10 $cm^3$) to give compound 12 (186 mg, 72%) as a black solid. $^1H$ NMR (400 MHz, 1,2-dichlorobenzene-d4, 100° C.) 9.02 (2H, s), 8.65 (2H, dd, J 14.7, 11.6), 8.39 (2H, d, J 11.5), 8.16 (2H, s), 7.68-7.79 (4H, m), 7.38-7.46 (6H, m), 7.10-7.15 (10H, m), 7.00 (2H, d, J 4.1), 6.96 (2H, d, J 4.0), 6.94 (4H, s), 2.51 (16H, t, J 7.5), 1.51-1.61 (16H, m), 1.18-1.30 (48H, m), 0.78-0.84 (24H, m).

Example 13

Intermediate 22

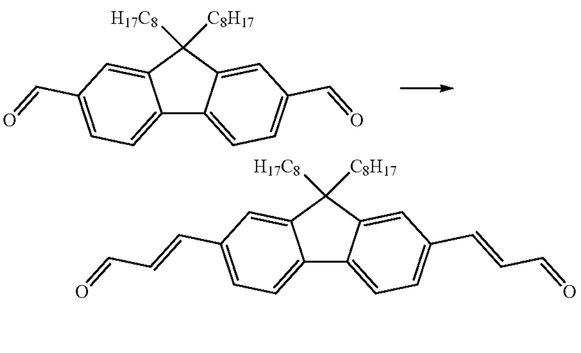

To a solution of tributyl(1,3-dioxolan-2-ylmethyl)-phosphonium bromide (3.64 g, 9.85 mmol), 9,9-dioctyl-9H-fluorene-2,7-dicarbaldehyde (2.00 g, 4.48 mmol) and anhydrous tetrahydrofuran (250 $cm^3$) is added sodium hydride (1.07 g, 26.9 mmol, 60% dispersion in mineral oil), initially at 23° C., but after the addition of ~50%, the reaction is cooled to 0° C. and the remainder added. The reaction is then stirred at 23° C. for 16 hours. The reaction is then cooled to 0° C. before the addition of hydrochloric acid (40 $cm^3$, 10% in water) which is then stirred at 0° C. for 35 minutes and then at 23° C. for a further 26 hours. Ethyl acetate (250 $cm^3$) and water (500 $cm^3$) are then added and the organic layer washed with water (500 $cm^3$) and brine (150 $cm^3$) before drying over anhydrous magnesium sulfate, filtered and the solvent removed in vacuo. The crude is partially purified by column chromatography using a graded solvent system (40-60 petrol:dichloromethane; 1:0 to 0:1) to give intermediate 22 (2.7 g) as a yellow solid. $^1$H NMR (400 MHz, $CDCl_3$) 9.75 (2H, d, J 7.6), 7.78 (2H, d, J 7.9), 7.52-7.62 (6H, m), 6.80 (2H, dd, J 15.9, 7.7), 1.97-2.04 (4H, m), 0.98-1.23 (20H, m), 0.80 (6H, t, J 7.1), 0.51-0.65 (4H, m).

Compound 13

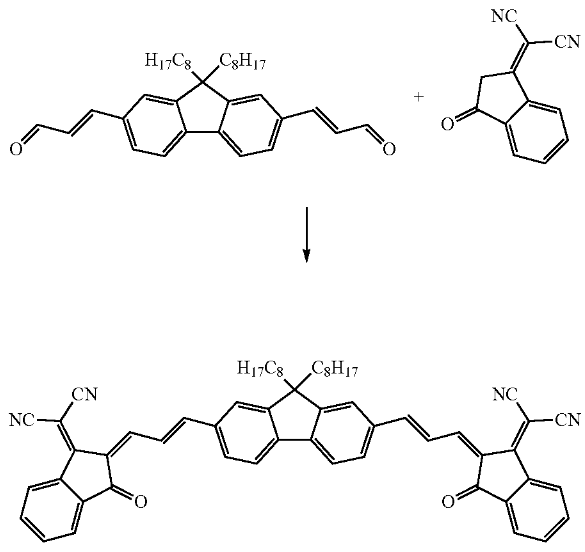

To a degassed solution of partially pure intermediate 22 (250 mg), chloroform (40 $cm^3$) and pyridine (2.8 $cm^3$) is added 2-(3-oxo-indan-1-ylidene)-malononitrile (389 mg, 2.01 mmol). The reaction is then cooled to 0° C. and stirred for 140 minutes. The reaction mixture is then concentrated in vacuo, added to stirred methanol (150 $cm^3$) and stirred for 35 minutes. The solid is collected by filtration and washed with methanol (4x10 $cm^3$), 40-60 petrol (4x10 $cm^3$), cyclohexane (4x10 $cm^3$) and acetonitrile (4x10 $cm^3$). The partially purified product is then triturated in boiling cyclohexane (2x50 cm 3) to give compound 13 (70 mg, 16%) as a black solid. $^1$H NMR (400 MHz, $CDCl_3$) 8.91 (2H, dd, J 15.3, 11.5), 8.70-8.74 (2H, m), 8.55 (2H, d, J 11.4), 7.94-7.98 (2H, m), 7.71-7.85 (8H, m), 7.66 (2H, s), 7.52 (2H, d, J 15.1), 2.02-2.13 (4H, m), 0.97-1.23 (20H, m), 0.78 (6H, t, J 7.0), 0.56-0.68 (4H, m).

Example 14

Intermediate 23

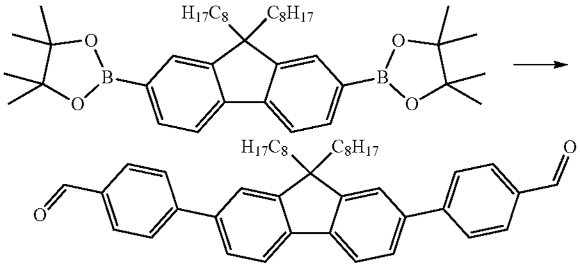

To a degassed mixture of 2-[9,9-dioctyl-7-(4,4,5,5-tetramethyl-1,3,2-dioxaborolan-2-yl)fluoren-2-yl]-4,4,5,5-tetramethyl-1,3,2-dioxaborolane (5.00 g, 7.78 mmol), 4-bromo-benzaldehyde (3.02 g, 16.3 mmol), toluene (100 $cm^3$) and [1,4]dioxane (100 $cm^3$) is added potassium phosphate tribasic (7.17 g, 33.8 mmol) and tetrakis(triphenylphosphine)palladium(0) (225 mg, 0.19 mmol). The mixture is further degassed and then heated at 100° C. for 16 hours. The reaction mixture allowed to cool to 23° C. and the solvent removed in vacuo. The crude is purified by column chromatography using a graded solvent system (40-60 petrol:ethyl acetate; 1:0 to 0:1) to give intermediate 23 (2.03 g, 44%) as a yellow oil. $^1$H NMR (400 MHz, $CDCl_3$) 10.08 (2H, s), 7.99-8.02 (4H, m), 7.81-7.87 (6H, m), 7.66 (2H, dd, J 7.9, 1.7), 7.62 (2H, d, J 1.6), 2.03-2.11 (4H, m), 1.01-1.21 (20H, m), 0.78 (6H, t, J 7.0), 0.66-0.75 (4H, m).

Intermediate 24

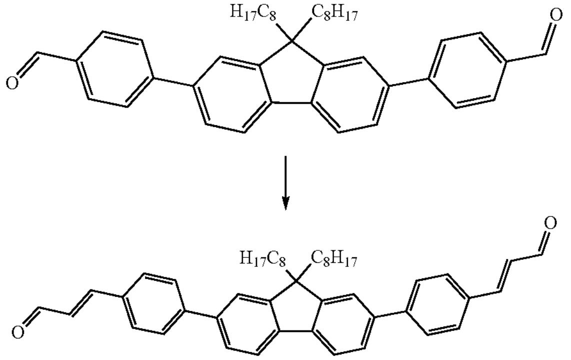

To a solution of tributyl(1,3-dioxolan-2-ylmethyl)-phosphonium bromide (1.75 g, 4.75 mmol), intermediate 23 (1.29 g, 2.16 mmol) and anhydrous tetrahydrofuran (120 $cm^3$) at 0° C. is added sodium hydride (518 mg, 12.9 mmol, 60% dispersion in mineral oil). The reaction is then stirred at 23° C. for 16 hours before hydrochloric acid (30 $cm^3$, 10% in water) is added at 0° C. The reaction is stirred at 0° C. for 20 minutes and at 23° C. for 4 hours. Ethyl acetate (100 $cm^3$) and water (100 $cm^3$) are then added and the organic layer washed with water (100 $cm^3$), brine (50 $cm^3$) before drying over anhydrous magnesium sulfate, filtered and the solvent removed in vacuo. The crude is purified by column chromatography using a graded solvent system (40-60 petrol:

ethyl acetate; 1:0 to 7:3) to give intermediate 24 (1.11 g, 79%) as a yellow solid. $^1$H NMR (400 MHz, $CDCl_3$) 9.75 (2H, d, J 7.7), 7.81 (2H, d, J 7.9), 7.73-7.78 (4H, m), 7.66-7.71 (4H, m), 7.64 (2H, dd, J 7.9, 1.6), 7.60 (2H, d, J 1.2), 7.55 (2H, d, J 15.9), 6.79 (2H, dd, J 15.9, 7.7), 2.01-2.10 (4H, m), 0.99-1.21 (20H, m), 0.78 (6H, t, J 7.0), 0.65-0.76 (4H, m).

Compound 14

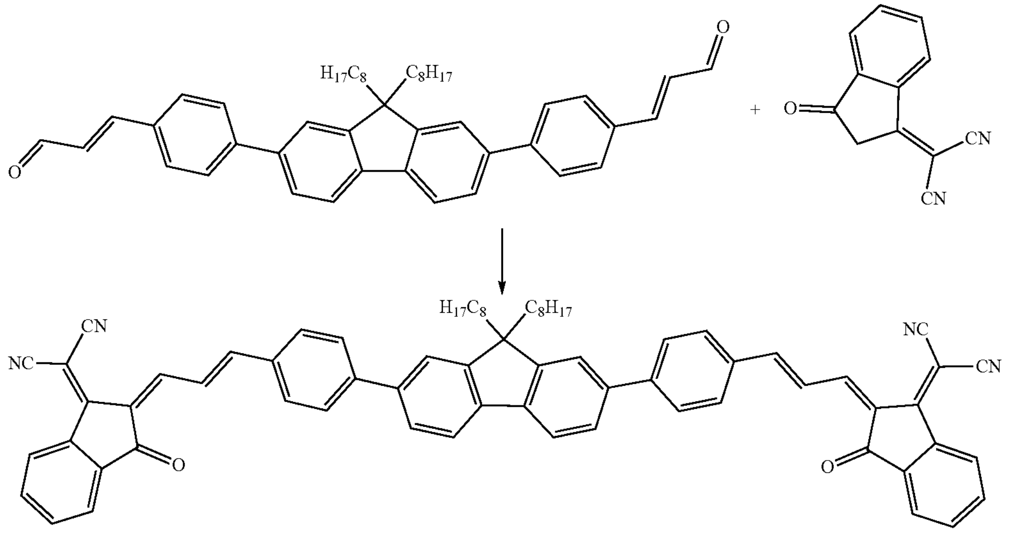

To a degassed solution of intermediate 24 (250 mg, 0.38 mmol), chloroform (46 cm$^3$) and pyridine (2.1 cm$^3$) at 0° C. is added of 2-(3-oxo-indan-1-ylidene)-malononitrile (298 mg, 1.54 mmol). The reaction is stirred for 3 hours and then partially concentrated in vacuo. The mixture is added to stirred methanol (150 cm$^3$) and the suspension stirred for 10 minutes. The solid is collected by filtration and washed with methanol (3x10 cm$^3$) 40-60 petrol (4x10 cm$^3$), cyclohexane (4x10 cm$^3$), acetonitrile (4x10 cm$^3$) and ether (4x10 cm$^3$). The solid is then recrystallized (acetone) to give compound 14 (51 mg, 13%) as a black powder. $^1$H NMR (400 MHz, $CDCl_3$) 8.89 (2H, dd, J 15.3, 11.5), 8.70-8.75 (2H, m), 8.55 (2H, d, J 11.5), 7.94-7.98 (2H, m), 7.85-7.87 (14H, m), 7.64-7.70 (2H, m), 7.63 (2H, s), 7.48 (2H, d, J 15.3), 2.01-2.14 (4H, m), 1.02-1.23 (20H, m), 0.79 (6H, t, J 7.0), 0.67-0.76 (4H, m).

Example 15

Intermediate 25

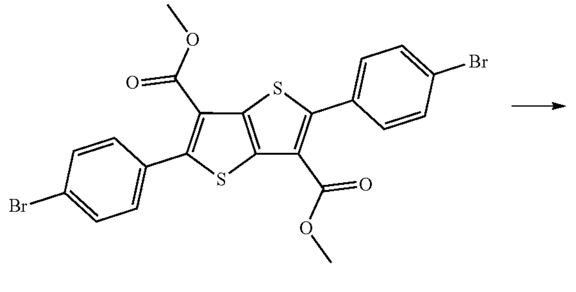

-continued

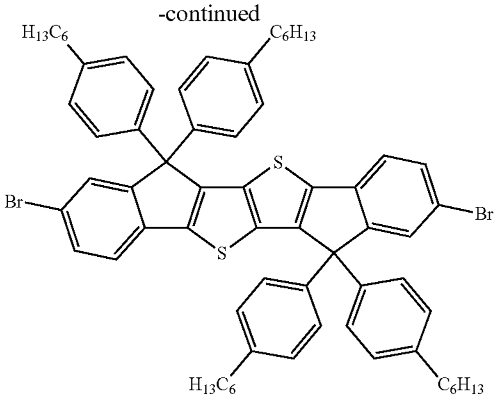

To a solution of 1-bromo-4-hexyl-benzene (10.0 g, 41.5 mmol) in anhydrous tetrahydrofuran (70 cm$^3$) at −78° C. is added n-butyllithium (16.6 cm$^3$, 41.5 mmol, 2.5 M in tetrahydrofuran) over 10 minutes. The reaction mixture is then stirred for 1 hour before methyl 5-bromo-2-[5-(4-bromo-2-methoxycarbonyl-phenyl)thieno[3,2-b]thiophen-2-yl]benzoate (4.70 g, 8.29 mmol) is added. The reaction mixture is then allowed to warm to 23° C. and stirred for 17 hours. Water (100 cm$^3$) is added and the mixture stirred for 1 hour. Ether (100 cm$^3$) is added and the organic washed with water (2x50 cm$^3$), brine (20 cm$^3$) and dried over anhydrous magnesium sulfate, filtered and the solvent removed in vacuo. The solid triturated in ice-cold 40-60 petrol (30 cm$^3$) to give a yellow solid. The solid is taken up in toluene (40 cm$^3$) and p-toluene sulfonic acid (2 g) is added. The reaction is stirred at 23° C. for 2 hours and at 50° C. for 1 hour. The mixture is filtered and the solvent removed in vacuo. The solid is triturated in acetone to give intermediate 25 (3.40 g, 37%) as a yellow solid. $^1$H NMR (400 MHz, $CDCl_3$) 7.44 (2H, s), 7.19 (2H, s), 7.12-7.14 (2H, m), 6.98-7.15 (16H, m), 2.42-2.53 (8H, m), 1.44-1.57 (8H, m), 1.12-1.28 (24H, m), 0.75-0.80 (12H, m).

Intermediate 26

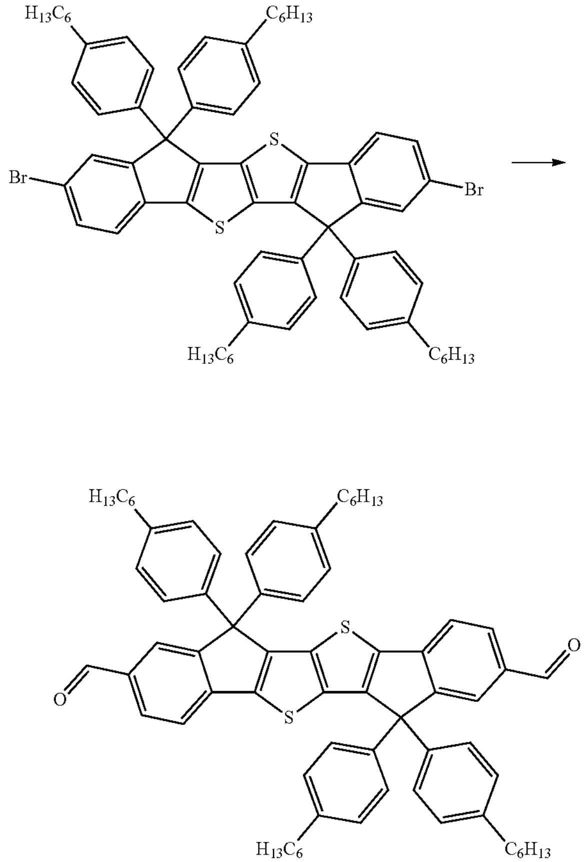

To a solution of intermediate 25 (8.75 g, 7.85 mmol) and anhydrous tetrahydrofuran (95 $cm^3$) at −78° C. is added dropwise n-butyllithium (7.2 $cm^3$, 18 mmol, 2.5 M in hexanes). The reaction mixture is stirred for 1 hour before N,N-dimethylformamide (1.5 $cm^3$, 20 mmol) is added dropwise. The reaction mixture is allowed to warm to 23° C. and stirred for 17 hours. Water (100 $cm^3$) is added and the aqueous extracted with dichloromethane (2×100 $cm^3$). The combined organics is washed with brine (50 $cm^3$), dried over anhydrous magnesium sulfate, filtered and the solvent removed in vacuo. The crude is purified by column chromatography using a graded solvent system (heptane:ethyl acetate, 9:1 then 8:2) to give intermediate 26 (3.30 g, 42%) as a yellow solid. $^1$H NMR (400 MHz, $CDCl_3$) 9.95 (2H, s), 7.94 (2H, s), 7.81-7.83 (2H, m), 7.49-7.54 (2H, m), 7.05-7.21 (16H, m), 2.51-2.62 (8H, m), 1.52-1.67 (8H, m), 1.25-1.41 (24H, m), 0.84-0.91 (12H, m).

Intermediate 27

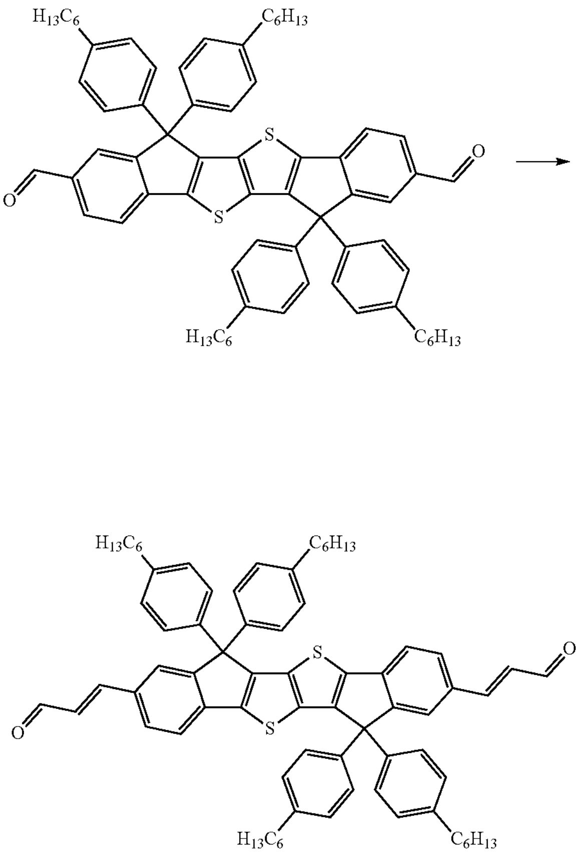

To a mixture of tributyl(1,3-dioxolan-2-ylmethyl)-phosphonium bromide (200 mg, 0.54 mmol), intermediate 26 (250 mg, 0.25 mmol) and anhydrous tetrahydrofuran (13 $cm^3$) at 0° C. is added sodium hydride (59 mg, 1.5 mmol, 60% dispersion in mineral oil). The reaction mixture is allowed to warm to 23° C. and stirred for 17 hours. Dichloromethane (20 $cm^3$) and hydrochloric acid (40 $cm^3$, 2N) are added and the mixture stirred for 30 minutes. The organic layer separated, washed with water (20 $cm^3$), dried over anhydrous magnesium sulfate, filtered and the solvent removed in vacuo. The crude is purified by column chromatography using a graded solvent system (40-60 petrol: dichloromethane; 9:11 to 7:13) to give intermediate 27 (228 mg, 87%) as a yellow solid. $^1$H NMR (400 MHz, $CDCl_3$) 9.68 (2H, d, J 7.7), 7.61 (2H, s), 7.39-7.56 (6H, m), 7.08-7.20 (16H, m), 6.68 (2H, dd, J 15.9, 7.6), 2.53-2.62 (8H, m), 1.56-1.66 (8H, m), 1.26-1.39 (24H, m), 0.84-0.92 (12H, m).

Compound 15

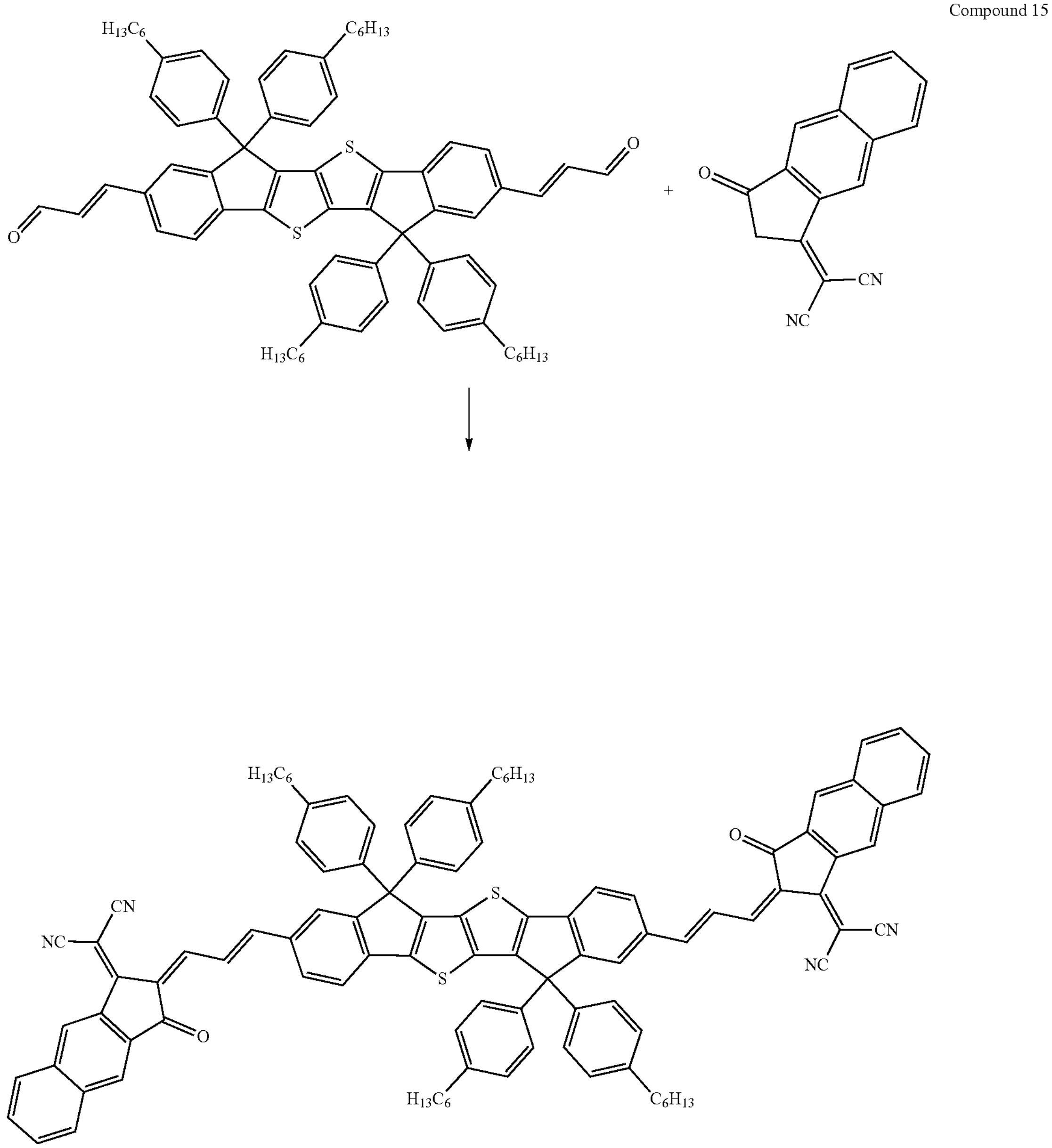

To a degassed mixture of 2-(3-oxo-2,3-dihydro-cyclopenta[b]naphthalen-1-ylidene)-malononitrile (115 mg, 0.469 mmol), intermediate 27 (100 mg, 0.094 mmol) and chloroform (10 $cm^3$) is added pyridine (520 mg) and the mixture further degassed. The reaction mixture is stirred for 17 hours and methanol (30 $cm^3$) added. The solid collected by filtration and the filtrate concentrated in vacuo. To the filtrate is added methanol (30 $cm^3$) and the solid collected by filtration. The combined solids are then purified by column chromatography using a graded solvent system (40-60 petrol:dichloromethane; 2:3 to 1:4) to give compound 15 (66 mg, 46%) as a green solid. $^1H$ NMR (400 MHz, $CDCl_3$) 9.13 (2H, s), 8.74-8.86 (2H, m), 8.48 (2H, d, J 11.6), 8.32 (2H, s), 7.96-8.05 (4H, m), 7.58-7.71 (8H, m), 7.33-7.42 (4H, m), 7.12 (8H, d, J 8.4), 7.06 (8H, d, J 8.4), 2.29-2.68 (8H, m), 1.53 (8H, t, J 7.5), 1.15-1.32 (24H, m), 0.72-0.84 (12H, m).

Example 16

Compound 16

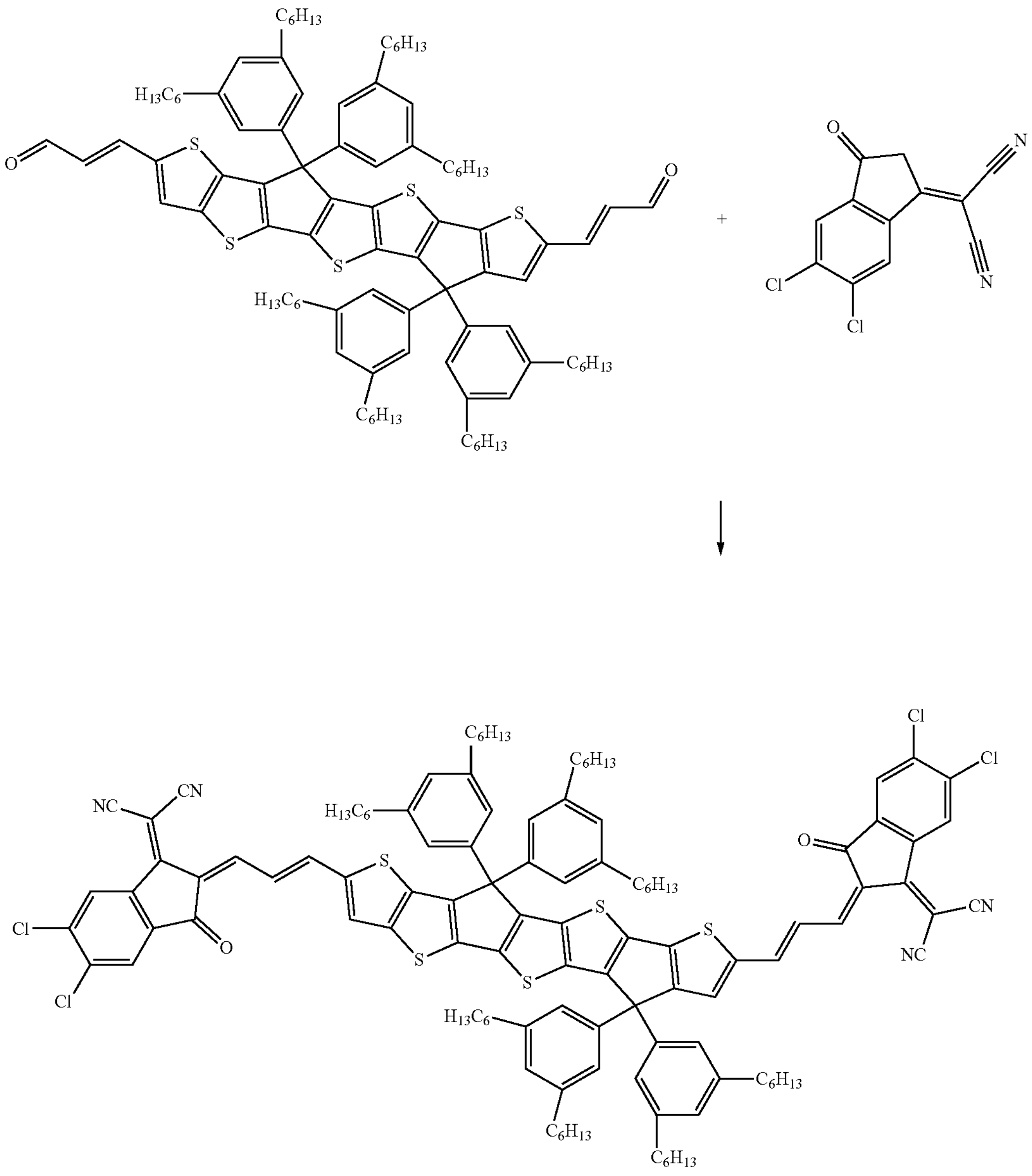

To a degassed solution of intermediate 18 (280 mg, 0.190 mmol) in anhydrous chloroform (15 $cm^3$) at 0° C. is added 2-(5,6-dichloro-3-oxo-2,3-dihydro-1H-inden-1-ylidene)propanedinitrile (250 mg, 0.952 mmol) and pyridine (1.1 $cm^3$, 13 mmol). The reaction mixture is then degassed for 25 minutes, the cooling removed, and the mixture stirred for 2.5 hours at 23° C. The reaction mixture is then poured into stirred acetonitrile (250 $cm^3$) and the solid collected by filtration. The crude is then purified by column chromatography using a graded solvent system (40-60 petrol:dichloromethane; 3:2 to 0:1) followed by trituration in acetone (100 $cm^3$) to give compound 16 (245 mg, 66%) as a black solid. $^1H$ NMR (400 MHz, $CDCl_3$) 8.72-8.81 (2H, m), 8.39-8.61 (4H, m), 7.87-7.95 (2H, m), 7.50-7.69 (3H, m), 7.39 (1H, s), 6.75-7.02 (12H, m), 2.54 (16H, q, J 8.0), 1.47-1.68 (16H, m), 1.18-1.36 (48H, m), 0.70-0.98 (24H, m).

Example 17

Intermediate 28

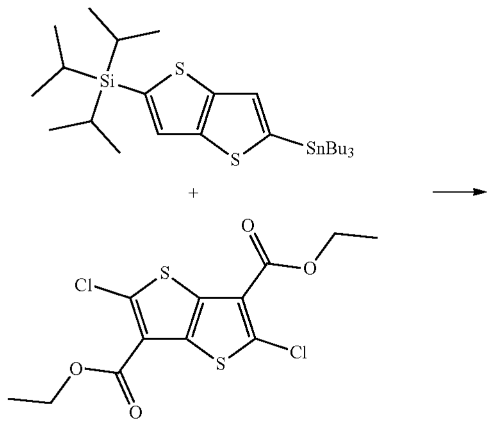

-continued

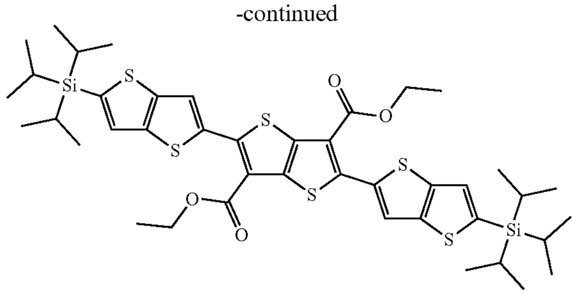

A mixture of 2,5-dichloro-3,6-diethyl ester-thieno[3,2-b]thiophene-3,6-dicarboxylic acid (7.5 g, 21 mmol), tributyl [5-[tris(1-methylethyl)silyl]thieno[3,2-b]thien-2-yl]-stanne (17.8 g, 30.4 mm) and anhydrous toluene (300 $cm^3$) is degassed for 25 minutes. To the mixture is added tetrakis (triphenylphosphine)palladium(0) (500 mg, 0.43 mmol) and the mixture further degassed for 15 minutes. The mixture is stirred at 85° C. for 17 hours and then filtered hot through a celite plug (hot toluene). The solvent reduced in vacuo to 100 $cm^3$ and cooled in an ice bath to form a suspension. The product is filtered, washed with water (100 $cm^3$) and methanol (100 $cm^3$) to give intermediate 28 (9.5 g, 71%) as a yellow crystalline solid. $^1H$ NMR (400 MHz, $CDCl_3$) 7.75 (2H, d, J 0.7), 7.30 (2H, d, J 0.7), 4.36 (4H, q, J 7.2), 1.23-1.43 (12H, m), 1.07 (36H, d, J 7.3).

Intermediate 29

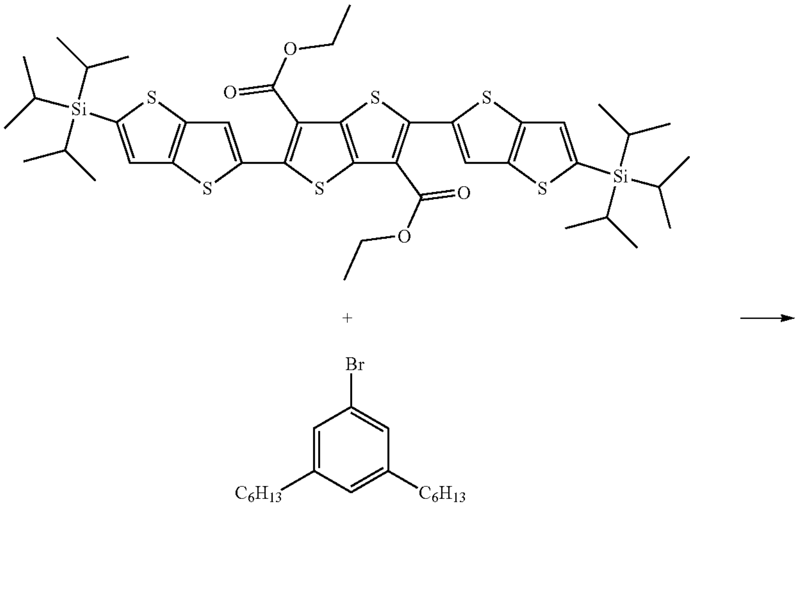

-continued

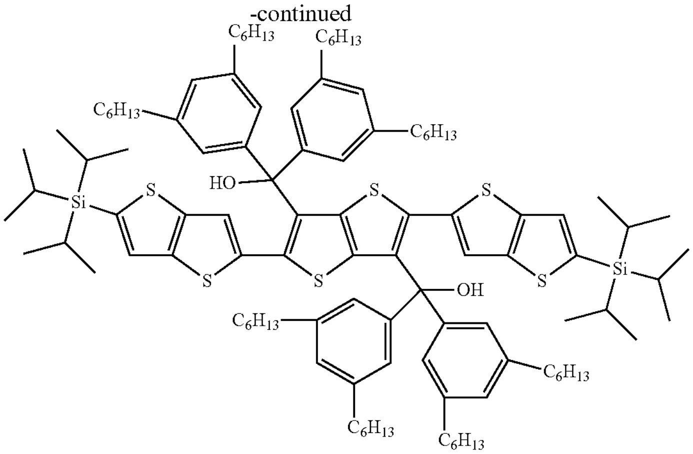

To a solution of 1-bromo-3,5-dihexyl-benzene (5.21 g, 16.0 mmol) in anhydrous tetrahydrofuran (100 $cm^3$) at −78° C. is added dropwise n-butyllithium (6.4 $cm^3$, 16 mmol, 2.5 M in haxane) over 30 minutes. The reaction mixture is then stirred for 2 hours. Intermediate 28 (2.80 g, 3.21 mmol) is then added and the reaction mixture allowed to warm to 23° C. and stirred for 17 hours. Water (100 $cm^3$) is added and the mixture stirred for a further 1 hour. Ether (100 $cm^3$) is added and the organic layer washed with water (2×50 $cm^3$), dried over anhydrous magnesium sulfate, filtered and the solvent removed in vacuo. The crude is purified by column chromatography using a graded solvent system (40-60 petrol: dichloromethane; 19:1 to 1:4) to give intermediate 29 (3.54 g, 63%) as a pale yellow oil. $^{1}H$ NMR (400 MHz, $CD_2Cl_2$) 7.23 (2H, s), 6.86-7.01 (12H, m), 6.51 (2H, s), 3.41 (2H, s), 2.42-2.61 (16H, m), 1.49-1.61 (16H, m), 1.22-1.45 (54H, m), 1.15 (36H, d, J 7.3), 0.78-0.95 (24H, m).

Intermediate 30

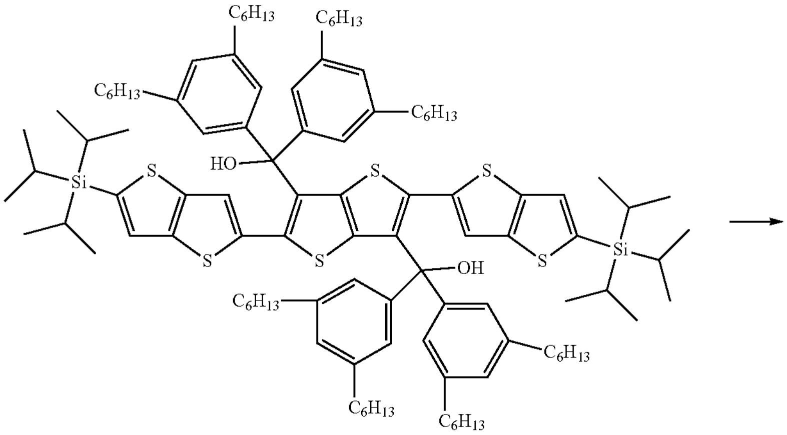

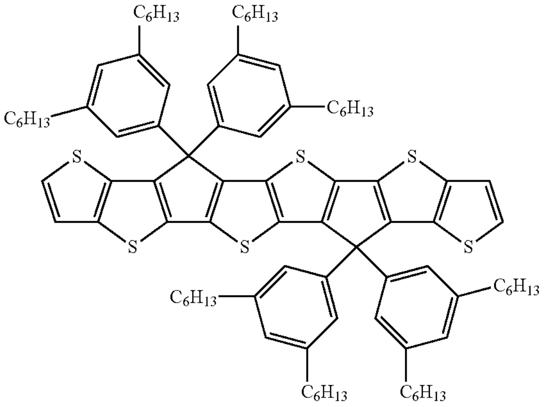

To a degassed suspension of amberlyst 15 strong acid (12 g) in anhydrous ether (100 $cm^3$) at 0° C. is added intermediate 29 (2.95 g, 1.67 mmol) followed by degassing for a further 30 minutes. The resulting suspension is allowed to warm to 23° C. and stirred for 1 hour. The reaction mixture is filtered through a thin celite plug and washed well with ether (200 $cm^3$). The crude is then purified by column chromatography (40-60 petrol) and then taken up in anhydrous tetrahydrofuran (50 $cm^3$) and cooled to 0° C. To the mixture is added a solution of tetrabutylammonium fluoride (3.34 $cm^3$, 3.34 mmol, 1 M in tetrahydrofuran) and the resulting mixture stirred for 30 minutes at 23° C. The solvent is then removed in vacuo and the residue suspended in methanol (200 $cm^3$) and stirred for 30 minutes. The solid collected by filtration to give intermediate 30 (2.02 g, 85%) as a dark orange solid. $^1$H NMR (400 MHz, $CDCl_3$) 7.13-7.21 (4H, m), 6.71-6.84 (12H, m), 2.33-2.49 (16H, m), 1.38-1.48 (16H, m), 1.08-1.22 (48H, m), 0.70-0.80 (24H, m).

Intermediate 31

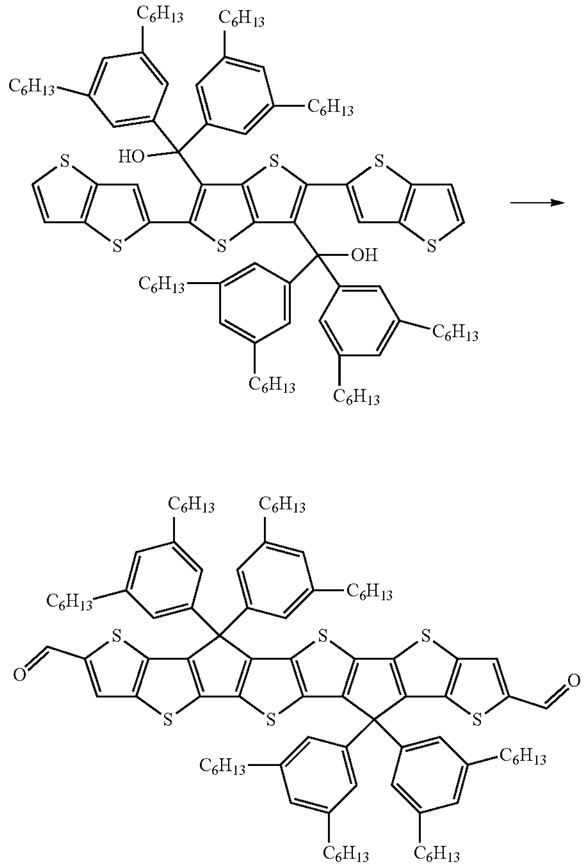

To a solution of intermediate 30 (600 mg, 0.42 mmol) in anhydrous tetrahydrofuran (25 $cm^3$) at −78° C. is added dropwise n-butyllithium (0.68 $cm^3$, 1.7 mmol, 2.5 M in hexane) over 10 minutes. The mixture is then stirred at −78° C. for 1 hour before anhydrous N,N-dimethylformamide (0.17 $cm^3$, 2.5 mmol) is added. The cooling is then removed and the reaction mixture stirred at 23° C. for 2 hours. Water (50 $cm^3$) is added and the mixture stirred for 30 minutes. The organics are extracted with ether (3×50 $cm^3$), combined, dried over anhydrous magnesium sulfate, filtered and the solvent removed in vacuo. The crude product is purified by column chromatography using a graded solvent system (40-60 petrol:dichloromethane; 1:0 to 4:1) to give intermediate 31 (450 mg, 72%) as a dark red sticky solid. $^1$H NMR (400 MHz, $CDCl_3$) 9.79 (2H, s), 7.85 (2H, s), 6.83 (4H, s), 6.71 (8H, d, J 1.0), 2.41 (16H, t, J 7.6), 1.39-1.50 (16H, m), 1.15 (48H, br. s), 0.70-0.80 (24H, m).

Intermediate 32

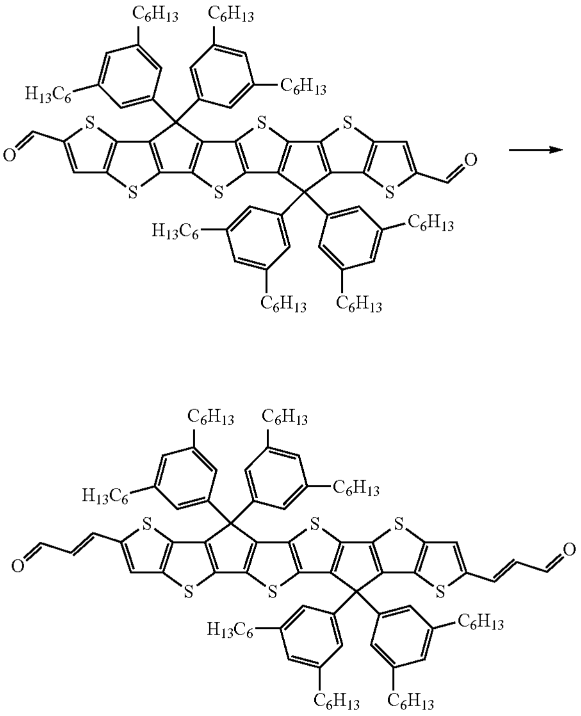

To a solution of intermediate 31 (500 mg, 0.34 mmol) and tributyl(1,3-dioxolan-2-ylmethyl)-phosphonium bromide (276 mg, 0.75 mmol) in tetrahydrofuran (19 $cm^3$) at 0° C. is added sodium hydride (81.4 mg, 2.03 mmol, 60% dispersion in mineral oil). The reaction is slowly warmed to 23° C. and stirred for 16 hours. Aqueous hydrochloric acid (60 $cm^3$, 10%) is added and the reaction mixture heated at 45° C. for 24 hours. The mixture allowed to cool, and the organics extracted with ether (40 $cm^3$). The organic layer is then washed with water (2×20 $cm^3$), dried over anhydrous magnesium sulphate and the solvent removed in vacuo. Purification by column chromatography using a graded solvent system (40-60 petrol:dichloromethane; 5:1 to 3:2) gives intermediate 32 (480 mg, 93%) as a purple solid. $^1$H NMR (400 MHz, $CDCl_3$) 9.62 (2H, d, J 7.6), 7.58 (2H, d, J 15.4), 7.54 (2H, s), 6.93 (4H, d, J 1.5), 6.82 (8H, d, J 1.5), 6.41 (2H, dd, J 15.4, 7.6), 2.51 (16H, t, J 7.6), 1.53 (16H, q, J 7.6, 7.0), 1.19-1.34 (48H, m), 0.80-0.88 (24H, m).

Compound 17

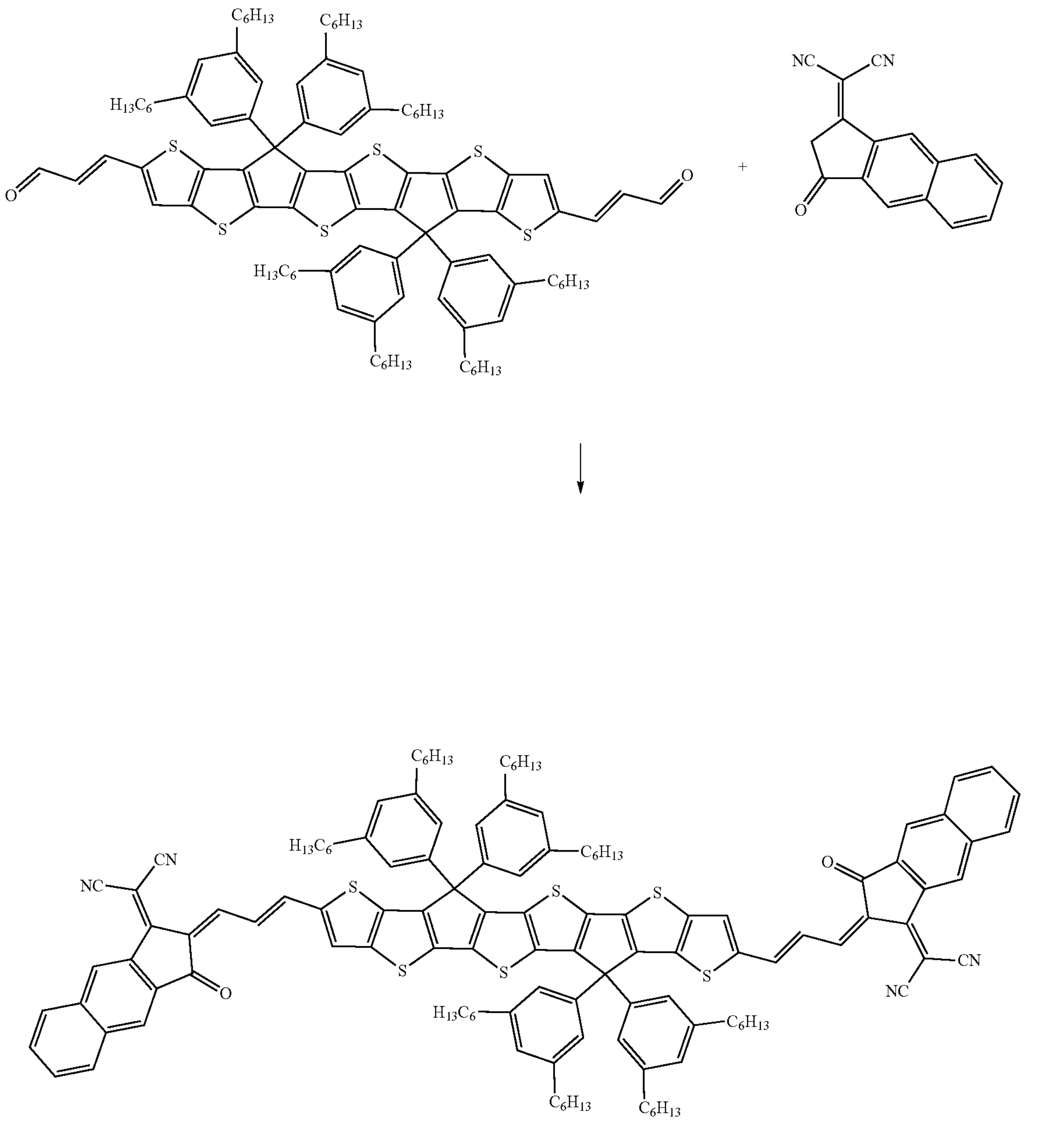

Intermediate 32 (100 mg, 0.066 mmol) and 2-(3-oxo-2,3-dihydro-cyclopenta[b]naphthalen-1-ylidene)-malononitrile (35.2 mg, 0.144 mmol) are suspended in chloroform (5.0 $cm^3$), pyridine (0.37 $cm^3$, 4.6 mmol) added and the reaction mixture stirred at 23° C. for 16 hours. Methanol (30 $cm^3$) is added, the solid collected by filtration and washed with methanol (10 $cm^3$). The crude is purified by column chromatography using a graded solvent system (40-60 petrol:dichloromethane; 5:1 to 3:7) to give compound 17 (68 mg, 53%) as a dark solid. $^1H$ NMR (400 MHz, $CDCl_3$) 9.20 (2H, s), 8.72 (2H, s), 8.53 (2H, d, J 11.7), 8.35 (2H, s), 8.00-8.18 (4H, m), 7.67-7.77 (4H, m), 7.65 (2H, s), 7.57 (2H, d, J 14.3), 6.96 (4H, s), 6.86 (8H, s), 2.56 (16H, t, J 7.6), 1.54-1.65 (16H, m), 1.19-1.40 (48H, m), 0.79-0.86 (24H, m).

Example 18

Compound 18

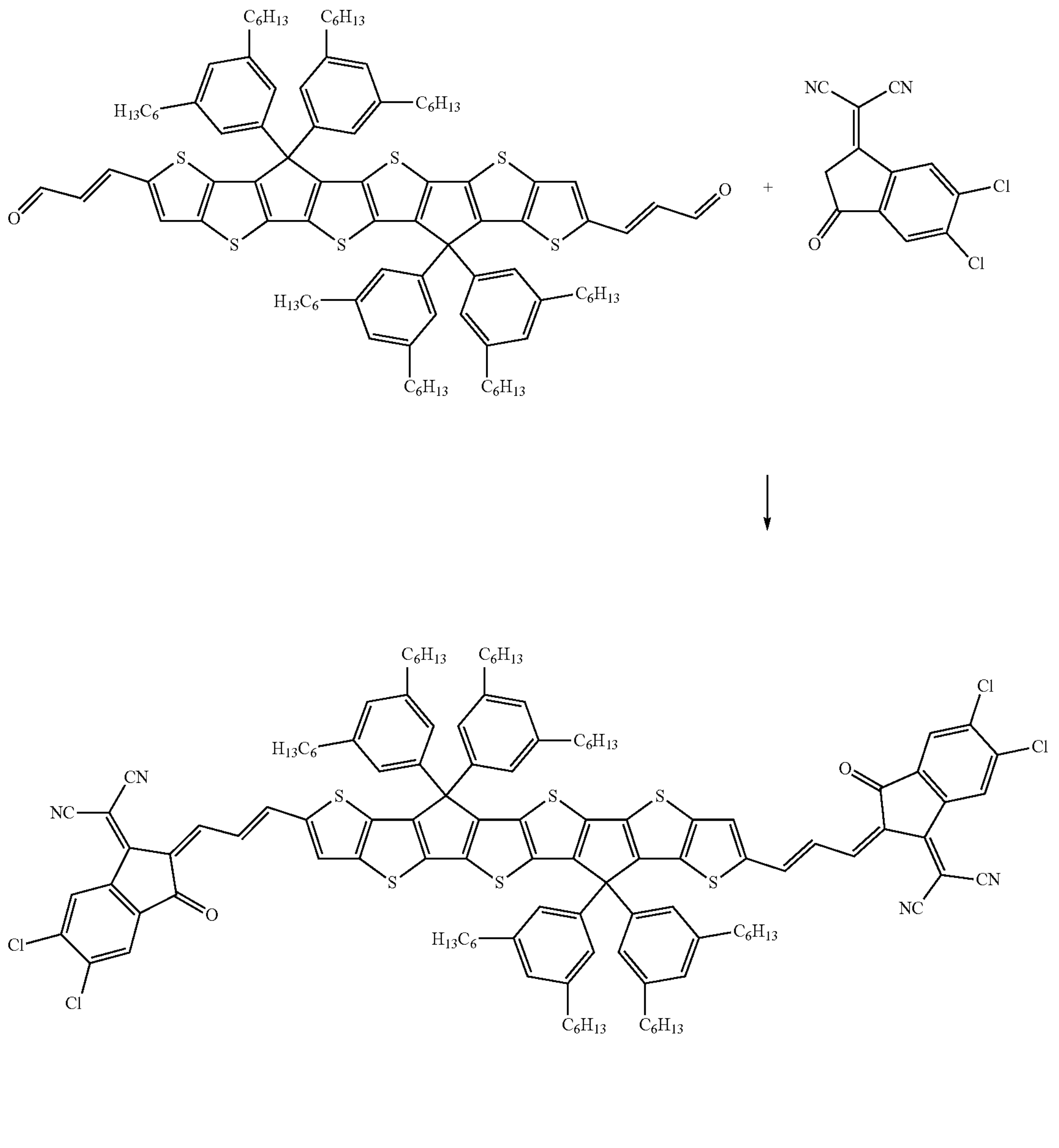

Intermediate 32 (100 mg, 0.066 mmol) and 2-(5,6-dichloro-3-oxo-2,3-dihydro-1H-inden-1-ylidene)propanedinitrile (37.9 mg, 0.144 mmol) are suspended in chloroform (5.0 $cm^3$), pyridine (0.37 $cm^3$, 4.6 mmol) added and the reaction mixture stirred at 23° C. for 16 hours. Methanol (30 $cm^3$) is added, the solid collected by filtration and washed with methanol (10 $cm^3$). The crude is purified by column chromatography using a graded solvent system (40-60 petrol:dichloromethane; 11:9 to 3:7) to give compound 18 (31 mg, 24%) as a dark solid. $^1H$ NMR (400 MHz, $CDCl_3$) 8.76 (2H, s), 8.41-8.58 (4H, m), 7.91 (2H, s), 7.53-7.72 (4H, m), 6.96 (4H, s), 6.83 (8H, s), 2.47-2.58 (16H, m), 1.48-1.62 (16H, m), 1.21-1.39 (48H, m), 0.75-0.82 (24H, m).

Example 19

Intermediate 33

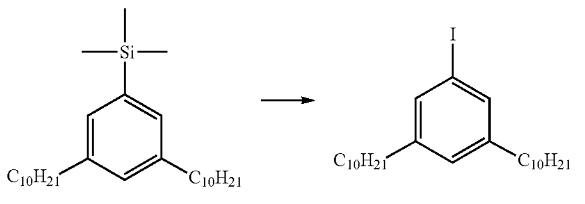

To a solution of 3,5-bis(decyl)phenyl]trimethylsilane (7.28 g, 16.9 mmol) in chloroform (10 $cm^3$) and methanol (10 $cm^3$) in the dark is added silver trifluoroacetate (7.84 g, 35.5 mmol). The mixture cooled to 0° C., iodine (8.58 g, 33.81 mmol) added and the mixture stirred for 90 minutes. The mixture is filtered through a plug of silica (40-60 petrol) and the organic phase washed with saturated aqueous sodium thiosulfate (100 $cm^3$), water (100 $cm^3$) and brine (100 $cm^3$). The organics are dried over anhydrous magnesium sulfate, filtered and the solvent removed in vacuo to give intermediate 33 (6.98 g, 85%) as a white solid. $^1H$ NMR (400 MHz, $CDCl_3$) 7.27 (2H, s), 6.85 (1H, s), 2.43 (4H, t, J 7.8), 1.44-1.55 (4H, m), 1.13-1.29 (28H, m), 0.78-0.84 (6H, m).

Intermediate 34

Intermediate 35

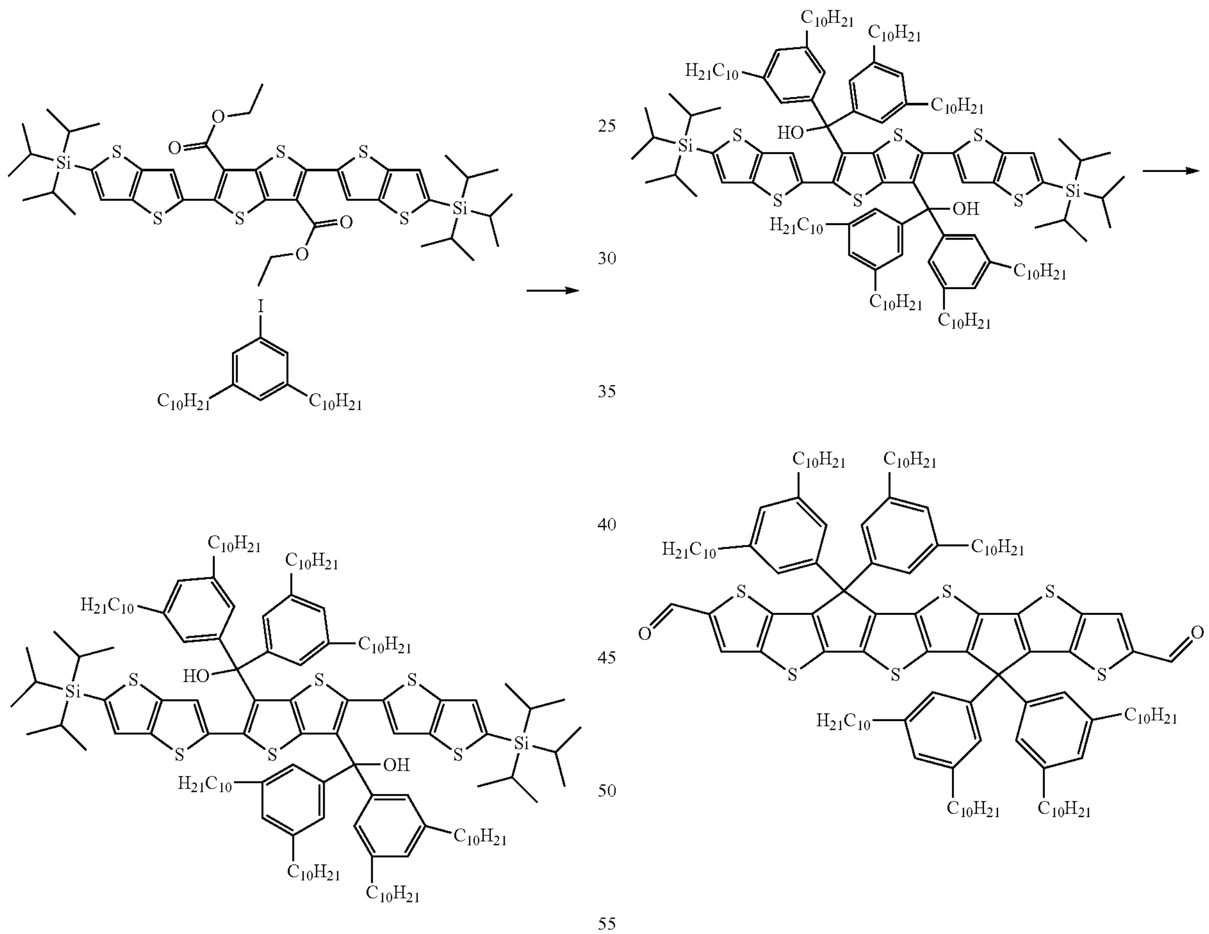

To a solution of intermediate 33 (4.99 g, 10.3 mmol) in anhydrous tetrahydrofuran (37.5 $cm^3$) at −78° C. is added dropwise t-butyllithium (12.1 $cm^3$, 20.6 mmol, 1.7 M in pentane) over 10 minutes. The reaction mixture is then stirred for 1 hour before the cooling is removed for 6 minutes and then the mixture cooled back to −78° C. Intermediate 28 (1.50 g, 1.71 mmol) is then added and the reaction mixture allowed to warm to 23° C. and stirred for 17 hours. Water (5 $cm^3$) is added and the mixture stirred for a further 10 minutes. Ether (100 $cm^3$) and water (50 $cm^3$) are added and the organic layer washed with water (3×20 $cm^3$), dried over anhydrous magnesium sulfate, filtered and the solvent removed in vacuo. The crude is purified by column chromatography using a graded solvent system (40-60 petrol:dichloromethane; 1:0 to 3:1) to give intermediate 34 (2.76 g, 73%) as a pale brown oil. $^1H$ NMR (400 MHz, $CDCl_3$) 7.17 (2H, s), 6.93 (8H, s), 6.88 (4H, s), 6.45 (2H, s), 3.39 (2H, s), 2.42-2.53 (16H, m), 1.48-1.61 (16H, m), 1.07-1.41 (118H, m), 0.83-0.94 (60H, m).

To a degassed solution of intermediate 34 (2.76 g, 1.25 mmol) in toluene (110 $cm^3$) at 60° C. is added Amberlyst 15 strong acid (10.0 g) and the reaction mixture stirred for 17 hours. The hot mixture is filtered and the filtered solid washed with with hot toluene (3×20 $cm^3$). The filtrates combined, and the solvent removed in vacuo. The intermediate is then purified by column chromatography using a graded solvent system (40-60 petrol:dichloromethane; 1:0 to 17:3). The solid is then dissolved in chloroform (55.2 $cm^3$) and N,N-dimethylformamide (1.46 g, 19.9 mmol) added. Phosphorus(V) oxychloride (2.86 g, 18.7 mmol) is then added slowly over 5 minutes and then the reaction mixture stirred for 30 minutes and heated at 55° C. for 17 hours. The reaction mixture is allowed to cool to 23° C. and aqueous potassium acetate (150 $cm^3$, 3 M) is added and the mixture stirred for 1 hour. The organics are extracted with dichloromethane (2×200 $cm^3$) and the combined organics washed with water (50 $cm^3$), dried over anhydrous magnesium sulfate, filtered and the solvent removed in vacuo. The crude is purified by column chromatography using a graded solvent system (40-60 petrol:dichloromethane; 9:1 to 3:1) to give intermediate 35 (1.37 g, 57%) as a red oil. $^1H$ NMR (400 MHz, $CDCl_3$) 9.89 (2H, s), 7.93 (2H, s), 6.92 (4H, s), 6.80 (8H, s), 2.50 (16H, t, J 7.7), 1.52 (16H, q, J 7.2), 1.09-1.40 (112H, m), 0.87 (24H, t, J 6.8).

Intermediate 36

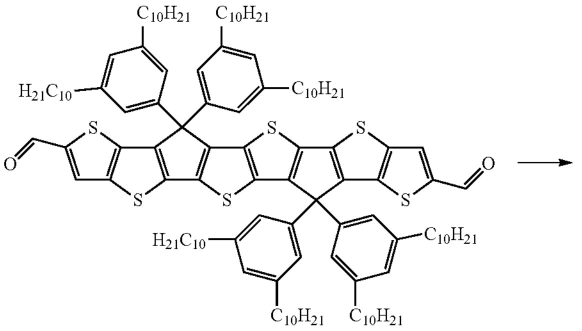

-continued

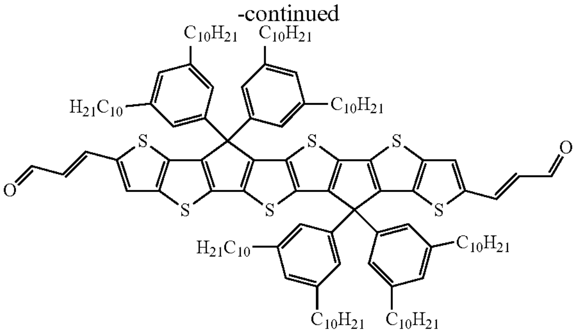

To a solution of intermediate 35 (400 mg, 0.208 mmol) and tributyl(1,3-dioxolan-2-ylmethyl)-phosphonium bromide (169 mg, 0.458 mmol) in anhydrous tetrahydrofuran (15 $cm^3$) is added sodium hydride (49.9 mg, 1.25 mmol, 60% dispersion in mineral oil). The reaction mixture is stirred for 18 hours and then cooled to 0° C. Aqueous hydrochloric acid (50 $cm^3$, 10%) is added and the reaction mixture stirred at 0° C. for 40 minutes and at 23° C. for 2 hours. Water (100 $cm^3$) is added and the organics extracted with ether (3×100 $cm^3$). The combined organic layer is then washed with brine (100 $cm^3$), dried over anhydrous magnesium sulphate and the solvent removed in vacuo. The crude is triturated in acetonitrile (50 $cm^3$), the solid collected by filtration and washed with methanol (50 $cm^3$) to give intermediate 36 (405 mg, 99%) as a red solid. $^1H$ NMR (400 MHz, $CDCl_3$) 9.52 (2H, d, J 7.6), 7.39-7.54 (4H, m), 6.68-6.87 (12H, m), 6.32 (2H, dd, J 15.4, 7.6), 2.41 (16H, t, J 7.5), 1.44 (16H, d, J 6.6), 1.06-1.24 (112H, m), 0.78 (24H, t, J 6.9).

Compound 19

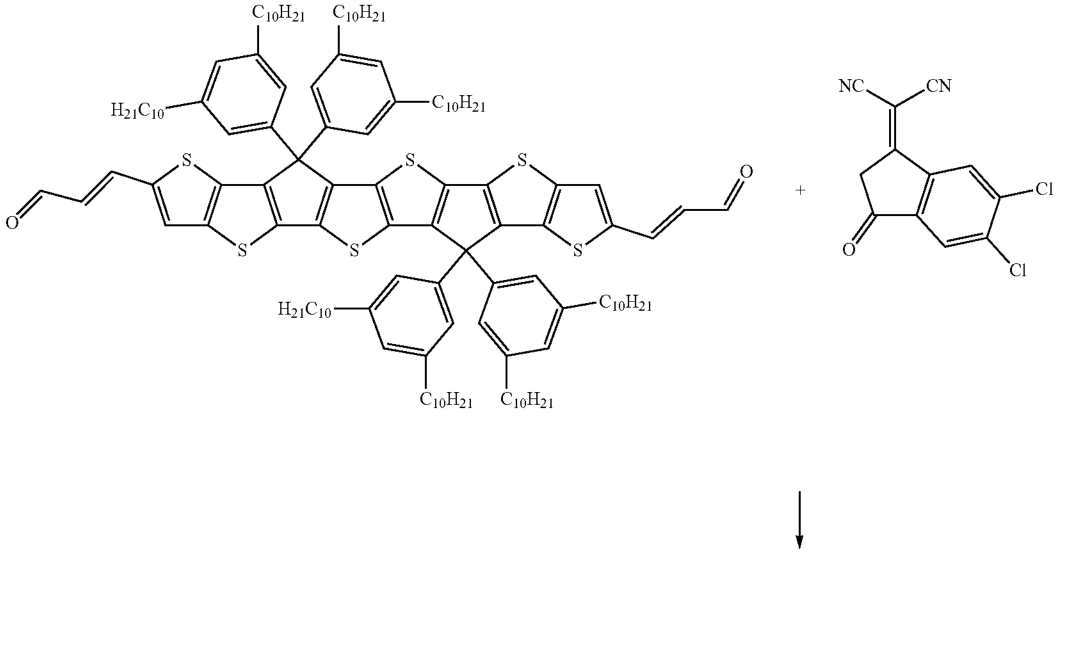

-continued

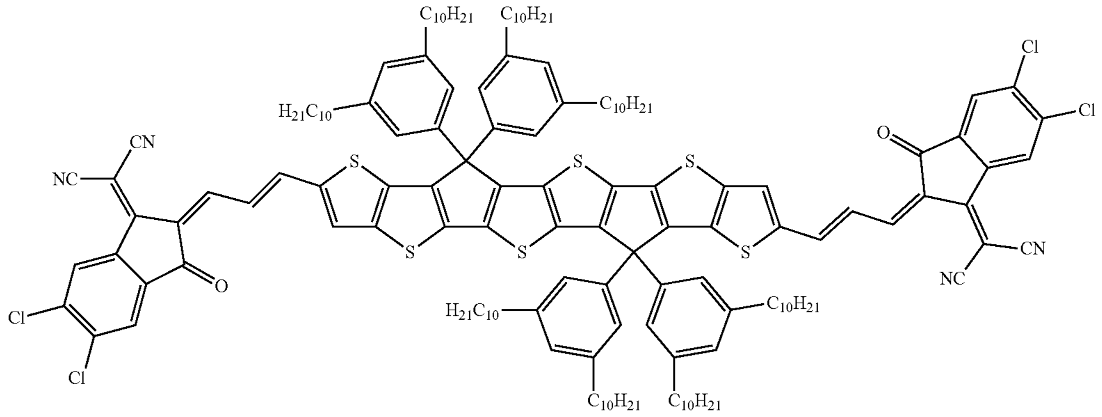

Intermediate 36 (150 mg, 0.076 mmol) and 2-(5,6-dichloro-3-oxo-2,3-dihydro-1H-inden-1-ylidene)propanedinitrile (79.9 mg, 0.304 mmol) are suspended in chloroform (6.0 $cm^3$), pyridine (0.43 $cm^3$, 5.3 mmol) added and the reaction mixture degassed for 15 minutes and then stirred at 23° C. for 35 minutes. Acetonitrile (130 $cm^3$) is added, the mixture stirred for 1 hour, the solid collected by filtration and washed with acetonitrile (50 $cm^3$). The crude is purified by column chromatography using a graded solvent system (40-60 petrol:dichloromethane; 9:1 to 6:4) followed by trituration in acetonitrile (50 $cm^3$) to give compound 19 (122 mg, 65%) as a dark green/blue solid. $^1H$ NMR (400 MHz, $CDCl_3$) 8.62-8.72 (2H, m), 8.31-8.51 (4H, m), 7.78-7.86 (2H, m), 7.44-7.58 (4H, m), 6.67-6.93 (12H, m), 2.45 (16H, t, J 7.5), 1.38-1.56 (16H, m), 1.02-1.25 (112H, m), 0.68-0.82 (24H, m).

Example 20

Intermediate 37

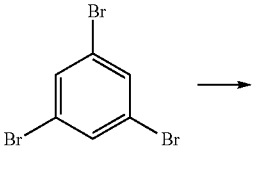

-continued

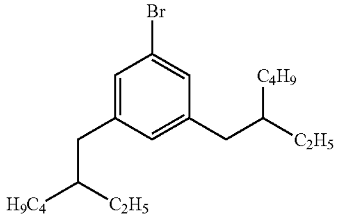

To a suspension of 1,3,5-tribromobenzene (10.0 g, 31.8 mmol) in ether (400 $cm^3$) at −78° C. is added t-butyllithium (74.7 $cm^3$, 127 mmol, 1.7 M in pentane) dropwise over 25 minutes. The reaction mixture is then stirred for 2 hours and 2-ethylhexanal (15.0 g, 117 mmol) is added over 20 minutes. The reaction mixture is allowed to warm to 23° C. and stirred for 16 hours. Water (20 $cm^3$) is slowly added followed by a saturated aqueous ammonium chloride solution (100 $cm^3$). The organic is washed with water (2×50 $cm^3$), dried over anhydrous magnesium sulphate, filtered and the solvent removed in vacuo. The crude material is purified by column chromatography using a graded solvent system (40-60 petrol:dichloromethane; 1:1 to 0:1). The purified material is then taken up in dichloromethane (42 $cm^3$), triethylsilane (14.2 g, 122 mmol) added and the mixture cooled to 0° C. Boron trifluoride diethyl etherate (8.65 g, 61.0 mmol) is then added portion wise over 1 hour, the mixture allowed to warm to 23° C. and stirred for 16 hours. The reaction mixture is then heated at 40° C. for 10 minutes, cooled to 23° C. and a saturated aqueous solution of sodium bicarbonate is added to reach ph ~8. The aqueous solution is extracted with dichloromethane (10 $cm^3$) and the combined organics dried over anhydrous magnesium sulphate, filtered and the solvent removed in vacuo. The crude is purified by column chromatography (40-60 petrol) to give intermediate 37 (2.39 g, 62%) as a colourless oil. $^1H$ NMR (400 MHz, $CDCl_3$) 7.12 (2H, s), 6.85 (1H, s), 2.48 (4H, d, J 7.1), 1.49-1.57 (2H, m), 1.18-1.36 (16H, m), 0.82-0.96 (12H, m).

Intermediate 38

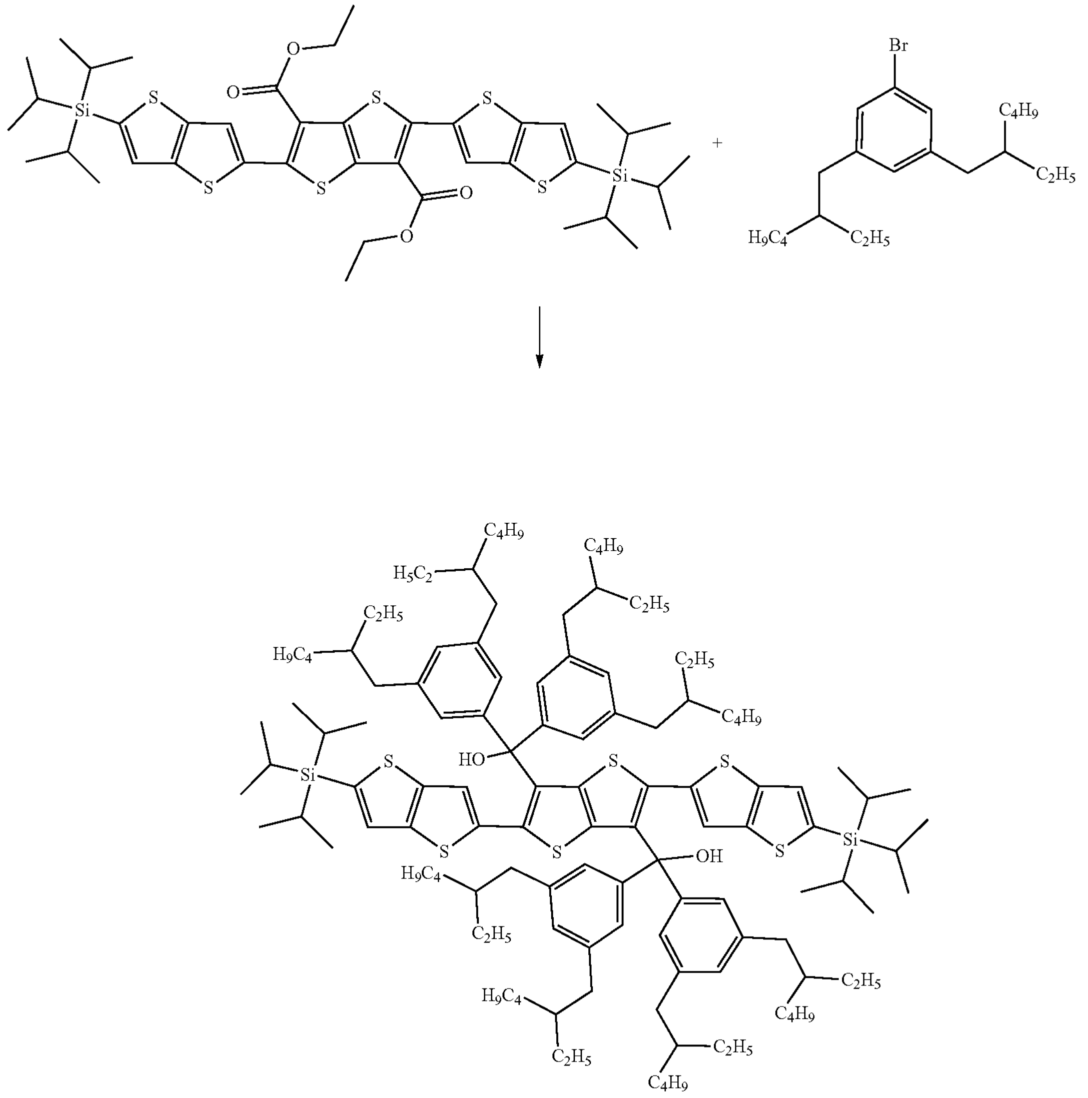

To a solution of intermediate 37 (2.25 g, 5.91 mmol) in anhydrous tetrahydrofuran (12.9 $cm^3$) at −78° C. is added dropwise t-butyllithium (6.95 $cm^3$, 11.8 mmol, 1.7 M in pentane). The reaction mixture is then stirred for 1 hour, warmed to −18° C. and then re-cooled to −78° C. A sonicated suspension of intermediate 28 (860 mg, 0.98 mmol) in anhydrous tetrahydrofuran (12.90 $cm^3$) is then added, the reaction mixture allowed to warm to 23° C. and stirred for 16 hours. Water (10 $cm^3$) is added and the biphasic mixture stirred for 5 minutes. Ether (100 $cm^3$) is added and the organic phase washed with water (3×30 $cm^3$), dried over anhydrous magnesium sulphate, filtered and the solvent removed in vacuo. The residue is purified by column chromatography using a graded solvent system (40-60 petrol:dichloromethane; 9:1 to 4:1) to give intermediate 38 (1.21 g, 62%) as an oil. $^1$H NMR (400 MHz, $CDCl_3$) 7.17 (2H, s), 6.89 (8H, s), 6.87 (4H, s), 6.58 (2H, s), 3.47-3.56 (2H, m), 2.34-2.53 (16H, m), 1.51 (4H, s), 1.05-1.41 (116H, m), 0.72-0.95 (48H, m).

Intermediate 39

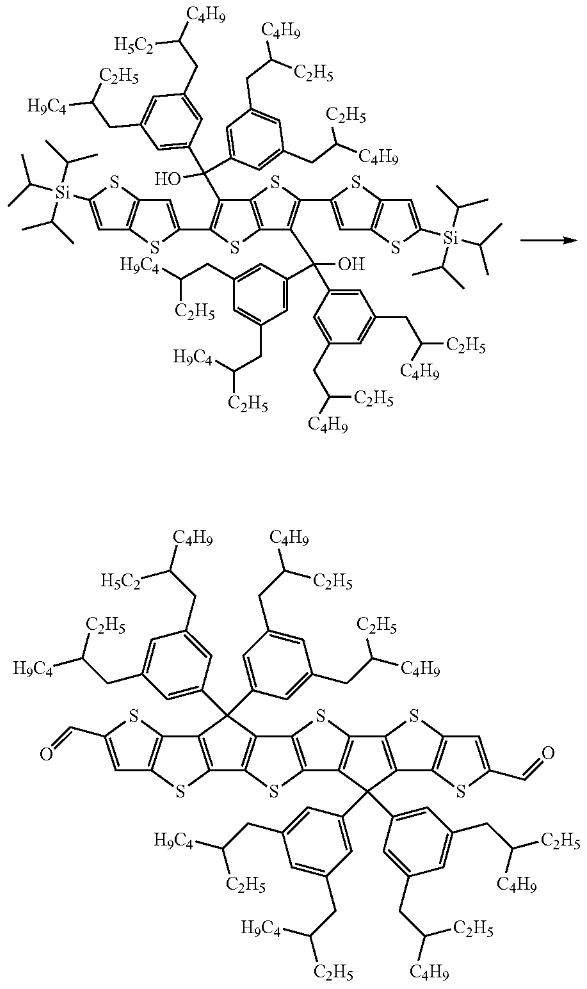

To a degassed mixture of intermediate 38 (1.20 g, 0.603 mmol) dissolved in toluene (48 $cm^3$) at 50° C. is added amberlyst 15 strong acid (4.0 g) and the reaction mixture stirred for 17 hours. The reaction mixture is filtered, the residue washed with hot toluene (2×20 $cm^3$) and the combined organic phases concentrated in vacuo. The residue is dissolved in chloroform (24 $cm^3$), N,N-dimethylformamide (0.70 g, 9.64 mmol) added and the reaction mixture cooled to 0° C. Phosphorus oxychloride (1.39 g, 9.04 mmol) is added over 5 minutes. The reaction mixture is warmed to 23° C. over 30 minutes and then heated at 55° C. for 16 hours before cooling to 23° C. Saturated potassium acetate (50 $cm^3$) is added and the biphasic solution stirred for 2 hours. The aqueous phase is extracted with chloroform (20 $cm^3$) and the combined organic phases washed with water (50 $cm^3$), dried over anhydrous magnesium sulphate, filtered and the solvent removed in vacuo. The residue is purified by column chromatography using a graded solvent system (40-60 petrol:dichloromethane; 9:1 to 3:1) to give intermediate 39 (730 mg, 71%) as a dark solid. $^1H$ NMR (400 MHz, $CDCl_3$) 9.88 (2H, s), 7.93 (2H, s), 6.86 (4H, s), 6.77 (8H, s), 2.37-2.45 (16H, m), 1.44-1.61 (8H, m), 1.11-1.39 (64H, m), 0.72-0.95 (48H, m).

Intermediate 40

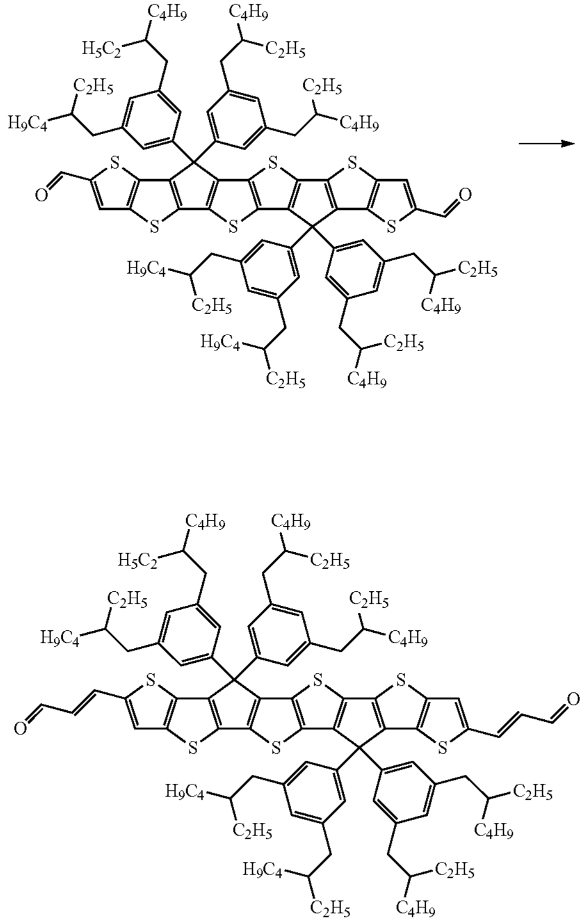

To a solution of intermediate 39 (200 mg, 0.118 mmol) and tributyl(1,3-dioxolan-2-ylmethyl)-phosphonium bromide (95.7 mg, 0.259 mmol) in tetrahydrofuran (8.6 $cm^3$) is added sodium hydride (28 mg, 0.71 mmol, 60% dispersion in mineral oil) and the reaction mixture stirred at 23° C. for 18 hours. The reaction mixture is cooled to 0° C. and aqueous hydrochloric acid (50 $cm^3$, 10%) added. The reaction mixture is stirred at 0° C. for 40 minutes and then at 23° C. for 2 hours. Water (100 $cm^3$) is added and the mixture extracted with ether (3×100 $cm^3$). The combined organic layer washed with brine (100 $cm^3$), dried over anhydrous magnesium sulfate, filtered and the solvent removed in vacuo. The crude is suspended in acetonitrile (40 $cm^3$), the solid collected by filtration and washed with methanol (100 $cm^3$) to give intermediate 40 (150 mg, 73%) as a dark red solid. $^1H$ NMR (400 MHz, $CDCl_3$) 9.52 (2H, d, J 7.8), 7.39-7.55 (4H, m), 6.61-6.84 (12H, m), 6.29 (2H, dd, J 15.4, 7.6), 2.23-2.42 (16H, m), 1.42 (8H, br. s.), 1.05-1.20 (64H, m), 0.62-0.78 (48H, m).

Compound 20

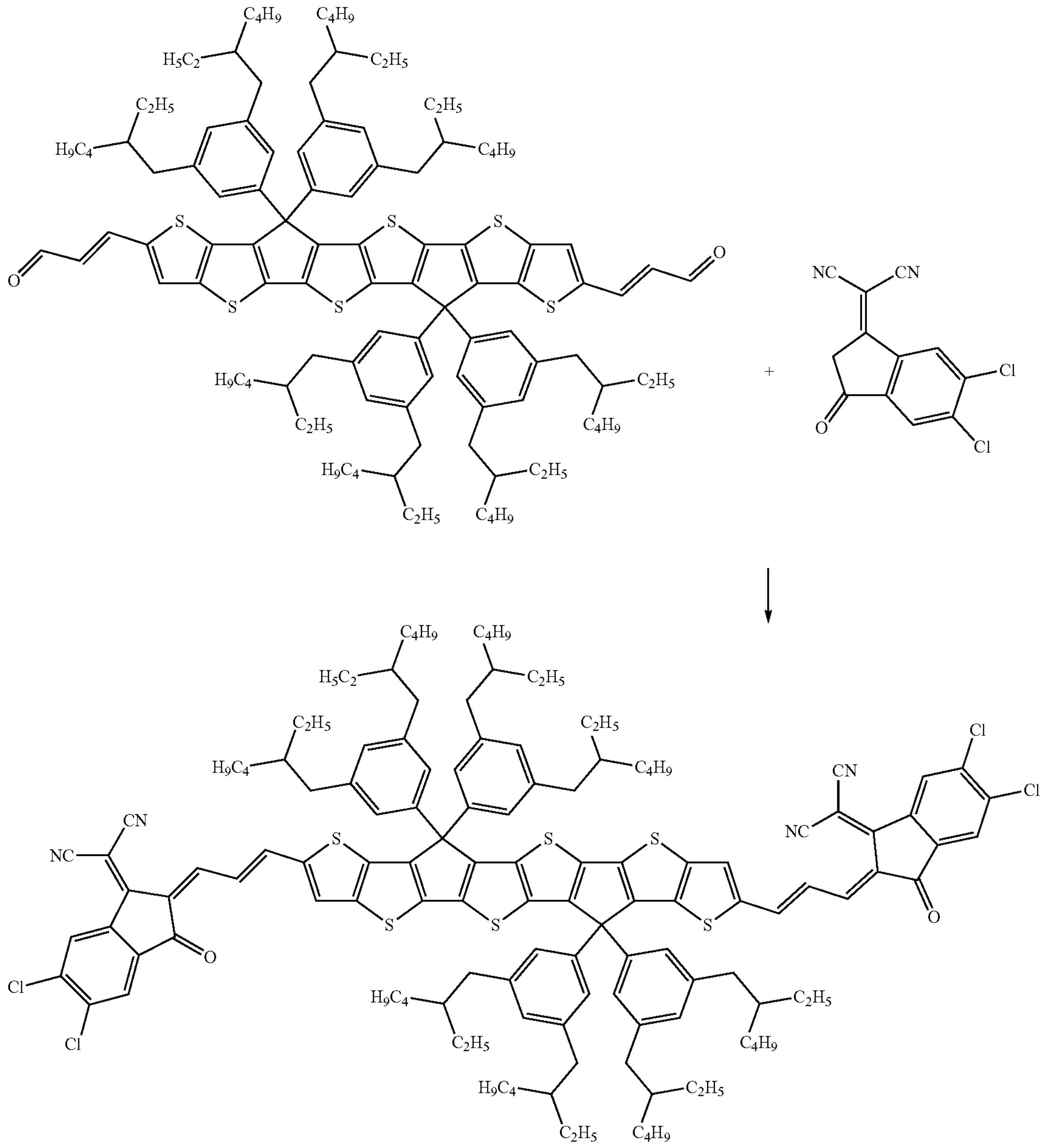

Intermediate 40 (150 mg, 0.086 mmol) and 2-(5,6-dichloro-3-oxo-2,3-dihydro-1H-inden-1-ylidene)propanedinitrile (90.2 mg, 0.343 mmol) are suspended in chloroform (6.9 $cm^3$), pyridine (0.48 $cm^3$, 6.0 mmol) added dropwise and the reaction mixture degassed for 15 minutes and then stirred at 23° C. for 35 minutes. Methanol (120 $cm^3$) is added, the mixture stirred for 1 hour, the solid collected by filtration and washed with acetonitrile (50 $cm^3$). The crude is purified by column chromatography using a graded solvent system (40-60 petrol:dichloromethane; 9:1 to 7:3) followed by trituration in acetonitrile (40 $cm^3$) to give compound 20 (124 mg, 65%) as a dark green/blue solid. $^1H$ NMR (400 MHz, $CDCl_3$) 8.62-8.72 (2H, m), 8.30-8.50 (4H, m), 7.76-7.84 (2H, m), 7.42-7.59 (4H, m), 6.65-6.83 (12H, m), 2.25-2.46 (16H, m), 1.47 (8H, d, J 19.3), 1.01-1.27 (64H, m), 0.61-0.78 (48H, m).

Example 21

Intermediate 41

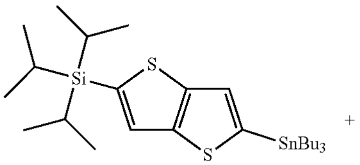

-continued

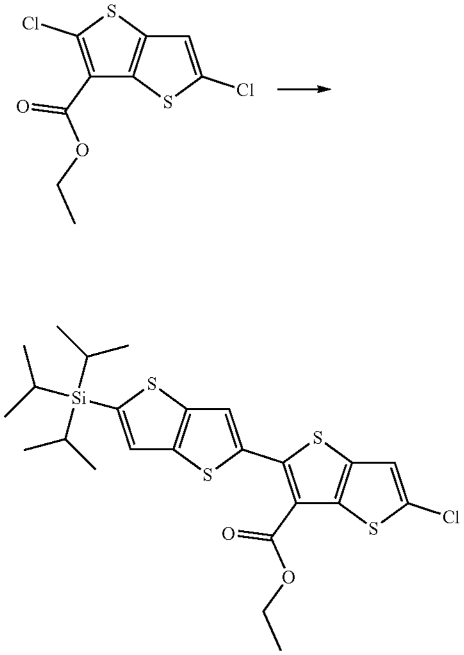

To a degassed solution of ethyl 2,5-dichlorothieno[3,2-b]thiophene-3-carboxylate (25.0 g, 88.9 mmol) in anhydrous toluene (650 $cm^3$) at 110° C. is added tris(dibenzylideneacetone)dipalladium (0) (0.81 g, 0.89 mmol), dicyclohexyl-(2,4,6-triisoprpopyl-biphenyl-2-yl-phosphane (0.85 g, 1.8 mmol) and a solution of tris(propan-2-yl)[5-(tributylstannyl)thieno[3,2-b]thiophen-2-yl]silane (41.3 g, 59.2 mmol) in anhydrous toluene (50 $cm^3$). The reaction mixture is stirred for 2 hours at 120° C. before allowing it to cool to 23° C. Water (750 $cm^3$) is added and the organic phase is separated, washed with brine (100 $cm^3$), dried over anhydrous magnesium sulfate and filtered off. Solvent is then removed in vacuo and the residue passed through a silica plug (heptane: dichloromethane; 1:5) to give intermediate 41 (28 g, 87%) as a yellow solid. $^1$H NMR (400 MHz, $CDCl_3$) 7.76 (1H, s), 7.36 (1H, s), 7.12 (1H, s), 4.38-4.50 (2H, m), 1.34-1.45 (3H, m), 1.10-1.22 (21, H).

Intermediate 42

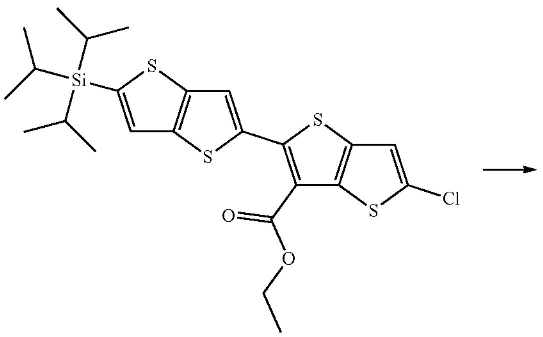

-continued

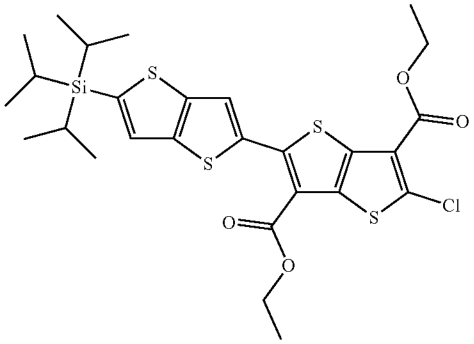

To a solution of intermediate 41 (51.2 g, 94.6 mmol) in anhydrous tetrahydrofuran (512 $cm^3$) at −8° C. is added tetramethylpiperidinyl-magnesium chloride lithium chloride complex (142 $cm^3$, 142 mmol, 1.0 M in tetrahydrofuran/toluene) dropwise over 50 minutes. The reaction mixture is stirred for 1 hour and then ethyl chloroformate (13.6 $cm^3$, 142 mmol) is added dropwise over 10 minutes. The reaction mixture is left stirring for 16 hours, warming up slowly to 23° C. Water (250 $cm^3$) is added followed by dichloromethane (250 $cm^3$). The aqueous layer is extracted with dichloromethane (2×250 $cm^3$) and then the combined organic layers are washed with brine (100 $cm^3$), dried over anhydrous magnesium sulfate and filtered off. Removal of the solvent in vacuo followed by repeated trituration in heptane gives intermediate 42 (41.8 g, 72%) as an orange solid. $^1$H NMR (400 MHz, $CDCl_3$) 7.80 (1H, s), 7.36 (1H, s), 4.32-4.52 (4H, m), 1.34-1.50 (6H, m), 1.10-1.22 (21, H).

Intermediate 43

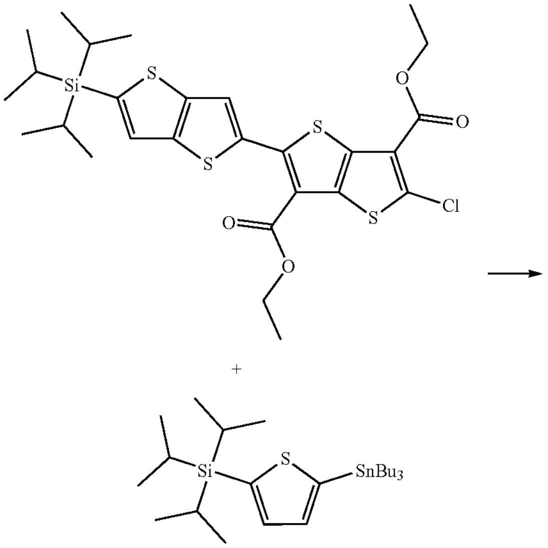

-continued

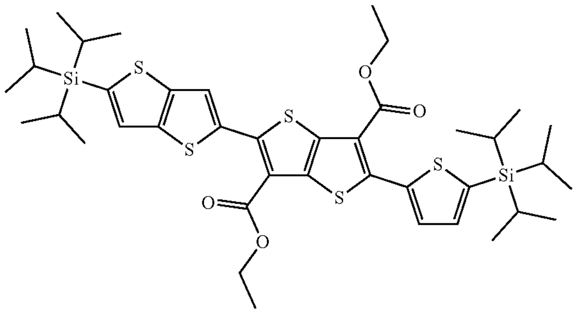

To intermediate 42 (48.0 g, 78.3 mmol) and toluene (480 $cm^3$) is added tris(propan-2-yl)[5-(tributylstannyl)thiophen-2-yl]silane (54.4 g, 82.2 mmol). The mixture is degassed for 1 hour before it is heated to 105° C. Then tris (dibenzylideneacetone)dipalladium (0) (1.79 g, 1.96 mmol) and dicyclohexyl-(2', 4',6'-triisopropylbiphenyl-2yl)-phosphane (1.87 g, 3.91 mmol) are added and the reaction mixture heated at 120° C. for 2 hours. After cooling down to 23° C., water (500 $cm^3$) is added and the aqueous layer is extracted with dichloromethane (3×250 $cm^3$). The combined organic layers are washed with brine (100 $cm^3$), dried over anhydrous magnesium sulfate and filtered off. The removal of the solvent in vacuo followed by column chromatography (heptane:dichloromethane;7:3) and trituation (heptane) gives intermediate 43 (41.5 g, 65%) as an orange solid. $^1H$ NMR (400 MHz, $CDCl_3$) 7.82 (1H, s), 7.68-7.72 (1H, d, J 3.5), 7.38 (1H, s), 7.25-7.29 (1H, m), 4.35-4.48 (4H, m), 1.34-1.50 (12H, m), 1.10-1.22 (36H, m).

Intermediate 44

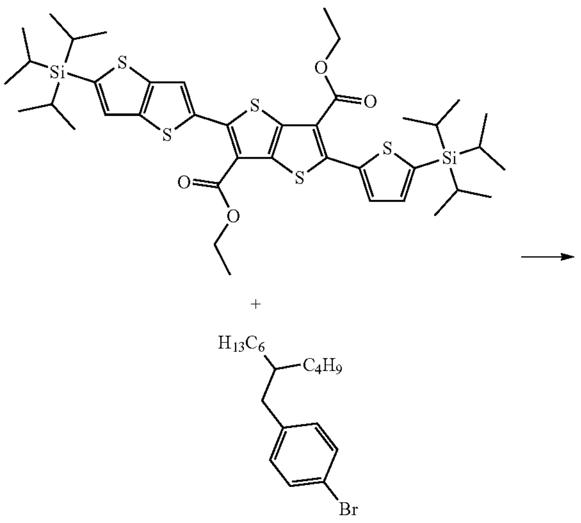

-continued

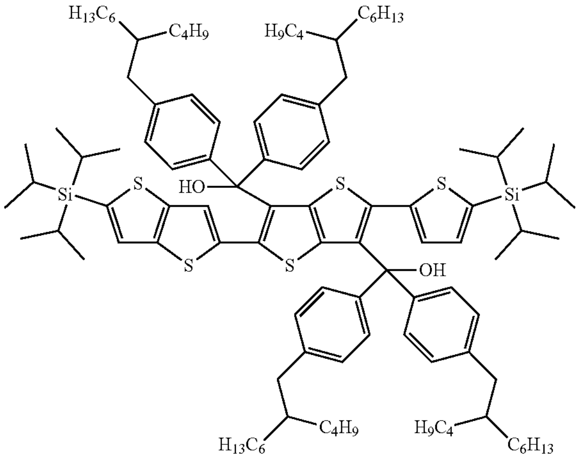

To a solution of 1-bromo-4-(2-butyloctyl)benzene (7.97 g, 0.024 mol) in anhydrous tetrahydrofuran (100 $cm^3$) at −78° C. is added dropwise t-butyllithium (29 $cm^3$, 0.049 mol, 1.7 M in pentane) over 70 minutes. The reaction mixture is then stirred for 2 hours. Intermediate 43 (4.00 g, 4.90 mmol) is then added and the reaction mixture allowed to warm to 23° C. and stirred for 17 hours. Water (100 $cm^3$) is added and the mixture stirred for a further 1 hour. Ether (100 $cm^3$) is added to the mixture, the organic layer separated, and the aqueous layer extracted with ether (2×100 $cm^3$).

The combined organics washed with water (2×50 $cm^3$), dried over anhydrous magnesium sulfate, filtered and the solvent removed in vacuo. The crude is purified by column chromatography (40-60 petrol) to give intermediate 44 (7.2 g, 86%) as a pale cream oil. H NMR (400 MHz, $CDCl_3$) 7.19-7.25 (8H, m), 7.17 (1H, s), 7.06-7.12 (8H, m), 6.90 (1H, d, J 3.5), 6.52-6.56 (2H, m), 3.54 (1H, s), 3.48 (1H, s), 2.47-2.60 (8H, m), 1.53-1.69 (4H, m), 0.99-1.42 (108H, m), 0.80-0.94 (24H, m).

Intermediate 45

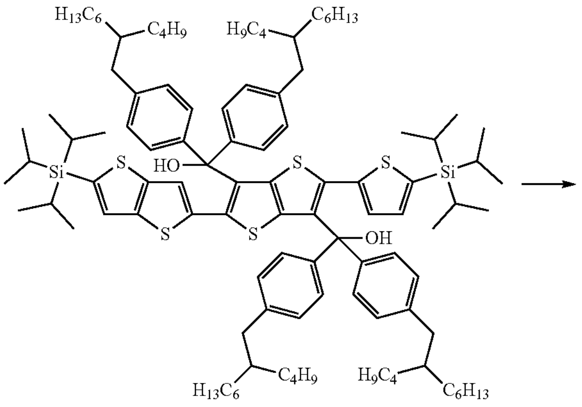

-continued

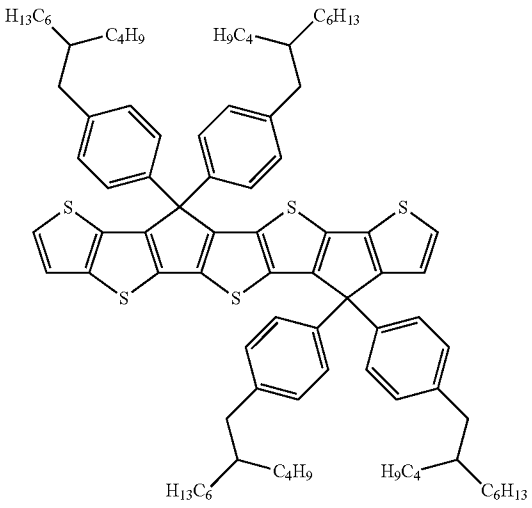

-continued

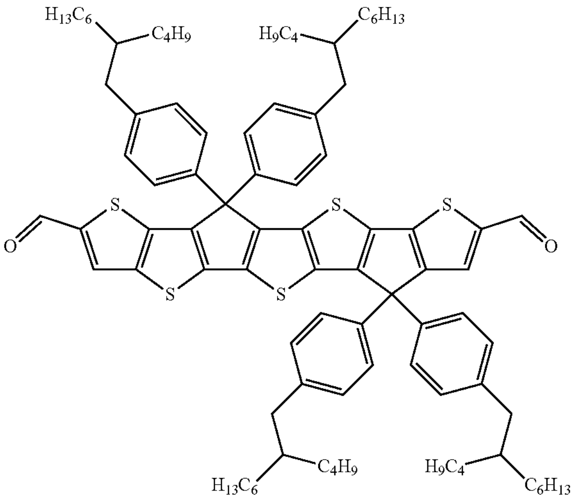

To a solution of 4-methylbenzene-1-sulfonic acid hydrate (4.27 g, 22.4 mmol) in dichloromethane (250 $cm^3$) at 0° C. is added a solution of intermediate 44 (6.40 g, 3.74 mmol) in dichloromethane (50 $cm^3$). The reaction mixture is allowed to warm to 23° C. and stirred for 17 hours. The solvent is removed in vacuo and the residue passed through a celite plug (pentane). The crude is purified by column chromatography (40-60 petrol) to give intermediate 45 (1.8 g, 35%) as a red oil. H NMR (400 MHz, $CDCl_3$) 7.19 (1H, d, 5.3), 7.15 (1H, d, 5.3), 7.09 (1H, d, 4.9), 7.04-7.08 (8H, m), 7.01 (1H, d, 4.9), 6.94-7.00 (8H, m), 2.35-2.43 (8H, m), 1.42-1.55 (4H, m), 1.06-1.28 (64H, m), 0.70-0.85 (24H, m).

Intermediate 46

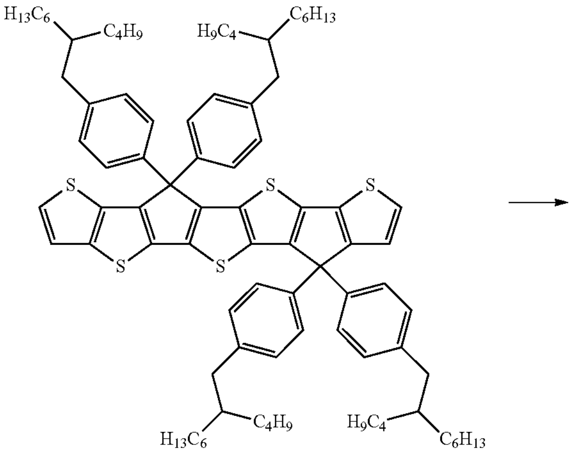

To a mixture of N,N-dimethylformamide (0.6 $cm^3$) and chloroform (100 $cm^3$) at 0° C. is added phosphoroxychloride (1.01 g, 6.61 mmol). The reaction mixture is allowed to warm to 23° C. and stirred for 1 hour before cooling to 0° C. Intermediate 45 (1.80 g, 1.32 mmol) is added, the reaction mixture allowed to warm to 23° C. and stirred for 72 hours. The reaction mixture is poured onto saturated aqueous sodium acetate (100 $cm^3$) and stirred for 30 minutes before heating to 50° C. and stirring for an additional 30 minutes. The aqueous layer is extracted with dichloromethane (100 $cm^3$). The organic layer is washed with water (100 $cm^3$), dried over anhydrous magnesium sulfate, filtered and the solvent removed in vacuo. The crude is purified by column chromatography using a graded solvent system (40-60 petrol:dichloromethane; 7:3 to 1:1) to give intermediate 46 (1.8 g, 96%) as an orange solid. $^1H$ NMR (400 MHz, $CDCl_3$) 9.90 (1H, s), 9.82 (1H, s), 7.94 (1H, s), 7.71 (1H, s), 7.04-7.18 (16H, m), 2.50 (8H, t, J 6.7), 1.52-1.62 (4H, m), 1.16-1.33 (64H, m), 0.79-0.91 (24H, m).

Intermediate 47

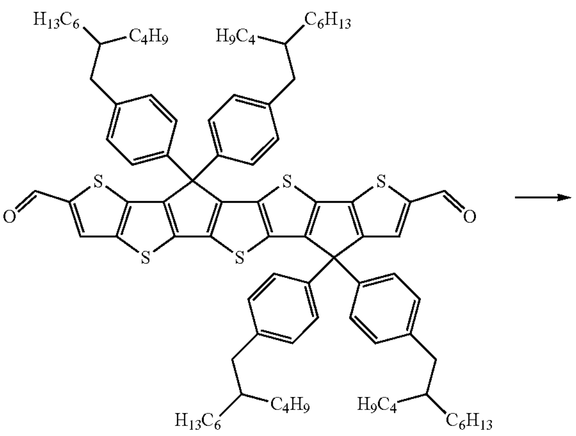

-continued

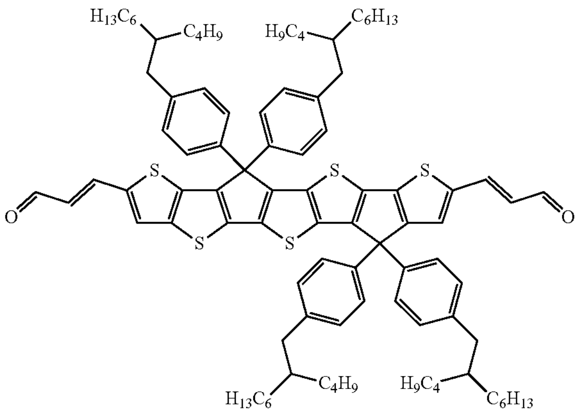

To a solution of intermediate 46 (1.40 g, 0.99 mmol) and tributyl(1,3-dioxolan-2-ylmethyl)-phosphonium bromide (802 mg, 2.17 mmol) in tetrahydrofuran (72 $cm^3$) is added sodium hydride (237 mg, 5.92 mmol, 60% dispersion in mineral oil) and the reaction mixture stirred at 23° C. for 18 hours. The reaction mixture is cooled to ° C. and aqueous hydrochloric acid (20 $cm^3$, 10%) added. The reaction mixture is stirred at 0° C. for 40 minutes and then at 23° C. for 2 hours. Water (100 $cm^3$) is added and the organics extracted with ether (3×100 $cm^3$). The combined organics washed with brine (100 $cm^3$), dried over anhydrous magnesium sulfate, filtered and the solvent removed in vacuo. The crude is triturated (acetonitrile), the solid collected by filtration and washed with methanol (100 $cm^3$) to give intermediate 47 (1.2 g, 83%) as a red solid. $^1H$ NMR (400 MHz, $CDCl_3$) 9.53 (1H, d, J 7.6), 9.50 (1H, d, J 7.6), 7.40-7.52 (3H, m), 7.24 (1H, s), 6.96-7.10 (8H, m), 6.30-6.41 (2H, m), 2.35-2.47 (8H, m), 1.43-1.55 (4H, m), 1.04-1.27 (64H, m), 0.68-0.84 (24H, m).

Compound 21

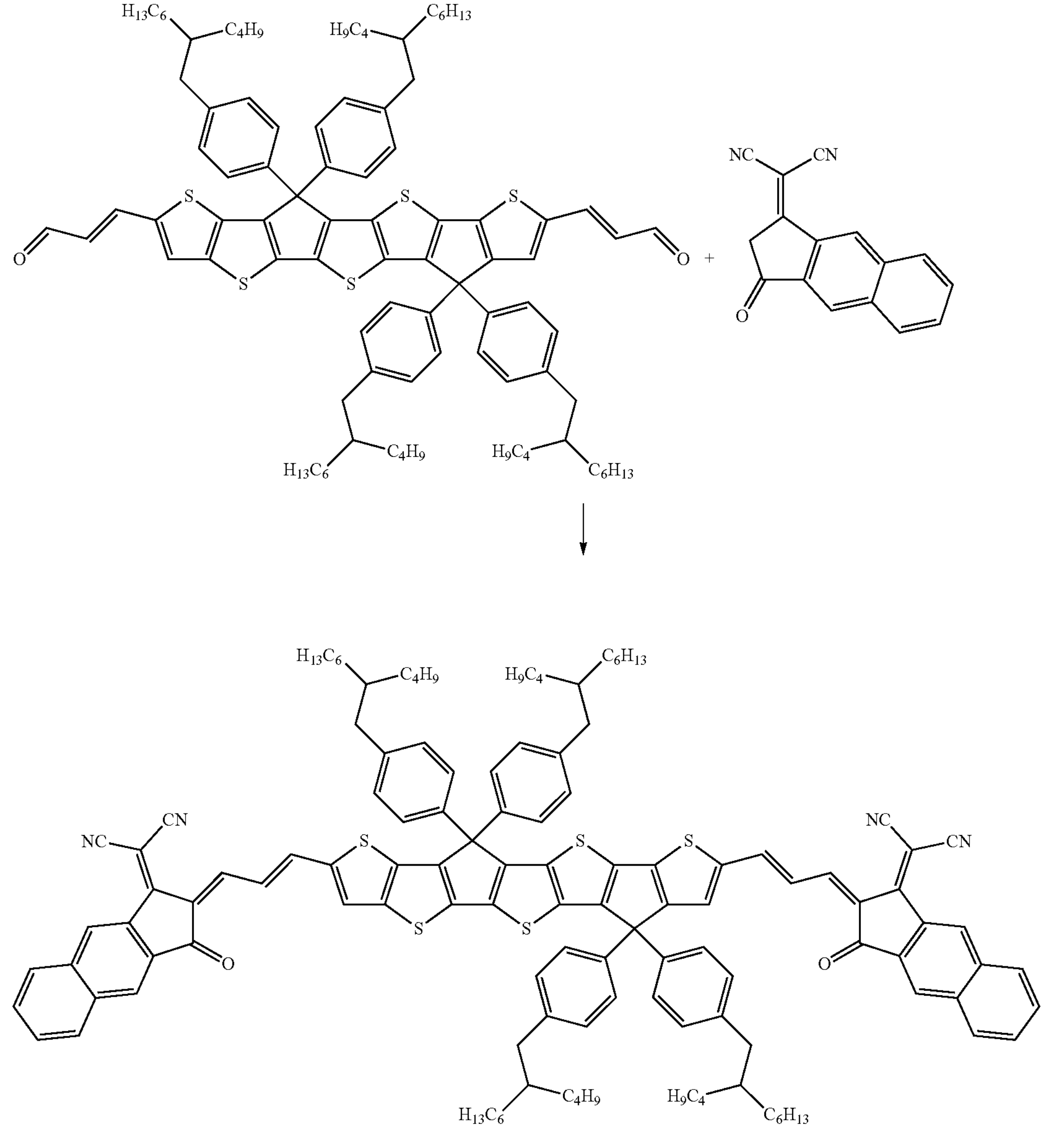

To a solution of intermediate 47 (250 mg, 0.17 mmol) in anhydrous chloroform (10 $cm^3$) is added 2-{3-oxo-1H,2H,3H-cyclopenta[b]naphthalen-1-ylidene}propanedinitrile (125 mg, 0.510 mmol) followed by pyridine (0.1 $cm^3$, 1.2 mmol). The resulting solution is stirred for 4 hours at 40° C. The mixture is allowed to cool to 23° C. and the volatiles removed in vacuo. The residue is triturated in methanol and the solid washed with further methanol until the filtrate runs colourless. The crude is purified by column chromatography (cyclohexane:chloroform; 7:13) to give compound 21 (94 mg, 29%) as a brown/green solid. $^1H$ NMR (400 MHz, $CDCl_3$) 9.05-9.11 (2H, m), 8.50-8.67 (2H, m), 8.38-8.47 (2H, m), 8.24-8.31 (2H, m), 7.93-8.04 (2H, m), 7.57-7.68 (4H, m), 7.36-7.54 (4H, m), 6.99-7.16 (16H, m), 2.37-2.51 (8H, m), 1.45-1.60 (4H, m), 1.08-1.27 (64H, m), 0.69-0.82 (24H, m).

Example 22

Compound 22

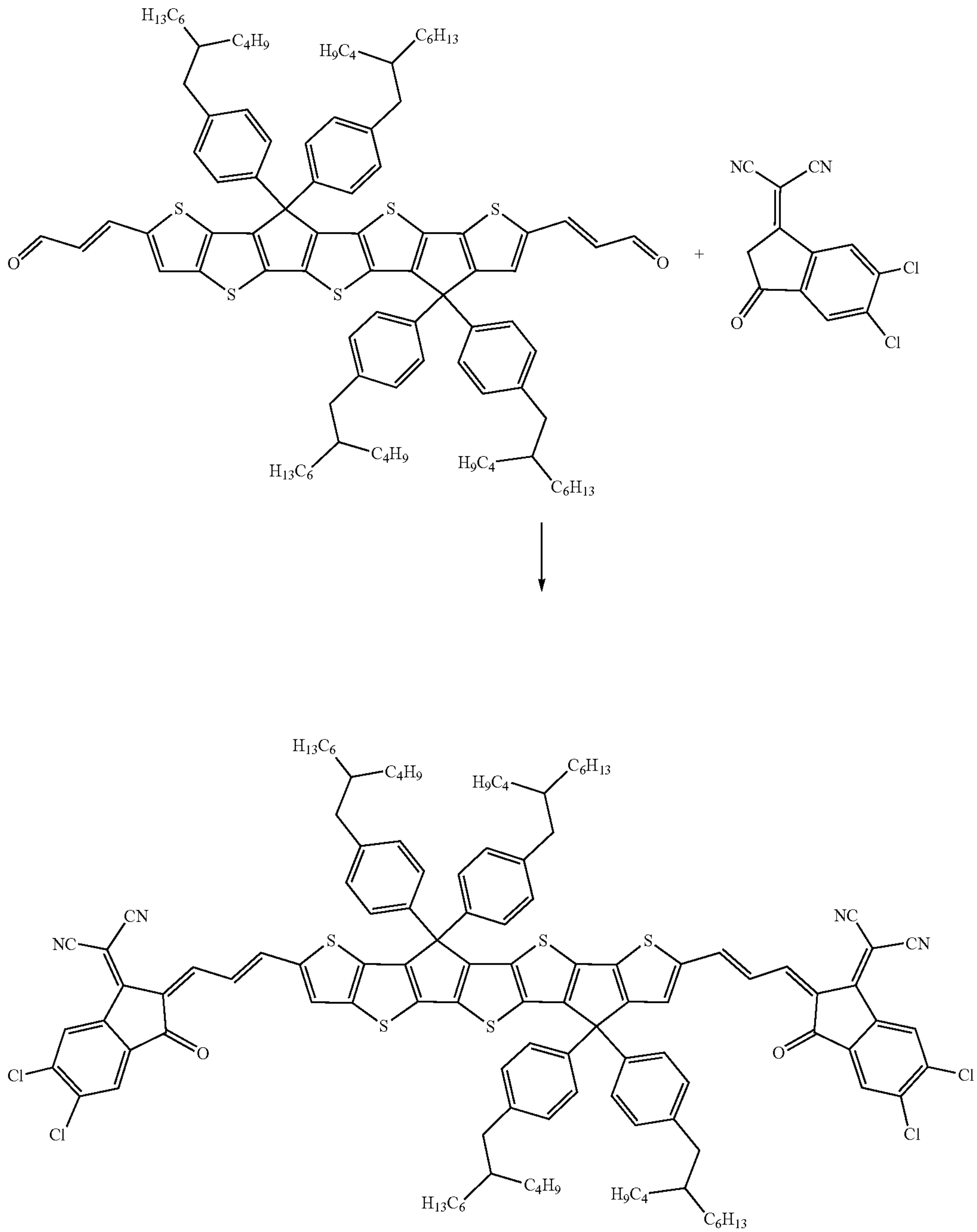

To a solution of intermediate 47 (220 mg, 0.15 mmol) in anhydrous chloroform (12 $cm^3$) is added 2-(5,6-dichloro-3-oxo-2,3-dihydro-1H-inden-1-ylidene)propanedinitrile (197 mg, 0.748 mmol) followed by pyridine (0.85 $cm^3$, 10.5 mmol). The resulting solution is degassed for 25 minutes and then stirred for 2 hours. Methanol (300 $cm^3$) is added and the solid collected by filtration. The crude is purified by column chromatography using a graded solvent system (40-60 petrol:dichloromethane; 7:3 to 0:1) followed by trituration in acetonitrile to give compound 22 (190 mg, 65%) as a dark solid. $^1H$ NMR (400 MHz, $CDCl_3$) 8.76 (2H, d, J 6.9), 8.38-8.60 (4H, m), 7.93 (2H, d, J 2,6), 7.43-7.71 (4H, m), 7.08-7.23 (16H, m), 2.47-2.58 (8H, m), 1.52-1.68 (4H, m), 1.15-1.41 (64H, m), 0.80-0.93 (24H, m).

Example 23

Compound 23

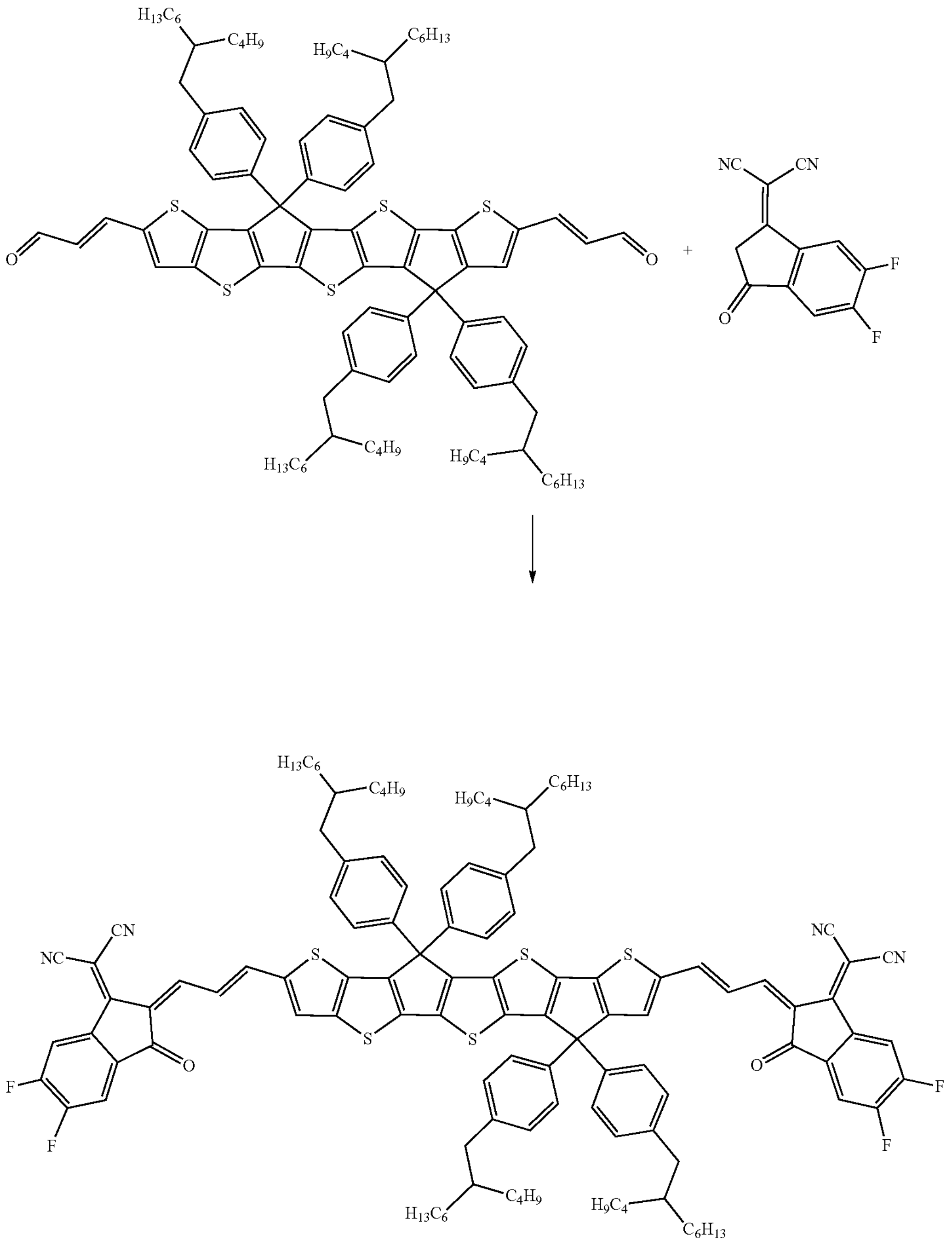

To a solution of intermediate 47 (220 mg, 0.15 mmol) in anhydrous chloroform (12 $cm^3$) is added 2-(5,6-difluoro-3-oxo-2,3-dihydro-1H-inden-1-ylidene)propanedinitrile (172 mg, 0.748 mmol) followed by pyridine (0.85 $cm^3$, 10.5 mmol). The resulting solution is degassed for 25 minutes and then stirred for 2 hours. Methanol (300 $cm^3$) is added and the solid collected by filtration to give compound 23 (240 mg, 85%) as a dark green solid. $^1H$ NMR (400 MHz, $CDCl_3$) 8.28-8.48 (6H, m), 7.36-7.61 (6H, m), 6.98-7.11 (16H, m), 2.39-2.48 (8H, m), 1.46-1.57 (4H, m), 1.08-1.26 (64H, m), 0.71-0.82 (24H, m).

Example 24

Intermediate 48

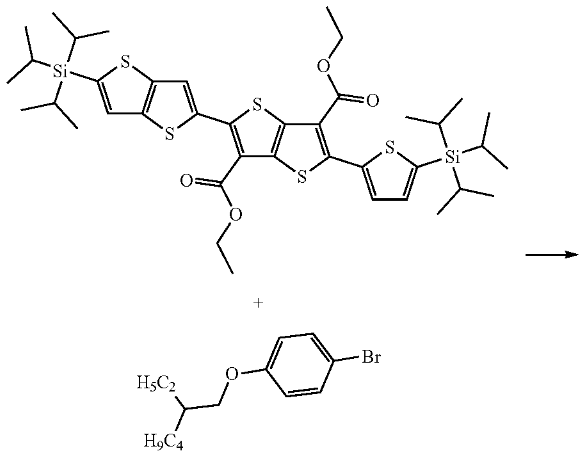

-continued

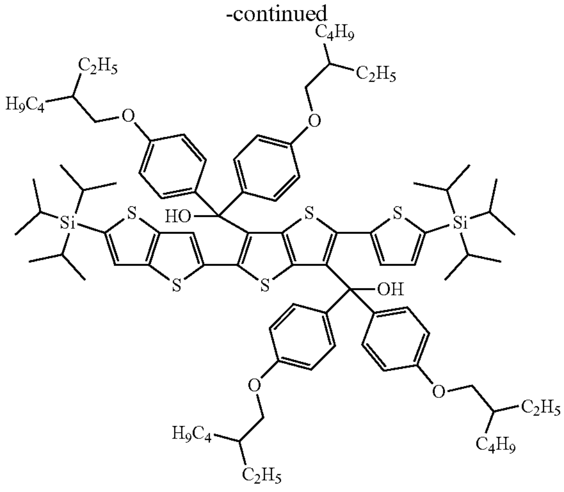

To a solution of 1-bromo-4-[(2-ethylhexyl)oxy]benzene (6.98 g, 24.5 mmol) in anhydrous tetrahydrofuran (100 $cm^3$) at −78° C. is added dropwise t-butyllithium (28.8 $cm^3$, 48.9 mmol, 1.7 M in pentane) over 70 minutes. The reaction mixture is then stirred for 2 hours. Intermediate 43 (4.00 g, 4.89 mmol) is then added as a single portion and the reaction mixture allowed to warm to 23° C. and stirred for 17 hours. Water (100 $cm^3$) is added and the mixture stirred for a further 1 hour. Ether (100 $cm^3$) is added and the aqueous layer extracted with ether (2×100 $cm^3$). The combined organic layers are washed with water (2×50 $cm^3$), dried over anhydrous magnesium sulfate, filtered and the solvent removed in vacuo. The crude is purified by column chromatography using a graded solvent system (pentane:dichloromethane; 1:0 to 0:1) to give intermediate 48 (6.70 g, 88%) as a yellow oil. $^1H$ NMR (400 MHz, $CD_2Cl_2$) 7.14 (1H, s), 7.04-7.12 (8H, m), 6.86 (1H, d, J 3.5), 6.69-6.75 (8H, m), 6.61 (1H, d, J 3.5), 6.54 (1H, m), 3.68-3.82 (8H, m), 3.30 (1H, s), 3.25 (1H, s), 1.56-1.68 (4H, m), 1.53-1.69 (4H, m), 1.11-1.42 (38H, m), 0.99-1.04 (18H, m), 0.92-0.97 (18H, m), 0.77-0.86 (24H, m).

Intermediate 49

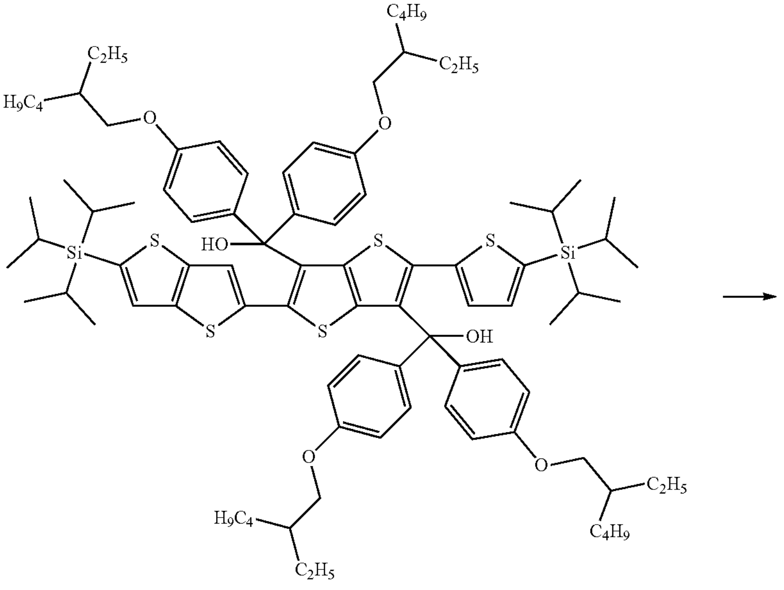

-continued

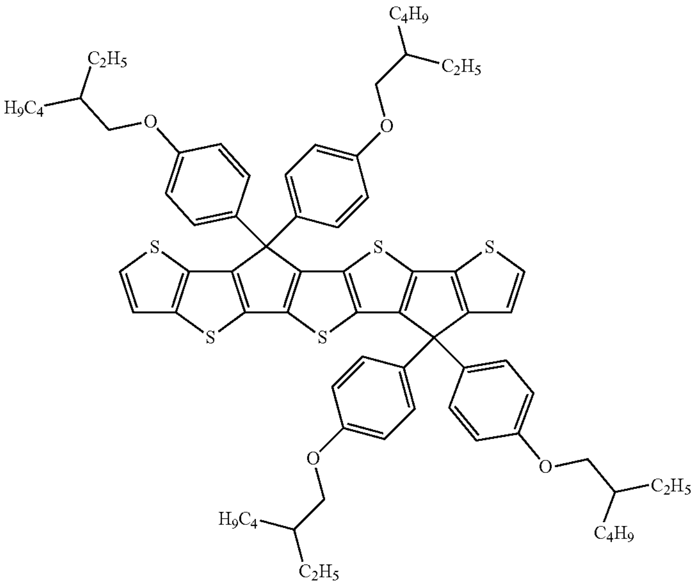

To a stirred solution of intermediate 48 (6.00 g, 3.87) in dichloromethane (50 $cm^3$) is added a solution of 4-methylbenzene-1-sulfonic acid hydrate (0.10 mg, 0.001 mmol) in acetic acid (1.0 $cm^3$). The mixture is then stirred at 40° C. for 12 hours. The mixture allowed to cool to 23° C. and the volatiles removed in vacuo. The residue taken up in ether (50 $cm^3$) and the solution washed with saturated aqueous potassium carbonate until the solution is basic. The solution is then dried over potassium carbonate, filtered and the solvent removed in vacuo. The residue is taken up in tetrahydrofuran (40 $cm^3$) and tetrabutylammonium fluoride (10 $cm^3$, 10 mmol, 1.0 M in tetrahydrofuran) is added. The mixture is stirred for 15 minutes and then the solvent removed in vacuo. The crude is purified by column chromatography using a graded solvent system (40-60 petrol:dichloromethane; 19:1 to 17:3) to give intermediate 49 (2.15 g, 46%) as a pale orange solid. $^1$H NMR (400 MHz, $CDCl_3$) 7.29 (1H, d, J 5.2), 7.25 (1H, d, J 5.2), 7.16-7.21 (9H, m), 7.06 (1H, d, J 4.9), 6.80-6.85 (8H, m), 3.76-3.83 (8H, m), 1.64-1.75 (4H, m), 1.24-1.54 (32H, m), 0.84-0.96 (24H, m).

Intermediate 50

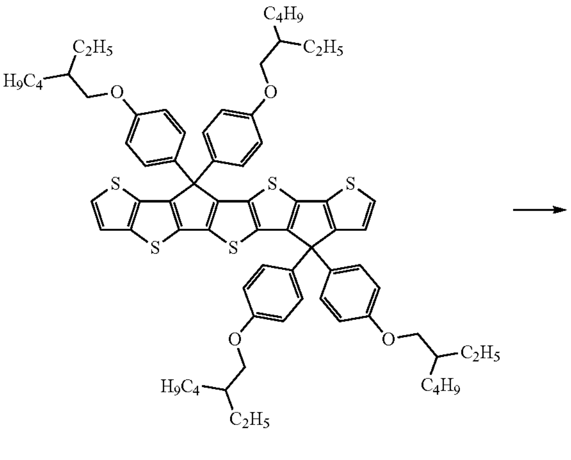

-continued

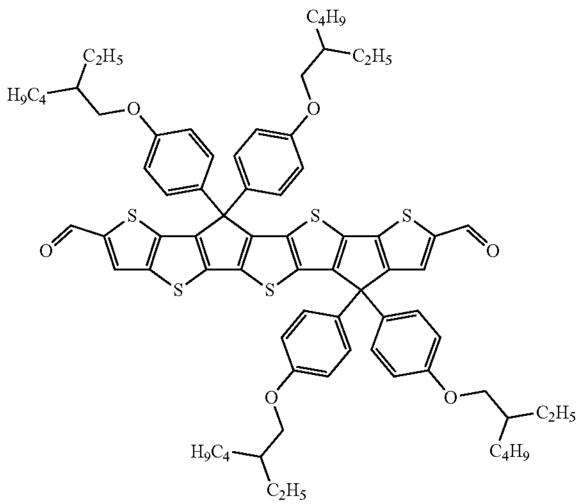

Intermediate 51

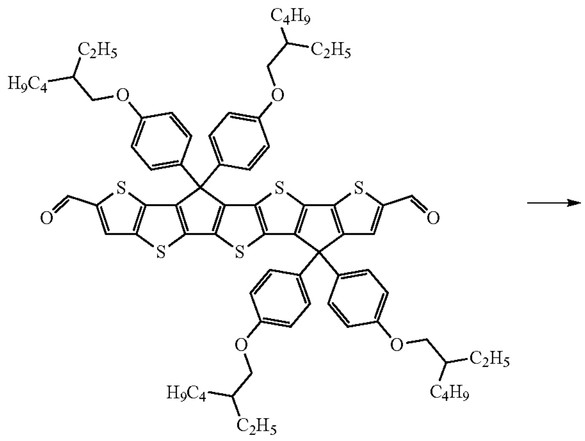

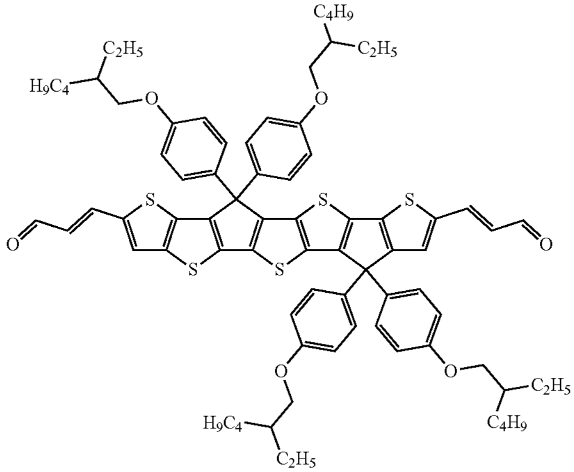

To a solution of intermediate 49 (1.98 g, 1.65 mmol), anhydrous N,N-dimethylformamide (0.65 $cm^3$, 8.4 mmol) and anhydrous chloroform (50 $cm^3$) at 0° C. is added phosphorus(V) oxychloride (0.80 $cm^3$, 8.6 mmol). The mixture is then stirred at 0° C. for 30 minutes and at 50° C. for 16 hours before allowing to cool to 23° C. The volatiles are removed in vacuo and tetrahydrofuran (25 $cm^3$) and water (5 $cm^3$) are added. The mixture is then stirred for 30 minutes before the volatiles are removed in vacuo. The residue is triturated (methanol), the solid collected by filtration and washed with methanol (50 $cm^3$) to give intermediate 50 (2.0 g, 99%) as an orange solid. $^1H$ NMR (400 MHz, $CD_2Cl_2$) 9.91 (1H, s), 9.83 (1H, s), 8.01 (1H, s), 7.72 (1H, s), 7.13-7.23 (8H, m), 6.81-6.91 (8H, m), 3.78-3.88 (8H, m), 1.69-1.79 (4H, m), 1.24-1.57 (32H, m), 0.85-1.00 (24H, m).

To a solution of intermediate 50 (1.70 g, 1.35 mmol) and tributyl(1,3-dioxolan-2-ylmethyl)-phosphonium bromide (1.50 g, 4.05 mmol) in tetrahydrofuran (25 $cm^3$) is added sodium hydride (270 mg, 6.76 mmol, 60% dispersion in mineral oil) and the reaction mixture stirred at 23° C. for 4 hours and at 40° C. for 2 hours. The reaction mixture is cooled to 0° C. and aqueous hydrochloric acid (4.6 $cm^3$, 10%) added. The reaction mixture is stirred at 0° C. for 10 minutes. The volatiles are removed in vacuo, the aqueous phase decanted, and the residue washed with water (2×10 $cm^3$). The crude is triturated (methanol), the solid collected by filtration and washed with methanol (50 $cm^3$). Itis further purified by column chromatography using a graded solvent system (40-60 petrol:dichloromethane;3:17 to 0:1) followed by recrystallisation (chloroform:acetonitrile) to give intermediate 51(1.63 g, 92%) as a red solid. $^1H$ NMR (400 MHz, $CD_2Cl_2$) 9.50 (1H, d, J 7.6), 9.48 (1H, d, J7.6), 7.41-7.54 (3H, in), 7.22 (1H, s), 7.00-7.10 (8H, in), 6.69-6.78 (8H, in), 6.26-6.39 (2H, in), 3.64-3.77 (8H, in), 1.52-1.65 (4H, in), 1.11-1.45 (32H, in), 0.72-0.86 (24H, in).

Compound 24

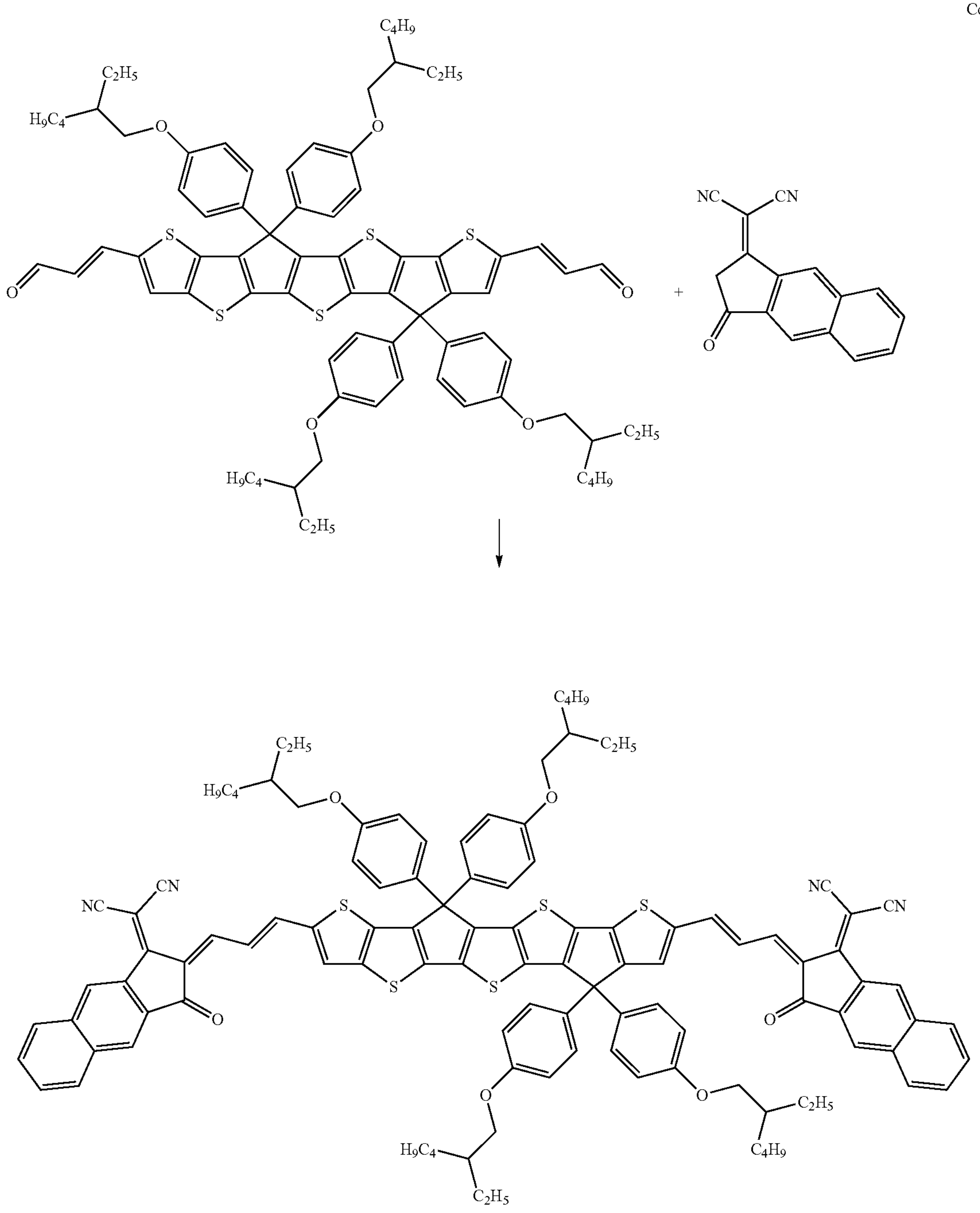

To a solution of intermediate 51 (250 mg, 0.191 mmol) in anhydrous chloroform (10 $cm^3$) and ethanol (0.5 $cm^3$) is added 2-{3-oxo-1H,2H,3H-cyclopenta[b]naphthalen-1-ylidene}propanedinitrile (140 mg, 0.573 mmol) followed by pyridine (0.1 $cm^3$, 1.2 mmol). The resulting solution is stirred for 12 hours at 40° C. The mixture is allowed to cool to 23° C. and the volatiles removed in vacuo. The residue is triturated in methanol and the solid washed with further methanol until the filtrate runs colourless. The crude is purified by column chromatography using a graded solvent system (40-60 petrol:chloroform;3:17 to 1:19) to give compound 24 (138 mg, 41%) as a dark green solid. $^1H$ NMR (400 MHz, $CDCl_3$) 9.15-9.19 (2H, m), 8.61-8.74 (2H, m), 8.47-8.54 (2H, m), 8.34-8.39 (2H, m), 8.03-8.11 (4H, m), 7.66-7.75 (4H, m), 7.49-7.63 (3H, m), 7.42 (1H, s), 7.14-7.22 (8H, m), 6.83-6.96 (8H, m), 3.77-3.90 (8H, m), 1.64-1.77 (4H, m), 1.23-1.59 (32H, m), 0.83-0.97 (24H, m).

Example 25

Compound 25

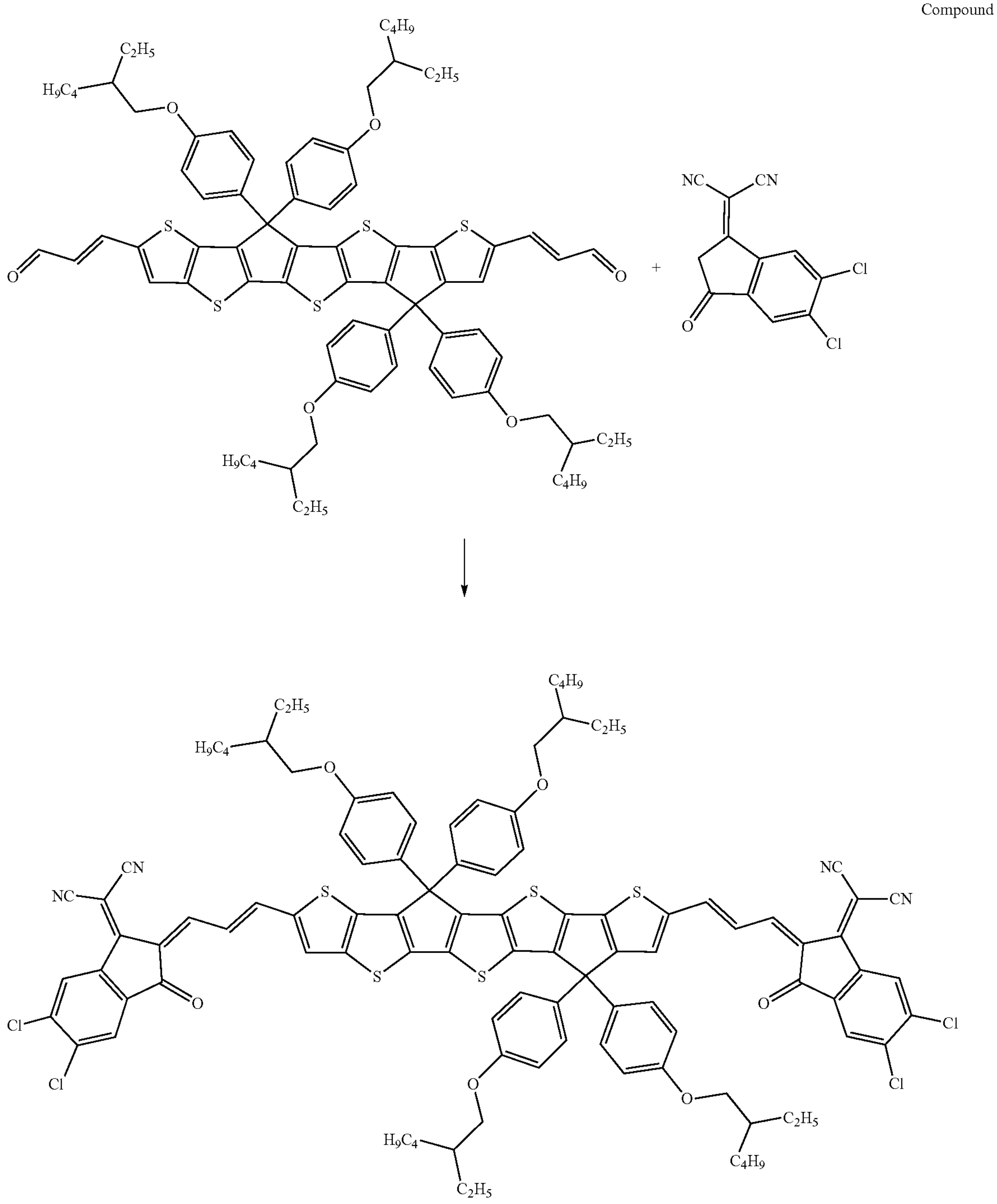

To a solution of intermediate 51 (200 mg, 0.153 mmol) in chloroform (10 $cm^3$) and ethanol (0.5 $cm^3$) is added pyridine (0.1 $cm^3$, 1 mmol) and 2-(5,6-dichloro-3-oxo-2,3-dihydro-1H-inden-1-ylidene)propanedinitrile (106 mg, 0.403 mmol). The solution is stirred at 40° C. for 6 hours and then allowed to cool to 23° C. The volatiles are removed in vacuo and the residue triturated with methanol. The solid is collected by filtration and washed with methanol until the filtrate is colourless. The crude is then further purified by column chromatography (cyclohexane:chloroform;7:13) to give compound 25 (204 mg, 74%) as a green solid. $^1$H NMR (400 MHz, $CDCl_3$) 8.74-8.78 (2H, m), 8.39-8.58 (4H, m), 7.90-7.96 (2H, m), 7.40-7.63 (4H, m), 7.12-7.24 (8H, m), 6.83-6.94 (8H, m), 3.83 (8H, t, J 5.7), 1.70 (4H, h, J 6.0), 1.23-1.55 (32H, m), 0.82-0.95 (24H, m).

Example 26

Compound 26

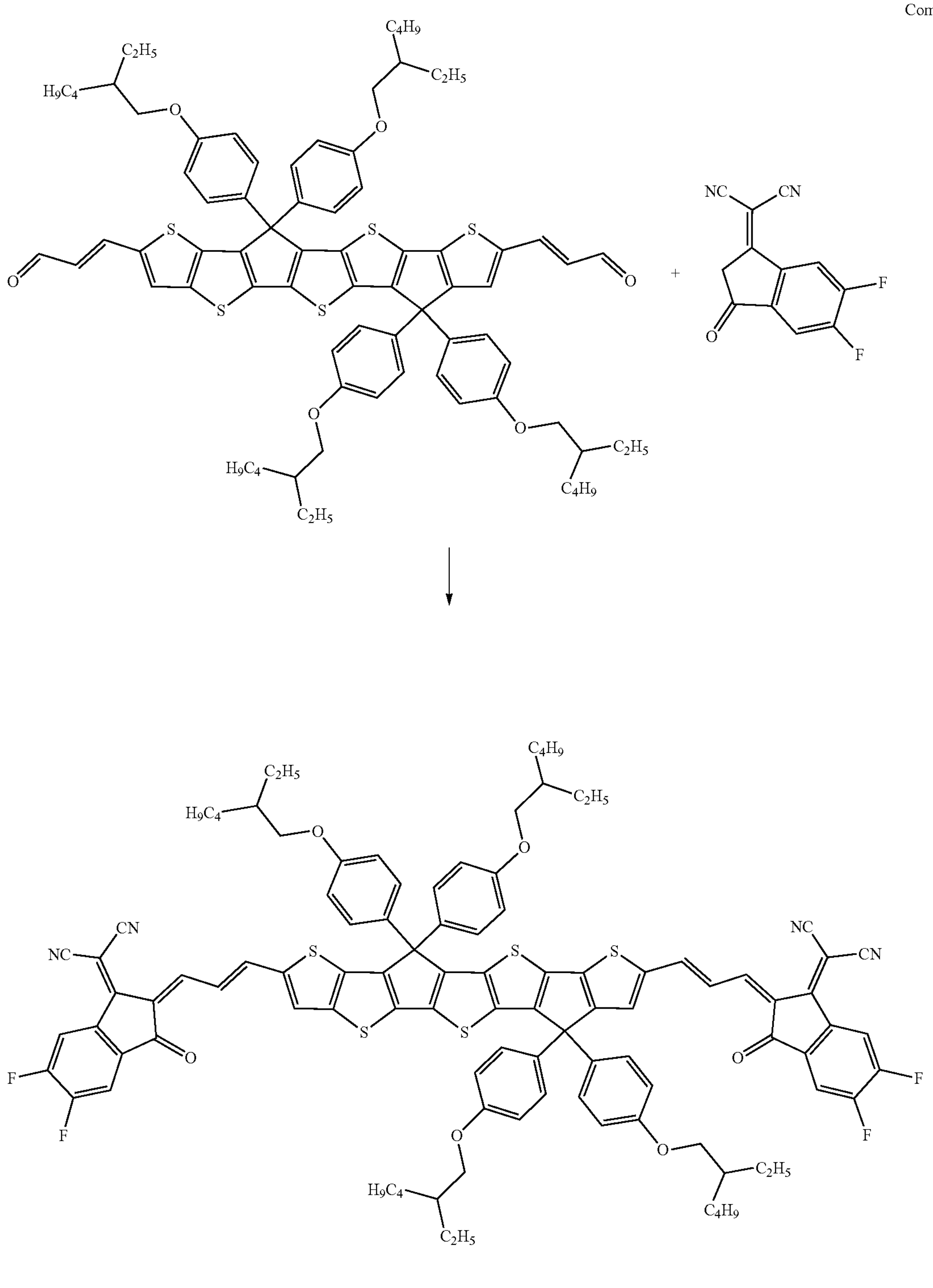

To a solution of intermediate 51 (200 mg, 0.153 mmol) in chloroform (10 $cm^3$) and ethanol (0.5 $cm^3$) is added pyridine (0.1 $cm^3$, 1 mmol) and 2-(5,6-difluoro-3-oxo-2,3-dihydro-1H-inden-1-ylidene)propanedinitrile (105 mg, 0.458 mmol). The solution is stirred at 40° C. for 6 hours and then allowed to cool to 23° C. The volatiles are removed in vacuo and the residue triturated with methanol. The solid is collected by filtration and washed with methanol until the filtrate is colourless. The crude is then further purified by column chromatography (cyclohexane:chloroform;7:13) to give compound 26 (113 mg, 43%) as a green solid. H NMR (400 MHz, $CD_2Cl_2$) 8.72-8.77 (1H, m), 8.28-8.49 (5H, m), 7.33-7.67 (6H, m), 7.04-7.17 (8H, m), 6.72-6.84 (8H, m), 3.68-3.81 (8H, m), 1.60 (4H, h, J 4.9), 1.10-1.49 (32H, m), 0.70-0.95 (24H, m).

Example 27

Intermediate 52

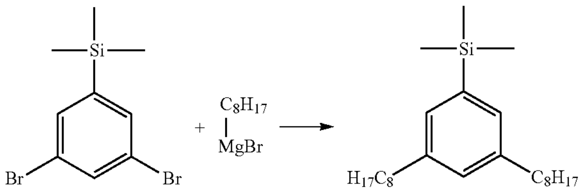

To octylmagnesium bromide solution (183 $cm^3$, 365 mmol, 2.0 M in ether) and tetrahydrofuran (450 $cm^3$) is added (3,5-dibromophenyl)trimethylsilane (45.0 g, 146 mmol) and [1,1'-bis(diphenylphosphino)ferrocene]dichloropalladium (II) (1.60 g, 2.19 mmol). The reaction mixture is heated at 55° C. for 16 hours before it is cooled to 0° C. and water (250 $cm^3$) added. The organics extracted with dichloromethane (2×250 $cm^3$). The combined organics are washed with brine (100 $cm^3$), dried over anhydrous magnesium sulfate, filtered and the solvent removed in vacuo. The crude is purified by column chromatography (heptane) to give intermediate 52 (22.2 g, 41%) as a colourless oil. $^1$H NMR (400 MHz, $CDCl_3$) 7.15 (2H, d, J 1.6), 7.00 (1H, s), 2.52-2.64 (4H, m), 1.55-1.68 (24H, m), 0.84-0.89-5 (6H, m), 0.22-0.31 (9H, m).

Intermediate 53

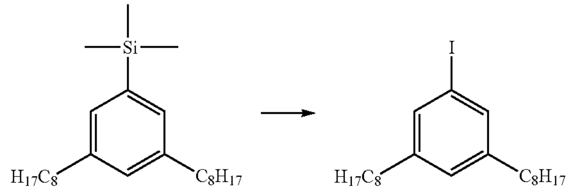

To a solution of intermediate 52 (10.0 g, 26.7 mmol), chloroform (100 $cm^3$) and methanol (100 $cm^3$) in the dark is added silver(I) trifluoroacetate (12.4 g, 56.0 mmol). The mixture is cooled to 0° C., iodine (13.5 g, 53.37 mmol) added and the mixture stirred for 90 minutes. The reaction mixture is filtered through a plug of silica (dichloromethane) and the organic phase washed with saturated aqueous sodium bisulfate (100 $cm^3$), water (100 $cm^3$) and brine (100 $cm^3$) before drying over anhydrous magnesium sulfate. The mixture is filtered, and the solvent removed in vacuo to give intermediate 53 (11.4 g, 99%) as a colourless liquid. $^1$H NMR (400 MHz, $CDCl_3$) 7.27 (2H, d, J 1.4), 6.85 (1H, d, J 1.5), 2.43 (4H, t, J 7.7), 1.07-1.34 (24H, m), 0.70-0.85 (6H, m).

Intermediate 54

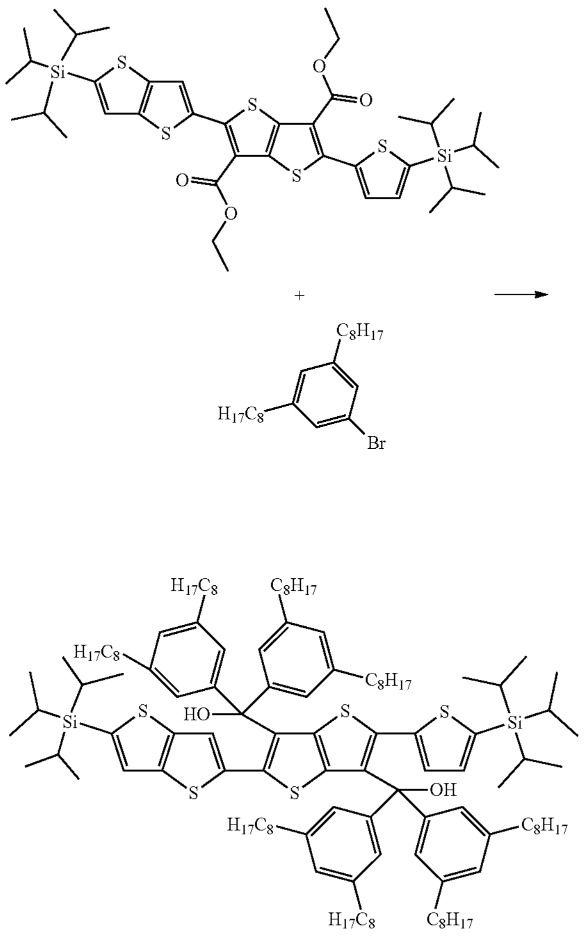

To a mixture of intermediate 53 (5.72 g, 15.0 mmol) and anhydrous tetrahydrofuran (40 $cm^3$) at −78° C. is added t-butyllithium (17.6 $cm^3$, 30.0 mmol, 1.7 M in pentane) over 10 minutes The mixture is then stirred for 2 hours before intermediate 43 (2.45 g, 3.00 mmol) is added, the mixture allowed to warm to 23° C. and stirred for 17 hours. Water (25 $cm^3$) is added and the mixture stirred for a further 1 hour. The aqueous layer is extracted with ether (2×50 $cm^3$) and the combined organics dried over anhydrous magnesium sulfate. Filtration and removal of the solvent in vacuo followed by column chromatography using a graded solvent system (40-60 petrol:dichloromethane; 1:0 to 17:3) gives intermediate 54 (3.03 g, 52%) as a yellow oil. $^1$H NMR (400 MHz, $CDCl_3$) 7.15 (1H, s), 6.95-7.00 (4H, m), 6.89-6.94 (6H, m), 6.89 (1H, d, J 3.4), 6.84-6.88 (2H, m), 6.62 (1H, d, J 3.4), 6.37 (1H, s), 3.50 (1H, s), 3.34 (1H, s), 2.40-2.59 (16H, m), 1.46-1.63 (16H, m), 1.19-1.42 (86H, m), 1.10-1.15 (18H, m), 1.02-1.07 (18H, m), 0.81-0.95 (24H, m).

Intermediate 55

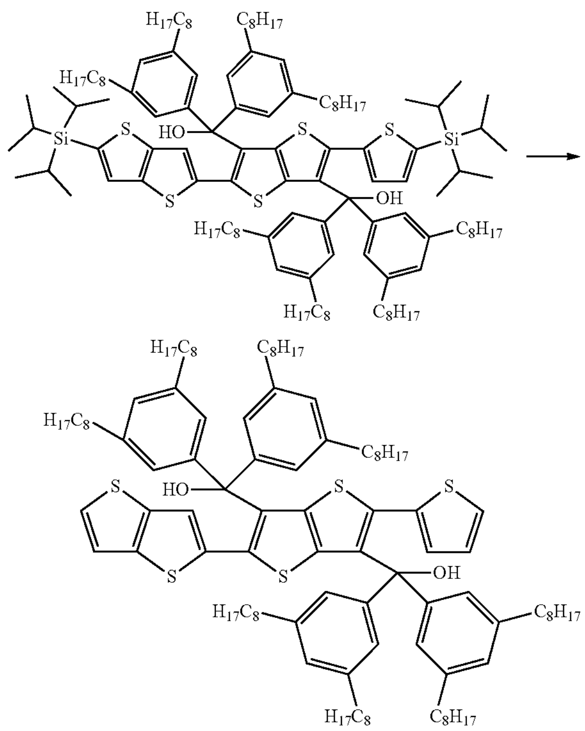

To a solution of intermediate 54 (2.20 g, 1.14 mmol) in tetrahydrofuran (20 $cm^3$) is added tetrabutylammonium fluoride (2.84 $cm^3$, 2.84 mmol, 1.0 M in tetrahydrofuran) and the mixture stirred for 2 hours. The volatiles are then removed in vacuo and the crude purified by column chromatography using a graded solvent system (40-60 petrol: dichloromethane; 9:1 to 3:1) to give intermediate 55 (1.64 g, 89%) as a pale yellow solid. $^1H$ NMR (400 MHz, $CDCl_3$) 7.25-7.27 (1H, m), 7.09-7.13 (1H, m), 7.03-7.05 (1H, m), 6.86-6.94 (12H, m), 6.68-6.72 (1H, m), 6.43-6.46 (2H, m), 3.34 (1H, s), 3.32 (1H, s), 2.42-2.55 (16H, m), 1.46-1.58 (16H, m), 1.14-1.34 (80H, m), 0.82-0.92 (24H, m).

Intermediate 56

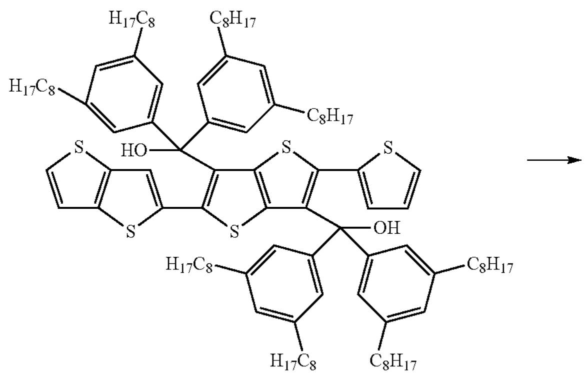

-continued

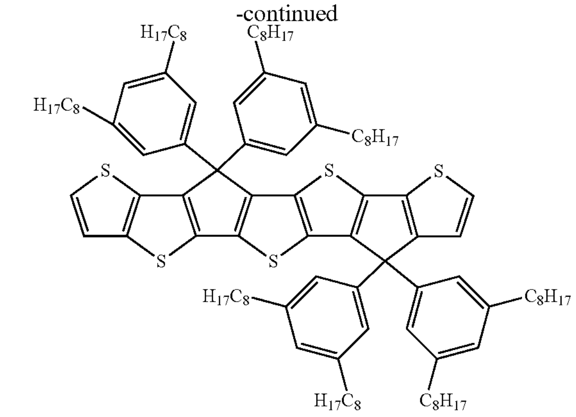

To a solution of intermediate 55 (910 mg, 0.560 mmol) in cyclohexane (50 $cm^3$) is added amberlyst 15 strong acid (3.50 g). The mixture is then heated at 50° C. for 25 minutes and the solution filtered. The volatiles are removed from the filtrate in vacuo and the residue purified by column chromatography (40-60 petrol) to give intermediate 56 (600 mg, 67%) as an orange oil. $^1H$ NMR (400 MHz, $CD_2Cl_2$) 7.21 (1H, d, 5.2), 7.17 (1H, d, 5.2), 7.13 (1H, d, 4.9), 6.98 (1H, d, 4.9), 6.78-6.82 (4H, m), 6.72-6.76 (8H, m), 2.33-2.44 (16H, m), 1.35-1.50 (16H, m), 1.04-1.27 (80H, m), 0.71-0.84 (24H, m).

Intermediate 57

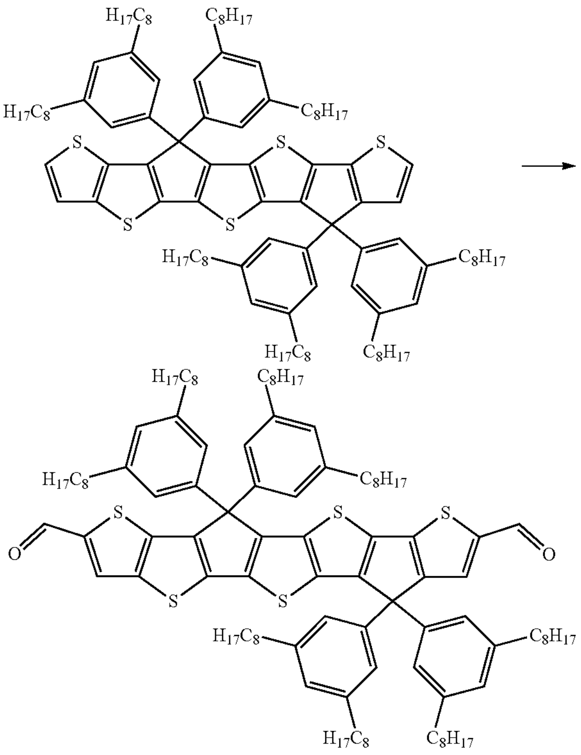

To a solution of intermediate 56 (590 mg, 0.372 mmol), anhydrous N,N-dimethylformamide (0.25 $cm^3$, 3.2 mmol) and anhydrous chloroform (20 $cm^3$) at 0° C. is added phosphorus(V) oxychloride (0.25 $cm^3$, 2.7 mmol). The mixture is then stirred at 0° C. for 30 minutes and at 60° C. for 16 hours before allowing to cool to 23° C. The volatiles are removed in vacuo and tetrahydrofuran (10 $cm^3$) and water (2 $cm^3$) are added. The mixture is then stirred for 15 minutes before the volatiles are removed in vacuo. The aqueous is decanted and the residue purified by column chromatography using a graded solvent system (cyclohexane:dichloromethane; 3:1 to 13:7) to give intermediate 57 (590 mg, 97%) as an orange solid. $^1H$ NMR (400 MHz, $CD_2Cl_2$) 9.78 (1H, s), 9.71 (1H, s), 7.88 (1H, s), 7.58 (1H, s), 6.84 (4H, s), 6.74 (4H, s), 6.70 (4H, s), 2.32-2.47 (16H, m), 1.30-1.50 (16H, m), 1.04-1.25 (80H, m), 0.67-0.83 (24H, m).

-continued

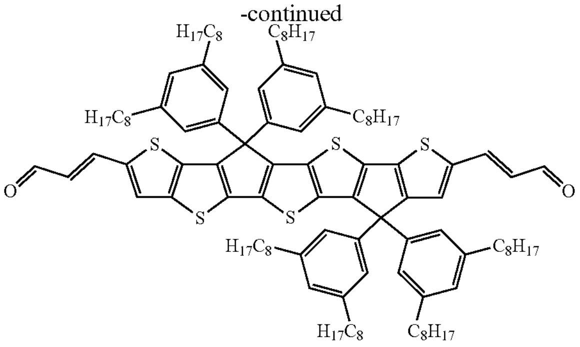

Intermediate 58

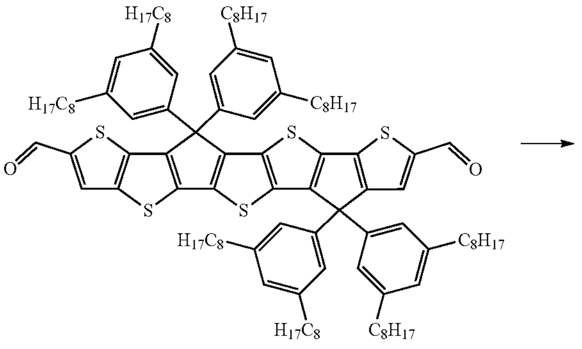

To a solution of intermediate 57 (630 mg, 0.384 mmol) and tributyl(1,3-dioxolan-2-ylmethyl)-phosphonium bromide (425 mg, 1.15 mmol) in tetrahydrofuran (10 $cm^3$) is added sodium hydride (77 mg, 1.9 mmol, 60% dispersion in mineral oil) and the reaction mixture stirred at 23° C. for 4 hours. The reaction mixture is cooled to 0° C. and aqueous hydrochloric acid (1.8 $cm^3$, 10%) added. The reaction mixture is stirred at 0° C. for 10 minutes. The volatiles are removed in vacuo, the aqueous phase decanted, and the residue washed with water (2×10 $cm^3$). The crude is then purified by column chromatography using a graded solvent system (40-60 petrol:dichloromethane; 11:9 to 2:3) to give intermediate 58 (460 mg, 71%) as an orange solid. $^1H$ NMR (400 MHz, $CD_2Cl_2$) 9.50 (1H, d, J 7.6), 9.47 (1H, d, J 7.6), 7.42-7.54 (3H, m), 7.21 (1H, s), 6.81-6.85 (4H, m), 6.69-6.75 (8H, m), 6.25-6.37 (2H, m), 2.34-2.45 (16H, m), 1.37-1.49 (16H, m), 1.05-1.23 (80H, m), 0.69-0.81 (24H, m).

Compound 27

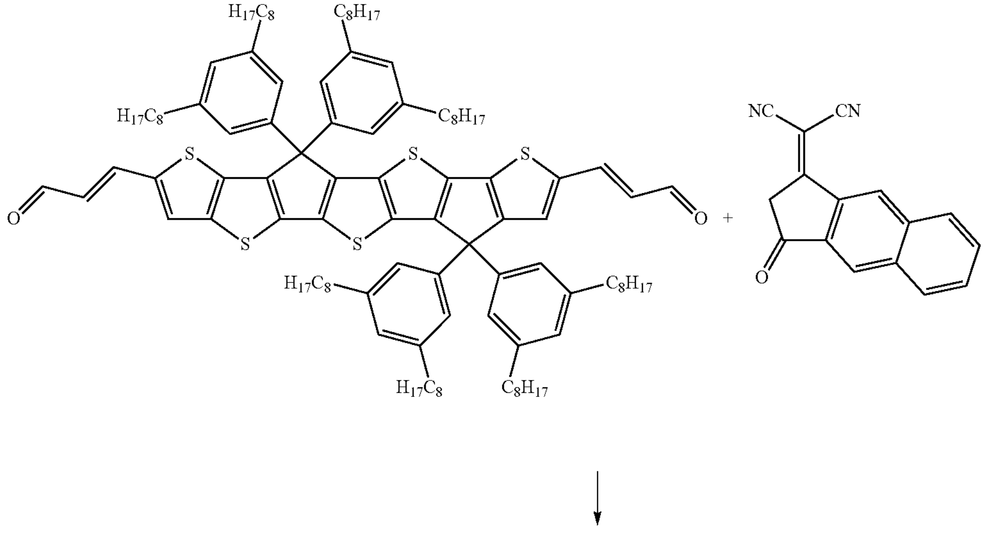

-continued

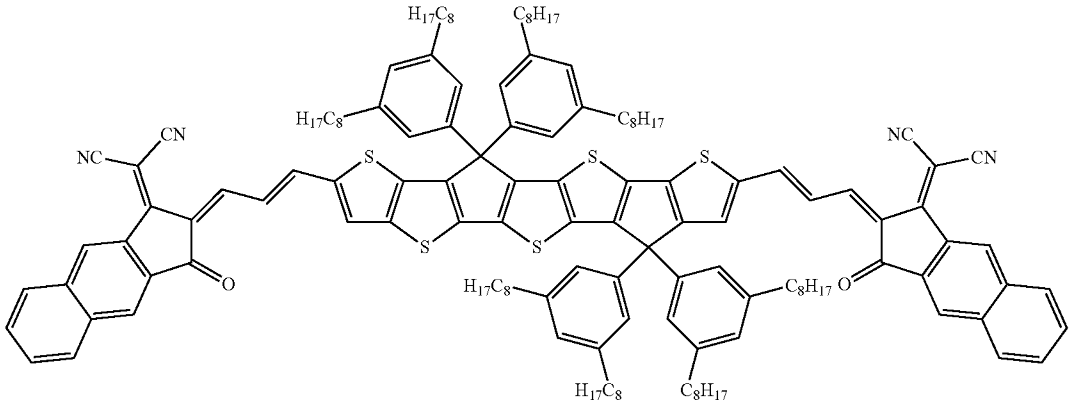

To a solution of intermediate 58 (139 mg, 0.082 mmol) in chloroform (10 $cm^3$) is added pyridine (0.1 $cm^3$, 1 mmol) and 2-{3-oxo-1H,2H,3H-cyclopenta[b]naphthalen-1-ylidene}propanedinitrile (59.0 mg, 0.241 mmol). The solution is stirred at 23° C. for 12 hours and at 40° C. for 3 hours and then allowed to cool to 23° C. The volatiles are removed in vacuo and the residue triturated with methanol. The solid is collected by filtration and washed with methanol until the filtrate is colourless. The crude is then further purified by column chromatography (chloroform) to give compound 27 (133 mg, 76%) as a green solid. $^1H$ NMR (400 MHz, $CDCl_3$) 9.06-9.13 (2H, m), 8.56-8.70 (2H, m), 8.39-8.47 (2H, m), 8.23-8.29 (2H, m), 7.92-8.07 (4H, m), 7.58-7.66 (4H, m), 7.55 (1H, s), 7.43-7.53 (2H, m), 7.30 (1H, s), 6.71-6.93 (12H, m), 2.39-2.51 (16H, m), 1.40-1.56 (16H, m), 1.00-1.28 (80H, m), 0.65-0.80 (24H, m).

Example 28

Compound 28

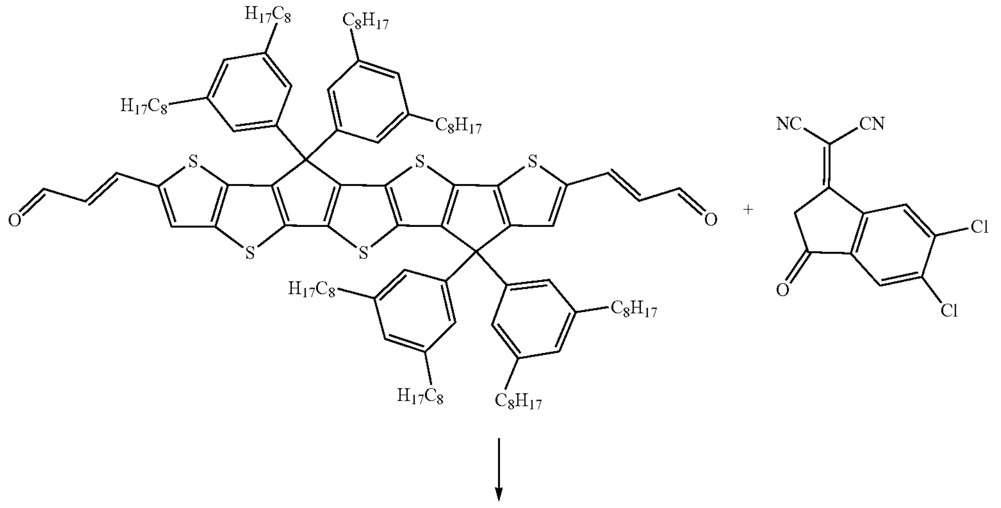

-continued

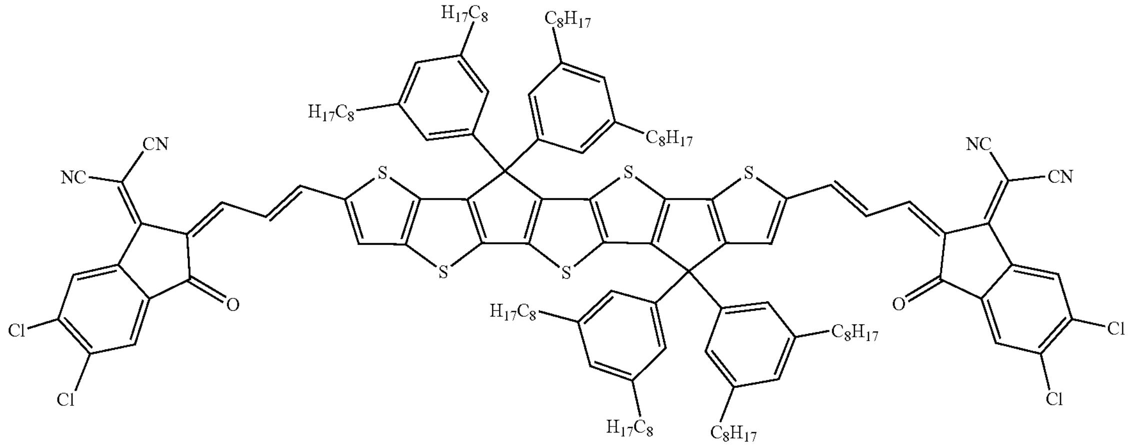

To a solution of intermediate 58 (130 mg, 0.077 mmol) in chloroform (10 $cm^3$) is added pyridine (0.1 $cm^3$, 1 mmol) and 2-(5,6-dichloro-3-oxo-2,3-dihydro-1H-inden-1-ylidene) propanedinitrile (60.5 mg, 0.230 mmol). The solution is stirred at 23° C. for 24 hours and at 40° C. for 1 hour and then allowed to cool to 23° C. The volatiles are removed in vacuo and the residue triturated with methanol. The solid is collected by filtration and washed with methanol until the filtrate is colourless. The crude is then further purified by column chromatography using a graded solvent system (cyclohexane:chloroform;13:7 to 1:1) to give compound 28 (87 mg, 52%) as a green solid. $^1$H NMR (400 MHz, $CD_2Cl_2$) 8.75-8.83 (1H, m), 8.62-8.68 (2H, m), 8.31-8.52 (3H, m), 8.02-8.07 (1H, m), 7.78-7.85 (2H, m), 7.45-7.70 (2H, m), 7.33-7.37 (1H, m), 6.83-6.90 (4H, m), 6.70-6.80 (8H, m), 2.35-2.50 (16H, m), 1.38-1.50 (16H, m), 1.02-1.25 (80H, m), 0.67-0.78 (24H, m).

Example 29

Compound 29

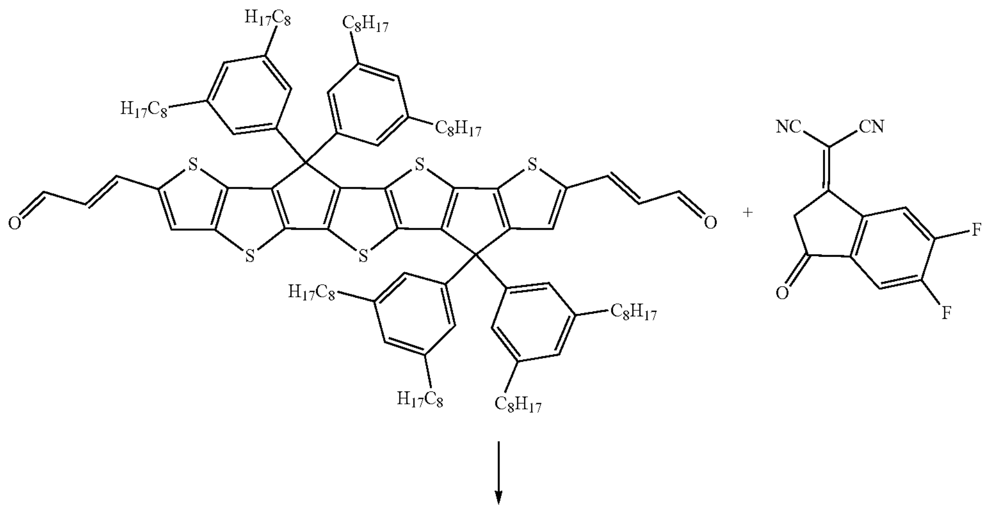

-continued

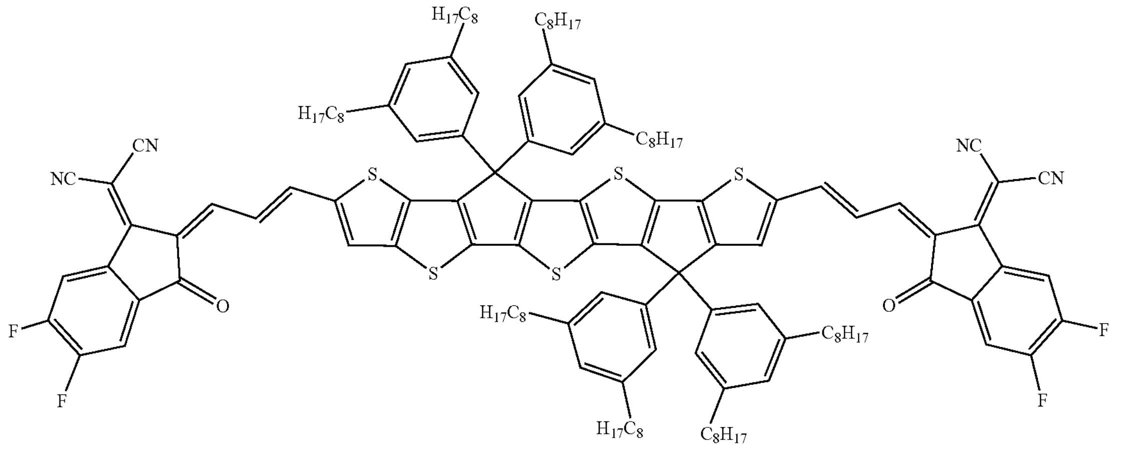

To a solution of intermediate 58 (130 mg, 0.077 mmol) in chloroform (10 $cm^3$) is added pyridine (0.1 $cm^3$, 1 mmol) and 2-(5,6-difluoro-3-oxo-2,3-dihydro-1H-inden-1-ylidene) propanedinitrile (53.0 mg, 0.230 mmol). The solution is stirred at 23° C. for 24 hours. The volatiles are removed in vacuo and the residue triturated with methanol. The solid is collected by filtration and washed with methanol until the filtrate is colourless. The crude is then further purified by column chromatography using a graded solvent system (cyclohexane:chloroform;13:7 to 1:1) to give compound 29 (85 mg, 52%) as a green solid. H NMR (400 MHz, $CD_2Cl_2$) 8.74-8.80 (1H, m), 8.02-8.51 (6H, m), 8.46-8.69 (4H, m), 7.31-7.36 (1H, m), 6.83-6.90 (4H, m), 6.70-6.80 (8H, m), 2.35-2.49 (16H, m), 1.37-1.52 (16H, m), 1.00-1.25 (80H, m), 0.65-0.79 (24H, m).

Use Example 1

Current-voltage characteristics are measured using a Keithley 2400 SMU while the solar cells are illuminated by a Newport Solar Simulator at 100 mWcm-2 white light. The solar simulator is equipped with AM1.5G filters. The illumination intensity is calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics are obtained for a composition, which contains Polymer 1 or Polymer 2 as shown below and an acceptor that is a compound of formula I, and is coated from an organic solution. Details of the solution composition are shown in Table 1.

Polymer 1

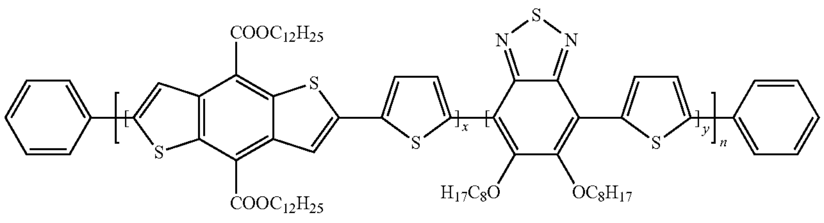

(x=y=1) and its preparation are disclosed in WO 2011/131280 A1.

Polymer 2

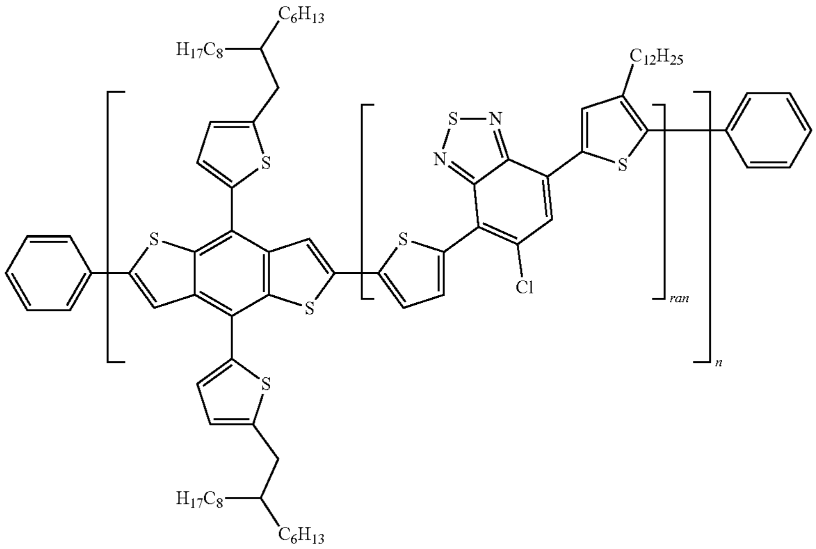

A1: Inverted Bulk Heterojunction Organic Photovoltaic Devices

Organic photovoltaic (OPV) devices are fabricated on pre-patterned ITO-glass substrates (13 Ω/sq.) purchased from LUMTEC Corporation. Substrates are cleaned using common solvents (acetone, iso-propanol, deionized-water) in an ultrasonic bath. A layer of commercially available aluminium zinc oxide (AlZnO, Nanograde) is applied as a uniform coating by doctor blade at 40° C. The AlZnO Films are then annealed at 100° C. for 10 minutes in air. Active material solutions (i.e. polymer+acceptor) are prepared to fully dissolve the solutes at a 23 mg·cm-3 solution concentration. Thin films are blade-coated in air atmosphere to achieve active layer thicknesses between 50 and 800 nm as measured using a profilometer. A short drying period follows to ensure removal of any residual solvent.

Typically, blade-coated films are dried at 70° C. for 2 minutes on a hotplate. Next the devices are transferred into an air atmosphere. On top of the active layer 0.1 mL of a conducting polymer poly(ethylene dioxythiophene) doped with poly(styrene sulfonic acid) [PEDOT:PSS Clevios HTL Solar SCA 434 (Heraeus)] is spread and uniformly coated by doctor blade at 70° C. Afterwards Ag (100 nm) cathodes are thermally evaporated through a shadow mask to define the cells.

Table 1 shows the characteristics of the individual photoactive formulations. The solvent is o-xylene (oXyl).

TABLE 1

Formulation characteristics

| No. | Acceptor | Polymer | Ratio Polymer: Acceptor | Concentration g/L | Solvent |
|---|---|---|---|---|---|
| 1 | Compound 3 | 1 | 1.00:1.30 | 23 | oXyl |
| 2 | Compound 3 | 2 | 1.00:1.30 | 23 | oXyl |
| 3 | Compound 7 | 2 | 1.00:1.30 | 23 | oXyl |

A2: Inverted Device Properties

Table 2 shows the device characteristics for the individual OPV devices comprising a photoactive layer with a BHJ formed from the photoactive acceptor/polymer formulations of Table 1.

TABLE 2

Photovoltaic cell characteristics under simulated solar irradiation at 1 sun (AM1.5G).

| | | Average Performance | | | |
|---|---|---|---|---|---|
| No. | Acceptor | Voc mV | Jsc $mA \cdot cm^{-2}$ | FF % | PCE % |
| 1 | Compound 3 | 690 | 15.4 | 55.4 | 5.48 |
| 2 | Compound 3 | 665 | 14.1 | 58.2 | 5.25 |
| 3 | Compound 7 | 657 | 11.0 | 47.2 | 3.40 |

From Table 2 it can be seen that OPV devices with a BHJ prepared from a solution of Polymer 1 or 2 and Compounds 3 or 7 show functional OPV devices.

Use Example 2 and 3

A1: Bulk Heterojunction Organic Photodetector Devices (OPDs)

Devices are fabricated onto glass substrates with six pre-patterned ITO dots of 5 mm diameter to provide the bottom electrode. The ITO substrates are cleaned using a standard process of ultrasonication in Decon90 solution (30 minutes) followed by washing with de-ionized water (×3) and ultrasonication in de-ionized water (30 minutes). The ZnO ETL layer is deposited by spin coating a ZnO nanoparticle dispersion onto the substrate and drying on a hotplate for 10 minutes at a temperature between 100 and 140° C. A formulation of Polymer 2, Polymer 3 (sourced from Merck KGaA) or Polymer 4 (Lisicon PV-D4650 (sourced from Merck KGaA)) and an acceptor which is a compound of formula I as disclosed herein is prepared at a ratio of 1:1 in o-xylene at a concentration of 20 mg/ml, and stirred for 17 hours at a temperature of between 23° C. and 60° C. The active layer is deposited using blade coating (K101 Control Coater System from RK). The stage temperature is set to between 20-60° C., the blade gap set between 2 and 200 μm and the speed set between 2 and 8 m/min, targeting a final dry film thickness of 500-1000 nm. Following coating the active layer is annealed at 100° C. for 10 minutes. The $MoO_3$ HTL layer is deposited by E-beam vacuum deposition from $MoO_3$ pellets at a rate of 1 Å/s, targeting 15 nm thickness. Finally, the top silver electrode is deposited by thermal evaporation through a shadow mask, to achieve Ag thickness between 30 and 80 nm.

Polymer 3

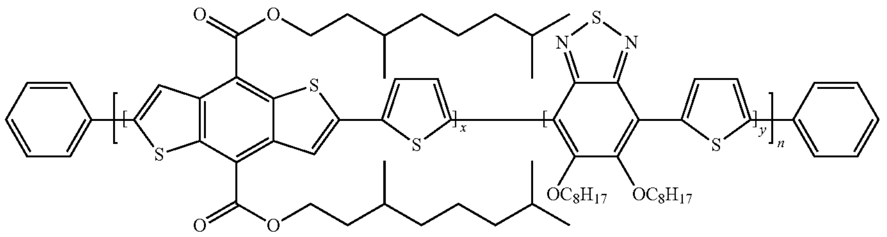

The J-V curves are measured using a Keithley 4200 system under light and dark conditions at a bias from +5 to −5 V. The light source is a 580 nm LED with power 0.5 mW/cm$^2$.

The EQE of OPD devices are characterized between 400 and 1100 nm under −2V bias, using an External Quantum Efficiency (EQE) Measurement System from LOT-QuantumDesign Europe.

Table 3 shows the characteristics of the individual formulations.

TABLE 3

| Formulation characteristics | | |
|---|---|---|
| No. | Acceptor | Polymer |
| 3 | Compound 1 | 4 |
| 4 | Compound 1 | 3 |
| 5 | Compound 3 | 4 |
| 6 | Compound 3 | 3 |
| 7 | Compound 4 | 2 |
| 8 | Compound 5 | 2 |
| 9 | Compound 6 | 2 |
| 10 | Compound 7 | 2 |
| 11 | Compound 8 | 4 |
| 12 | Compound 8 | 2 |

Tables 4, 5 and 6 show the EQE values for the individual OPD devices comprising a photoactive layer with a BHJ formed from the photoactive acceptor/polymer formulations of Table 3.

TABLE 4

| EQEs for the devices at 650 nm | | | | | | | | | | |
|---|---|---|---|---|---|---|---|---|---|---|
| No. | 3 | 4 | 5 | 6 | 7 | 8 | 9 | 10 | 11 | 12 |
| EQE % | 46 | 57 | 23 | 47 | 42 | 44 | 23 | 29 | 28 | 63 |

TABLE 5

| EQEs for the devices at 850 nm | | | | | | | | | | |
|---|---|---|---|---|---|---|---|---|---|---|
| No. | 3 | 4 | 5 | 6 | 7 | 8 | 9 | 10 | 11 | 12 |
| EQE % | 40 | 49 | 18 | 38 | 36 | 38 | 9 | 23 | 24 | 57 |

TABLE 6

| EQEs for the devices at 940 nm | | | | | | | | | | |
|---|---|---|---|---|---|---|---|---|---|---|
| No. | 3 | 4 | 5 | 6 | 7 | 8 | 9 | 10 | 11 | 12 |
| EQE % | 34 | 42 | 14 | 25 | 32 | 31 | 7 | 15 | 20 | 52 |

The invention claimed is:

1. A compound of formula I1

I1

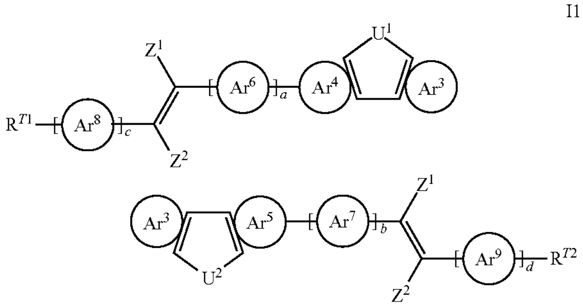

wherein the individual radicals, independently of each other and on each occurrence identically or differently, have the following meanings $Ar^3$ heteroarylene that has from 5 to 20 ring atoms, is mono- or polycyclic, optionally contains fused rings, and is unsubstituted or substituted by one or more identical or different groups $R^1$ or $L^S$, $Ar^{4-5}$ arylene or heteroarylene that has from 5 to 20 ring atoms, is mono-or polycyclic, optionally contains fused rings, and is unsubstituted or substituted by one or more identical or different groups $R^1$ or $L^S$, $Ar^{6-9}$ arylene or heteroarylene that has from 5 to 20 ring atoms, is mono-or polycyclic, optionally contains fused rings, and is unsubstituted or substituted by one or more identical or different groups $R^1$ or $L^S$, or $CY^1{=}CY^2$ or —C≡C—, $U^1$, $U^2$ $CR^1R^2$, $SiR^1R^2$, $GeR^1R^2$, $C{=}CR^1R^2$ or C═O, $R^W$ an electron withdrawing group, which has one of the meanings given for an electron withdrawing group $R^{T1}$, $Z^1$, $Z^2$ $R^1$ or $Y^1$, $Y^1$, $Y^2$ H, F, Cl or CN, $R^1$, $R^2$ $R^W$, H, F, Cl, CN, or straight-chain, branched or cyclic alkyl with 1 to 30, in which one or more $CH_2$ groups are optionally replaced by —O—, —S—, —C(═O)—, —C(═S)—, —C(═O)—O—, —O—C(═O)—, —$NR^0$—, —$SiR^0R^{00}$—, —$CF_2$—, —$CR^0{=}CR^{00}$—, —$CY^1{=}CY^2$— or —C≡C— in such a manner that O and/or S atoms are not linked directly to one another, and in which one or more H atoms are optionally replaced by F, Cl, Br, I or CN, and in which one or more $CH_2$ or $CH_3$ groups are optionally replaced by a cationic or anionic group, or aryl, heteroaryl, arylalkyl, heteroarylalkyl, aryloxy or heteroaryloxy, wherein each of the aforementioned cyclic groups has 5 to 20 ring atoms, is mono-or polycyclic, does optionally contain fused rings, and is unsubstituted or substituted by one or more identical or different groups $L^S$, and the pair of $R^1$ and $R^2$, together with the C, Si or Ge atom to which they are attached, may also form a spiro group with 5 to 20 ring atoms which is mono-or polycyclic, does optionally contain fused rings, and is unsubstituted or substituted by one or more identical or different groups $L^S$, $L^S$ F, Cl, —$NO_2$, —CN, —NC, —NCO, —NCS, —OCN, —SCN, $R^0$, $OR^0$, $SR^0$, —C(═O) $X^0$, —C(═O) $R^0$, —C(═O)—$OR^0$, —O—C(═O)—$R^0$, —$NH_2$, —$NHR^0$, —$NR^0R^{00}$, —C(═O) $NHR^0$, —C(═O) $NR^0R^{00}$, —$SO_3R^0$, —$SO_2R^0$, —OH, —$NO_2$, —$CF_3$, —$SF_5$, or optionally substituted silyl, or carbyl or hydrocarbyl with 1 to 30 C, a, b, c, d 0 or an integer from 1 to 10, wherein at least one of $R^{T1}$ and $R^{T2}$ is an electron withdrawing group, and $R^{T1}$ and $R^{T2}$ are selected from the group consisting of F, Cl, Br, —$NO_2$, —CN, —$CF_3$, —$CF_2$—R*, —O—R*, —S—R*, —$SO_2$—R*, —$SO_3$—R*, —C(═O)—H, —C(═O)—R*, —C(═S)—R*, —C(═O)—$CF_2$—R*, —C(═O)—OR*, —C(═S)—OR*, —O—C(═O)—R*, —O—C(═S)—R*, —C(═O)—SR*, —S—C(═O)—R*, —C(═O)NR*R**, —NR*—C(═O)—R*, —NHR*, —NR*R**, —CR*═CR*R**, —C═C—R*, —C≡C—SiR*RR*, —SiR*RR*, —CH═CH (CN), —C(CN)═C$(CN)_2$, —CH═C (CN)($R^a$), CH═C(CN)—C(═O)—OR*, —CH═C$(CO—OR^*)_2$, —CH═C$(CO—NR^*R^{**})_2$, and the group consisting of the following formulae,

T1

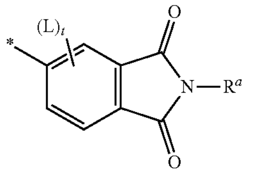

-continued

T2

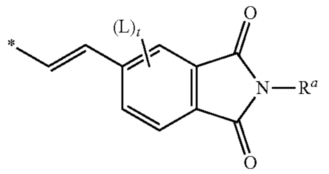

T3

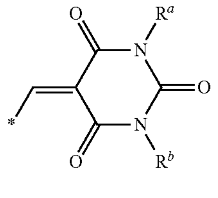

T4

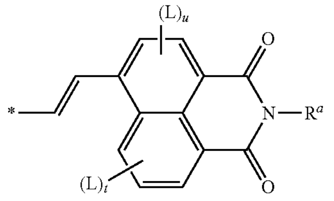

T5

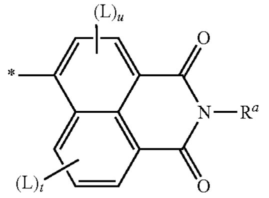

T6

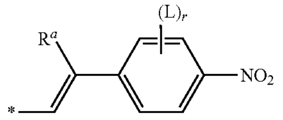

T7

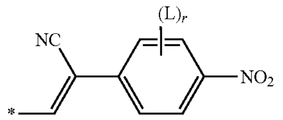

T8

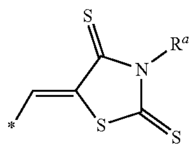

T9

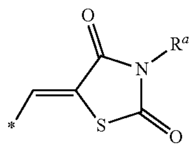

T10

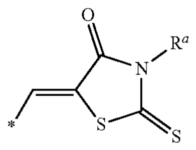

-continued
T11
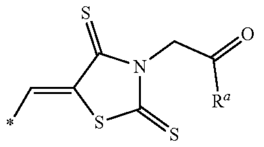
T12
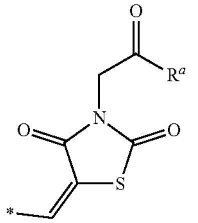
T13
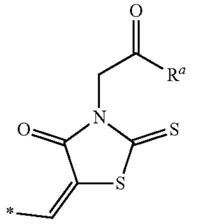
T14
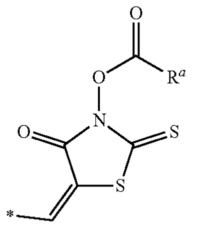
T15
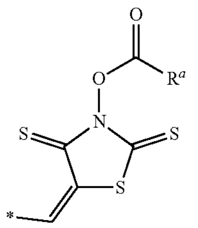
T16
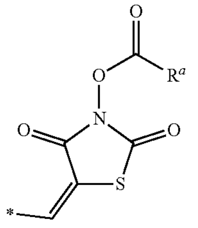
T17
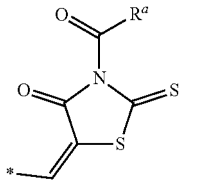
-continued
T18
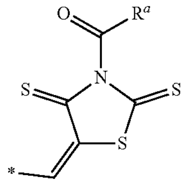
T19
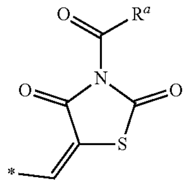
T20
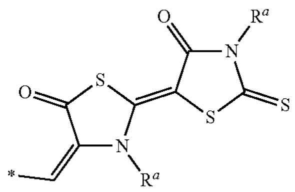
T21
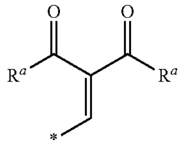
T22
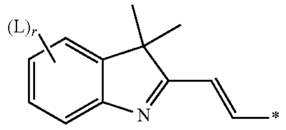
T23
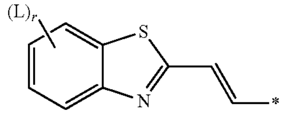
T24
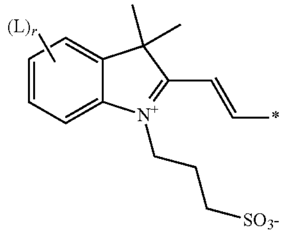
T25
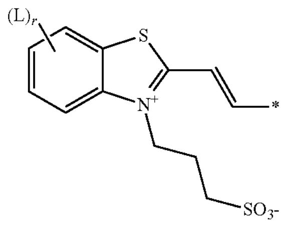

-continued
T26
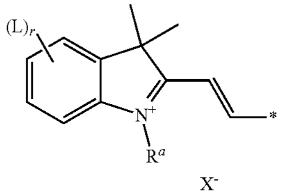
T27
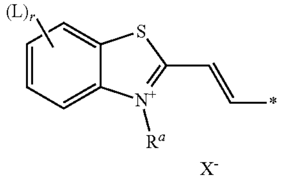
T28
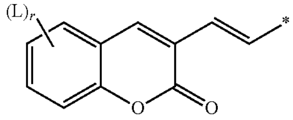
T29
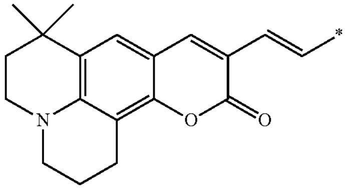
T30
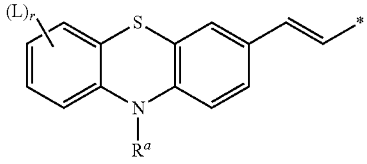
T31
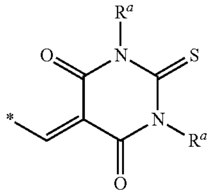
T32
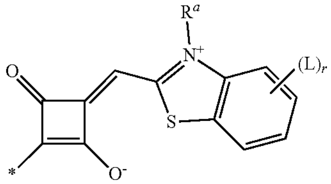
T33
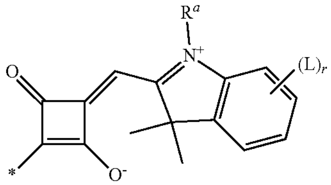
T34
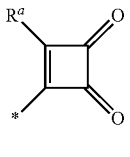
-continued
T35
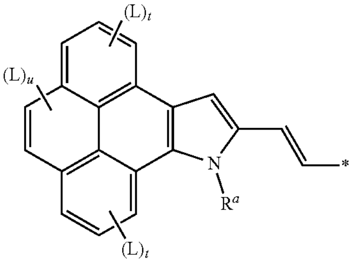
T36
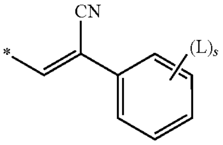
T37
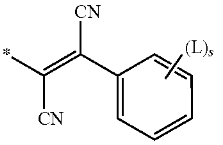
T39
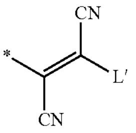
T40
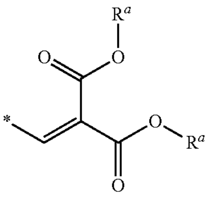
T41
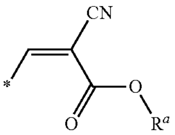
T42
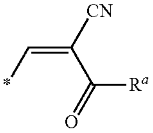
T43
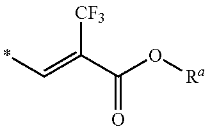
T44
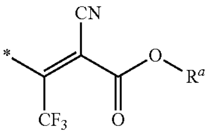

-continued
T45
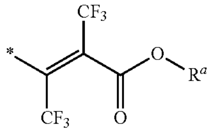
T46
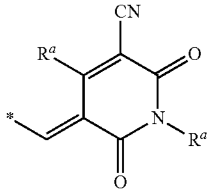
T47
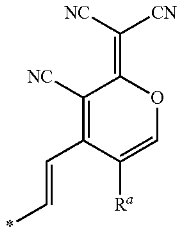
T48
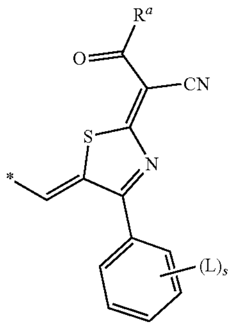
T49
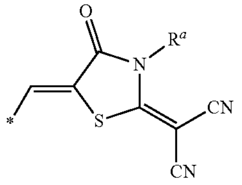
T50
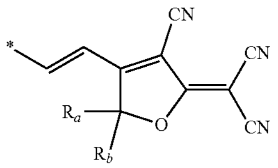
T51
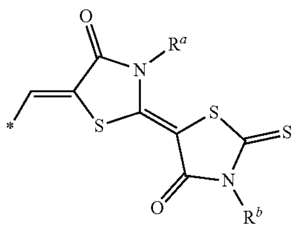
-continued
T52
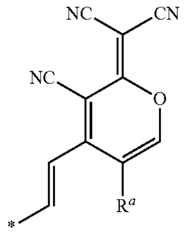
T53
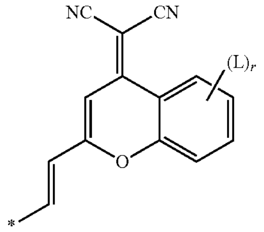
T54
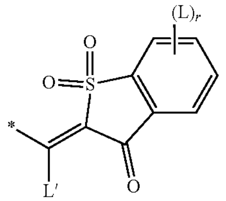
T55
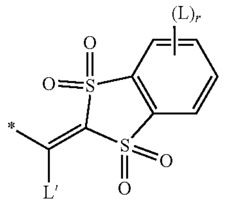
T56
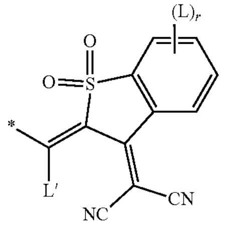
T57
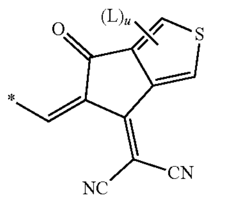
T58
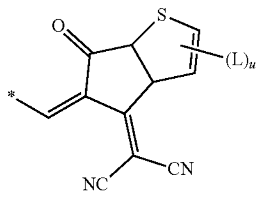

-continued
T59
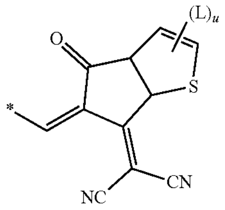
T60
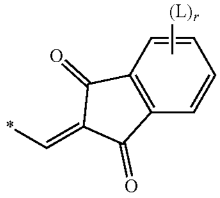
T61
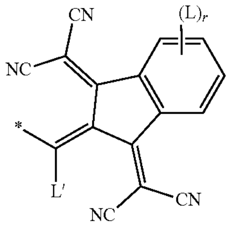
T62
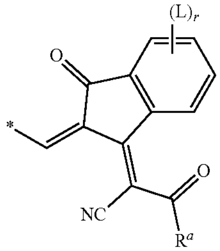
T63
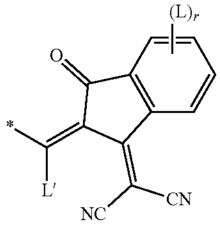
T64
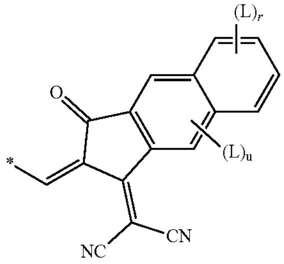
-continued
T65
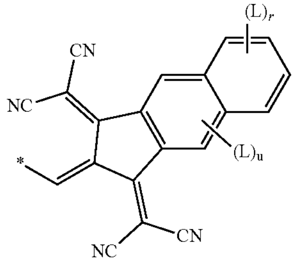
T66
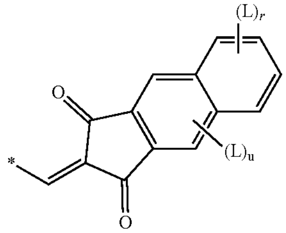
T67
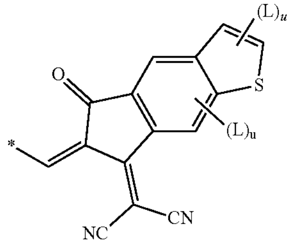
T68
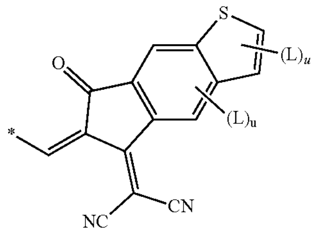
T69
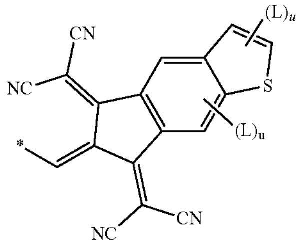
T70
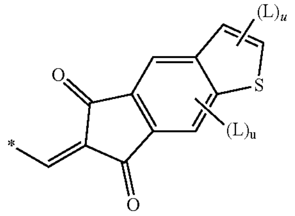

-continued

T71

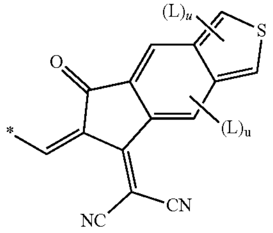

T72

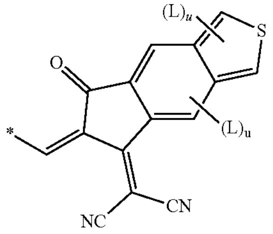

T73

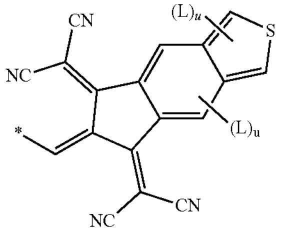

T74

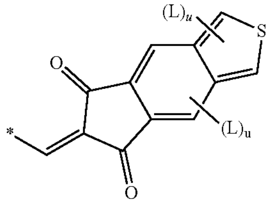

T75

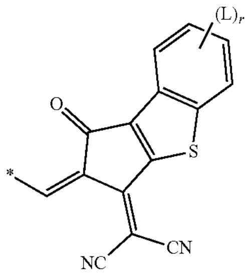

T76

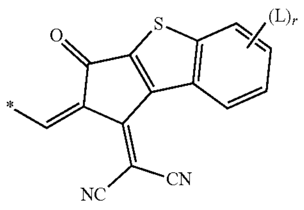

-continued

T77

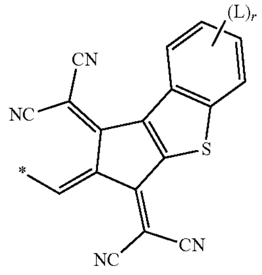

T78

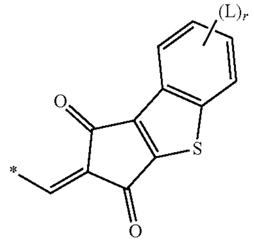

wherein the individual radicals, independently of each other and on each occurrence identically or differently, have the following meanings $R^a$, $R^b$ aryl or heteroaryl, each having from 4 to 30 ring atoms, or containing fused rings or being unsubstituted or substituted with one or more groups L, or one of the meanings given for L, R*, R, R* alkyl with 1 to 20 C atoms which is straight-chain, branched or cyclic, and is unsubstituted, or substituted with one or more For Cl atoms or CN groups, or perfluorinated, and in which one or more C atoms are optionally replaced by —O—, —S—, —C(═O)—, —C(═S)—, —$SiR^0R^{00}$, —$NR^0R^{00}$, —$CHR^0$═$CR^{00}$, or —C≡C— such that O- and/or S-atoms are not directly linked to each other, L F, Cl, —$NO_2$, —CN, —NC, —NCO, —NCS, —OCN, —SCN, $R^0$, $OR^0$, $SR^0$, —C(═O) $X^0$, —C(═O) $R^0$, —C(═O)—$OR^0$, —O—C(═O)—$R^0$, —$NH_2$, —$NHR^0$, —$NR^0R^{00}$, —C(═O)$NHR^0$, —C(═O) $NR^0R^{00}$, —$SO_3R^0$, —$SO_2R^0$, —OH, —$NO_2$, —$CF_3$, —$SF_5$, or optionally substituted silyl, or carbyl or hydrocarbyl with 1 to 30 C, L' H or one of the meanings of L, $R^0$, $R^{00}$ H or straight-chain or branched alkyl with 1 to 20 C atoms, or 1 to 12 C atoms that is fluorinated, $Y^1$, $Y^2$ H, F, Cl or CN, $X^0$ halogen, r 0, 1, 2, 3 or 4, S 0, 1, 2, 3, 4 or 5, t 0, 1, 2 or 3, u 0, 1 or 2.

2. The compound according to claim 1, characterized in that the groups $Ar^3$ are on each occurrence identically or differently selected from the following formulae and their mirror images A3a

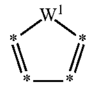

-continued

A3b

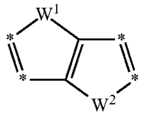

A3c

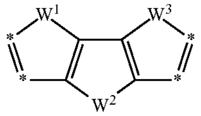

A3d

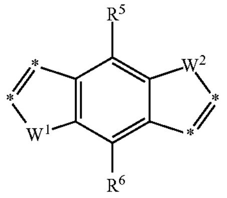

A3e

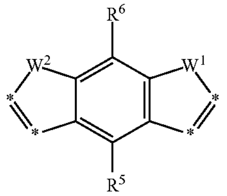

A3f

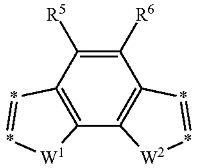

A3g

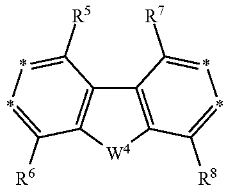

A3h

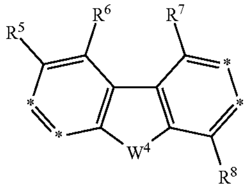

A3i

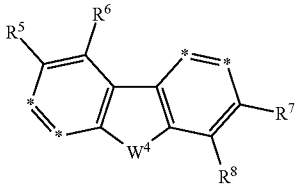

-continued

A3j

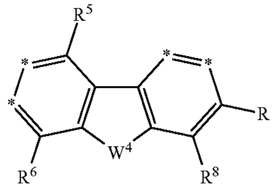

A3k

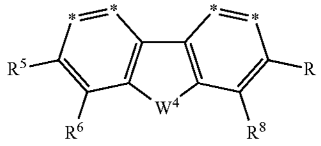

A3l

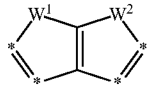

A3m

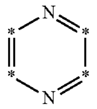

A3n

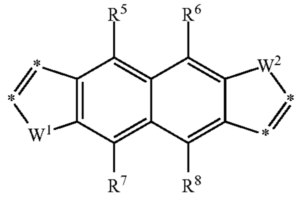

A3o

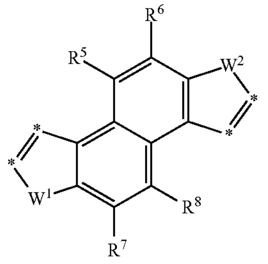

wherein the individual radicals, independently of each other and on each occurrence identically or differently, have the following meanings $W^1$, $W^2$, $W^3$ S, O or Se, $W^4$ S, O or $NR^3$, $R^{3-8}$ one of the meanings given for $R^1$ in claim 1.

3. The compound according to claim 1, characterized in that the groups $Ar^3$ are on each occurrence identically or differently selected from the following formulae and their mirror images A3a1

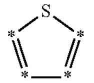

A3b1

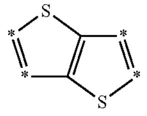

-continued
A3c1
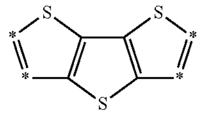
A3d1
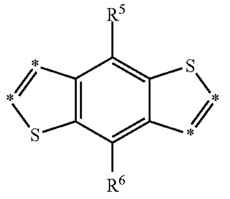
A3e1
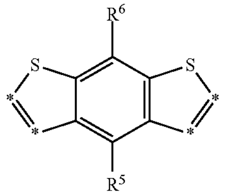
A3f1
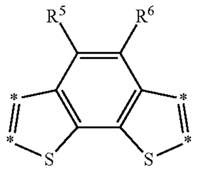
A3j1
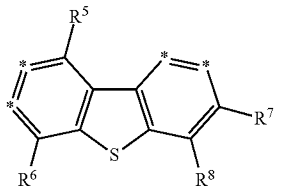
A3g2
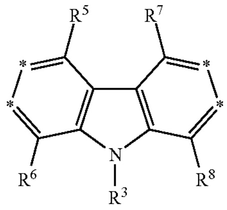
A3h2
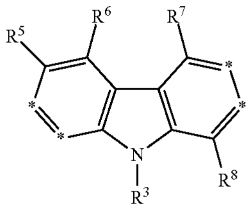
A3i2
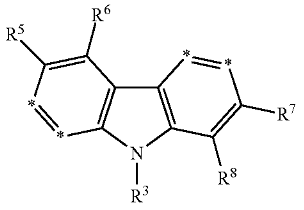
-continued
A3j2
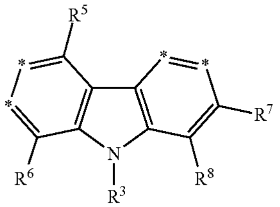
A3l1
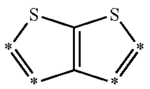
A3j1
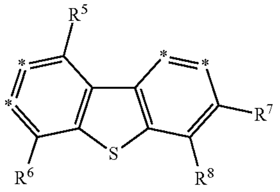
A3g2
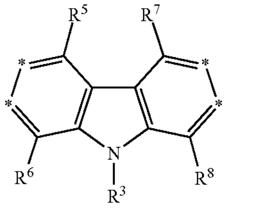
A3h2
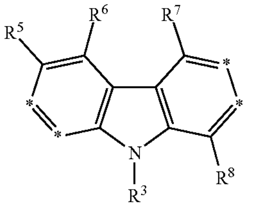
wherein $R^{3-8}$ have the meanings given in claim 2.
4. The compound according to claim 1, characterized in that the groups $Ar^4$ are on each occurrence identically or differently selected from the following formulae and their mirror images
A4a
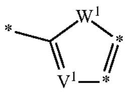
A4b
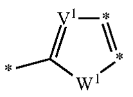
A4c
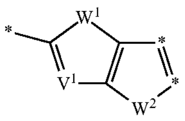
A4d
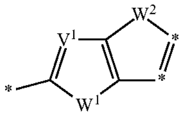

-continued
A4e
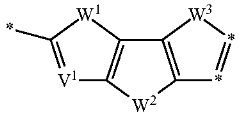
A4f
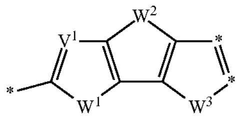
A4g
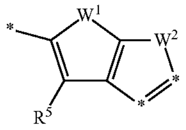
A4h
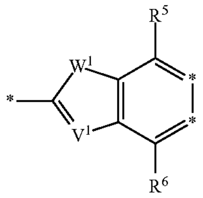
A4i
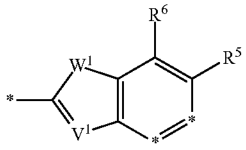
A4j
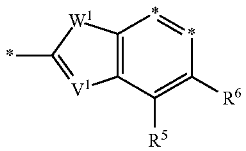
A4k
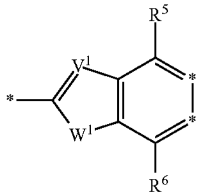
A4l
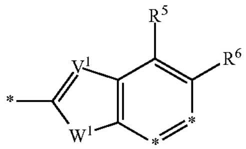
A4m
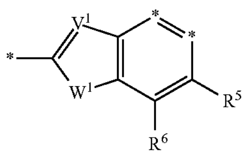
-continued
A4n
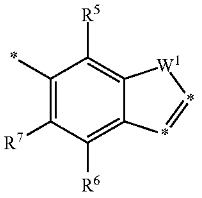
A4o
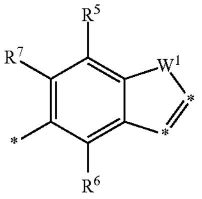
A4p
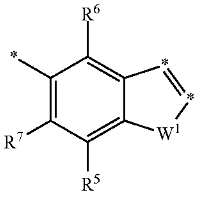
A4q
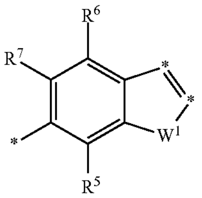
A4r
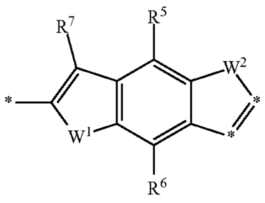
A4s
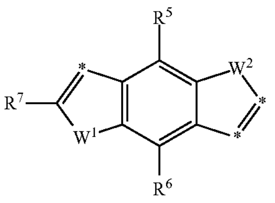
A4t
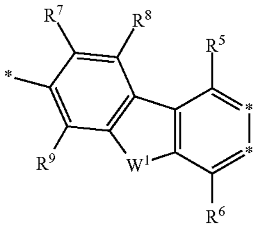

-continued

A4u

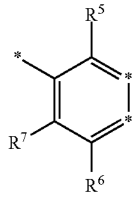

A4v

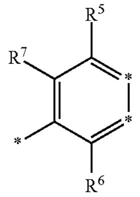

A4w

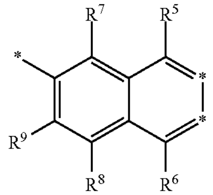

A4x

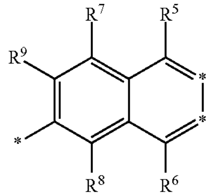

wherein $W^{1-3}$ and $R^{5-8}$ have the meanings given in claim 2, $V^1$ is $CR^5$ or N, and $R^9$ has one of the meanings given for $R^5$.

5. The compound according to claim 1, characterized in that the groups $Ar^4$ are on each occurrence identically or differently selected from the following formulae and their mirror images A4a1

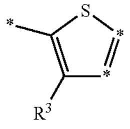

A4b1

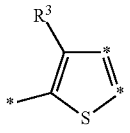

A4c1

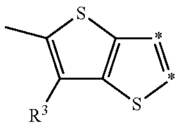

A4d1

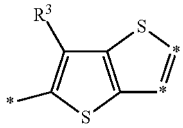

-continued

A4e1

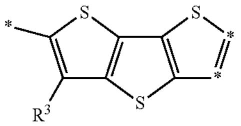

A4f1

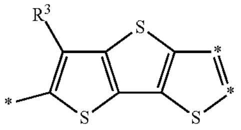

A4g1

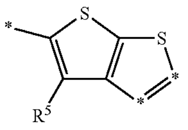

A4h1

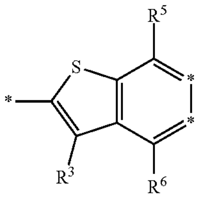

A4i1

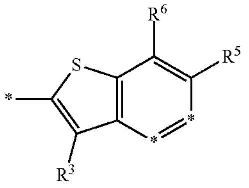

A4j1

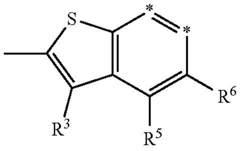

A4k1

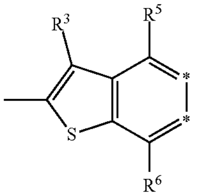

A4l1

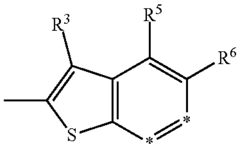

A4m1

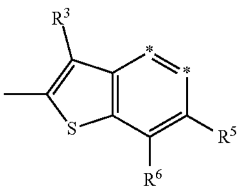

-continued
A4n1
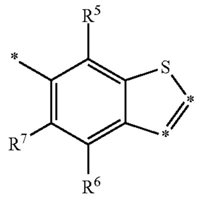
A4o1
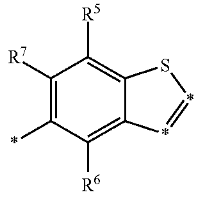
A4p1
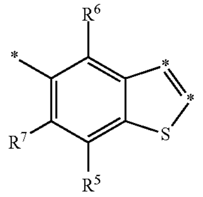
A4q1
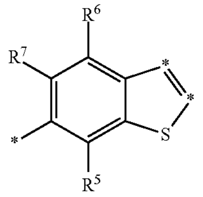
A4r1
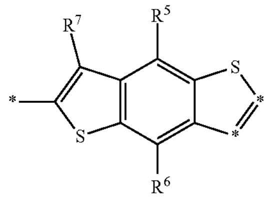
A4s1
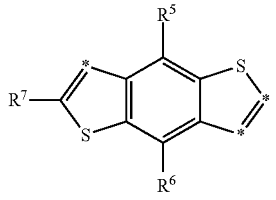
A4t1
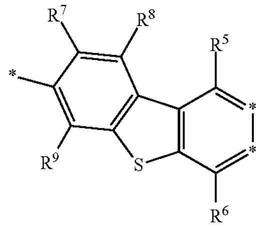
-continued
A4u
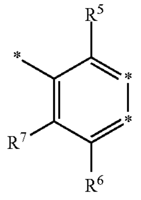
A4v
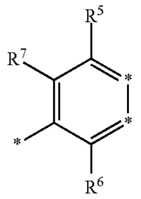
A4w
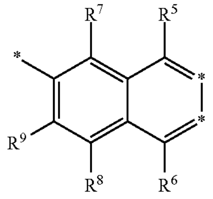
A4x
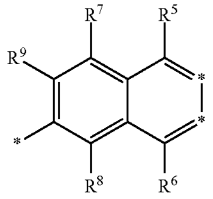
wherein $R^{5-9}$ have the meanings given in claim 4.
6. The compound according to claim 1, characterized in that the groups $Ar^5$ are on each occurrence identically or differently selected from the following formulae and their mirror images
A5a
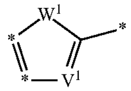
A5b
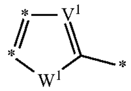
A5c
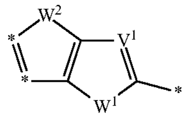
A5d
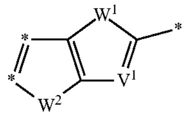
A5e
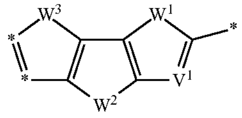

-continued
A5f
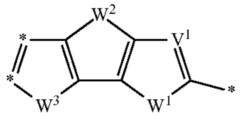
A5g
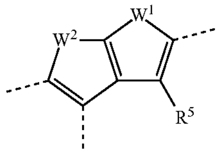
A5h
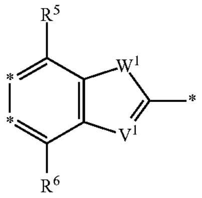
A5i
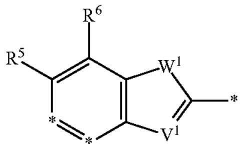
A5j
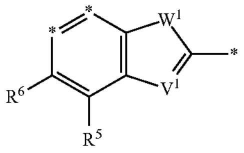
A5k
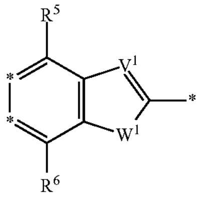
A5l
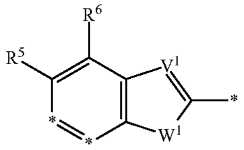
A5m
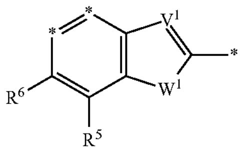
A5n
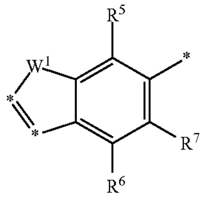
-continued
A5o
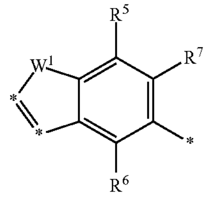
A5p
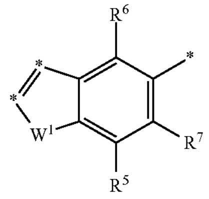
A5q
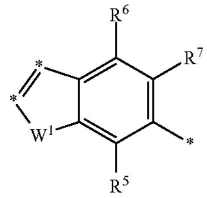
A5r
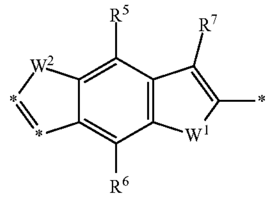
A5s
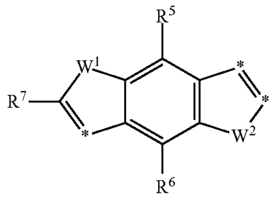
A5t
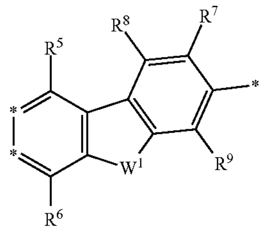
A5u
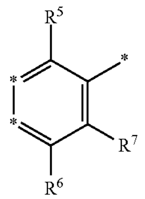

-continued
A5v
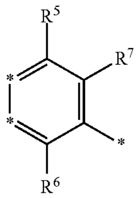
A5w
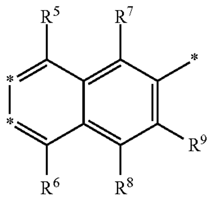
A5x
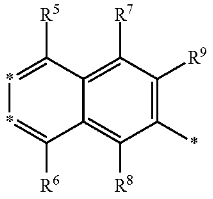
wherein $V^1$, $W^{1-3}$, and $R^{5-9}$ have the meanings given in claim 5.
7. The compound according to claim 1, characterized in that the groups $Ar^5$ are on each occurrence identically or differently selected from the following formulae and their mirror images
A5a1
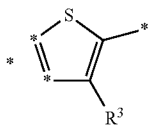
A5b1
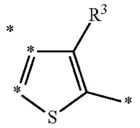
A5c1
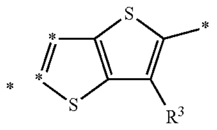
A5d1
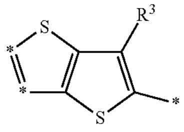
A5e1
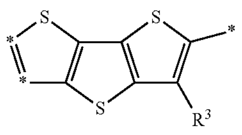
-continued
A5f1
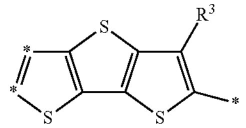
A5g1
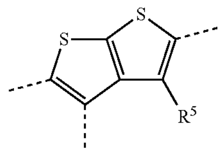
A5h1
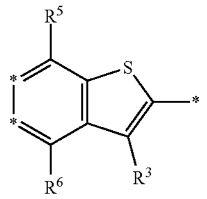
A5i1
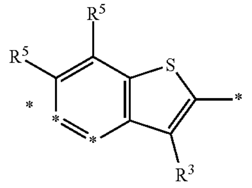
A5j1
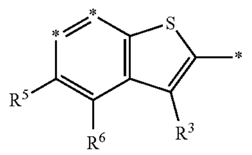
A5k1
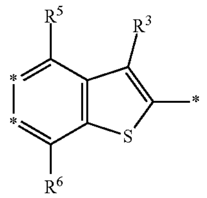
A5l1
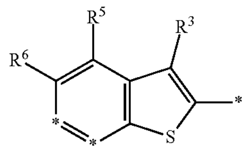
A5m1
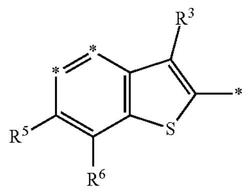
A5n1
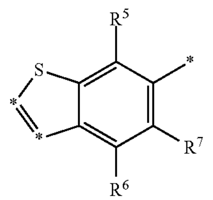

-continued
A5o1
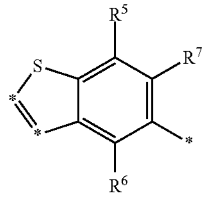
A5p1
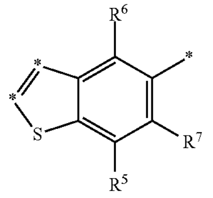
A5q1
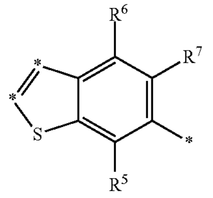
A5r1
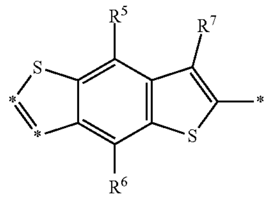
A5s1
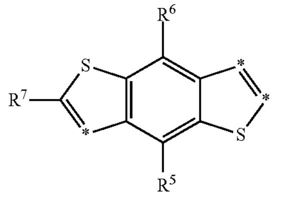
A5t1
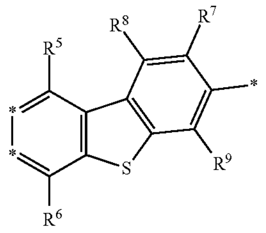
A5u
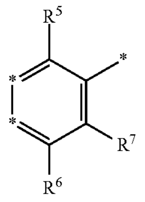
-continued
A5v
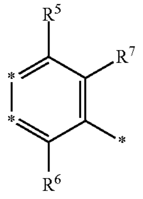
A5w
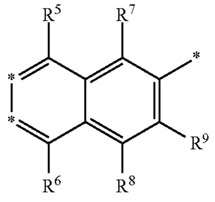
A5x
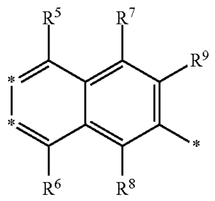
wherein $R^{5-9}$ have the meanings given in claim 4.
8. The compound according to claim 1, characterized in that the groups $Ar^{6-9}$ are on each occurrence identically or differently selected from the following formulae and their mirror images
AR1
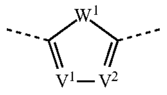
AR2
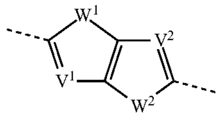
AR3
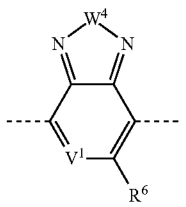
AR4
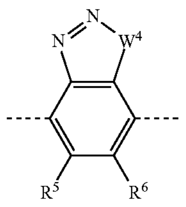

-continued

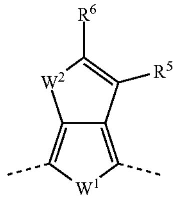

AR5

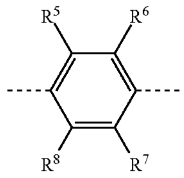

AR6

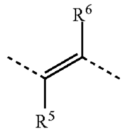

AR7 wherein, independently of each other and on each occurrence identically or differently, $V^2$ is $CR^5$ or N, and $V^1$, $W^{1-3}$ and $R^{5-8}$ are as defined in claim 2.

9. The compound according to claim 1, characterized in that both $R^{T1}$ and $R^{T2}$ denote an electron withdrawing group.

10. A composition comprising one or more compounds according to claim 1, and further comprising one or more compounds having one or more of a semiconducting, hole or electron transporting, hole or electron blocking, electrically conducting, photoconducting, photoactive or light emitting property, and/or a binder.

11. The composition of claim 10, comprising one or more n-type semiconductors, at least one of which is a compound according to claim 1, and further comprising one or more p-type semiconductors, selected from conjugated polymers.

12. The composition according to claim 10, comprising one or more n-type semiconductors selected from fullerenes or fullerene derivatives.

13. Use of a compound according to claim 1, or of a composition according to claim 10, in an electronic or optoelectronic device, or in a component of such a device or in an assembly comprising such a device.

14. A formulation comprising one or more compounds according to claim 1, or a composition according to claim 10, and further comprising one or more solvents selected from organic solvents.

15. An electronic or optoelectronic device, or a component thereof, or an assembly comprising it, which comprises a compound according to claim 1, or a composition according to claim 10.

16. The electronic or optoelectronic device according to claim 15, which is selected from organic field effect transistors (OFET), organic thin film transistors (OTFT), organic light emitting diodes (OLED), organic light emitting transistors (OLET), organic light emitting electro-chemical cells (OLEC), organic photovoltaic devices (OPV), organic photodetectors (OPD), organic solar cells, dye-sensitized solar cells (DSSC), perovskite-based solar cells (PSC), organic photoelectrochemical cells (OPEC), laser diodes, Schottky diodes, photoconductors, photodetectors, thermoelectric devices.

17. The component according to claim 15, which is selected from charge injection layers, charge transport layers, interlayers, planarizing layers, antistatic films, polymer electrolyte membranes (PEM), conducting substrates and conducting patterns.

18. The assembly according to claim 15, which is selected from integrated circuits (IC), radio frequency identification (RFID) tags, security markings, security devices, flat panel displays, LC windows, backlights of flat panel displays, electrophotographic devices, electrophotographic recording devices, organic memory devices, sensor devices, biosensors and biochips.

* * * * *